US006824981B2

(12) United States Patent
Chait et al.

(10) Patent No.: US 6,824,981 B2
(45) Date of Patent: Nov. 30, 2004

(54) ULTRA-SENSITIVE DETECTION SYSTEMS USING ALTERABLE PEPTIDE TAGS

(75) Inventors: Brian T. Chait, New York, NY (US); Darin R. Latimer, East Haven, CT (US); Paul M. Lizardi, Wallingford, CT (US); Eric R. Kershnar, New Haven, CT (US); Jon S. Morrow, Madison, CT (US); Matthew E. Roth, Branford, CT (US); Martin J. Mattessich, Woodbridge, CT (US); Kevin J. McConnell, Branford, CT (US)

(73) Assignee: Agilix Corporation, New Haven, CT (US)

( * ) Notice: Subject to any disclaimer, the term of this patent is extended or adjusted under 35 U.S.C. 154(b) by 164 days.

(21) Appl. No.: 09/929,266

(22) Filed: Aug. 13, 2001

(65) Prior Publication Data

US 2003/0045694 A1 Mar. 6, 2003

Related U.S. Application Data

(60) Provisional application No. 60/283,498, filed on Apr. 12, 2001, and provisional application No. 60/224,939, filed on Aug. 11, 2000.

(51) Int. Cl.[7] .............................. C12Q 1/68; C07K 7/00
(52) U.S. Cl. ........................ 435/6; 435/252.3; 536/234; 530/300; 530/344; 530/350; 530/412
(58) Field of Search ................................ 530/300, 344, 530/350, 412; 536/234; 435/252.3, 6

(56) References Cited

U.S. PATENT DOCUMENTS

| | | | |
|---|---|---|---|
| 4,086,254 A | 4/1978 | Wierenga | |
| 4,868,116 A | 9/1989 | Morgan et al. | |
| 4,980,286 A | 12/1990 | Morgan et al. | |
| 5,429,807 A | 7/1995 | Matson et al. | |
| 5,599,695 A | 2/1997 | Pease et al. | |
| 5,654,413 A | 8/1997 | Brenner et al. | |
| 5,780,232 A | 7/1998 | Arlinghaus | |
| 5,871,928 A | 2/1999 | Fodor et al. | |
| 6,117,631 A | 9/2000 | Nilsen | |
| 6,156,527 A * | 12/2000 | Schnidt et al. | 435/24 |
| 6,184,344 B1 | 2/2001 | Kent et al. | |
| 6,203,989 B1 | 3/2001 | Goldberg et al. | |
| 6,312,893 B1 | 11/2001 | Van Ness et al. | 435/6 |
| 6,312,904 B1 | 11/2001 | Schmidt et al. | 435/6 |
| 6,329,180 B1 * | 12/2001 | Garvin | 435/91.2 |
| 6,344,335 B1 | 2/2002 | Tausk et al. | |
| 6,403,309 B1 * | 6/2002 | Iris et al. | 435/6 |
| 6,562,567 B2 | 5/2003 | Wold | 435/6 |
| 6,613,508 B1 | 9/2003 | Ness et al. | 435/6 |
| 6,613,523 B2 | 9/2003 | Fischer | 435/6 |
| 6,629,040 B1 | 9/2003 | Goodlett et al. | 702/23 |
| 2003/0022225 A1 | 1/2003 | Monforte et al. | 435/6 |

FOREIGN PATENT DOCUMENTS

| | | |
|---|---|---|
| GB | 0006141.6 | 3/2000 |
| WO | WO 89/07136 | 8/1989 |
| WO | WO 90/02806 | 3/1990 |
| WO | WO 97/11958 | 4/1997 |
| WO | WO 98/28434 | 7/1998 |
| WO | WO 98/31830 | 7/1998 |
| WO | WO 99/05319 | 2/1999 |
| WO | WO 00/04036 | 1/2000 |
| WO | WO 00/11208 | 3/2000 |
| WO | WO00/23622 | * 4/2000 ............ C12Q/1/68 |
| WO | WO 01/68664 | 9/2001 |
| WO | WO 03/025576 | 3/2003 |

OTHER PUBLICATIONS

Geysen et al., "Isotope or Mass Encoding of Combinatorial Libaries" *Chemistry & Biology*, vol. 3, No. 8, 679–688 (1996).

Metzer et al., "Electrospray Mass Spectrometry and Tandem Mass Spectrometry of Synthetic Multicomponent Peptide Mixtures: Determination of Composition and Purity," *Analytical Biochemistry*, vol. 219, 219–277 (1994).

Nawrocki et al., "Analysis of Combinatorial Libraries Using Electrospray Fourier Transform Ion Cyclotron Resonance Mass Spectrometry," *Rapid Communications in Mass Spectrometry*, vol. 10, 1860–1864 (1996).

Nikolaiev et al., "Peptide–Encoding for Structure Determination of Nonsequenceable Polymers within Libraries Synthesized and Tested on Solid–Phase Supports,", *Peptide Research*, vol. 6, No. 3, 161–170 (1993).

(List continued on next page.)

*Primary Examiner*—Kenneth R. Horlick
(74) *Attorney, Agent, or Firm*—Needle & Rosenberg, PC

(57) ABSTRACT

Disclosed are compositions and methods for sensitive detection of one or multiple analytes. In general, the methods involve the use of special label components, referred to as reporter signals, that can be associated with, incorporated into, or otherwise linked to the analytes. In some embodiments, the reporter signals can be altered such that the altered forms of different reporter signals can be distinguished from each other. In some embodiments, sets of reporter signals can be used where two or more of the reporter signals in a set have one or more common properties that allow the reporter signals having the common property to be distinguished and/or separated from other molecules lacking the common property. In other embodiments, sets of reporter signal/analyte conjugates can be used where two or more of the reporter signal/analyte conjugates in a set have one or more common properties that allow the reporter signal/analyte conjugates having the common property to be distinguished and/or separated form other molecules lacking the common property. Reporter signals can also be in conjunction with analytes (such as in mixtures of reporter signals and analytes), where no significant physical association between the reporter signals and analytes occurs; or alone, where no analyte is present.

513 Claims, 10 Drawing Sheets

OTHER PUBLICATIONS

Wentworth, Jr. and Janda, "Generating and Analyzing Combinatorial Chemistry Libraries," *Analytical Biotechnology*, 109–115.

Winger and Campana, "Characterization of Combinatorial Peptide Libraries by Electrospray Ionization Fourier Transform Mass Spectrometry," *Rapid Communications in Mass Spectrometry*, vol. 10, 1811–1813 (1996).

Olejnik et al. Photocleavable biotin phosphoramidite for 5'—end–labelling, affinity purification and phosphorylation of synthetic oligonucleotides *Nucleic Acids Research, Oxford University Press, Surrey, GB* 24(2):361–366 (1996), XP002084583.

Alagon et al. Activation of polysacchirides with 2–iminothiolane and its uses. *Biochemistry* 19:4341–4345 (1980).

Alonso et al. Lipid chain dynamics in *stratum corneum* studied by spin label electron paramagnetic resonance. *Chem. Phys. Lipids* 104:101–111 (2000).

Andresen et al. Medium–chain acyl–CoA dehydrogenase (MCAD) mutations identified by MS/MS–based prospective screening of newborns differ from those observed in patients with clinical symptoms: identification and characterization of a new, prevalent mutation that results in mild MCAD deficiency. *Am. J. Hum. Genet.* 68:1408–1418 (2001).

Annan et al. A multidimensional electrospray MS–based appraoch to phosphopeptide mapping. *Anal. Chem.* 73:393–404 (2001).

Arora et al. Selectivity of lipid–protein interactions with trysinized Na, K–ATPase studies by spin–label ERP. *Biochim. Biophys. Acta.* 1371:163–167 (1998).

Banerji et al. A Lymphocyte–Specific Cellular Enhancer Is Located Downstream of the Joining Region in Immunoglobulin Heavy Chain Genes. *Cell* 33:729–740 (1983).

Berkner et al. Abundant Expression of Polyomavirus Middle T Antigen and Dihydrofolate Reductase in an Adenovirus Recombinant. *J. Virol.* 61:1213–1220 (1987).

Birkenmeyer et al. DNA Probe Amplification Methods. *J. Virol. Meth.* 35:117–126 (1991).

Black. Protein diversity from alternative splicing: a challenge for bioinformatics and post–genome biology. *Cell* 103:367–370 (2000).

Bout et al. Lung Gene Therapy: In Vivo Adenovirus–Mediated Gene Transfer to Rhesus Monkey Airway Epithelium. *Hum. Gene Ther.* 5:3–10 (1994).

Brdicka et al. *Phosphoprotein associated with glycosphingolipid–enriched microdomains (PAG), a novel ubiquitously* expressed transmembrane adaptor protein, binds the protein tyrosine kinase csk and is involved in regulation of T cell activation. *J. Exp. Med.* 191:1591–1604 (2000).

Breslauer et al. Predicting DNA duplex stability from the base sequence. *Proc. Natl. Acad. Sci. USA* 83:3746–3750 (1986).

Brizard et al. Immunoaffinity purifaction of FLAG epitode–tagged bacterial alkaline phosphatase using a novel monoclonal antibody and peptide elution. *Biotechnology* 16:730–735 (1994).

Brown et al. Penetration of Host Cell Membranes by Adenovirus 2. *Journal of Virology* 12(2):386–396 (1973).

Caillaud et al. Adenoviral Vector as a Gene Delivery System into Cultured Rat Neuronal and Glial Cells.. *Eur. J. Neurosci.* 5:1287–1291 (1993).

Cantrell. Phosphoinositide 3–kinase signalling pathways. *J. Cell. Sci.* 114:1439–1445 (2001).

Chandrasegaran et al. Chimeric restriction enzymes: what is next? *Biol. Chem.* 380(7–8):841–848 (1999).

Chardonnet et al. Early Events in the Interaction of Adenoviruses with HeLa Cells. *Virology* 40:462–477 (1970).

Chatterjee et al. In vivo Analysis of nuclear protein traffic in mammalian cells. *Exp. Cell. Res.* 236(1):346–350 (1997).

Chong et al. Utilizing the C–terminal cleavage activity of a protein splicing element to purify recombinant proteins in a single chromatographic step. *Nucl. Acids. Res.* 26(22):5109–5115 (1998).

Cianci et al. Brain and muscle express a unique alternative transcript of αII spectrin. *Biochemistry* 38:15721–15730 (1999).

Conrads et al. Utility of Accurate Mass Tags for Proteome–Wide Protein Identification *Anal. Chem.* 72:3349–3354 (2000).

Cowie et al. Biosynthesis by *Escherichia coli* of active altered proteins containing selenium instead of sulfur. *Biochimica. Et Biophsyica Acta.* 26:252–261 (1957).

Davidson et al. Overproduction of Polyomavirus Middle T Antigen in Mammalian Cells through the Use of an Adenovirus Vector. *J. Virol.* 61:1226–1239 (1987).

Dawson et al. Synthesis of proteins by native chemical ligation. *Science* 266:776–779 (1994).

Dawson et al. Synthesis of Native Proteins by Chemical Ligation. *Ann. Rev. Biochem.* 69:923–960 (2000).

DeGnore et al. Fragmentation of phosphopetides in an ion trap mass spectrometer. *J. Am. Soc. Mass Spectrom.* 9:1175–1188 (1998).

Dervan et al. Sequence–specific DNA recognition by polyamides. *Curr. Opin. Chem. Biol.* 3(6):688–693 (1999).

Dhandayuthapani et al. Green fluorescent protein as a marker for gene expression and cell biology of mycobacterial interactions with macrophages. *Mol. Microbiol.* 17(5):901–912 (1995).

Dikler et al. *J. Mass. Spectrom.* 32:1337–1349 (1997).

Drysdale et al. Complex promoter and coding region $\beta_2$–adrenergic receptor haplotypes alter receptor expression and predict in vivo responsiveness. *Proc. Natl. Acad. Sci. USA.* 97(19):10483–10488 (2000).

Engvall et al. Enzyme–linked immunosorbent assay (ELISA). Quantitive assay of immunoglobulin G. *Immunochemistry* 8:871–874 (1971).

Fields et al. A novel genetic system to detect protein–protein interactions. *Nature* 340:245–246 (1989).

Fiers et al. Complete nucleotide sequence of SV40 DNA. *Nature* 273:113–129 (1978).

Freier et al. Improved free–energy parameters for predictions of RNA duplex stability. *Proc. Natl. Acad. Sci. USA* 83:9373–9377 (1986).

Gasparro et al. Site–Specific targeting of psoralen photoadducts with a triple helix–forming oligonucleotide: characterization of psoralen monoadduct and crosslink formation. *Nucl. Acids Res.* 22(14):2845–2852 (1994).

Gee et al. Alternative splicing of protein 4.1R exon 16: ordered excision of flanking introns ensures proper splice site choice. *Blood* 95:692–699 (2000).

Godi et al. ARF mediates recruitment of PtdIns–4–OH kinase–beta and stimulates synthesis of PtdIns(4,5)P2 on the Golgi complex. *Nat. Cell. Biol.* 1:280–287 (1999) (Abstract).

Glatthar et al. A New Photocleavable Linker in Solid–Phase Chemistry for Ether Cleavage. *Org. Lett.* 2(15):2315–2317 (2000).

Gomez–Foix et al. Adenovirus–mediated Transfer of the Muscle Glycogen Phosphorylase Gene into Hepatocytes Confers Altered Regulation of Glycogen Metabolism. *J. Biol. Chem.* 267(35):25129–25134 (1992).

Greenaway et al. Human cytomegalovirus DNA: *Bam* HI, *Eco* RI and *Pst* I restriction endonuclease cleavage maps. *Gene* 18:355–360 (1982).

Griffin et al. Quantitative proteomic analysis using a MALDI quadrupole time–of–flight mass spectrometer. *Anal. Chem.* 73:978–986 (2001).

Groth et al. A phage integrase directs efficient site–specific integration in human cells. *Proc. Natl. Acad. Sci.* USA 97(11):5995–6000 (2000).

Guillier et al. Linkers and Cleavage Strategies in Solid–Phase Organic Synthesis and Combinatorial Chemistry. *Chem. Rev.* 100:2091–2157 (2000).

Guo et al. Direct Flourescence Analysis of Genetic Polymorphisms by Hybridization with Oligonucleotide Arrays on Glass Supports. *Nucl. Acids Res.* 22(24):5456–5465 (1994).

Guzman et al. Efficient Gene Transfer Into Myocardium by Direct Injection of Adenovirus Vectors. *Circul. Res.* 73:1202–1207 (1993).

Gygi et al. Quantitative analysis of complex protein mixtures using isotope–coded affinity tags. *Nat. Biotechnol.* 17:994–999 (1999).

Hackeng et al. Chemical synthesis and spontaneous folding of a multidomain protein anticoagulo dictopatent S. *Proc Natl. Sci. USA* 97(26):14074–14078 (2000).

Hage. Affinity chromatography: a review of clinical applications. *Clin. Chem.* 45(5):593–615 (1999).

Hage et al. Chromatographic Immunoassays. *Anal. Chem.* 73(7):198A–205A (2001).

Haj–Ahmad et al. Development of a Helper–Independent Human Adenovirus Vector and Its Use in the Transfer of the Herpes Simplex Virus Thymidine Kinase Gene. *J. Virol.* 57(1):267–274 (1986).

Harth–Fritschy et al Esterification of 9–Fluorenylmethoxy-carbonyl–glycosylated serine and cysteine derivatives with an hydroxymethyl resin. *Pet. Res.* 50:415 (1997).

Hayes et al. Desorption–ionization mass spectrometry using deposited nanostructured silicon films. *Anal. Chem.* 73:1292–1295 (2001).

Haynes et al. Proteome profiling–pitfalls and progress. *Yeast* 17(2):81–87 (2000).

Hendrickson et al. Selenomethionyl proteins produced for analysis by multiwavelength anomalous diffraction (MAD): a vehicle for direct determination of three–dimensional structure. *Embo. J.* 9(5):1665–1672 (1990).

Hendrickson et al. High sensitivity multianalyte immunoassay using covalent DNA–labeled antibodies and polymerase chain reaction. *Nucl. Acids Res.* 23(3):522–529 (1995).

Hermanson. Bioconjugate techniques, Academic Press, pp. 528–569 (1996).

Hobbs et al. Development of a bicistronic vector driven by the human polypeptide chain elongation factor 1α promoter for creation of stable mammalian cell lines that express very high levels of recombinant proteins. *Biochem. Biophys. Res. Commun.* 252:368–372 (1998).

Hoheisel. Sequence–independent and linear variation of oligonucleotide DNA binding stabilities. *Nucl. Acid. Res.* 24(3):430–432 (1996).

Hong et al. Development of two bacterial articial chromosome shuttle vectors for a recombination–based cloning and regulated expression of large genes in mammalian cells. *Anal. Biochem.* 291:142–148 (2001).

Hope et al. Production of large unilamellar vesicles by a rapid extrusion procedure. Characterization of size distribution, trapped volume and ability to maintain a membrane potential. *Biochimica et Biophysica Acta.* 812:55–65 (1985).

Horn et al. An improved divergent synthesis of comb–type branched oligodeoxyribonucleotides (bDNA) containing multiple secondary sequences. *Nucl. Acids Res.* 23(25):4835–4841 (1997).

Hou et al. Regulation of alternative pre–mRNA splicing during erythroid differentiation. *Curr. Opin. Hematol.* 8(2):74–79 (2001) (Abstract).

Jamieson et al. In vitro selection of zinc fingers with altered DNA –binding specificity. *Biochemistry* 33(19):5689–5895 (1994).

Johnstone et al. Immunochemistry In Practice (Blackwell Scientific Publications, Oxford, England, pp. 30–85 (1987).

Kershnar et al. Immunoaffinity purification and functional characterization of human transcription factor IIH and RNA polymerase II from clonal cell lines that conditionally express epitope–tagged subunits of the multiprotein complexes. *J. Biol. Chem.* 273:34444–34453 (1998).

Kikumori et al. Promiscuity of pre–mRNA spliceosome–mediated trans splicing: a problem for gene therapy? *Hum. Gene. Ther.* 12:1429–1441 (2001).

Kirshenbaum et al. Highly Efficient Gene Transfer into Adult Ventricular Myocytes by Recombinant Adenovirus. *J. Clin. Invest.* 92:381–387 (1993).

Kornberg et al. Inside–outside transitions of phospholipids in vesicle membranes. *Biochemistry* 10(7):1111–1120(1971).

Kornberg et al. Lateral diffusion of phospholipids in a vesicle membrane. *Proc. Natl. Acad. Sci. USA* 68(10):2564–2568 (1971).

Khrapko et al. Hybridization of DNA with oligonucleotides immobilized in gel: a convenient method for recording single base replacements. *Mol. Biol.* (*Mosk*) 25(3):718–730 (1991).

Kremer et al. Green fluorescent protein as a new expression marker in mycrobacteria. *Mol. Microbiol.* 17(5):913–922 (1995).

Krull et al. Labeling reactions applicable to chromatography and electrophoresis of minute amounts of proteins. *J. Chromatogr. B. Biomed. Sci. Appl.* 699:173–208 (1997).

Krull et al. Specific applications of capillary electrochromatography to biopolymers, including proteins, nucleic acids, peptide mapping, antibodies, and so forth. *J. Chromatogr. A.* 887:137–163 (2000).

Krutchinsky et al. Rapid, Automatic Identification of proteins utilizing a novel MALDI–Ion Trap Mass Spectrometer, *Abstract of the 49th ASMS Conference on Mass Spectrometry and Allied Topics* (May 27–31, 2001).

Krutchinsky et al. Rapidly Switchable Matrix–Assisted Desorption/Ionization and Electrospray Quadrupole–Time-of–Flight Mass Spectrometry for Protein Identification. *J. AM. Soc. Mass Spectrum.* 11(6):493–504 (2000).

Kunkel et al. Inducible isopentenyl tranferase as a high–efficency marker for plant transformation. *Nat. Biotech.* 17:916–919 (1999).

Laimins et al. Osmotic control of kdp operon expression in *Escherichia coli*. *Proc. Natl. Acad. Sci. USA* 78:464–468 (1981).

La Salle et al. An Adenovirus Vector for Gene Transfer into Neurons and Glia in the Brain. *Science* 259:988–990 (1993).

Landergren. Molecular Mechanics of Nucleic Acids Sequence Amplification. *Trends Genet.* 9(6):199–202 (1993).

Lipshutz et al. High density synthetic olinucleotide arrays. *Nat. Genetic.* 21(1 Suppl):20–24 (1999).

Loboda et al. Atandemquadrupole/time–of–flight mass spectrometer (QqTOF) with a MALDI source: design and performance. *Rapid Comm. Mass Spectrom.* 14(12)1047–1057 (2000).

Lusky et al. Bovine Papilloma Virus Contains an Activator of Gene Expression at the Distal End of the Early Transcription Unit. *Mol. Cell. Biol.* 3(6):1108–1122 (1983).

MacDonald et al. Small–volume extrusion apparatus for preparation of large, unilamellar vesicles. *Biochimia et Biophysica Acta* 1061:297–303 (1991).

Maier et al. Application of robotic technology to automated sequence fingerprint analysis by oligonucleotide hybridisation. *J. Biotechnol.* 35(2–3):191–203 (1994).

Maiolini et al. A sandwich method for enzmye immunoassay. I. Application to rat and human alpha–fetoprotein. *J. Immuno. Meth.* 8:223–234 (1975).

Malik et al. Effects of a second intron on recombinant MFG retroviral vector. *Arch. Virol.* 146:601–609 (2001).

Mankertz et al. Expression from the human occludin promoter is affected by tumor necrosis factor α and interferon Y. *J. Cell. Sci.* 113:2085–2090 (2000).

March et al. A simplified method for cyanogen bromide activation of agarose for affinity chromatography. *Anal. Biochem.* 60:149–152 (1974).

Marriot et al. Synthesis and applications of heterobifunctional photocleavable cross–linking reagents. *Meth. Enzymol.* 291:155–175 (1998).

Massie et al. Construction of a Helper–Free Recombinant Adenovirus That Expresses Polyomavirus Large T Antigen. *Mol. Cell. Biol.* 6(8):2872–2883 (1986).

Matsumoto et al. Suppression of STAT5 functions in liver, mammary glands, and T cells in cytokine–inducible SH2–containing protein 1 transgenic mice. *Mol. Cell. Biol.* 19(9):6396–6407 (1999).

Morsy et al. Efficient Adenoviral–mediated Ornithine Transcarbamylase Expression in Deficient Mouse and Human Hepatocytes. *J. Clin. Invest.* 92:1580–1586 (1993).

Moullier et al. Correction of lysosomal storage in the liver and spleen of MPS VII mice by implantation of genetically modified skin fibroblasts. *Nat. Genet.* 4:154–159 (1993).

Mulligan et al. Expression of a Bacterial Gene in Mammalian Cells. *Science* 209:1422–1427 (1980).

Mulligan. The Basic Science of Gene Therapy. *Science* 260:926–932 (1993).

Nardelli et al. Zinc finger–DNA recognition: analysis of base specificity by site–directed mutagenesis. *Nucl. Acids Res.* 20(16):4137–4144 (1992).

Nguyen et al. Modification of DNA duplexed to smooth their thermal stability independently of their base content for DNA sequencing by hybridization. *Nucl. Acid. Res.* 25(15)3059–3065 (1997).

Nguyen et al. Smoothing of the thermal stability of DNA duplexes by using modified mucleosides and chaotropic agents. *Nucl. Acids Res.* 27(6):1492–1498 (1999).

Niemeyer et al. Oligonucleotide–directed self–assembly of proteins: semisynthetic DNA–streptavidin hybrid molecules as connectors for the generation of macroscopic arrays and the construction of supramolecular bioconjugates. *Nucl. Acids. Res.* 22(25):5530–5539 (1994).

Nizectic et al. Construction, arraying, and high–density screening of large insert libraries of human chromosomes X and 21: their potential use as reference libraries. *Proc. Natl. Sci. USA* 88:3233–3237 (1991).

Oda et al. Accurate quantitation of protein expression and site–specific phosphorylation. *Proc. Natl. Acad. Sci. USA* 96:6591–6596 (1999).

Oda et al. Enrichment analysis of phosphorylated proteins as a tool for probing the phosphoproteome. *Nat. Biotech.* 19:379–382 (2001).

Oikawa et al. Metalloselenonein, the selenium analogue of metallothionein: synthesis andcharacterization of its complex with copper ions. *Proc. Natl. Acad. Sci. USA* 88:3057–3059 (1991).

Olejnik et al. Photocleavable peptide–DNA conjugates: synthesis and applications to DNA analysis using MALDI–MS. *Nucl. Acids Res.* 27(23):4626–4631 (1999).

Orentas et al. Detection of Epstein–Barr virus EBER sequence in post–transplant lymphoma patients with DNA dendrimers. *J. Virol. Meth.* 77:153–163 (1999).

Osborne et al. Transcription Control Region Within the Protein–Coding Portion of Adenovirus E1A Genes. *Mol. Cell Biol.* 4(7):1293–1305 (1984).

Patterson et al. Quantitative imaging of TATA–binding protein in living yeast cells. *Yeast* 14:813–825 (1998).

Patton. Making Blind Robots See: The Synergy Between Fluorescent Dyes and Imaging Devices in Automated Proteomics. *Biotech.* 28(5):944–957 (2000).

Payrastre et al. Phosphoinositides: key players in cell signalling, in time and space. *Cell Signal* 13:377–387 (2001).

Pease et al. Light–generated oligonucleotide arrays for rapid DNA sequence analysis. *Proc. Natl. Acad. Sci USA* 91:5022–5026 (1994).

Qin et al. Identification and characterization of posttranslational modifications of proteins by MALDI ion trap mass spectrometry. *Anal. Chem.* 69:4002–4009 (1997).

Ragot et al. Replication–defective recombinant adenovirus expressing the Epstein–Barr virus (EBV) envelope glycoprotein gp340/220 induces protective immunity against EBV–induced lymphomas in the cottontop tamarin. *J. Gen. Virol.* 74:501–507 (1993).

Ram et al. In Situ Retroviral–mediated Gene Transfer for the Treatment of Brain Tumors in Rats. *Cancer Res.* 53:83–88 (1993).

Ramsay. DNA chips: State–of–the art. *Nat. Biotechnol.* 16(1):40–44 (1998).

Reilander et al. Functional expression of the *Aequorea victoria* green fluorescent protein in insect cells using the baculovirus expression system. *Biochem. Biophys. Res. Commun.* 219:14–20 (1996).

Rich et al. Development and Analysis of Recombinant Adenoviruses for Gene Therapy of Cystic Fibrosis. *Hum. Gene Ther.* 4:461–476 (1993).

Roessler et al. Adenoviral–mediated Gene Transfer to Rabbit Synovium In Vivo. *J. Clin. Invest.* 92:1085–1092 (1993).

Rong et al. A Targeted Gene Knockout in Drosophila. *Genetics* 157:1307–1312 (2001).

Sano et al. Immuno–PCR: Very Sensitive Antigen Detection by Means of Specific Antibody–DNA Conjugates. *Science* 258:120–122 (1992).

Santa Lucia et al. Improved Nearest–Neighbor Parameters for Predicting DNA Duplex Stability. *Biochemistry.* 35:3555–3562 (1996).

Sawin et al. Identification of fission yeast nuclear markers using random polypeptide fusion with green fluorescent protein. *Proc. Natl. Acad. Sci. USA* 94:15146–15151 (1996).

Scheffold et al. High–sensitivity immunofluorescence for detection of the pro– and anti–inflammatory cytokines gamma interferon and interleukin–10 on the surface of cytokine–secreting cells. *Nat. Med.* 6(1):107–110 (2000).

Schena et al. Parallel human genome analysis: microarray–based expression monitoring of 1000 genes. *Proc. Natl. Acad. Sci. USA* 93:10614–10619 (1996).

Seth et al. Evidence that the Penton Base of Adenovirus Is Involved in Potentiation of Toxiicity of *Pseudomonas* Exotoxin Conjugated to Epidermal Growth Factor. *Mol. Cell. Biol.* 4(8):1528–1533 (1984).

Seth et al. Role of a Low–pH Environment in Adenovirus Enhancement of the Toxicity of a *Pseudomonas* Exotoxin–Epidermal Growth Factor Conjugate. *J. Virol.* 51(3):650–655 (1984).

Shalon et al. A DNA microarray system for analyzing complex DNA samples using two–color fluorescent probe hybridation. *Genome. Res.* 6:639–645 (1996).

Shchepinov et al. Oligonucleotide dendrimers: synthesis and use as polylabelled DNA probes. *Nucl. Acids Res.* 25(22):4447–4454 (1997).

Shevchenko et al. MALDI Quadrupole Time–of–Flight Mass Spectrometry: A Powerful Tool for Proteomic Research. *Anal. Chem.* 72:2132–2142 (2000).

Shevchenko et al. Rapid 'de novo' peptide sequencing by a combination of nanoeletrospray, isotoopic labeling and a quadrupole/time–of–flight mass spectrometer. *Rapid Commun. Mass Spectrom.* 11(9):1015–1024 (1997).

Singh–Gasson et al. Maskless fabrication of light–directed oligonucleotide microarrays using a micromirror array. *Nat. Biotechnol.* 17:974–978 (1999).

Smith et al. Identification of Hydrogen Peroxide Oxidation Sites of αA– and αB–Crystallins. *Free Rad. Res.* 26:103–111 (1997).

Smith et al. A detailed study of the substrate specificity of a chimeric restriction enzyme. *Nucl. Acids Res.* 27(2):674–681 (1999).

Southern et al. Analyzing and comparing nucleic acid sequences by hybridization to arrays of oligonucleotides: evaluation using experimental models. *Genomics* 13:1008–1017 (1992).

Southern et al. Transformation of Mammalian Cells to Antibiotic Resistance with a Bacterial Gene Under Control of the SV40 Early Region Promoter. *Molec. Appl. Genet.* 1:327 (1982).

Stimpson et al. Real–Time Detection of DNA Hybridization and Melting on Oligonucleotide Arrays by using Optical Wave Guides. *Proc. Natl. Acad. Sci. USA* 92:6379–6383 (1995).

Sudgen et al. A Vector That Replicates as a Plasmid and Can Be Efficiently Selected in B–Lymphoblasts Transformed by Epstein–Barr Virus. *Mol. Cell. Biol.* 5(2):410–413 (1985).

Svensson. Role of Vesicles During Adenovirus 2 Internalization into HeLa Cells. *J. Virol* 55(2):442–449 (1985).

Syvanen et al. Fast Qualification of nucleic acid hybrids by affinity–based hybrid collection. *Nucl. Acids Res.* 14(12):5037–5049 (1986).

Templeton et al. Efficient gene targeting in mouse embryonic stem cells. *Gene Ther.* 4(7):700–709 (1997) (Abstract).

Uetz et al. A comprehensive analysis of protein–protein interactions in *Saccharomyces cerevisiae*. *Nature* 403:623–627 (2000).

Urdea. Branched DNA Signal Amplification. *Biotechnology* 12:926–928 (1994).

Uto et al. Determination of urinary Tamm–Horsfall protein by ELISA using a maleimide method for enzyme–antibody conjugation. *J. Immunol. Meth.* 138:87–94 (1991).

Van Criekinge et al. Yeast two–hybrid: state of the art. *Biol. Proc. Online* 2(1) (1999).

Van Oss et al. Mechanism of DNA (Southern) and protein (Western) blotting on cellulose nitrate and other membranes. *J. Chromatogr.* 391:53–65 (1987).

Varga et al. Infectious Entry Pathway of Adenovirus Type 2. *J. Virol.* 65(11):6061–6070 (1991).

Vasiliskov et al. Fabrication of microarray of gel–immobilized compounds on a chip by copolymerization. *Biotechniques* 27(3):592–594,596–598, 600 (1999).

Vergunst et al. Site–specific integration of *Agrobecterium* T–DNA in *Arabidopsis thaliana* mediated by Cre recombinase. *Nucl. Acids. Res.* 26(11):2729–2734 (1998).

Virts et al. The role of intron sequences in high level expression from CD45 cDNA constructs. *J. Biol. Chem.* 276(23):19913–19920 (2001).

Wemmer et al. Targeting the minor grove of DNA.. *Curr Opin. Struct Biol.* 7:355–361 (1997).

White et al. Real–time analysis of the transcriptional regulation of HIV and hCMV promoters in single mammalian cells. *J. Cell. Sci.* 108:441–455 (1995).

Thompson et al., Tandem Mass Tags: A Novel Quantification Strategy for Comparative Analysis of Complex Protein Mixtures by MS/MS. *Anal. Chem.* 75: 1895–1904 (2003).

* cited by examiner

Figure 1. Representation of the mass spectra for the "before fragmentation", left, and "after fragmentation" right. In the fragmentation spectrum representation there are three ions shown, the parent ion {C(CGAGSDPLAGSLR)IK$^+$, 1536 amu}, the parent ion after loss of PLAGSLR {C(CGAGSD)IK$^+$, 851 amu} and PLAGSLR$^+$ (712 amu).

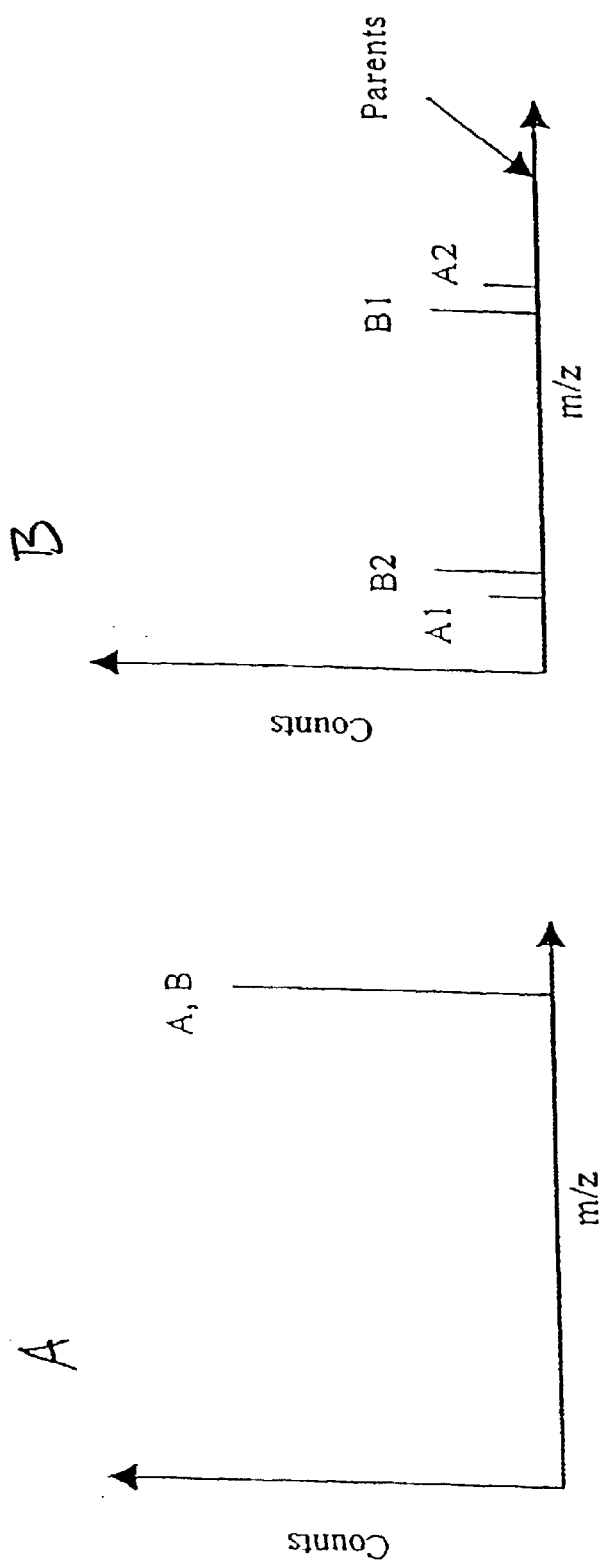

Figure 2. Schematic representation of the mass spectra of the solution of peptides A and B (The spectrum indicates there is twice as much B as A in the original sample). In the case of very low pressure in the collision cell the parent ions will pass through Q2 without fragmenting (left), with gas pressure in the collision cell the peptides will fragment at the labile bonds (right). Note the correlation (intensities are the same, and the sum of the masses is equal to the parent ion mass-to-charge) of the $A^+$ daughters and the $B^+$ daughters.

FIG. 2

SEQUENCE LISTING

```
<160> NUMBER OF SEQ ID NOS: 33

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 1

Cys Gly Gly Gly Gly Asp Pro Gly Gly Gly Gly Arg
 1               5                  10

<210> SEQ ID NO 2
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 2

Ala Gly Ser Leu Asp Pro Ala Gly Ser Leu Arg
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 3

Ala Gly Ser Met Leu Asp Pro Ala Gly Ser Met Leu Arg
 1               5                  10

<210> SEQ ID NO 4
<211> LENGTH: 11
```

```
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 4

Ala Gly Ser Leu Ala Asp Pro Gly Ser Leu Arg
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 5

Ala Leu Ser Leu Ala Asp Pro Gly Ser Gly Arg
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 6

Ala Leu Ser Leu Gly Asp Pro Ala Ser Gly Arg
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 7

Ala Gly Ser Asp Pro Leu Ala Gly Ser Leu Arg
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 8

Ala Asp Pro Gly Ser Leu Ala Gly Ser Leu Arg
 1               5                  10

<210> SEQ ID NO 9
<211> LENGTH: 357
<212> TYPE: PRT
<213> ORGANISM: Homo sapiens

<400> SEQUENCE: 9

Met Ser Ala Ile Gln Ala Ala Trp Pro Ser Gly Thr Glu Cys Ile Ala
 1               5                  10                  15

Lys Tyr Asn Phe His Gly Thr Ala Glu Gln Asp Leu Pro Phe Cys Lys
```

```
                     20                  25                  30
Gly Asp Val Leu Thr Ile Val Ala Val Thr Lys Asp Pro Asn Trp Tyr
         35                  40                  45

Lys Ala Lys Asn Lys Val Gly Arg Glu Gly Ile Ile Pro Ala Asn Tyr
 50                  55                  60

Val Gln Lys Arg Glu Gly Val Lys Ala Gly Thr Lys Leu Ser Leu Met
 65                  70                  75                  80

Pro Trp Phe His Gly Lys Ile Thr Arg Glu Gln Ala Glu Arg Leu Leu
                 85                  90                  95

Tyr Pro Pro Glu Thr Gly Leu Phe Leu Val Arg Glu Ser Thr Asn Tyr
            100                 105                 110

Pro Gly Asp Tyr Thr Leu Cys Val Ser Cys Asp Gly Lys Val Glu His
            115                 120                 125

Tyr Arg Ile Met Tyr His Ala Ser Lys Leu Ser Ile Asp Glu Glu Val
            130                 135                 140

Tyr Phe Glu Asn Leu Met Gln Leu Val Glu His Tyr Thr Ser Asp Ala
145                 150                 155                 160

Asp Gly Leu Cys Thr Arg Leu Ile Lys Pro Lys Val Met Glu Gly Thr
                165                 170                 175

Val Ala Ala Gln Asp Glu Phe Tyr Arg Ser Gly Trp Ala Leu Asn Met
            180                 185                 190

Lys Glu Leu Lys Leu Leu Gln Thr Ile Gly Lys Gly Glu Phe Gly Asp
            195                 200                 205

Val Met Leu Gly Asp Tyr Arg Gly Asn Lys Val Ala Val Lys Cys Ile
            210                 215                 220

Lys Asn Asp Ala Thr Ala Gln Ala Phe Leu Ala Glu Ala Ser Val Met
225                 230                 235                 240

Thr Gln Leu Arg His Ser Asn Leu Val Gln Leu Leu Gly Val Ile Val
                245                 250                 255

Glu Glu Lys Gly Gly Leu Tyr Ile Val Thr Glu Tyr Met Ala Lys Gly
            260                 265                 270

Ser Leu Val Asp Tyr Leu Arg Ser Arg Gly Arg Ser Val Leu Gly Gly
            275                 280                 285

Asp Cys Leu Leu Lys Phe Ser Leu Asp Val Cys Glu Ala Met Glu Tyr
290                 295                 300

Leu Glu Gly Asn Asn Phe Val His Arg Asp Leu Ala Ala Arg Asn Val
305                 310                 315                 320

Leu Val Ser Glu Asp Asn Val Ala Lys Val Ser Asp Phe Gly Leu Thr
                325                 330                 335

Lys Glu Ala Ser Thr Pro Arg Thr Arg Ala Ser Cys Gln Ser Ser Gly
            340                 345                 350

Gln Pro Leu Arg Pro
        355

<210> SEQ ID NO 10
<211> LENGTH: 536
<212> TYPE: PRT
<213> ORGANISM: Homo sapiens

<400> SEQUENCE: 10

Met Gly Ser Asn Lys Ser Lys Pro Lys Asp Ala Ser Gln Arg Arg Arg
  1               5                  10                  15

Ser Leu Glu Pro Ala Glu Asn Val His Gly Ala Gly Gly Gly Ala Phe
                 20                  25                  30
```

```
Pro Ala Ser Gln Thr Pro Ser Lys Pro Ala Ser Ala Asp Gly His Arg
            35                  40                  45

Gly Pro Ser Ala Ala Phe Ala Pro Ala Ala Glu Pro Lys Leu Phe
     50                  55                  60

Gly Gly Phe Asn Ser Ser Asp Thr Val Thr Ser Pro Gln Arg Ala Gly
65                  70                  75                  80

Pro Leu Ala Gly Gly Val Thr Thr Phe Val Ala Leu Tyr Asp Tyr Glu
                85                  90                  95

Ser Arg Thr Glu Thr Asp Leu Ser Phe Lys Lys Gly Glu Arg Leu Gln
            100                 105                 110

Ile Val Asn Asn Thr Glu Gly Asp Trp Trp Leu Ala His Ser Leu Ser
            115                 120                 125

Thr Gly Gln Thr Gly Tyr Ile Pro Ser Asn Tyr Val Ala Pro Ser Asp
    130                 135                 140

Ser Ile Gln Ala Glu Glu Trp Tyr Phe Gly Lys Ile Thr Arg Arg Glu
145                 150                 155                 160

Ser Glu Arg Leu Leu Leu Asn Ala Glu Asn Pro Arg Gly Thr Phe Leu
                165                 170                 175

Val Arg Glu Ser Glu Thr Thr Lys Gly Ala Tyr Cys Leu Ser Val Ser
            180                 185                 190

Asp Phe Asp Asn Ala Lys Gly Leu Asn Val Lys His Tyr Lys Ile Arg
        195                 200                 205

Lys Leu Asp Ser Gly Gly Phe Tyr Ile Thr Ser Arg Thr Gln Phe Asn
    210                 215                 220

Ser Leu Gln Gln Leu Val Ala Tyr Tyr Ser Lys His Ala Asp Gly Leu
225                 230                 235                 240

Cys His Arg Leu Thr Thr Val Cys Pro Thr Ser Lys Pro Gln Thr Gln
                245                 250                 255

Gly Leu Ala Lys Asp Ala Trp Glu Ile Pro Arg Glu Ser Leu Arg Leu
            260                 265                 270

Glu Val Lys Leu Gly Gln Gly Cys Phe Gly Glu Val Trp Met Gly Thr
        275                 280                 285

Trp Asn Gly Thr Thr Arg Val Ala Ile Lys Thr Leu Lys Pro Gly Thr
    290                 295                 300

Met Ser Pro Glu Ala Phe Leu Gln Glu Ala Gln Val Met Lys Lys Leu
305                 310                 315                 320

Arg His Glu Lys Leu Val Gln Leu Tyr Ala Val Val Ser Glu Glu Pro
                325                 330                 335

Ile Tyr Ile Val Thr Glu Tyr Met Ser Lys Gly Ser Leu Leu Asp Phe
            340                 345                 350

Leu Lys Gly Glu Thr Gly Lys Tyr Leu Arg Leu Pro Gln Leu Val Asp
        355                 360                 365

Met Ala Ala Gln Ile Ala Ser Gly Met Ala Tyr Val Glu Arg Met Asn
    370                 375                 380

Tyr Val His Arg Asp Leu Arg Ala Ala Asn Ile Leu Val Gly Glu Asn
385                 390                 395                 400

Leu Val Cys Lys Val Ala Asp Phe Gly Leu Ala Arg Leu Ile Glu Asp
                405                 410                 415

Asn Glu Tyr Thr Ala Arg Gln Gly Ala Lys Phe Pro Ile Lys Trp Thr
            420                 425                 430

Ala Pro Glu Ala Ala Leu Tyr Gly Arg Phe Thr Ile Lys Ser Asp Val
        435                 440                 445

Trp Ser Phe Gly Ile Leu Leu Thr Glu Leu Thr Thr Lys Gly Arg Val
```

-continued

```
         450             455             460
Pro Tyr Pro Gly Met Val Asn Arg Glu Val Leu Asp Gln Val Glu Arg
465                 470                 475                 480

Gly Tyr Arg Met Pro Cys Pro Pro Glu Cys Pro Glu Ser Leu His Asp
                485                 490                 495

Leu Met Cys Gln Cys Trp Arg Lys Glu Pro Glu Glu Arg Pro Thr Phe
            500                 505                 510

Glu Tyr Leu Gln Ala Phe Leu Glu Asp Tyr Phe Thr Ser Thr Glu Pro
        515                 520                 525

Gln Tyr Gln Pro Gly Glu Asn Leu
    530                 535

<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 11

Cys Gly Ala Gly Ser Asp Pro Leu Ala Gly Ser Leu Arg
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 12

Gly Ser Trp Phe Ser Gly Met Cys Ala Arg
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 13

Tyr Phe Met Thr Ser Gly Cys Asp Pro Gly Gly Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 14

Tyr Phe Met Thr Ser Gly Asp Pro Cys Gly Gly Arg
1               5                   10

<210> SEQ ID NO 15
<211> LENGTH: 12
<212> TYPE: PRT
<213> ORGANISM: Artificial Sequence
<220> FEATURE:
```

<223> OTHER INFORMATION: Description of Artificial Sequence; Note=
      synthetic construct

<400> SEQUENCE: 15

Tyr Phe Met Thr Ser Asp Pro Gly Cys Gly Gly Arg
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 16

Tyr Phe Met Thr Asp Pro Ser Gly Cys Gly Gly Arg
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 17

Tyr Phe Met Asp Pro Thr Ser Gly Cys Gly Gly Arg
 1               5                  10

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 18

Ala Gly Ser Leu Ala Gly Ser Leu Asp Pro Ala Gly Ser Leu Ala Gly
 1               5                  10                  15

Ser Leu Arg

<210> SEQ ID NO 19
<211> LENGTH: 18
<212> TYPE: DNA
<213> ORGANISM: Artificial Sequence
<220> FEATURE:
<223> OTHER INFORMATION: Description of Artificial Sequence; Note=
      synthetic construct

<400> SEQUENCE: 19
gattagccac gtcgccgt                                                 18

<210> SEQ ID NO 20
<211> LENGTH: 18
<212> TYPE: DNA
<213> ORGANISM: Artificial Sequence
<220> FEATURE:
<223> OTHER INFORMATION: Description of Artificial Sequence; Note=
      synthetic construct

<400> SEQUENCE: 20
gcatatagct agctctcg                                                 18

```
<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence; Note=
      synthetic construct

<400> SEQUENCE: 21
gacgacggcg acgtggctgc gc                                              22

<210> SEQ ID NO 22
<211> LENGTH: 18
<212> TYPE: DNA
<213> ORGANISM: Artificial Sequence
<220> FEATURE:
<223> OTHER INFORMATION: Description of Artificial Sequence; Note=
      synthetic construct

<400> SEQUENCE: 22
acggcgacgt ggctaatc                                                   18

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence; Note=
      synthetic construct

<400> SEQUENCE: 23
cgtcatcgta g                                                          11

<210> SEQ ID NO 24
<211> LENGTH: 15
<212> TYPE: PRT
<213> ORGANISM: Artificial Sequence
<220> FEATURE:
<223> OTHER INFORMATION: Description of Artificial Sequence; Note=
      synthetic construct
<221> NAME/KEY: VARIANT
<222> LOCATION: 1-15
<223> OTHER INFORMATION: Xaa = any amino acid

<400> SEQUENCE: 24

Cys Phe Xaa Xaa Xaa Xaa Xaa Asp Pro Xaa Xaa Xaa Xaa Xaa Arg
 1               5                  10                  15

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence; Note=
      synthetic construct
<221> NAME/KEY: VARIANT
<222> LOCATION: 1-35
<223> OTHER INFORMATION: Xaa = any amino acid

<400> SEQUENCE: 25

Xaa Xaa Xaa Xaa Xaa Xaa Xaa Xaa Asp Pro Xaa Xaa Xaa Xaa Xaa
 1               5                  10                  15

Xaa Xaa Xaa Xaa Xaa Asp Pro Xaa Xaa Xaa Xaa Xaa Xaa Arg Xaa
                 20                  25                  30

Xaa Xaa Xaa
         35
```

```
<210> SEQ ID NO 26
<211> LENGTH: 34
<212> TYPE: PRT
<213> ORGANISM: Artificial Sequence
<220> FEATURE:
<223> OTHER INFORMATION: Description of Artificial Sequence; Note=
      synthetic construct
<221> NAME/KEY: VARIANT
<222> LOCATION: 1-34
<223> OTHER INFORMATION: Xaa = any amino acid

<400> SEQUENCE: 26

Xaa Xaa Xaa Xaa Xaa Xaa Xaa Xaa Xaa Asp Pro Xaa Xaa Xaa Xaa Xaa
 1               5                  10                  15

Xaa Xaa Xaa Xaa Xaa Phe Xaa Xaa Xaa Xaa Xaa Xaa Xaa Arg Xaa Xaa
            20                  25                  30

Xaa Xaa

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 27

Ala Gly Ser Leu Ala Gly Ser Leu Asp Pro Arg
      1               5                  10

SEQ ID NO 28

LENGTH: 14
TYPE: PRT

ORGANISM: Artificial Sequence
FEATURE:
<223> OTHER INFORMATION: Description of Artificial Sequence; Note=
      synthetic construct

<400> SEQUENCE: 28

Cys Gly Trp Ala Gly Ser Asp Pro Leu Ala Gly Ser Leu Arg
 1               5                  10

<210> SEQ ID NO 29
<211> LENGTH: 14
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 29

Cys Gly Trp Ala Gly Ser Leu Asp Pro Ala Gly Ser Leu Arg
 1               5                  10

<210> SEQ ID NO 30
<211> LENGTH: 14
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 30

Cys Gly Trp Ala Gly Ser Leu Ala Asp Pro Gly Ser Leu Arg
 1               5                  10
```

```
<210> SEQ ID NO 31
<211> LENGTH: 28
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 31

Cys Gly Trp Ala Gly Ser Leu Ala Gly Asp Pro Ser Leu Arg Cys Gly
 1               5                  10                  15

Trp Ala Gly Ser Leu Ala Gly Ser Asp Pro Leu Arg
            20                  25

<210> SEQ ID NO 32
<211> LENGTH: 14
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 32

Cys Gly Trp Ala Gly Ser Leu Ala Gly Ser Asp Pro Leu Arg
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Description of Artificial Sequence; Note=
      synthetic construct

<400> SEQUENCE: 33

Arg Leu Ser Gly Ala Asp Pro Leu Ser Gly Ala Trp Gly Cys
 1               5                  10
```

ULTRA-SENSITIVE DETECTION SYSTEMS USING ALTERABLE PEPTIDE TAGS

CROSS-REFERENCE TO RELATED APPLICATIONS

This application claims benefit of U.S. Provisional Application No. 60/224,939, filed Aug. 11, 2000, and U.S. Provisional Application No. 60/283,498, filed Apr. 12, 2001. Application Ser. No. 60/224,939, filed Aug. 11, 2000, and application Ser. No. 60/283,498, filed Apr. 12, 2001, are hereby incorporated herein by reference.

FIELD OF THE INVENTION

This invention is generally in the field of detection of analytes and biomolecules, and more specifically in the field of multiplex detection and analysis of analytes and biomolecules.

BACKGROUND OF THE INVENTION

Detection of molecules is an important operation in the biological and medical sciences. Such detection often requires the use of specialized label molecules, amplification of a signal, or both, because many molecules of interest are present in low quantities and do not, by themselves, produce detectable signals. Many labels, labeling systems, and signal amplification techniques have been developed. For example, nucleic acid molecules and sequences have been amplified and/or detected using polymerase chain reaction (PCR), ligase chain reaction (LCR), self-sustained sequence replication (3SR), nucleic acid sequence based amplification (NASBA), strand displacement amplification (SDA), and amplification with Qβ replicase (Birkenmeyer and Mushahwar, *J. Virological Methods*, 35:117–126 (1991); Landegren, *Trends Genetics* 9:199–202 (1993)). Proteins have been detected using antibody-based detection systems such as sandwich assays (Mailini and Maysef, "A sandwich method for enzyme immunoassay. I. Application to rat and human alpha-fetoprotein" J. Immunol. Methods 8:223–234 (1975)) and enzyme-linked immunosorbent assays (Engvall and Perlmann, "Enzyme-linked immunosorbent assay (ELISA). Quantitative assay of immunoglobulin" Immunochemistry 8:871–874 (1971)), and two-dimensional (2-D) gel electrophoresis (Patton, *Biotechniques* 28: 944–957 (2000)). Although these techniques are useful, most have significant drawbacks and limitations. For example, radioactive labels are dangerous and difficult to handle, fluorescent labels have limited capacity for multiplex detection because of limitations on distinguishable labels, and amplification methods can be subject to spurious signal amplification. There is a need for improved detection labels and detection techniques that can detect minute quantities of specific molecules and that can be highly multiplexed.

Analysis of protein expression and presence, such as proteome profiling or proteomics, requires sensitive detection of multiple proteins. Current methods in proteome profiling suggests that there is a shortage of tools necessary for such detection (Haynes and Yates, *Proteome profiling-pitfalls and progress*. Yeast 17(2):81–87 (2000)). While the techniques of chromatography and capillary electrophoresis are amenable to proteomic studies and have seen significant development efforts (see for example, Krull et al., *Specific applications of capillary electrochromatography to biopolymers, including proteins, nucleic acids, peptide mapping, antibodies, and so forth*. J Chromatogr A, 887:137–63 (2000), Hage, *Affinity chromatography: a review of clinical applications*. Clin Chem, 45(5):593–615 (1999), Hage et al., *Chromatographic Immunoassays.*, Anal Chem, 73(07):198 A-205 A, (2001), Krull et al., *Labeling reactions applicable to chromatography and electrophoresis of minute amounts of proteins*. J Chromatogr B Biomed Sci Appl, 699:173–208 (1997)), the workhorse of the industry remains two dimensional electrophoresis where the two dimensions are isoelectric focusing and molecular size. Haynes and Yates point out the significant shortcomings of the technique but discuss the utility of the method in light of such shortcomings. Hayes and Yates also discuss the techniques of Isotope Coded Affinity Tags (ICAT), LC-LC-MS/MS, and stable isotope labeling techniques (Shevchenko et al., *Rapid 'de novo' peptide sequencing by a combination of nanoelectrospray, isotopic labeling and a quadrupole/time-of-flight mass spectrometer*. Rapid Commun Mass Spectrom 11(9):1015–1024 (1997); Oda et al., *Accurate quantitation of protein expression and site-specific phosphorylation*. Proc Natl Acad Sci USA 96(12):6591–6596 (1999)).

Aebersold et al. (WO 00/11208) have described labels of the composition PRG-L-A, where PRG is a protein reactive group, L is a linker (that may contain isotopically distinguishable composition), and A is an affinity moiety. Aebersold et al. describes a method where the protein reactive group is used to attach the label to a protein, an affinity capture molecule is used to capture the affinity moiety, the remaining proteins are discarded, then the affinity moiety is released and the labeled proteins are detected by mass spectrometry. The method of Aebersold et al. does not involve fragmentation or other modification of the labels or proteins.

The technique of ICAT, where cysteine residues are labeled with heavy or light tags that each contain affinity moieties, in control and tester samples, has received significant interest and holds potential for protein profiling (Gygi et al., *Quantitative analysis of complex protein mixtures using isotope-coded affinity tags*. Nat. Biotechnol. 17(10): 994–999 (1999), Griffin et al., *Quantitative proteomic analysis using a MALDI quadrupole time-of-flight mass spectrometer.*, Anal. Chem., 73:978–986 (2001)). Gygi et al. and Griffin et al. have demonstrated relative profiling of two protein samples, where the two samples are distinguished utilizing linkers containing either eight normal hydrogen or eight heavy hydrogen (deuterium) atoms. The relative concentrations of labeled proteins are determined by ratio of peaks that are separated by the corresponding 8 amu difference in the linker molecules. Current implementations have been limited to two labels. This technique does not involve fragmentation or other modification of the labels or proteins.

Mass spectrometry has been used to detect phosphorylated proteins (DeGnore and Qin, *Fragmentation of phosphopeptides in an ion trap mass spectrometer*. J. Am. Soc. Mass Spectrom. 9:1175–1188 (1998); Qin and Chait, *Identification and characterization of posttranslational modifications of proteins by MALDI ion trap mass spectrometry*. Anal Chem, 69:4002–9 (1997); Annan et al., *A multidimensional electrospray MS-based approach to phosphopeptide mapping*. Anal. Chem. 73:393–404 (2001)). The methods make use of a signature mass to indicate the presence of a phosphate group, for example m/z=63 and/or m/z=79 corresponding to $PO_2^{31}$ and $PO_3^-$ ions in negative ion mode, or the neutral loss of 98 Daltons from the parent ion indicates the loss of $H_3PO_4$ from the phosphorylated peptide, indicate phosphorylated Ser, Tyr, Thr. Once phosphorylated amino acids are identified, the peptide containing the modification is sequenced by standard MS/MS techniques. There is a need for a high reliability, highly multiplexed readout system for proteomics.

The status of any living organism may be defined, at any given time in its lifetime, by the complex constellation of proteins that constitute its "proteome."While the complete status of the proteome could be defined by listing all proteins present (including modified variants) as well as their intracellular locations and concentrations, such a task is beyond the capabilities of any current single analytical method. However, attempts have been made to define the status of a cell or tissue by identifying and measuring the relative concentrations of a small subset of proteins. For example, Conrads et al., Analytical Chemistry, 72:3349–3354 (2000), have described the use of "Accurate Mass Tags" (AMT) for proteome-wide protein identification. Conrads et al. show, for a simple organism, that a mass spectrometer of sufficient mass accuracy and resolution can be used to detect certain tryptic digest fragments from proteins. Once identified, the AMTs may be directly detected in samples by tryptic digest of the proteins, and high accuracy, high resolution mass spectrometry.

While the concept of Accurate Mass Tags is useful for protein discovery, as well as for generating peptide patterns in conventional biological experiments, it does not solve the problem of sensitivity that is at the heart of a truly useful diagnostic multi-protein assessment. A useful assessment consisting of AMTs will require samples containing a minimum of 2000 to 10,000 cells in order to permit reliable readout. This is so because many important cellular proteins are present at levels of only 500 to 5000 molecules per cell. If a clinically relevant protein is present in 500 copies per cell, and a precious clinical sample from a cancer patient contains only 1000 cells, the total number of proteins is 500,000, an amount that lies below the limit of detection by conventional mass spectrometry. Thus, the types of measurements proposed by Conrads et al. for the study of proteomes after identification of AMTs are not suitable for addressing important clinical problems such as the diagnosis of cancer.

BRIEF SUMMARY OF THE INVENTION

Disclosed are compositions and methods for sensitive detection of one or multiple analytes. In general, the methods involve the use of special label components, referred to as reporter signals, that can be associated with, incorporated into, or otherwise linked to the analytes. Reporter signals can also be used merely in conjunction with analytes, with no significant association between the analytes and reporter signals. Compositions where reporter signals are associated with, incorporated into, or otherwise linked to the analytes are referred to as reporter signal/analyte conjugates. Such conjugates include reporter signals associated with analytes, such as a reporter signal probe hybridized to a nucleic acid sequence; reporter signals covalently coupled to analytes, such as reporter signals linked to proteins via a linking group; and reporter signals incorporated into analytes, such as fusions between a protein of interest and a peptide reporter signal.

In some embodiments, the reporter signals can be altered such that the altered forms of different reporter signals can be distinguished from each other. Reporter signal/analyte conjugates can be altered, generally through alteration of the reporter signal portion of the conjugate, such that the altered forms of different reporter signals, altered forms of different reporter signal/analyte conjugates, or both, can be distinguished from each other. Where the reporter signal or reporter signal/analyte conjugate is altered by fragmentation, any, some, or all of the fragments can be distinguished from each other, depending on the embodiment. For example, where reporter signals fragmented into two parts, either or both parts of the reporter signals can be distinguished. Where reporter signal/analyte conjugates are fragmented into two parts (with the break point in the reporter signal portion), either the reporter signal fragment, the reporter signal/analyte fragment, or both can be distinguished. In some embodiments, only one part of a fragmented reporter signal will be detected and so only this part of the reported signals need be distinguished.

In some embodiments, sets of reporter signals can be used where two or more of the reporter signals in a set have one or more common properties that allow the reporter signals having the common property to be distinguished and/or separated from other molecules lacking the common property. In other embodiments, sets of reporter signal/analyte conjugates can be used where two or more of the reporter signal/analyte conjugates in a set have one or more common properties that allow the reporter signal/analyte conjugates having the common property to be distinguished and/or separated form other molecules lacking the common property. In still other embodiments, analytes can be fragmented (prior to or following conjugation) to produce reporter signal/analyte fragment conjugates (which can be referred to as fragment conjugates). In such cases, sets of fragment conjugates can be used where two or more of the fragment conjugates in a set have one or more common properties that allow the fragment conjugates having the common property to be distinguished and/or separated from other molecules lacking the common property. It should be understood that fragmented analytes can be considered analytes in their own right. In this light, reference to fragmented analytes is made for convenience and clarity in describing certain embodiments and to allow reference to both the base analyte and the fragmented analyte.

As indicated above, reporter signals conjugated with analytes can be altered while in the conjugate and distinguished. Conjugated reporter signals can also be dissociated or separated, in whole or in part, from the conjugated analytes prior to their alteration. Where the reporter signals are dissociated (in whole or in part) from the analytes, the method can be performed such that the fact of association between the analyte and reporter signal is part of the information obtained when the reporter signal is detected. In other words, the fact that the reporter signal may be dissociated from the analyte for detection does not obscure the information that the detected reporter signal was associated with the analyte.

Reporter signals can also be in conjunction with analytes (such as in mixtures of reporter signals and analytes), where no significant physical association between the reporter signals and analytes occurs; or alone, where no analyte is present. In such cases, where reporter signals are not or are no longer associated with analytes, sets of reporter signals can be used where two or more of the reporter signals in a set have one or more common properties that allow the reporter signals having the common property to be distinguished and/or separated from other molecules lacking the common property.

Detection of the reporter signals indicates the presence of the corresponding analytes. The reporter signals preferably can have two key features. First, the reporter signals can be used in sets where all the reporter signals in the set have similar properties (for example, mass spectrometry reporter signals may have similar mass-to-charge ratios). The similar properties allow the reporter signals to be distinguished and/or separated from other molecules lacking one or more of the properties. Second, all the reporter signals in a set can be fragmented, decomposed, reacted, derivatized, or otherwise modified to distinguish the different reporter signals in the set. Preferably, mass spectrometry reporter signals are fragmented to yield fragments of similar charge but different mass.

Differential distribution of mass in the fragments of the reporter signals can be accomplished in a number of ways. For example, reporter signals of the same nominal structure (for example, peptides having the same amino acid sequence) can be made with different distributions of heavy isotopes, such as deuterium; reporter signals of the same nominal structure can be made with different distributions of modifications, such as methylation, phosphorylation, sulphation, and use of seleno-methionine for methionine; reporter signals of the same nominal composition (for example, made up of the same amino acids) can be made with different ordering of the subunits or components of the reporter signal; and reporter signals having the same nominal composition can be made with a labile or scissile bond at a different location in the reporter signal. Each of these modes can be combined with each other and/or one or more of the other modes to produce differential distribution of mass in the fragments of the reporter signals.

The reporter signals are preferably detected using mass spectrometry which allows sensitive distinctions between molecules based on their mass-to-charge ratios. The disclosed reporter signals can be used as general labels in myriad labeling and/or detection techniques. A set of isobaric reporter signals can be used for multiplex labeling and/or detection of many analytes since the reporter signal fragments can be designed to have a large range of masses, with each mass individually distinguishable upon detection.

The disclosed method has advantageous properties which can be used as a detection system in a number of fields, including antibody or protein microarrays, DNA microarrays, expression profiling, comparative genomics, immunology, diagnostic assays, and quality control.

A. Reporter Molecule Labeling

In one form of the disclosed method, referred to as reporter molecule labeling (RML), reporter signals are first associated with the analytes and then dissociated and detected. The reporter signals preferably are associated with the analytes via interaction of specific binding molecules with the analytes. The reporter signals are either directly or indirectly associated with the specific binding molecules such that interaction of the specific binding molecules with the analytes allows the reporter signals to be associated with the analytes. The method can be performed such that the fact of association between the analyte and reporter signal is part of the information obtained when the reporter signal is detected. In other words, the fact that the reporter signal may be dissociated from the analyte for detection does not obscure the information that the detected reporter signal was associated with the analyte.

B. Reporter Signal Labeling

In another form of the disclosed method, referred to as reporter signal labeling (RSL), reporter signals are used for sensitive detection of one or multiple analytes. In the method, analytes labeled with reporter signals are analyzed using the reporter signals to distinguish the labeled analytes (where the analytes are labeled with the reporter signals). Detection of the reporter signals indicates the presence of the corresponding analyte(s). The detected analyte(s) can then be analyzed using known techniques. The labels provide a unique analyte/label composition that can specifically identify the analyte(s). This is accomplished through the use of the specialized reporter signals as the labels. The labeled analyte(s) can be fragmented prior to analysis. An analyte sample to be analyzed can also be subjected to fractionation or separation to reduce the complexity of the samples. Fragmentation and fractionation can also be used together in the same assay. Such fragmentation and fractionation can simplify and extend the analysis of the analytes.

Reporter signals can be coupled or directly associated with an analyte. For example, a reporter signal can be coupled to an analyte via reactive groups, or a reporter molecule (composed of a specific binding molecule and a reporter signal) can be associated with an analyte. The reporter signals can be attached to analytes in any manner. For example, reporter signals can be covalently coupled to proteins through a sulfur—sulfur bond between a cysteine on the protein and a cysteine on the reporter signal. Many other chemistries and techniques for coupling compounds to analytes are known and can be used to couple reporter signals to analytes. For example, coupling can be made using thiols, epoxides, nitrites for thiols, NHS esters, isothiocyanates for amines, and alcohols for carboxylic acids. Reporter signals can be attached to analytes either directly or indirectly, for example, via a linker.

Alternatively, a reporter signal can be associated with an analyte indirectly. In this mode, a "coding" molecule containing a specific binding molecule and a coding tag can be associated with the analyte (via the specific binding molecule). Alternatively, a coding tag can be coupled or directly associated with the analyte. Then a reporter signal associated with a decoding tag (such a combination is another form of reporter molecule) is associated with the coding molecule through an interaction between the coding tag and the decoding tag. An example of this interaction is hybridization where the coding and decoding tags are complementary nucleic acid sequences. The result is an indirect association of the reporter signal with the analyte. This mode has the advantage that all of the interactions of the reporter signals with the coding molecule can be made chemically and physically similar by using the same types of coding tags and decoding tags for all of the coding molecules and reporter molecules in a set.

Reporter signals can be fragmented, decomposed, reacted, derivatized, or otherwise modified, preferably in a characteristic way. This allows an analyte to which the reporter signal is attached to be identified by the correlated detection of the labeled analyte and one or more of the products of the labeled analyte following fragmentation, decomposition, reaction, derivatization, or other modification of the reporter signal (the labeled analyte is the analyte/reporter signal combination). The alteration of the reporter signal will alter the labeled analyte in a characteristic and detectable way. Together, the detection of a characteristic labeled analyte and a characteristic product of the labeled analyte can uniquely identify the analyte. In this way, using the disclosed method and materials, one or more analytes can be detected, either alone or together (for example, in a multiplex assay). Further, one or more analytes in one or more samples can be detected in a multiplex manner. Preferably, for mass spectrometry reporter signals, the reporter signals are fragmented to yield fragments of similar charge but different mass.

In preferred embodiments, reporter signals are used in sets where all the reporter signals in the set have similar properties (such as similar mass-to-charge ratios). The similar properties allow the reporter signals to be distinguished and/or separated from other molecules lacking one or more of the properties. Alternatively, or in addition, reporter signals can be used in sets such that the resulting labeled analytes will have similar properties allowing the labeled analytes to be distinguished and/or separated from other molecules lacking one or more of the properties.

Analytes can be detected using the disclosed reporter signals in a variety of ways. For example, the analyte and attached reporter signal can be detected together, one or more fragments of the analyte and the attached reporter signal(s) can be detected together, the fragments of the reporter signal can be detected, or a combination. Preferred detection involves detection of the analyte/reporter signal both before and after fragmentation of the reporter signal.

A preferred form of the disclosed method involves correlated detection of the reporter signals both before and after fragmentation of the reporter signal. This allows labeled analytes to be detected and identified via the change in labeled analyte. That is, the nature of the reporter signal detected (non-fragmented versus fragmented) identifies the analyte as labeled. Where the analytes and reporter signals are detected by mass-to-charge ratio, the change in mass-to-charge ratio between fragmented and non-fragmented samples provides the basis for comparison. Such mass-to-charge ratio detection is preferably accomplished with mass spectrometry.

As an example, an analyte in a sample can be labeled with reporter signal designed as a mass spectrometry label. The labeled analyte can be subjected to mass spectrometry. A peak corresponding to the analyte/reporter signal will be detected. Fragmentation of the reporter signal in a collision cell in the mass spectrometer would result in a shift in the peak corresponding to the loss of a portion of the attached reporter signal, the appearance of a peak corresponding to the lost fragment, or a combination of both events. Significantly, the shift observed will depend on which reporter signal is on the analyte since different reporter signals will, by design, produce fragments with different mass-to-charge ratios. The combination event of detection of the parent mass-to-charge (with no collision gas) and the mass-to-charge corresponding to the loss of the fragment from the reporter signal (with collision gas) indicates a labeled analyte. The identity of the analyte can be determined by standard mass spectrometry techniques, such as compositional analysis.

A powerful form of the disclosed method is use of analytes labeled with reporter signals to assay multiple samples (for example, time series assays or other comparative analyses). Knowledge of the temporal response of a biological system following perturbation is a very powerful process in the pursuit of understanding the system. To follow the temporal response, a sample of the system is obtained (for example, cells from a cell culture, mice initially synchronized and sacrificed) at determined times following the perturbation. Knowledge of spatial analyte profiles (for example, relative position within a tissue section) is a very powerful process in the pursuit of understanding the biological system.

In the disclosed method a series of samples can each be labeled with a different reporter signal from a set of reporter signals. Preferred reporter signals for this purpose would be those using differentially distributed mass. In particular, the use of stable isotopes is preferred to ensure that members of the set of reporter signals would behave chemically identically and yet would be distinguishable.

The labeled analytes are preferably detected using mass spectrometry which allows sensitive distinctions between molecules based on their mass-to-charge ratios. The disclosed reporter signals can be used as general labels in myriad labeling and/or detection techniques. A set of isobaric reporter signals can be used for multiplex labeling and/or detection of many analytes since the reporter signal fragments can be designed to have a large range of masses, with each mass individually distinguishable upon detection. Where the same analyte or type of analyte is labeled with a set of isobaric reporter signals (by, for example, labeling the same analyte in different samples), the set of labeled analytes that results from use of an isobaric set of reporter signals will also be isobaric. Fragmentation of the reporter signals will split the set of labeled analytes into individually detectable labeled proteins of characteristically different mass.

The disclosed method can be used in many modes. For example, the disclosed method can be used to detect a specific analyte (in a specific sample or in multiple samples) or multiple analytes (in a single sample or multiple samples). In each case, the analyte(s) to be detected can be separated either from other, unlabeled analytes or from other molecules lacking a property of the labeled analyte(s) to be detected. For example, analytes in a sample can be generally labeled with reporter signals and some analytes can be separated on the basis of some property of the analytes. For example, the separated analytes could have a certain mass-to-charge ratio (separation based on mass-to-charge ratio will select both labeled and unlabeled analytes having the selected mass-to-charge ratio). As another example, all of the labeled analytes can be distinguished and/or separated from unlabeled molecules based on a feature of the reporter signal such as an affinity tag. Where different affinity tags are used, some labeled analytes can be distinguished and/or separated from others. Reporter signal labeling allows profiling of analytes and cataloging of analytes.

In one mode of the disclosed method, multiple analytes in multiple samples are labeled where all of the analytes in a given sample are labeled with the same reporter signal. That is, the reporter signal is used as a general label of the analytes in a sample. Each sample, however, uses a different reporter signal. This allows samples as a whole to be compared with each other. By additionally separating or distinguishing different analytes in the samples, one can easily analyze many analytes in many samples in a single assay. For example, proteins in multiple samples can be labeled with reporter signals as described above, and the samples mixed together. If some or all of the various labeled proteins are separated by, for example, association of the proteins with antibodies on an array, the presence and amount of a given protein in each of the samples can be determined by identifying the reporter signals present at each array element. If the protein corresponding to a given array element was present in a particular sample, then some of the protein associated with that array element will be labeled with the reporter signal used to label that particular sample. Detection of that reporter signal will indicate this. This same relationship holds true for all of the other samples. Further, the amount of reporter signal detected can indicate the amount of a given protein in a given sample, and the simultaneous quantitation of protein in multiple samples can provide a particularly accurate comparison of the levels of the proteins in the various samples.

In one form of reporter signal labeling, referred to as reporter signal protein labeling (RSPL), reporter signals are used for sensitive detection of one or multiple proteins. In the method, proteins labeled with reporter signals are analyzed using the reporter signals to distinguish the labeled proteins. Detection of the reporter signals indicates the presence of the corresponding protein(s). The detected protein(s) can then be analyzed using known techniques.

The labels provide a unique protein/label composition that can specifically identify the protein(s). This is accomplished through the use of the specialized reporter signals as the labels. The labeled protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

C. Reporter Signal Calibration

In another form of the method, referred to as reporter signal calibration (RSC), a form of reporter signals referred to as reporter signal calibrators are mixed with analytes or analyte fragments, the reporter signal calibrators and the analytes or analyte fragments are altered, and the altered forms of the reporter signal calibrators and altered forms of the analytes or analyte fragments are detected. Reporter signal calibrators are useful as standards for assessing the amount of analytes present. That is, one can add a known amount of a reporter signal calibrator in order to assess the amount of analyte present comparing the amount of altered analyte or analyte fragment detected with the amount of altered reporter signal calibrator detected and calibrating these amounts with the known amount of reporter signal calibrator added (and thus the predicted amount of altered reporter signal calibrator).

In some embodiments, each analyte or analyte fragment can share one or more common properties with at least one reporter signal calibrator such that the reporter signal calibrators and analytes or analyte fragments having the common property can be distinguished and/or separated from other molecules lacking the common property.

In some embodiments, reporter signal calibrators and analytes and analyte fragments can be altered such that the altered form of an analyte or analyte fragment can be distinguished from the altered form of the reporter signal calibrator with which the analyte or analyte fragment shares a common property. In some embodiments, the altered forms of different reporter signal calibrators can be distinguished from each other. In some embodiments, the altered forms of different analytes or analyte fragments can be distinguished from each other.

In some embodiments of reporter signal calibration, the analyte or analyte fragment is not altered and so the altered reporter signal calibrators and the analytes or analyte fragments are detected. In this case, the analyte or analyte fragment can be distinguished from the altered form of the reporter signal calibrator with which the analyte or analyte fragment shares a common property.

In some embodiments the analyte or analyte fragment may be a reporter signal or a fragment of a reporter signal. In this case, the reporter signal calibrators serve as calibrators for the amount of reporter signal detected.

Reporter signal calibration is preferably used in connection with proteins and peptides (as the analytes). This form of reporter signal calibration is referred to as reporter signal protein calibration. Reporter signal protein calibration is useful, for example, for producing protein signatures of protein samples. As used herein, a protein signature is the presence, absence, amount, or presence and amount of a set of proteins or protein surrogates.

In some embodiments of reporter signal protein calibration, the presence of labile, scissile, or cleavable bonds in the proteins to be detected can be exploited. Peptides, proteins, or protein fragments (collectively referred to, for convenience, as protein fragments in the remaining description) containing such bonds can be altered by fragmentation at the bond. In this way, reporter signal calibrators having a common property (such as mass-to-charge ratio) with the protein fragments can be used and the altered forms of the reporter signal calibrators and the altered (that is, fragmented) forms of the protein fragments can be detected and distinguished. In this regard, although the protein fragments share a common property with their matching reporter signal calibrators, the altered forms of the reporter signal calibrators and altered forms of protein fragments can be distinguished (because, for example, the altered forms have different properties, such as different mass-to-charge ratios).

D. Reporter Signal Fusions

In another form of the disclosed method and compositions, referred to as reporter signal fusions (RSF), reporter signal peptides are joined with a protein or peptide of interest in a single amino acid segment. Such fusions of proteins with reporter signal peptides can be expressed from a nucleic acid molecule encoding the amino acid segment that constitutes the fusion. The fusion protein is referred to herein as a reporter signal fusion. The reporter signal peptides allow for sensitive monitoring and detection of the proteins and peptides to which they are fused, and of expression of the genes, vectors, expression constructs, and nucleic acids that encode them. In particular, the reporter signal fusions allow sensitive and multiplex detection of expression of particular proteins and peptides of interest, and/or of the genes, vectors, and expression constructs encoding the proteins and peptides of interest.

The disclosed reporter signal fusions also are useful for creating cells, cell lines, and organisms that have particular protein(s), gene(s), vector(s), and/or expression sequence(s) labeled (that is, associated with or involved in) reporter signal fusions. For example, a set of nucleic acid constructs, each encoding a reporter signal fusion with a different reporter signal peptide, can be used to uniquely label a set of cells, cell lines, and/or organisms. Processing of a sample from any of the labeled sources can result in a unique altered form of the reporter signal peptide (or the amino acid segment or an amino acid subsegment) for each of the possible sources that can be distinguished from the other altered forms. Detection of a particular altered form identifies the source from which it came.

The disclosed reporter signal fusions also can be used to "label" particular pathways, regulatory cascades, and other suites of genes, proteins, vectors, and/or expressions sequences. Such labeling can be within the same cell, cell line, or organism, or across a set of cells, cell lines, or organisms. For example, nucleic acid segments encoding reporter signal fusions can be associated with endogenous expression sequences of interest, endogenous genes of interest, exogenous expression sequences of interest, exogenous genes of interest, or a combination. The exogenous constructs then are introduced into the cells or organisms of interest. The association with endogenous expression sequences or genes can be accomplished, for example, by introducing a nucleic acid molecule (encoding the reporter signal fusion) for insertion at the site of the expression sequences or gene of interest, or by creating a vector or other nucleic acid construct (containing both the endogenous expression sequences or gene and a nucleic acid segment encoding the reporter signal fusion) in vitro and introducing the construct into the cells or organisms of interest. Many other uses and modes of use are possible, a number of which are described in the illustrations below. In particular, the disclosed reporter signal fusions can be used in any context and for any purpose that green fluorescent protein and green fluorescent protein fusions are used. However, the disclosed reporter signal proteins have more uses and are more useful than green fluorescent protein at least because of the ability to multiplex the disclosed reporter signal fusions.

The reporter signal peptides can be used for sensitive detection of one or multiple proteins (that is, the proteins to which the reporter signal peptides are fused). In the method, proteins fused with reporter signal peptides are analyzed using the reporter signal peptides to distinguish the reporter signal fusions. Detection of the reporter signal peptides indicates the presence of the corresponding protein(s). The detected protein(s) can then be analyzed using known techniques. The reporter signal fusions provide a unique protein/label composition that can specifically identify the protein (s). This is accomplished through the use of the specialized reporter signal peptides as the labels.

The reporter signal fusions can be produced by expression from nucleic acid molecules encoding the fusions. Thus, the disclosed fusions generally can be designed by designing nucleic acid segments that encode amino acid segments where the amino acid segments comprise a reporter signal peptide and a protein or peptide of interest. A given nucleic acid molecule can comprise one or more nucleic acid segments. A given nucleic acid segment can encode one or more amino acid segments. A given amino acid segment can include one or more reporter signal peptides and one or more proteins or peptides of interest. The disclosed amino acid segments consist of a single, contiguous polypeptide chain. Thus, although multiple amino acid segments can be part of the same contiguous polypeptide chain, all of the components (that is, the reporter signal peptide(s) and protein(s) and peptide(s) of interest) of a given amino acid segment are part of the same contiguous polypeptide chain.

Reporter signal peptides can be fragmented, decomposed, reacted, derivatized, or otherwise modified, preferably in a characteristic way. This allows a protein to which the reporter signal peptide is fused to be identified by detection of one or more of the products of the reporter signal fusion following fragmentation, decomposition, reaction, derivatization, or other modification of the reporter signal peptide. Expression of one or more proteins in one or more samples can be detected in a multiplex manner. Preferably, for mass spectrometry reporter signals, the reporter signal peptides are fragmented to yield fragments of similar charge but different mass.

Preferably, the reporter signal peptides are fragmented to yield fragments of similar charge but different mass. This allows each reporter signal fusion (and/or each reporter signal peptide) in a set to be distinguished by the different mass-to-charge ratios of the fragments of (that is, altered forms of) the reporter signal peptides or reporter signal fusions. This is possible since the fragments of the different reporter signal peptides (or the fragments of the reporter signal fusions) can be designed to have different mass-to-charge ratios. In the disclosed method, this allows each reporter signal fusion to be distinguished by the mass-to-charge ratios of the reporter signal fusions after fragmentation of the reporter signal peptide.

Alteration of reporter signals peptides in reporter signal fusions can produce a variety of altered compositions. Any or all of these altered forms can be detected. For example, the altered form of the reporter signal peptide can be detected, the altered form of the amino acid segment (which contains the reporter signal peptide) can be detected, the altered form of a subsegment of the amino acid segment can be detected, or a combination of these can be detected.

Where the reporter signal peptide is altered by fragmentation, the result generally will be a fragment of the reporter signal peptide and an altered form of the amino acid segment containing the protein or peptide of interest and a portion of the reporter signal peptide (that is, the portion not in the reporter signal peptide fragment). The protein or peptide of interest also can be fragmented. The result would be a subsegment of the amino acid segment. The amino acid subsegment would contain the reporter signal peptide and a portion of the protein or peptide of interest. When the reporter signal peptide in an amino acid subsegment is altered (which can occur before, during, or after fragmentation of the amino acid segment), the result is an altered form of the amino acid subsegment (and an altered form of the reporter signal peptide). This altered form of amino acid subsegment can be detected.

As with reporter signals generally, reporter signal peptides can be used in sets where the reporter signal peptides in a set can have one or more common properties that allow the reporter signal peptides to be separated or distinguished from molecules lacking the common property. In the case of reporter signal fusions, amino acid segments and amino acid subsegments can be used in sets where the amino acid segments and amino acid subsegments in a set can have one or more common properties that allow the amino acid segments and amino acid subsegments, respectively, to be separated or distinguished from molecules lacking the common property. In general, the component(s) of the reporter signal fusions having common properties can depend on the component(s) to be detected and/or the mode of the method being used.

Nucleic acid molecules encoding reporter signal fusions can be used in sets where the reporter signal peptides in the reporter signal fusions encoded by a set of nucleic acid molecules can have one or more common properties that allow the reporter signal peptides to be separated or distinguished from molecules lacking the common property. Similarly, nucleic acid segments (which, generally, are part of nucleic acid molecules) encoding reporter signal fusions can be used in sets where the reporter signal peptides in the reporter signal fusions encoded by a set of nucleic acid segments can have one or more common properties that allow the reporter signal peptides to be separated or distinguished from molecules lacking the common property. Other relationships between members of the sets of nucleic acid molecules, nucleic acid segments, amino acid segments, reporter signal peptides, and proteins of interest are contemplated.

Cells, cell lines, organisms, and expression of genes and proteins can be detected using the disclosed reporter signal fusions in a variety of ways. For example, the protein and attached reporter signal peptide can be detected together, one or more peptides of the protein and the attached reporter signal peptide(s) can be detected together, the fragments of the reporter signal peptide can be detected, or a combination. Preferred detection involves detection of the reporter signal fusion both before and after fragmentation of the reporter signal peptide.

A powerful form of the disclosed method is use of reporter signal fusions to assay multiple samples (for example, time series assays or other comparative analyses). Knowledge of the temporal response of a biological system following perturbation is a very powerful process in the pursuit of understanding the system. To follow the temporal response a sample of the system is obtained (for example, cells from a cell culture, mice initially synchronized and sacrificed) at determined times following the perturbation. Knowledge of spatial protein profiles (for example, relative position within a tissue section) is a very powerful process in the pursuit of understanding the biological system.

The reporter signal fusions are preferably detected using mass spectrometry which allows sensitive distinctions between molecules based on their mass-to-charge ratios. A set of isobaric reporter signal peptides or reporter signal fusions can be used for multiplex labeling and/or detection of the expression of many genes, proteins, vectors, expression constructs, cells, cell lines, and organisms since the reporter signal peptide fragments can be designed to have a large range of masses, with each mass individually distinguishable upon detection. Where the same gene, protein, vector, expression construct, cell, cell line, or organism (or the same type of gene, protein, vector, expression construct, cell, cell line, or organism) is labeled with a set of reporter signal fusions that are isobaric or that include isobaric reporter signal peptides (by, for example, "labeling" the same gene, protein, vector, expression construct, cell, cell line, or organism in different samples), the set of reporter signal fusions or reporter signal peptides that results will also be isobaric. Fragmentation of the reporter signal peptides will split the set of reporter signal peptides into individually detectable reporter signal fusion fragments and reporter signal peptide fragments of characteristically different mass.

A preferred form of the disclosed method involves filtering of isobaric reporter signal fusions or reporter signal peptides from other molecules based on mass-to-charge ratio, fragmentation of the reporter signal peptides to produce fragments having different masses, and detection of the different fragments based on their mass-to-charge ratios. The method is best carried out using a tandem mass spectrometer as described elsewhere herein.

It is an object of the present invention to provide a method for the multiplexed determination of presence, amount, or presence and amount of analytes.

It is an object of the present invention to provide labeled proteins such that the presence, amount, or presence and amount of the proteins can be determined.

It is another object of the present invention to provide a method for labeling proteins so as to allow the multiplexed determination of presence, amount, or presence and amount of proteins.

It is another object of the present invention to provide a method for the multiplexed determination of presence, amount, or presence and amount of proteins.

It is an object of the present invention to provide a method for detecting a mass tag signature.

It is an object of the present invention to provide a method for detecting a protein signature.

It is another object of the present invention to provide an assessment of the identity and purity of the peptides comprising a protein signature.

It is another object of the present invention to provide a method for detecting phosphopeptides, or other posttranslational protein modifications, among the peptides comprising a protein signature.

It is another object of the present invention to provide kits for generating mass tag signatures.

It is another object of the present invention to provide kits for generating protein signatures.

BRIEF DESCRIPTION OF THE DRAWINGS

FIG. 1A shows the results where there is no fragmentation of the reporter signal. A single peak represents the parent ion. FIG. 1B shows the results where the reporter signal is fragmented. The parent ion along with two fragmentation ions are detected.

FIGS. 2A and 2B are graphs of mass-to-charge ratio (m/z) versus detected counts. FIG. 2A shows the results where no fragmentation of reporter signals A and B occurs. FIG. 2B shows the results where all of the reporter signals are fragmented (A fragments to A1 and A2, B fragments to B1 and B2).

FIG. 9B is an expanded view of the peak. Selection was not perfect in this example as the finite resolution of the filter allowed three peaks to pass.

DETAILED DESCRIPTION OF THE INVENTION

Figure 1:
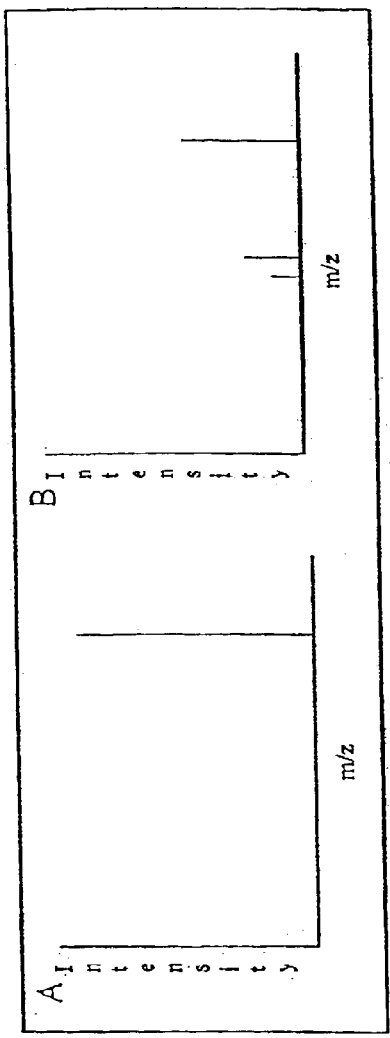
FIGS. 1A and 1B are graphs of mass-to-charge ratio (m/z) versus signal intensity.

Disclosed are compositions and methods for sensitive detection of one or multiple analytes. In general, the methods involve the use of special label components, referred to as reporter signals, that can be associated with, incorporated into, or otherwise linked to the analytes. Reporter signals can also be used merely in conjunction with analytes, with no significant association between the analytes and reporter signals. Compositions where reporter signals are associated with, incorporated into, or otherwise linked to the analytes are referred to as reporter signal/analyte conjugates. Such conjugates include reporter signals associated with analytes, such as a reporter signal probe hybridized to a nucleic acid sequence; reporter signals covalently coupled to analytes, such as reporter signals linked to proteins via a linking group; and reporter signals incorporated into analytes, such as fusions between a protein of interest and a peptide reporter signal.

In some embodiments, the reporter signals can be altered such that the altered forms of different reporter signals can be distinguished from each other. Reporter signal/analyte conjugates can be altered, generally through alteration of the reporter signal portion of the conjugate, such that the altered forms of different reporter signals, altered forms of different reporter signal/analyte conjugates, or both, can be distinguished from each other. Where the reporter signal or reporter signal/analyte conjugate is altered by fragmentation, any, some, or all of the fragments can be distinguished from each other, depending on the embodiment. For example, where reporter signals fragmented into two parts, either or both parts of the reporter signals can be distinguished. Where reporter signal/analyte conjugates are fragmented into two parts (with the break point in the reporter signal portion), either the reporter signal fragment, the reporter signal/analyte fragment, or both can be distinguished. In some embodiments, only one part of a fragmented reporter signal will be detected and so only this part of the reported signals need be distinguished.

In some embodiments, sets of reporter signals can be used where two or more of the reporter signals in a set have one or more common properties that allow the reporter signals having the common property to be distinguished and/or separated from other molecules lacking the common property. In other embodiments, sets of reporter signal/analyte conjugates can be used where two or more of the reporter signal/analyte conjugates in a set have one or more common properties that allow the reporter signal/analyte conjugates having the common property to be distinguished and/or separated form other molecules lacking the common property. In still other embodiments, analytes can be fragmented (prior to or following conjugation) to produce reporter signal/analyte fragment conjugates (which can be referred to as fragment conjugates). In such cases, sets of fragment conjugates can be used where two or more of the fragment conjugates in a set have one or more common properties that allow the fragment conjugates having the common property to be distinguished and/or separated form other molecules lacking the common property. It should be understood that fragmented analytes can be considered analytes in their own right. In this light, reference to fragmented analytes is made for convenience and clarity in describing certain embodiments and to allow reference to both the base analyte and the fragmented analyte.

As indicated above, reporter signals conjugated with analytes can be altered while in the conjugate and distinguished. Conjugated reporter signals can also be dissociated or separated, in whole or in part, from the conjugated analytes prior to their alteration. Where the reporter signals are dissociated (in whole or in part) from the analytes, the method can be performed such that the fact of association between the analyte and reporter signal is part of the information obtained when the reporter signal is detected. In other words, the fact that the reporter signal may be dissociated from the analyte for detection does not obscure the information that the detected reporter signal was associated with the analyte.

Reporter signals can also be in conjunction with analytes (such as in mixtures of reporter signals and analytes), where no significant physical association between the reporter signals and analytes occurs; or alone, where no analyte is present. In such cases, where reporter signals are not or are no longer associated with analytes, sets of reporter signals can be used where two or more of the reporter signals in a set have one or more common properties that allow the reporter signals having the common property to be distinguished and/or separated from other molecules lacking the common property.

Detection of the reporter signals indicates the presence of the corresponding analytes. The reporter signals can have two key features. First, the reporter signals can be used in sets where all the reporter signals in the set have similar properties. The similar properties allow the reporter signals to be distinguished and/or separated from other molecules lacking one or more of the properties. Preferably, the reporter signals in a set have the same mass-to-charge ratio (m/z). That is, the reporter signals in a set are isobaric. This allows the reporter signals to be separated precisely from other molecules based on mass-to-charge ratio. The result of the filtering is a huge increase in the signal to noise ratio (S/N) for the system, allowing more sensitive and accurate detection.

Second, all the reporter signals in a set can be fragmented, decomposed, reacted, derivatized, or otherwise modified to distinguish the different reporter signals in the set. For example, the reporter signals can be fragmented to yield fragments having the same charge but different mass. This allows each reporter signal in a set to be distinguished by the different mass-to-charge ratios of the fragments of the reporter signals. This is possible since, although the unfragmented reporter signals in a set are isobaric, the fragments of the different reporter signals are not. Reporter signals to be detected on the basis of mass-to-charge ratio and/or to be detected with the use of a mass spectrometer, can be referred to as mass spectrometer reporter signals.

Differential distribution of mass in the fragments of the reporter signals can be accomplished in a number of ways. For example, reporter signals of the same nominal structure (for example, peptides having the same amino acid sequence), can be made with different distributions of heavy isotopes, such as deuterium. All reporter signals in the set would have the same number of a given heavy isotope, but the distribution of these would differ for different reporter signals. Similarly, reporter signals of the same general structure (for example, peptides having the same amino acid sequence), can be made with different distributions of modifications, such as methylation, phosphorylation, sulphation, and use of seleno-methionine for methionine. All reporter signals in the set would have the same number of a given modification, but the distribution of these would differ for different reporter signals. Reporter signals of the same nominal composition (for example, made up of the same amino acids), can be made with different ordering of the subunits or components of the reporter signal. All reporter signals in the set would have the same number of subunits or components, but the distribution of these would be different for different reporter signals. Reporter signals having the same nominal composition (for example, made up of the same amino acids), can be made with a labile or scissile bond at a different location in the reporter signal. All reporter signals in the set would have the same number and order of subunits or components. Where the labile or scissile bond is present between particular subunits or components, the order of subunits or components in the reporter signal can be the same except for the subunits or components creating the labile or scissile bond. Each of these modes can be combined with one or more of the other modes to produce differential distribution of mass in the fragments of the reporter signals. For example, different distributions of heavy isotopes can be used in reporter signals where a labile or scissile bond is placed in different locations.

The reporter signals are preferably detected using mass spectrometry which allows sensitive distinctions between molecules based on their mass-to-charge ratios. The disclosed reporter signals can be used as general labels in myriad labeling and/or detection techniques. A set of isobaric reporter signals can be used for multiplex labeling and/or detection of many analytes since the reporter signal fragments can be designed to have a large range of masses, with each mass individually distinguishable upon detection.

Current technologies are limited in their ability to multiplex labels. In contrast, the disclosed method allows the readout of many samples simultaneously and high internal accuracy in comparison to a sequential readout system.

A preferred form of the disclosed method involves filtering of isobaric reporter signals from other molecules based on mass-to-charge ratio, fragmentation of the reporter signals to produce fragments having different masses, and detection of the different fragments based on their mass-to-charge ratios. The method is best carried out using a tandem mass spectrometer where the isobaric reporter signals are passed through a filtering quadrupole, the reporter signals are fragmented in a collision cell, and the fragments are distinguished and detected in a time-of-flight (TOF) stage. In such an instrument the sample is ionized in the source (for example, in a MALDI ion source) to produce charged ions. It is preferred that the ionization conditions are such that primarily a singly charged parent ion is produced. A first quadrupole, Q0, is operated in radio frequency (RF) mode only and acts as an ion guide for all charged particles. The second quadrupole, Q1, is operated in RF+DC mode to pass only a narrow range of mass-to-charge ratios (that includes the mass-to-charge ratio of the reporter signals). This quadrupole selects the mass-to-charge ratio of interest. Quadrupole Q2, surrounded by a collision cell, is operated in RF only mode and acts as ion guide. The collision cell surrounding Q2 will be filled to appropriate pressure with a gas to fracture the input ions by collisionally induced dissociation. The collision gas preferably is chemically inert, but reactive gases can also be used. Preferred molecular systems utilize reporter signals that contain scissile bonds, labile bonds, or combinations, such that these bonds will be preferentially fractured in the Q2 collision cell.

A. Reporter Molecule Labeling

In one form of the disclosed method, referred to as reporter molecule labeling (RML), reporter signals are associated with analytes to be detected and/or quantitated. For example, a reporter signal can be associated with a specific binding molecule that interacts with the analyte of interest. Such a combination is referred to as a reporter molecule. The specific binding molecule in the reporter molecule interacts with the analyte thus associating the reporter signal with the analyte. Alternatively, a reporter signal can be associated with an analyte indirectly. In this mode, a "coding" molecule containing a specific binding molecule and a coding tag is associated with the analyte (via the specific binding molecule). Alternatively, a coding tag can be coupled or directly associated with the analyte. Then a reporter signal associated with a decoding tag (such a combination is another form of reporter molecule) is associated with the coding molecule through an interaction between the coding tag and the decoding tag. An example of this interaction is hybridization where the coding and decoding tags are complementary nucleic acid sequences. The result is an indirect association of the reporter signal with the analyte. This mode has the advantage that all of the interactions of the reporter signals with the coding molecule can be made chemically and physically similar by using the same types of coding tags and decoding tags for all of the coding molecules and reporter molecules in a set.

B. Reporter Signal Labeling

In another form of the disclosed method, referred to as reporter signal labeling (RSL), reporter signals are used for sensitive detection of one or multiple analytes. In the method, analytes labeled with reporter signals are analyzed using the reporter signals to distinguish the labeled analytes (where the analytes are labeled with the reporter signals). Detection of the reporter signals indicates the presence of the corresponding analyte(s). The detected analyte(s) can then be analyzed using known techniques. The labels provide a unique analyte/label composition that can specifically identify the analyte(s). This is accomplished through the use of the reporter signals as the labels. The labeled analyte(s) can be fragmented prior to analysis. An analyte sample to be analyzed can also be subjected to fractionation or separation to reduce the complexity of the samples. Fragmentation and fractionation can also be used together in the same assay. Such fragmentation and fractionation can simplify and extend the analysis of the analytes.

Reporter signals can be coupled or directly associated with an analyte. For example, a reporter signal can be coupled to an analyte via reactive groups, or a reporter molecule (composed of a specific binding molecule and a reporter signal) can be associated with an analyte. The reporter signals can be attached to analytes in any manner. For example, reporter signals can be covalently coupled to proteins through a sulfur—sulfur bond between a cysteine on the protein and a cysteine on the reporter signal. Many other chemistries and techniques for coupling compounds to analytes are known and can be used to couple reporter signals to analytes. For example, coupling can be made using thiols, epoxides, nitriles for thiols, NHS esters, isothiocyanates for amines, and alcohols for carboxylic acids. Reporter signals can be attached to analytes either directly or indirectly, for example, via a linker.

Reporter signals, or constructs containing reporters signals, also can be attached or coupled to analytes by ligation. Methods for ligation of nucleic acids are well known (see, for example, Sambrook et al. Molecular Cloning: A Laboratory Manual, second edition, 1989, Cold Spring Harbor Laboratory Press, New York.), and efficient protein ligation is known (see, for example, Dawson et al., "Synthesis of proteins by native chemical ligation" Science 266, 776–9 (1994); Hackeng et al., "Chemical synthesis and spontaneous folding of a multidomain protein: anticoagulant microprotein S" Proc Natl Acad Sci USA 97:14074–8 (2000); Dawson et al., "Synthesis of Native Proteins by Chemical Ligation" Ann. Rev. Biochem. 69:923–960 (2000); U.S. Pat. No. 6,184,344; PCT Publication WO 98/28434).

Alternatively, a reporter signal can be associated with an analyte indirectly. In this mode, a "coding" molecule containing a specific binding molecule and a coding tag can be associated with the analyte (via the specific binding molecule). Alternatively, a coding tag can be coupled or directly associated with the analyte. Then a reporter signal associated with a decoding tag (such a combination is another form of reporter molecule) is associated with the coding molecule through an interaction between the coding tag and the decoding tag. An example of this interaction is hybridization where the coding and decoding tags are complementary nucleic acid sequences. The result is an indirect association of the reporter signal with the analyte. This mode has the advantage that all of the interactions of the reporter signals with the coding molecule can be made chemically and physically similar by using the same types of coding tags and decoding tags for all of the coding molecules and reporter molecules in a set.

Reporter signals can be fragmented, decomposed, reacted, derivatized, or otherwise modified, preferably in a characteristic way. This allows an analyte to which the reporter signal is attached to be identified by the correlated detection of the labeled analyte and one or more of the products of the labeled analyte following fragmentation, decomposition, reaction, derivatization, or other modification of the reporter signal (the labeled analyte is the analyte/reporter signal combination). The alteration of the reporter signal will alter the labeled analyte in a characteristic and detectable way. Together, the detection of a characteristic labeled analyte and a characteristic product of the labeled analyte can uniquely identify the analyte. In this way, using the disclosed method and materials, one or more analytes can be detected, either alone or together (for example, in a multiplex assay). Further, one or more analytes in one or more samples can be detected in a multiplex manner. Preferably, for mass spectrometry reporter signals, the reporter signals are fragmented to yield fragments of similar charge but different mass.

Preferably, the reporter signals are fragmented to yield fragments of similar charge but different mass. This allows each labeled analyte (and/or each reporter signal) in a set to be distinguished by the different mass-to-charge ratios of the fragments of the reporter signals. This is possible since, although the unfragmented reporter signals in a set are isobaric, the fragments of the different reporter signals are not. In the disclosed method, this allows each analyte/reporter signal combination to be distinguished by the mass-to-charge ratios of the analyte/reporter signals after fragmentation of the reporter signal.

In preferred embodiments, reporter signals are used in sets where all the reporter signals in the set have similar properties (such as similar mass-to-charge ratios). The similar properties allow the reporter signals to be distinguished and/or separated from other molecules lacking one or more of the properties. Preferably, the reporter signals in a set have the same mass-to-charge ratio (m/z). That is, the reporter signals in a set are isobaric. This allows the reporter signals (or any analytes to which they are attached) to be separated precisely from other molecules based on mass-to-charge ratio. The result of the filtering is a huge increase in the signal to noise ratio (S/N) for the system, allowing more sensitive and accurate detection. Alternatively, or in addition, reporter signals can be used in sets such that the resulting labeled analytes will have similar properties allowing the labeled analytes to be distinguished and/or separated from other molecules lacking one or more of the properties.

Analytes can be detected using the disclosed reporter signals in a variety of ways. For example, the analyte and attached reporter signal can be detected together, one or more fragments of the analyte and the attached reporter signal(s) can be detected together, the fragments of the reporter signal can be detected, or a combination. Preferred detection involves detection of the analyte/reporter signal both before and after fragmentation of the reporter signal.

A preferred form of the disclosed method involves correlated detection of the reporter signals both before and after fragmentation of the reporter signal. This allows labeled analytes to be detected and identified via the change in labeled analyte. That is, the nature of the reporter signal detected (non-fragmented versus fragmented) identifies the analyte as labeled. Where the analytes and reporter signals are detected by mass-to-charge ratio, the change in mass-to-charge ratio between fragmented and non-fragmented samples provides the basis for comparison. Such mass-to-charge ratio detection is preferably accomplished with mass spectrometry.

As an example, an analyte in a sample can be labeled with reporter signal designed as a mass spectrometry label. The labeled analyte can be subjected to mass spectrometry. A peak corresponding to the analyte/reporter signal will be detected. Fragmentation of the reporter signal in the mass spectrometer (preferably in a collision cell) would result in a shift in the peak corresponding to the loss of a portion of the attached reporter signal, the appearance of a peak corresponding to the lost fragment, or a combination of both events. Significantly, the shift observed will depend on which reporter signal is on the analyte since different reporter signals will, by design, produce fragments with different mass-to-charge ratios. The combination event of detection of the parent mass-to-charge (with no collision gas) and the mass-to-charge corresponding to the loss of the fragment from the reporter signal (with collision gas) indicates a labeled analyte. The identity of the analyte can be determined by standard mass spectrometry techniques, such as compositional analysis.

A powerful form of the disclosed method is use of analytes labeled with reporter signals to assay multiple samples (for example, time series assays or other comparative analyses). Knowledge of the temporal response of a biological system following perturbation is a very powerful process in the pursuit of understanding the system. To follow the temporal response, a sample of the system is obtained (for example, cells from a cell culture, mice initially synchronized and sacrificed) at determined times following the perturbation. Knowledge of spatial analyte profiles (for example, relative position within a tissue section) is a very powerful process in the pursuit of understanding the biological system.

In the disclosed method a series of samples can each be labeled with a different reporter signal from a set of reporter signals. Preferred reporter signals for this purpose would be those using differentially distributed mass. In particular, the use of stable isotopes is preferred to ensure that members of the set of reporter signals would behave chemically identically and yet would be distinguishable.

The labeled analytes are preferably detected using mass spectrometry which allows sensitive distinctions between molecules based on their mass-to-charge ratios. The disclosed reporter signals can be used as general labels in myriad labeling and/or detection techniques. A set of isobaric reporter signals can be used for multiplex labeling and/or detection of many analytes since the reporter signal fragments can be designed to have a large range of masses, with each mass individually distinguishable upon detection. Where the same analyte or type of analyte is labeled with a set of isobaric reporter signals (by, for example, labeling the same analyte in different samples), the set of labeled analytes that results from use of an isobaric set of reporter signals will also be isobaric. Fragmentation of the reporter signals will split the set of labeled analytes into individually detectable labeled proteins of characteristically different mass.

A preferred form of the disclosed method involves filtering of isobaric reporter signals (and the attached analytes) from other molecules based on mass-to-charge ratio, fragmentation of the reporter signals to produce fragments having different masses, and detection of the different fragments based on their mass-to-charge ratios. This form of the method is best carried out using a tandem mass spectrometer as described elsewhere herein.

The disclosed method can be used in many modes. For example, the disclosed method can be used to detect a specific analyte (in a specific sample or in multiple samples) or multiple analytes (in a single sample or multiple samples). In each case, the analyte(s) to be detected can be separated either from other, unlabeled analytes or from other molecules lacking a property of the labeled analyte(s) to be detected. For example, analytes in a sample can be generally labeled with reporter signals and some analytes can be separated on the basis of some property of the analytes. For example, the separated analytes could have a certain mass-to-charge ratio (separation based on mass-to-charge ratio will select both labeled and unlabeled analytes having the selected mass-to-charge ratio). As another example, all of the labeled analytes can be distinguished and/or separated from unlabeled molecules based on a feature of the reporter signal such as an affinity tag. Where different affinity tags are used, some labeled analytes can be distinguished and/or separated from others. Reporter signal labeling allows profiling of analytes and cataloging of analytes.

In one mode of the disclosed method, multiple analytes in multiple samples are labeled where all of the analytes in a given sample are labeled with the same reporter signal. That is, the reporter signal is used as a general label of the analytes in a sample. Each sample, however, uses a different reporter signal. This allows samples as a whole to be compared with each other. By additionally separating or distinguishing different analytes in the samples, one can easily analyze many analytes in many samples in a single assay. For example, proteins in multiple samples can be labeled with reporter signals as described above, and the samples mixed together. If some or all of the various labeled proteins are separated by, for example, association of the proteins with antibodies on an array, the presence and amount of a given protein in each of the samples can be determined by identifying the reporter signals present at each array element. If the protein corresponding to a given array element was present in a particular sample, then some of the protein associated with that array element will be labeled with the reporter signal used to label that particular sample. Detection of that reporter signal will indicate this. This same relationship holds true for all of the other samples. Further, the amount of reporter signal detected can indicate the amount of a given protein in a given sample, and the simultaneous quantitation of protein in multiple samples can provide a particularly accurate comparison of the levels of the proteins in the various samples.

1. Reporter Signal Protein Labeling

In one form of reporter signal labeling, referred to as reporter signal protein labeling (RSPL), reporter signals are used for sensitive detection of one or multiple proteins. In the method, proteins labeled with reporter signals are analyzed using the reporter signals to distinguish the labeled proteins. Detection of the reporter signals indicates the presence of the corresponding protein(s). The detected protein(s) can then be analyzed using known techniques. The labels provide a unique protein/label composition that can specifically identify the protein(s). This is accomplished through the use of the specialized reporter signals as the labels.

Although reference is made above and elsewhere herein to detection of a "protein" or "proteins," the disclosed method and compositions encompass proteins, peptides, and fragments of proteins or peptides. Thus, reference to a protein herein is intended to refer to proteins, peptides, and fragments of proteins or peptides unless the context clearly indicates otherwise. As used herein "labeled protein" refers to a protein, peptide, or fragment of a protein or peptide to which a reporter signal is attached unless the context clearly indicates otherwise. The labeled protein(s) can be fragmented, such as by protease digestion, prior to analysis. A protein sample to be analyzed can also be subjected to fractionation or separation to reduce the complexity of the samples. Fragmentation and fractionation can also be used together in the same assay. Such fragmentation and fractionation can simplify and extend the analysis of the proteins.

The reporter signals can be attached to proteins in any manner. For example, reporter signals can be covalently coupled to proteins through a sulfur—sulfur bond between a cysteine on the protein and a cysteine on the reporter signal. Many other chemistries and techniques for coupling compounds to proteins are known and can be used to couple reporter signals to proteins. For example, coupling can be made using thiols, epoxides, nitrites for thiols, NHS esters, isothiocyanates for amines, and alcohols for carboxylic acids. Reporter signals can be attached to proteins either directly or indirectly, for example, via a linker. Reporter signals also can be attached to proteins by ligation (for example, protein ligation of a reporter signal peptide to a protein).

It is possible to form labeled proteins where the reporter signal is specifically attached to phosphopeptides. Chemistry for specific derivatization of phosphoserine or phosphotyrosine residues has been described (Zhou et al. *A systematic approach to the problem of protein phosphorylation.*, Nat. Biotech. 19:375–378 (2001), Oda et al., *Enrichment analysis of phosphorylated proteins as a tool for probing the phosphoproteome.*, Nat. Biotech. 19:379–382 (2001)). Tryptic peptides treated according to either of these two protocols will display reactive sulfhydryls at sites of protein phosphorylation. These sites may be reacted with reporter signals to generate a labeled protein. Non-phosphorylated peptides will not be derivatized.

Reporter signals can be fragmented, decomposed, reacted, derivatized, or otherwise modified, preferably in a characteristic way. This allows a protein to which the reporter signal is attached to be identified by the correlated detection of the labeled protein and one or more of the products of the labeled protein following fragmentation, decomposition, reaction, derivatization, or other modification of the reporter signal (the labeled protein is the protein/reporter signal combination). The alteration of the reporter signal will alter the labeled protein in a characteristic and detectable way. Together, the detection of a characteristic labeled protein and a characteristic product of the labeled protein can uniquely identify the protein. In this way, using the disclosed method and materials, one or more proteins can be detected, either alone or together (for example, in a multiplex assay). Further, one or more proteins in one or more samples can be detected in a multiplex manner. Preferably, for mass spectrometry reporter signals, the reporter signals are fragmented to yield fragments of similar charge but different mass.

Preferably, the reporter signals are fragmented to yield fragments of similar charge but different mass. This allows each labeled protein (and/or each reporter signal) in a set to be distinguished by the different mass-to-charge ratios of the fragments of the reporter signals. This is possible since, although the unfragmented reporter signals in a set are isobaric, the fragments of the different reporter signals are not. In the disclosed method, this allows each protein/reporter signal combination to be distinguished by the mass-to-charge ratios of the protein/reporter signals after fragmentation of the reporter signal.

In preferred embodiments, reporter signals are used in sets where all the reporter signals in the set have similar properties (such as similar mass-to-charge ratios). The similar properties allow the reporter signals to be distinguished and/or separated from other molecules lacking one or more of the properties. Preferably, the reporter signals in a set have the same mass-to-charge ratio (m/z). That is, the reporter signals in a set are isobaric. This allows the reporter signals (or any proteins to which they are attached) to be separated precisely from other molecules based on mass-to-charge ratio. The result of the filtering is a huge increase in the signal to noise ratio (S/N) for the system, allowing more sensitive and accurate detection. Alternatively, or in addition, reporter signals can be used in sets such that the resulting labeled proteins will have similar properties allowing the labeled proteins to be distinguished and/or separated from other molecules lacking one or more of the properties.

Proteins can be detected using the disclosed reporter signals in a variety of ways. For example, the protein and attached reporter signal can be detected together, one or more peptides of the protein and the attached reporter signal(s) can be detected together, the fragments of the reporter signal can be detected, or a combination. Preferred detection involves detection of the protein/reporter signal or peptide/reporter signal both before and after fragmentation of the reporter signal.

A preferred form of the disclosed method involves correlated detection of the reporter signals both before and after fragmentation of the reporter signal. This allows labeled proteins to be detected and identified via the change in labeled protein. That is, the nature of the reporter signal detected (non-fragmented versus fragmented) identifies the protein as labeled. Where the proteins and reporter signals are detected by mass-to-charge ratio, the change in mass-to-charge ratio between fragmented and non-fragmented samples provides the basis for comparison. Such mass-to-charge ratio detection is preferably accomplished with mass spectrometry.

As an example, a protein in a sample can be labeled with reporter signal designed as a mass spectrometry label. The labeled protein can be subjected to tryptic digest followed by mass spectrometry of the resulting materials. A peak corresponding to the tryptic fragment containing the reporter signal will be detected. Fragmentation of the reporter signal in the mass spectrometer (preferably in a collision cell) would result in a shift in the peak corresponding to the loss of a portion of the attached reporter signal, the appearance of a peak corresponding to the lost fragment, or a combination of both events. Significantly, the shift observed will depend on which reporter signal is on the protein since different reporter signals will, by design, produce fragments with different mass-to-charge ratios. The combination event of detection of the parent mass-to-charge (with no collision gas) and the mass-to-charge corresponding to the loss of the fragment from the reporter signal (with collision gas) indicates a labeled protein. The combination event may be carried out in an analogous fashion to the detection of phosphorylation sites described above. The identity of the tryptic fragment of the protein can be determined by standard mass spectrometry techniques, such as compositional analysis and peptide sequencing.

Not all labeled protein fragments that can be made in the disclosed method from a protein sample will be unique. Because some proteins have common motifs that may be identical in different proteins, some protein fragments or peptides produced from a sample will be identical although they were derived from different proteins. For example, some families of related proteins have such common motifs or common amino acid sequences. Thus, in some embodiments of the disclosed method, detection of a characteristic labeled protein may be the result of detection of a common portion of related proteins. Such a result can be an advantage when detection of the family of proteins is desired. Alternatively, such collective detection of related proteins can be avoided by focusing on detection of unique fragments (that is, non-identical portions) of the proteins in the family. For convenience, as used herein, detection of a common portion of multiple related proteins is intended to be encompassed by reference to detection of a unique protein, labeled protein, or other component, unless the context clearly indicates otherwise.

A powerful form of the disclosed method is use of proteins labeled with reporter signals to assay multiple samples (for example, time series assays or other comparative analyses). Knowledge of the temporal response of a biological system following perturbation is a very powerful process in the pursuit of understanding the system. To follow the temporal response a sample of the system is obtained (for example, cells from a cell culture, mice initially synchronized and sacrificed) at determined times following the perturbation. Knowledge of spatial protein profiles (for example, relative position within a tissue section) is a very powerful process in the pursuit of understanding the biological system.

In the disclosed method a series of samples can each be labeled with a different reporter signal from a set of reporter signals. Preferred reporter signals for this purpose would be those using differentially distributed mass. In particular, the use of stable isotopes is preferred to ensure that members of the set of reporter signals would behave chemically identically and yet would be distinguishable. An exemplary set of labels could be as shown in Table 1, where each of five time points could be labeled with one of the five indicated labels and the mixture of the samples could be read out simultaneously. The unfragmented labels are SEQ ID NO:1 and the fragmented labels are amino acids 7–12 of SEQ ID NO:1.

TABLE 1

| Sequence | Mass (amu) | Fragment Sequence | Fragment mass (amu) |
|---|---|---|---|
| CG*G*G*G*DPGGGGR | 949 | PGGGGR | 499 |
| CG*G*G*GDPGGGG*R | 949 | PGGGG*R | 500 |
| CG*G*GGDPGGG*G*R | 949 | PGGG*G*R | 501 |
| CG*GGGDPGG*G*G*R | 949 | PGG*G*G*R | 502 |
| CGGGGDPG*G*G*G*R | 949 | PG*G*G*G*R | 503 |

The labeled proteins are preferably detected using mass spectrometry which allows sensitive distinctions between molecules based on their mass-to-charge ratios. The disclosed reporter signals can be used as general labels in myriad labeling and/or detection techniques. A set of isobaric reporter signals can be used for multiplex labeling and/or detection of many proteins since the reporter signal fragments can be designed to have a large range of masses, with each mass individually distinguishable upon detection. Where the same protein or type of protein is labeled with a set of isobaric reporter signals (by, for example, labeling the same protein in different samples), the set of labeled proteins that results from use of an isobaric set of reporter signals will also be isobaric. Fragmentation of the reporter signals will split the set of labeled proteins into individually detectable labeled proteins of characteristically different mass.

A preferred form of the disclosed method involves filtering of isobaric reporter signals (and the attached proteins) from other molecules based on mass-to-charge ratio, fragmentation of the reporter signals to produce fragments having different masses, and detection of the different fragments based on their mass-to-charge ratios. The method is best carried out using a tandem mass spectrometer as described elsewhere herein.

The method allows detection of proteins, peptides and protein fragments where detection provides some information on the sequence or other structure of the protein or peptide detected. For example, the mass or mass-to-charge ratio, the amino acid composition, or amino acid sequence can be determined. The set of proteins, peptides and/or protein fragments detected in a sample using particular reporter signals will produce characteristic sets of protein and peptide information. The method allows a complex sample of proteins to be cataloged quickly and easily in a reproducible manner. The disclosed method also should produce two "signals" for each protein, peptide, or peptide fragment in the sample: the original labeled protein and the altered form of the labeled protein. This can allow comparisons and validation of a set of detected proteins and peptides.

Reporter signal protein labeling allows profiling of proteins, de novo discovery of proteins, and cataloging of proteins. The method has advantageous properties which can be used as a detection and analysis system for protein analysis, proteome analysis, proteomic, protein expression profiling, de novo protein discovery, functional genomics, and protein detection.

C. Reporter Signal Calibration

In another form of the method, referred to as reporter signal calibration (RSC), a form of reporter signals referred to as reporter signal calibrators are mixed with analytes or analyte fragments, the reporter signal calibrators and the analytes or analyte fragments are altered, and the altered forms of the reporter signal calibrators and altered forms of the analytes or analyte fragments are detected. Reporter signal calibrators are useful as standards for assessing the amount of analytes present. That is, one can add a known amount of a reporter signal calibrator in order to assess the amount of analyte present comparing the amount of altered analyte or analyte fragment detected with the amount of altered reporter signal calibrator detected and calibrating these amounts with the known amount of reporter signal calibrator added (and thus the predicted amount of altered reporter signal calibrator).

The disclosed reporter signal calibration method generates, with high sensitivity, unique protein signatures related to the relative abundance of different proteins in tissue, microorganisms, or any other biological sample. The disclosed method allows one to define the status of a cell or tissue by identifying and measuring the relative concentrations of a small but highly informative subset of proteins. Such as measurement is known as a protein signature. Protein signatures are useful, for example, in the diagnosis, grading, and staging of cancer, in drug screening, and in toxicity testing.

In some embodiments, each analyte or analyte fragment can share one or more common properties with at least one reporter signal calibrator such that the reporter signal calibrators and analytes or analyte fragments having the common property can be distinguished and/or separated from other molecules lacking the common property.

In some embodiments, reporter signal calibrators and analytes and analyte fragments can be altered such that the altered form of an analyte or analyte fragment can be distinguished from the altered form of the reporter signal calibrator with which the analyte or analyte fragment shares a common property. In some embodiments, the altered forms of different reporter signal calibrators can be distinguished from each other. In some embodiments, the altered forms of different analytes or analyte fragments can be distinguished from each other.

In some embodiments of reporter signal calibration, the analyte or analyte fragment is not altered and so the altered reporter signal calibrators and the analytes or analyte fragments are detected. In this case, the analyte or analyte fragment can be distinguished from the altered form of the reporter signal calibrator with which the analyte or analyte fragment shares a common property.

In some embodiments the analyte or analyte fragment may be a reporter signal or a fragment of a reporter signal. In this case, the reporter signal calibrators serve as calibrators for the amount of reporter signal detected.

Reporter signal calibration is preferably used in connection with proteins and peptides (as the analytes). This form of reporter signal calibration is referred to as reporter signal protein calibration. Reporter signal protein calibration is useful, for example, for producing protein signatures of protein samples. As used herein, a protein signature is the presence, absence, amount, or presence and amount of a set of proteins or protein surrogates.

In some embodiments of reporter signal protein calibration, the presence of labile, scissile, or cleavable bonds in the proteins to be detected can be exploited. Peptides, proteins, or protein fragments (collectively referred to, for convenience, as protein fragments in the remaining description) containing such bonds can be altered by fragmentation at the bond. In this way, reporter signal calibrators having a common property (such as mass-to-charge ratio) with the protein fragments can be used and the altered forms of the reporter signal calibrators and the altered (that is, fragmented) forms of the protein fragments can be detected and distinguished. In this regard, although the protein fragments share a common property with their matching reporter signal calibrators, the altered forms of the reporter signal calibrators and altered forms of protein fragments can be distinguished (because, for example, the altered forms have different properties, such as different mass-to-charge ratios).

As an example of reporter signal protein calibration, a protein sample of interest can be digested with a serine protease, preferably trypsin. The digest generates a complex mixture of protein fragments. Among these protein fragments, there will exist a subset (approximately one protein fragment among every 400) that contains the dipeptide Asp-Pro. This dipeptide sequence is uniquely sensitive to fragmentation during mass spectrometry, an thus produces a high yield of ions in fragmentation mode. Since the human proteome consists of at least 2,000,000 distinct tryptic peptides, the number of protein fragments containing the Asp-Pro sequence is of the order of 5,000. Since some of these may exist as phosphopeptides or other modified forms, the number may be even higher. This number is sufficiently high to permit the selection of a subset (perhaps 50 to 100 or so) of fragmentable protein fragments that is suitable for generating a highly informative protein signature. Peptides that contain the Asp-Pro dipeptide sequence, peptides that contain amino acids that are modified by phosphorylation inside the cell, or peptides that contain an internal methionine are particularly preferred for use in reporter signal calibration. Alternatively, tryptic peptides terminating in arginine may be modified by reaction with acetylacetone (pentane-2,4-dione) to increase the frequency of fragment ions (Dikler et al., J Mass Spectrom 32:1337–49 (1997)). Selection of the subsets of protein fragments can be performed using bioinformatics in order to maximize the information content of the protein signatures.

For this form of reporter signal protein calibration, the protein digest can be mixed with a specially designed set of reporter signal calibrators, and then is analyzed using tandem mass spectrometry. In the case of a tandem in space instrument (for example, Q-Tof™ from Micromass), using first quadrupole settings for single-ion filtering (defined by the molecular mass of each unique fragment, which can be obtained from sequence data), followed by a collision stage for ion fragmentation, and finally TOF spectrometry of the peptide fragments (generated by cleavage at fragile bonds, such as Asp-Pro, bonds involving a phosphorylated amino acid, or bonds adjacent to an oxidized amino-acid such as methionine sulfoxide, Smith et al., Free Radic Res. 26:103–11 (1997)) that arise from the original single-ion. In the second stage, signal to noise of the TOF measurement is much larger than in a conventional MS experiment. In general, one reporter signal calibrator can be used for each protein fragment in the sample that will be used to make up the protein signature (such protein fragments are referred to as signature protein fragments), and each is designed to fragment in an easily detectable pattern of masses, distinct from the fragment masses of the unfragmented signature protein fragments. The quadrupole filtering settings are then varied in sequence over a range of values (fifty, for example), corresponding to the masses of each of the protein fragments previously chosen to comprise the protein signature (that is, the signature protein fragments). At each filtered mass setting, there will be two types of signals detectable by TOF after fragmentation, one set derived from the tryptic peptide (that is, the original protein fragment), and another set corresponding to the reporter signal calibrator. The reporter signal calibrator permits one to calculate relative abundance for each of the signature protein fragments. These relative abundance ratios, determined for a given sample, constitute the protein signature. The detection limit of the tandem mass spectrometer in MS/MS mode, is remarkably good, perhaps of the order of 500 molecules of peptide. This level of detection is approximately 1,000 times better than that for MALDI-TOF mass spectrometry, and should permit the generation of protein signatures from single cells.

As can be seen, for this form of reporter signal calibration, the availability of the sequence of the entire human genome, as well as the genomes of many other organisms, can facilitate the identification of protein fragments that are unique in the context of all known proteins. That is, the sequence information can be used to identify peptides that will be generated in a protein signature and guide selection of reporter signal calibrators.

D. Reporter Signal Fusions

In another form of the disclosed method and compositions, referred to as reporter signal fusions (RSF), reporter signal peptides are joined with a protein or peptide of interest in a single amino acid segment. Such fusions of proteins and peptides of interest with reporter signal peptides can be expressed as a fusion protein or peptide from a nucleic acid molecule encoding the amino acid segment that constitutes the fusion. The fusion protein or peptide is referred to herein as a reporter signal fusion. The reporter signal peptides, a form of reporter signal, allow for sensitive monitoring and detection of the proteins and peptides to which they are fused. In particular, the reporter signal fusions allow sensitive and multiplex detection of expression of particular proteins and peptides of interest, and/or of the genes, vectors, and expression constructs encoding the proteins and peptides of interest. The disclosed reporter signal fusions can also be used for any purpose including as a source of reporter signals for other forms of the disclosed method and compositions.

The disclosed reporter signal fusions also are useful for creating cells, cell lines, and organisms that have particular protein(s), gene(s), vector(s), and/or expression sequence(s) labeled (that is, associated with or involved in) reporter signal fusions. For example, a set of nucleic acid constructs, each encoding a reporter signal fusion with a different reporter signal peptide, can be used to uniquely label a set of cells, cell lines, and/or organisms. Processing of a sample from any of the labeled sources can result in a unique altered form of the reporter signal peptide (or the amino acid segment or an amino acid subsegment) for each of the possible sources that can be distinguished from the other altered forms. Detection of a particular altered form identifies the source from which it came. As a more specific example, a nucleic acid construct encoding a reporter signal fusion can be introduced into a genetically modified plant line (for example, a Roundup resistant corn line) and the plant line can then be identified by detecting the reporter signal fusion. Preferred reporter signal peptides for use in reporter signal fusions used in or associated with different genes, proteins, vectors, constructs, cells, cell lines, or organisms would be those using differentially distributed mass. In particular, the use of alternative amino acid sequences using the same amino acid composition is preferred.

The disclosed reporter signal fusions also can be used to "label" particular pathways, regulatory cascades, and other suites of genes, proteins, vectors, and/or expressions sequences. Such labeling can be within the same cell, cell line, or organism, or across a set of cells, cell lines, or organisms. For example, nucleic acid segments encoding reporter signal fusions can be associated with endogenous expression sequences of interest, endogenous genes of interest, exogenous expression sequences of interest, exogenous genes of interest, or a combination. The exogenous constructs then are introduced into the cells or organisms of interest. The association with endogenous expression sequences or genes can be accomplished, for example, by introducing a nucleic acid molecule (encoding the reporter signal fusion) for insertion at the site of the expression sequences or gene of interest, or by creating a vector or other nucleic acid construct (containing both the endogenous expression sequences or gene and a nucleic acid segment encoding the reporter signal fusion) in vitro and introducing the construct into the cells or organisms of interest. Many other uses and modes of use are possible, a number of which are described in the illustrations below. The disclosed reporter signal fusions can be used, for example, in any context and for any purpose that green fluorescent protein and green fluorescent protein fusions are used. However, the disclosed reporter signal proteins have more uses and are more useful than green fluorescent protein at least because of the ability to multiplex more highly the disclosed reporter signal fusions.

Nucleic acid sequences encoding reporter signal peptides can be engineered into particular exons of a gene. This would be the normal situation when the gene encoding the protein to be fused contains introns, although sequence encoding a reporter signal peptide can be split between different exons to be spliced together. Placement of nucleic acid sequences encoding reporter signal peptides into particular exons is useful for monitoring and analyzing alternative splicing of RNA. The appearance of a reporter signal peptide in the final protein indicates that the exon encoding the reporter signal peptide was spliced into the mRNA.

The reporter signal peptides can be used for sensitive detection of one or multiple proteins (that is, the proteins to which the reporter signal peptides are fused). In the method, proteins fused with reporter signal peptides are analyzed using the reporter signal peptides to distinguish the reporter signal fusions. Detection of the reporter signal peptides indicates the presence of the corresponding protein(s). The detected protein(s) can then be analyzed using known techniques. The reporter signal fusions provide a unique protein/label composition that can specifically identify the protein(s). This is accomplished through the use of the specialized reporter signal peptides as the labels.

Although reference is made above and elsewhere herein to detection of, and fusion with, a "protein" or "proteins," the disclosed method and compositions encompass proteins, peptides, and fragments of proteins or peptides. Thus, reference to a protein herein is intended to refer to proteins, peptides, and fragments of proteins or peptides unless the context clearly indicates otherwise. As used herein "reporter signal fusion" refers to a protein, peptide, or fragment of a protein or peptide to which a reporter signal peptide is fused (that is, joined by peptide bond(s) in the same polypeptide chain) unless the context clearly indicates otherwise. The reporter signal fusion(s) can be fragmented, such as by protease digestion, prior to analysis. An expression sample to be analyzed can also be subjected to fractionation or separation to reduce the complexity of the samples. Fragmentation and fractionation can also be used together in the same assay. Such fragmentation and fractionation can simplify and extend the analysis of the expression. The reporter signal peptide(s) can be fused to a protein in any arrangement, such as at the N-terminal end of the protein, at the C-terminal end of the protein, in or at domain junctions, or at any other appropriate location in the protein. In some forms of the method, it is desirable that the protein remain functional. In such cases, terminal fusions or inter-domain fusions are preferable. Those of skill in the art of protein fusions generally know how to design fusions where the protein of interest is expected to remain functional. In other embodiments, it is not necessary that the protein remain functional in which case the reporter signal peptide and protein can have any desired structural organization.

The reporter signal fusions can be produced by expression from nucleic acid molecules encoding the fusions. Thus, the disclosed fusions generally can be designed by designing nucleic acid segments that encode amino acid segments where the amino acid segments comprise a reporter signal peptide and a protein or peptide of interest. A given nucleic acid molecule can comprise one or more nucleic acid segments. A given nucleic acid segment can encode one or more amino acid segments. A given amino acid segment can include one or more reporter signal peptides and one or more proteins or peptides of interest. The disclosed amino acid segments consist of a single, contiguous polypeptide chain. Thus, although multiple amino acid segments can be part of the same contiguous polypeptide chain, all of the components (that is, the reporter signal peptide(s) and protein(s) and peptide(s) of interest) of a given amino acid segment are part of the same contiguous polypeptide chain.

Reporter signal peptides can be fragmented, decomposed, reacted, derivatized, or otherwise modified, preferably in a characteristic way. This allows a protein to which the reporter signal peptide is fused to be identified by detection of one or more of the products of the reporter signal fusion following fragmentation, decomposition, reaction, derivatization, or other modification of the reporter signal peptide. The protein can also be identified by the correlated detection of the reporter signal fusion and one or more of the products of the reporter signal fusion following fragmentation, decomposition, reaction, derivatization, or other modification of the reporter signal peptide. The alteration of the reporter signal peptide will alter the reporter signal fusion in a characteristic and detectable way. Together, the detection of a characteristic reporter signal fusion and a characteristic product of (that is, altered form of) the reporter signal fusion can uniquely identify the protein (although the altered form alone can be detected, if desired). In this way, using the disclosed method and materials, expression of one or more proteins can be detected, either alone or together (for example, in a multiplex assay). Further, expression of one or more proteins in one or more samples can be detected in a multiplex manner. Preferably, for mass spectrometry reporter signals, the reporter signal peptides are fragmented to yield fragments of similar charge but different mass.

Preferably, the reporter signal peptides are fragmented to yield fragments of similar charge but different mass. This allows each reporter signal fusion (and/or each reporter signal peptide) in a set to be distinguished by the different mass-to-charge ratios of the fragments of (that is, altered forms of) the reporter signal peptides. This is possible since the fragments of the different reporter signal peptides (or the fragments of the reporter signal fusions) can be designed to have different mass-to-charge ratios. In the disclosed method, this allows each reporter signal fusion to be distinguished by the mass-to-charge ratios of the reporter signal fusions after fragmentation of the reporter signal peptide.

Alteration of reporter signals peptides in reporter signal fusions can produce a variety of altered compositions. Any or all of these altered forms can be detected. For example, the altered form of the reporter signal peptide can be detected, the altered form of the amino acid segment (which contains the reporter signal peptide) can be detected, the altered form of a subsegment of the amino acid segment can be detected, or a combination of these can be detected. Where the reporter signal peptide is altered by fragmentation, the result generally will be a fragment of the reporter signal peptide and an altered form of the amino acid segment containing the protein or peptide of interest and a portion of the reporter signal peptide (that is, the portion not in the reporter signal peptide fragment).

The protein or peptide of interest also can be fragmented. The result would be a subsegment of the amino acid segment. The amino acid subsegment would contain the reporter signal peptide and a portion of the protein or peptide of interest. When the reporter signal peptide in an amino acid subsegment is altered (which can occur before, during, or after fragmentation of the amino acid segment), the result is an altered form of the amino acid subsegment (and an altered form of the reporter signal peptide). This altered form of amino acid subsegment can be detected. Where the reporter signal peptide is altered by fragmentation, the result generally will be a fragment of the reporter signal peptide and an altered form of (that is, fragment of) the amino acid subsegment. In this case, the altered form of the amino acid subsegment will contain a portion of the protein or peptide of interest and a portion of the reporter signal peptide (that is, the portion not in the reporter signal peptide fragment).

As with reporter signals generally, reporter signal peptides can be used in sets where the reporter signal peptides in a set can have one or more common properties that allow the reporter signal peptides to be separated or distinguished from molecules lacking the common property. In the case of reporter signal fusions, amino acid segments and amino acid subsegments can be used in sets where the amino acid segments and amino acid subsegments in a set can have one or more common properties that allow the amino acid segments and amino acid subsegments, respectively, to be separated or distinguished from molecules lacking the common property. In general, the component(s) of the reporter signal fusions having common properties can depend on the component(s) to be detected and/or the mode of the method being used.

Nucleic acid molecules encoding reporter signal fusions can be used in sets where the reporter signal peptides in the reporter signal fusions encoded by a set of nucleic acid molecules can have one or more common properties that allow the reporter signal peptides to be separated or distinguished from molecules lacking the common property. Similarly, nucleic acid molecules encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid molecules encoding amino acid segments can be used in sets where the amino acid segments encoded by a set of nucleic acid molecules can have one or more common properties that allow the amino acid segments to be separated or distinguished from molecules lacking the common property.

Nucleic acid segments (which, generally, are part of nucleic acid molecules) encoding reporter signal fusions can be used in sets where the reporter signal peptides in the reporter signal fusions encoded by a set of nucleic acid segments can have one or more common properties that allow the reporter signal peptides to be separated or distinguished from molecules lacking the common property. Similarly, nucleic acid segments encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid segments encoding amino acid segments can be used in sets where the amino acid segments encoded by a set of nucleic acid molecules can have one or more common properties that allow the amino acid segments to be separated or distinguished from molecules lacking the common property. Other relationships between members of the sets of nucleic acid molecules, nucleic acid segments, amino acid segments, reporter signal peptides, and proteins of interest are contemplated.

Reporter signal fusions can include other components besides a protein of interest and a reporter signal peptide. For example, reporter signal fusions can include epitope tags or flag peptides (see, for example, Brizzard et al. (1994) Immunoaffinity purification of FLAG epitope-tagged bacterial alkaline phosphatase using a novel monoclonal antibody and peptide elution. Biotechniques 16:730–735). Epitope tags and flag peptides can serve as tags by which reporter signal fusions can be manipulated. The use of epitope tags and flag peptides generally is known and can be adapted for use in the disclosed reporter signal fusions.

In preferred embodiments, reporter signal peptides, reporter signal fusions (or amino acid segments), nucleic acid segments encoding reporter signal fusion, and/or nucleic acid molecules comprising nucleic acid segments encoding reporter signal fusions are used in sets where the reporter signal peptides, the reporter signal fusions, and/or subsegments of the reporter signal fusions constituting or present in the set have similar properties (such as similar mass-to-charge ratios). The similar properties allow the reporter signals, the reporter signal fusions, or subsegments of the reporter signal fusions to be distinguished and/or separated from other molecules lacking one or more of the properties. Preferably, the reporter signals, the reporter signal fusions, or subsegments of the reporter signal fusions constituting or present in a set have the same mass-to-charge ratio (m/z). That is, the reporter signals, the reporter signal fusions, or subsegments of the reporter signal fusions in a set are isobaric. This allows the reporter signals, the reporter signal fusions, or subsegments of the reporter signal fusions to be separated precisely from other molecules based on mass-to-charge ratio. The result of the filtering is a huge increase in the signal to noise ratio (S/N) for the system, allowing more sensitive and accurate detection.

Cells, cell lines, organisms, and expression of genes and proteins can be detected using the disclosed reporter signal fusions in a variety of ways. For example, the protein and attached reporter signal peptide can be detected together, one or more peptides of the protein and the attached reporter signal peptide(s) can be detected together, the fragments of the reporter signal peptide can be detected, or a combination. Preferred detection involves detection of the reporter signal fusion both before and after fragmentation of the reporter signal peptide.

A preferred form of the disclosed method involves correlated detection of the reporter signal peptides both before and after fragmentation of the reporter signal peptide. This allows genes, proteins, vectors, and expression constructs "labeled" with a reporter signal peptide to be detected and identified via the change in the reporter signal fusion and/or reporter signal peptide. That is, the nature of the reporter signal fusion or reporter signal peptide detected (non-fragmented versus fragmented) identifies the gene, protein, vector, or nucleic acid construct from which it was derived. Where the reporter signal fusions and reporter signal peptides are detected by mass-to-charge ratio, the change in mass-to-charge ratio between fragmented and non-fragmented samples provides the basis for comparison. Such mass-to-charge ratio detection is preferably accomplished with mass spectrometry.

As an example, a fusion between a protein of interest and a reporter signal peptide designed as a mass spectrometry label can be expressed. The reporter signal fusion can be subjected to tryptic digest followed by mass spectrometry of the resulting materials. A peak corresponding to the tryptic fragment containing the reporter signal peptide will be detected. Fragmentation of the reporter signal peptide in the mass spectrometer (preferably in a collision cell) would result in a shift in the peak corresponding to the loss of a portion of the attached reporter signal peptide, the appearance of a peak corresponding to the lost fragment, or a combination of both events. Significantly, the shift observed will depend on which reporter signal peptide is fused to the protein since different reporter signal peptides will, by design, produce fragments with different mass-to-charge ratios. The combination event of detection of the parent mass-to-charge (with no collision gas) and the mass-to-charge corresponding to the loss of the fragment from the reporter signal peptide (with collision gas) indicates a reporter signal fusion (thus indicating expression of the reporter signal fusion and of the gene, vector, or construct encoding it).

A powerful form of the disclosed method is use of reporter signal fusions to assay multiple samples (for example, time series assays or other comparative analyses). Knowledge of the temporal response of a biological system following perturbation is a very powerful process in the pursuit of understanding the system. To follow the temporal response a sample of the system is obtained (for example, cells from a cell culture, mice initially synchronized and sacrificed) at determined times following the perturbation. Knowledge of spatial protein profiles (for example, relative position within a tissue section) is a very powerful process in the pursuit of understanding the biological system.

The reporter signal fusions are preferably detected using mass spectrometry which allows sensitive distinctions between molecules based on their mass-to-charge ratios. A set of isobaric reporter signal peptides or reporter signal fusions can be used for multiplex labeling and/or detection of the expression of many genes, proteins, vectors, expression constructs, cells, cell lines, and organisms since the reporter signal peptide fragments can be designed to have a large range of masses, with each mass individually distinguishable upon detection. Where the same gene, protein, vector, expression construct, cell, cell line, or organism (or the same type of gene, protein, vector, expression construct, cell, cell line, or organism) is labeled with a set of reporter signal fusions that are isobaric or that include isobaric reporter signal peptides (by, for example, "labeling" the same gene, protein, vector, expression construct, cell, cell line, or organism in different samples), the set of reporter signal fusions or reporter signal peptides that results will also be isobaric. Fragmentation of the reporter signal peptides will split the set of reporter signal peptides into individually detectable reporter signal fusion fragments and reporter signal peptide fragments of characteristically different mass.

A preferred form of the disclosed method involves filtering of isobaric reporter signal fusions or reporter signal peptides from other molecules based on mass-to-charge ratio, fragmentation of the reporter signal peptides to produce fragments having different masses, and detection of the different fragments based on their mass-to-charge ratios. The method is best carried out using a tandem mass spectrometer as described elsewhere herein.

Nucleic acid sequences and segments encoding reporter signal fusions can be expressed in any suitable manner. For example, the disclosed nucleic acid sequences and nucleic acid segments can be expressed in vitro, in cells, and/or in cells in organism. Many techniques and systems for expression of nucleic acid sequences and proteins are known and can be used with the disclosed reporter signal fusions. For example, many expression sequences, vector systems, transformation and transfection techniques, and transgenic organism production methods are known and can be used with the disclosed reporter signal peptide method and compositions.

For example, kits for the in vitro transcription/translation of DNA constructs containing promoters and nucleic acid sequence to be transcribed and translated are known (for example, PROTEINscript-PRO™ from Ambion, Inc. Austin Tex. Wilkinson (1999) "Cell-Free And Happy: In Vitro Translation And Transcription/Translation Systems", The Scientist 13[13]:15, Jun. 21, 1999). Such constructs can be used in the genomic DNA of an organism, in a plasmid or other vector that may be transfected into an organism, or in in vitro systems. For example, constructs containing a promoter sequence and a nucleic acid sequence that, following transcription and translation, results in production of green fluorescence protein or luciferase as a reporter/marker in in vivo systems are known (for example, Sawin and Nurse, "Identification of fission yeast nuclear markers using random polypeptide fusions with green fluorescent protein." Proc Natl Acad Sci USA 93(26): 15146–51 (1996); Chatterjee et al., "In vivo analysis of nuclear protein traffic in mammalian cells." Exp Cell Res 236(1):346–50 (1997); Patterson et al., "Quantitative imaging of TATA-binding protein in living yeast cells." Yeast 14(9):813–25 (1998); Dhandayuthapani et al., "Green fluorescent protein as a marker for gene expression and cell biology of mycobacterial interactions with macrophages." Mol Microbiol 17(5): 901–12 (1995); Kremer et al., "Green fluorescent protein as a new expression marker in mycobacteria." Mol Microbiol 17(5):913–22 (1995); Reiländer et al., "Functional expression of the Aequorea victoria green fluorescent protein in insect cells using the baculovirus expression system." Biochem Biophys Res Commun 219(1): 14-20 (1996); Mankertz et al., "Expression from the human occludin promoter is affected by tumor necrosis factor alpha and interferon gamma" J Cell Sci, 113:2085–90 (2000); White et al., "Real-time analysis of the transcriptional regulation of HIV and hCMV promoters in single mammalian cells" J Cell Sci, 108:441–55 (1995)). Green fluorescence protein, or variants, have been shown to be stably incorporated and not interfere with the organism—generally GFP is larger relative to the disclosed reporter signal peptides (GFP from Aequorea Victoria is 238 amino acids in size; NCBI GI:606384), and thus the generally smaller reporter signal peptides are less likely to disrupt an expression system to which they are added.

Techniques are known for modifying promoter regions such that the endogenous promoter is replaced with a promoter-reporter construct, for example, where the reporter is green fluorescent protein (Patterson et al., "Quantitative imaging of TATA-binding protein in living yeast cells." Yeast 14(9): 813–25 (1998)) or luciferase. Transcription factor concentrations are followed by monitoring the GFP or luciferase. These techniques can be used with the disclosed reporter signal fusions and reporter signal fusion constructs. Techniques are also known for targeted knock-in of nucleic acid sequences into a gene of interest, typically under control of the endogenous promoter. Such techniques, which can be used with the disclosed method and compositions, have been used to introduce reporter/markers of the transcription and translation of the gene where the nucleic acid was inserted. The same techniques can be used to place the disclosed reporter signal fusions under control of endogenous expression sequences. Alternately, non-targeted knock-ins (techniques for which are also known; Hobbs et al. "Development of a bicistronic vector driven by the human polypeptide chain elongation factor 1alpha promoter for creation of stable mammalian cell lines that express very high levels of recombinant proteins" Biochem Biophys Res Commun, 252:368–72 (1998); Kershnar et al., "Immunoaffinity purification and functional characterization of human transcription factor IIH and RNA polymerase II from clonal cell lines that conditionally express epitope-tagged subunits of the multiprotein complexes" J Biol Chem, 273:34444–53 (1998); Wu and Chiang, "Establishment of stable cell lines expressing potentially toxic proteins by tetracycline-regulated and epitope-tagging methods" Biotechniques 21:718–22, 724–5 (1996)) can be used to follow the level or activity of transcription factors—reporter signal peptide fusions associated with the inserted nucleic acid code can directly indicate the transcription/translation activity.

The disclosed reporter signal fusions also can be used in the detection and analysis of protein interactions with other proteins and molecules. For example interaction traps for protein—protein interactions include the well known yeast two-hybrid (Fields and Song, "A novel genetic system to detect protein—protein interactions" Nature 340:245–6 (1989); Uetz et al., "A comprehensive analysis of protein—protein interactions in *Saccharomyces cerevisiae*" Nature 403:623–7 (2000)) and related systems (Ausubel et al., Current Protocols in Molecular Biology, John Wiley & Sons, Inc., 2001; Van Criekinge and Beyaert, "Yeast two-hybrid: state of the art" Biological Procedures Online, 2(1), 1999). Incorporation of nucleic acid sequence encoding a peptide reporter signal can be introduced into these systems, for example at a terminus of the ordinarily used LacZ selection region (LacZ selection is described in, for example, Sambrook et al., Molecular Cloning: A Laboratory Manual, second edition, 1989, Cold Spring Harbor Laboratory Press, New York). A set of such incorporated sequences (for example, in a set of such plasmids, where each plasmid has a reporter signal coding sequence and the LacZ functionality), allows the unambiguous detection of many interactions simultaneously rather (as many different interactions as reporter signals used).

In another mode of reporter signal fusions, a nucleic acid sequence encoding a reporter signal could be added to sequence encoding the constant (C) region of T cell and B cell receptors. The reporter signal would appear in T or B cell receptors when that C region is spliced to a J region following transcription.

In another mode of reporter signal fusions, referred to as reporter signal presentation, the presentation of specific antigenic peptides by major histocompatibility (MHC) and non-major histocompatibility molecules can be detected and analyzed. It is well known that protein antigens are processed by antigen presenting cells and that small peptides, typically 8–12 amino acids are presented by Class I and Class II MHC molecules for recognition by T cells. The study of specific T cell/peptide-MHC complexes is technically challenging due various labeling requirements (either radioactive or fluorescence) and the common reliance on antibody reagents that recognize specific receptors and/or peptide-MHC complexes.

There is a need to be able to further expand our knowledge of antigen processing and antigen presentation. Reporter signals that have been engineered into specific protein antigens could provide novel insight into this process and enable new experimental approaches. For instance, consider two viral or bacterial proteins, protein A and protein B, that differ by only a few amino acids. It would be useful to know if they are processed and presented to immune cells (for example, T cells) with the same efficiency. By engineering reporter signals into protein A and engineered protein B to antigen presenting cells, one could test for the presence of the different reporter signals presented on and thus determine if the proteins are efficiently processed and presented. The presence of reporter signal A (present in protein A) but not reporter signal B (present in protein B), indicates that protein A is processed and that protein B is not. The lack of antigen processing of protein B may then be an explanation of why a virus or bacteria escapes immune surveillance by the immune system. Antigenic peptides are characterized by conserved anchor residues near both the amino and carboxy ends, with more heterogeneity tolerated in the middle. This middle heterogeneity is thus a preferred site for addition of a reporter signal peptide.

E. Rearranging Reporter Signals

Another embodiment of the disclosed method and compositions, referred to as rearranging reporter signals, enables one to detect the occurrence of specific gene rearrangement events, their protein products, and specific cell populations bearing those receptors. Rearranging reporter signals will also allow one to follow the progression or development of certain receptors and cells or populations of cells by monitoring the presence and/or absence of a reporter signal. Design considerations for rearranged reporter signals are analogous to those required for reporter signal fusions as described elsewhere herein.

Most embodiments of the disclosed method involve intact reporter signals that are associated with analytes in various ways. Rearranging reporter signals make use of processes, such as biological processes, to form reporter signals by specific rearrangement of the reporter signal pieces or rearrangement of nucleic acid segments encoding only portions of reporter signals. One form of rearranging reporter signals utilizes endogenous biological systems, such as the variable-diversity-joining (V-D-J) gene rearrangement machinery present in the mammalian immune system. In this system, short stretches of germline DNA (the V, D & J gene fragments) that are not contiguous, are brought together (recombined) prior to serving as a template for transcription. Gene rearrangement occurs in white blood cells such as T and B lymphocytes and is a key mechanism for generating diversity of T cell and B cell antigen receptors. Theoretically, billions of different receptors can be generated. This level of complexity makes it difficult to detect the presence of rare rearrangement events, or receptors. PCR based assays and flow cytometry approaches are now used to study receptor diversity. However, PCR approaches are laborious and do not provide any information on the status of expressed protein. Flow cytometry approaches have limited multiplexing capabilities due to emission spectra overlap of the fluorescent probes used.

If one desired to test for 50–100 T cell or B cell receptors, one would need to make use of a similar number of antibodies to those receptors, something that in practice is not done. Therefore, there is a real need for methods that would allow highly sensitive and specific detection of specific receptors in a highly complex pool of receptors. The ability to highly multiplex this approach would enable currently unattainable experimental approaches. The disclosed reporter signal technology allows large scale multiplexing of signals for detection.

As an example of rearranging reporter signals, transgenic mice can be generated in which nucleic acid sequences encoding reporter signals have been engineered into the mouse germline. Methods for doing this are well known in the art and include using standard molecular biology methods to engineer rearranging reporter signal into, for example, yeast or bacterial artificial chromosomes (YACs or BACs) and then using these constructs to generate transgenic mice.

As an example of the use of immunoglobulin rearrangement for rearranging reporter signals, part of a reporter signal could be encoded on the D region and another part of the reporter signal could be encoded on the J region. Upon a rearrangement event that joined the D and J regions encoding these "partial" reporter signals, a coding sequence for a "complete" reporter signal would be generated. Following transcription and translation, the reporter signal would be encoded within the protein product. The reporter signal could then be detected as described elsewhere herein. In the absence of a rearrangement event that joins the engineered D and J region, no reporter signal would be detected. By including sequences encoding parts of a variety of reporter signals with different D and J regions, a variety of different reporter signals can be generated by rearrangement, a different, and diagnostic, reporter signal for each of the different possible rearrangements. This system also could be extended to include, for example, reporter signals split among three or more gene regions (for example, V-D-J, V-D-D-J, etc) with the result that multiple rearrangement events would produce the reporter signal. In this mode, the combinations of rearrangements of the reporter signal parts can give rise to an large number of different reporter signals, each characterized by the specific reporter signal parts rearranged to form the reporter signal.

Transgenic mice carrying rearranging reporter signals would enable one to address questions that would otherwise be very difficult or impossible to address. For instance, one could dissect what specific T and B cell receptors (out of the thousands or millions possible) respond to specific stimuli or what cell types are present at certain stages of development.

F. Mass Spectrometers

The disclosed methods can make use of mass spectrometers for analysis of reporter signals, altered forms of reporters signals, and various analytes and analyte fragments. Mass spectrometers are generally available and such instruments and their operations are known to those of skill in the art. Fractionation systems integrated with mass spectrometers are commercially available, exemplary systems include liquid chromatography (LC) and capillary electrophoresis (CE).

The principle components of a mass spectrometer include: (a) one or more sources, (b) one or more analyzers and/or cells, and (c) one or more detectors. Types of sources include Electrospray Ionization (ESI) and Matrix Assisted Laser Desorption Ionization (MALDI). Types of analyzers and cells include quadrupole mass filter, hexapole collision cell, ion cyclotron trap, and Time-of-Flight (TOF). Types of detectors include Multichannel Plates (MCP) and ion multipliers. A preferred mass spectrometer for use with the disclosed method is described by Krutchinsky et al., Rapid Automatic Identification of Proteins Utilizing a Novel MALDI-Ion Trap Mass Spectrometer, Abstract of the 49$^{th}$ ASMS Conference on Mass Spectrometry and Allied Topics (May 27–31, 2001), The Rockefeller University, New York, N.Y.

Mass spectrometers with more than one analyzer/cell are known as tandem mass spectrometers. There are two types of tandem mass spectrometers, as well as hybrids and combinations of these types: "tandem in space" spectrometers and "tandem in time" spectrometers. Tandem mass spectrometers where the ions traverse more than one analyzer/cell are known as tandem in space mass spectrometers. Tandem in space spectrometers utilize spatially ordered elements and act upon the ions in turn as the ions pass through each element. Tandem mass spectrometers where the ions remain primarily in one analyzer/cell are known as tandem in time mass spectrometers. Tandem in time spectrometers utilize temporally ordered manipulations on the ions as the ions are contained in a space. Hybrid systems and combinations of these types are known. The ability to select a particular mass-to-charge ratio of interest in a mass analyzer is typically characterized by the resolution (reported as the centroid mass-to-charge divided by the full width at half maximum of the selected ions of interest). Thus resolution is an indicator of the narrowness of the ion mass-to-charge distribution passed through the analyzer to the detector. Reference to such resolution is generally noted herein by referring to the ability of a mass spectrometer to pass only a narrow range of mass-to-charge ratios.

A preferred form of mass spectrometer for use in the disclosed methods is a tandem mass spectrometer, such as a tandem in space tandem mass spectrometer. As an example of the use of a tandem in space class of instrument, the isobaric reporter signals can be first passed through a filtering quadrupole, the reporter signals are fragmented (preferably in a collision cell), and the fragments are distinguished and detected in a time-of-flight (TOF) stage. In such an instrument the sample is ionized in the source (for example, in a MALDI ion source) to produce charged ions. It is preferred that the ionization conditions are such that primarily a singly charged parent ion is produced. A first quadrupole, Q0, is operated in radio frequency (RF) mode only and acts as an ion guide for all charged particles. The second quadrupole, Q1, is operated in RF+DC mode to pass only a narrow range of mass-to-charge ratios (that includes the mass-to-charge ratio of the reporter signals). This quadrupole selects the mass-to-charge ratio of interest. Quadrupole Q2, surrounded by a collision cell, is operated in RF only mode and acts as ion guide. The collision cell surrounding Q2 can be filled to appropriate pressure with a gas to fracture the input ions by collisionally induced dissociation when fragmentation of the reporter signals is desired. The collision gas preferably is chemically inert, but reactive gases can also be used. Preferred molecular systems utilize reporter signals that contain scissile bonds, labile bonds, or combinations, such that these bonds will be preferentially fractured in the Q2 collision cell.

Tandem instruments capable of $MS^N$ can be used with the disclosed method. As an example consider; a method where one selects a set of molecules using a first stage filter (MS), photocleaves these molecules to yield a set of reporter signals, selects these reporter signals using a second stage (MS/MS), alters these reporter signals by collisional fragmentation, detects by time of flight (MS3). Many other combinations are possible and the disclosed method can be adapted for use with such systems. For example, extension to more stages, or analysis of reporter signal fragments is within the skill of those in the art.

Materials

A. Reporter Signals

Reporter signals are molecules that can be preferentially fragmented, decomposed, reacted, derivatized, or otherwise modified or altered for detection. Detection of the modified reporter signals is preferably accomplished with mass spectrometry. The disclosed reporter signals are preferably used in sets where members of a set have the same mass-to-charge ratio (m/z). This facilitates sensitive filtering or separation of reporter signals from other molecules based on mass-to-charge ratio. Reporter signals can have any structure that allows modification of the reporter signal and identification of the different modified reporter signals. Reporter signals preferably are composed such that at least one preferential bond rupture can be induced in the molecule. A set of reporter signals having nominally the same molecular mass and arbitrarily chosen internal fragmentation points may be constructed such that upon fragmentation each member of the set will yield unique correlated daughter fragments. For convenience, reporter signals that are fragmented, decomposed, reacted, derivatized, or otherwise modified for detection are referred to as fragmented reporter signals.

Preferred reporter signals are made up of chains of subunits such as peptides, oligonucleotides, peptide nucleic acids, oligomers, carbohydrates, polymers, and other natural and synthetic polymers and any combination of these. Most preferred chains are peptides, and are referred to herein as reporter signal peptides. Chains of subunits and subunits have a relationship similar to that of a polymers and mers. The mers are connected together to form a polymer. Likewise, subunits are connected together to form chains of subunits. Preferred reporter signals are made up of chains of similar or related subunits. These are termed homochains or homopolymers. For example, nucleic acids are made up of phosphonucleosides and peptides are made up of amino acids.

Reporter signals can also be made up of heterochains or heteropolymers. A heterochain is a chain or a polymer where the subunits making up the chain are different types or the mers making up the polymer are different types. For example, a heterochain could be guanosine-alanine, which is made up of one nucleoside subunit and one amino acid subunit. It is understood that any combination of types of subunits can be used within the disclosed compositions, sets, and methods. Any molecule having the required properties can be used as a reporter signal. Preferred reporter signals can be fragmented in tandem mass spectrometry.

Reporter signals preferably are used in sets where all the reporter signals in the set have similar physical properties. The similar (or common) properties allow the reporter signals to be distinguished and/or separated from other molecules lacking one or more of the properties. Preferably, the reporter signals in a set have the same mass-to-charge ratio (m/z). That is, the reporter signals in a set are isobaric. This allows the reporter signals (and/or the proteins to which they are attached) to be separated precisely from other molecules based on mass-to-charge ratio. The result of the filtering is a huge increase in the signal to noise ratio (S/N) for the system, allowing more sensitive and accurate detection. Sets of reporter signals can have any number of reporter signals. For example, sets of reporter signals can have one, two or more, three or more, four or more, five or more, six or more, seven or more, eight or more, nine or more, ten or more, twenty or more, thirty or more, forty or more, fifty or more, sixty or more, seventy or more, eighty or more, ninety or more, one hundred or more, two hundred or more, three hundred or more, four hundred or more, or five hundred or more different reporter signals. Although specific numbers of reporter signals and specific endpoints for ranges of the number of reporter signals are recited, each and every specific number of reporter signals and each and every specific endpoint of ranges of numbers of reporter signals are specifically contemplated, although not explicitly listed, and each and every specific number of reporter signals and each and every specific endpoint of ranges of numbers of reporter signals are hereby specifically described.

The sets of reporter signals can be made up of reporter signals that are made up of chains or polymers. The set of reporter signals can be homosets which means that the set is made up of one type of reporter signal or that the reporter signal is made up of homochains or homopolymers. The set of reporter signals can also be a heteroset which means that the set is made up of different reporter signals or of reporter signals that are made up of different types of chains or polymers. A special type of heteroset is one in which the set is made up of different homochains or homopolymers, for example one peptide chain and one nucleic acid chain. Another special type of heteroset is one where the chains themselves are heterochains or heteropolymers. Still another type of heteroset is one which is made up of both heterochains/heteropolymers and homochains/homopolymers.

A variety of different properties can be used as the common physical property used to separate reporter signals from other molecules lacking the common property. For example, other physical properties useful as common properties include mass, charge, isoelectric point, hydrophobicity, chromatography characteristics, and density. It is preferred that the physical property shared by reporter signals in a set (and used to distinguish or separate the reporter signals from other molecules) is an overall property of the reporter signal (for example, overall mass, overall charge, isoelectric point, overall hydrophobicity, etc.) rather than the mere presence of a feature or moiety (for example, an affinity tag, such as biotin). Such properties are referred to herein as "overall" properties (and thus, reporter signals in a set would be referred to as sharing a "common overall property"). It should be understood that reporter signals can have features and moieties, such as affinity tags, and that such features and moieties can contribute to the common overall property (by contributing mass, for example). However, such limited and isolated features and moieties would not serve as the sole basis of the common overall property.

A preferred common overall property is the property of subunit isomers. This property occurs when a set of at least two reporter signals (which typically are made up of subunit chains which are in turn made up of subunits, for example, like the relationship between a polymer and the units that make up a polymer) is made up of subunit isomers, and the set could then be called subunit isomeric or isomeric for subunits. Subunits are discussed elsewhere herein, but reporter signals can be made up of any type of chain, such as peptides or nucleic acids or polymer (general) which are in turn made up of subunits for example amino acids and phosphonucleosides, and mers (general) respectively. Within each type of subunit there are typically multiple members that are all the same type of subunit, but differ. For example, within the subunit type "amino acids," there are many members, for example, ala, tyr, and ser, or any other combination of amino acids.

When a set of reporter signals is subunit isomeric or is made up of subunit isomers this means that each individual of the set is a subunit isomer of every other individual subunit in the set. Isomer or isomeric means that the makeup of the subunits forming the subunit chain (i.e., distribution or array) is the same but the overall connectivity of the subunits, forming the chain, is different. Thus, for example, a first reporter signal could be the chain, ala-ser-lys-gln, a second reporter signal could be the chain ala-lys-ser-gln, and a third reporter signal could be the chain ala-ser-lys-pro. If a set of reporter signals was made that contained the first reporter signal and the second reporter signal, the set would be subunit isomeric because the first reporter signal and the second reporter signal have the same makeup, i.e. each has one ala, one ser, one lys, and one gln, but each chain has a different connectivity. If, however, the set of reporter signals were made which contained the first, second, and third reporter signals the set would not be isomeric because the make up of each chain would not be the same because the first and second chains do not have a pro and the third chain does not have a gln.

Another illustration is the following: a first reporter signal could be the chain, ala-guanosine-lys-adenosine, a second reporter signal could be the chain ala-adenosine-lys-guanosine, and a third reporter signal could be the chain ala-ser-lys-pro. If a set of reporter signals was made that contained the first reporter signal and the second reporter signal, the set would be subunit isomeric because the first reporter signal and the second reporter signal have the same makeup, i.e. each has one ala, one guanosine, one lys, and one adenosine, but each chain has a different connectivity. If, however, the set of reporter signals were made which contained the first, second, and third reporter signals the set would not be isomeric because the makeup of each chain would not be the same because the first and second chains do not have a pro or a ser and the third chain does not have a guanosine or adenosine. This illustration shows that the sets can be made up of, or include, heterochains and still be considered subunit isomers.

It is preferred that the common property of reporter signals is not an affinity tag. Nevertheless, even in such a case, reporter signals that otherwise have a common property may also include an affinity tag—and in fact may all share the same affinity tag—so long as another common property is present that can be (and, in some embodiments of the disclosed method, is) used to separate reporter signals sharing the common property from other molecules lacking the common property. With this in mind, it is preferred that, if chromatography or other separation techniques are used to separate reporter signals based on the common property, the affinity be based on an overall physical property of the reporter signals and not on the presence of, for example, a feature or moiety such as an affinity tag. As used herein, a common property is a property shared by a set of components (such as reporter signals). That is, the components have the property "in common." It should be understood that reporter signals in a set may have numerous properties in common. However, as used herein, the common properties of reporter signals referred to are only those used in the disclosed method to distinguish and/or separate the reporter signals sharing the common property from molecules that lack the common property.

Reporter signals in a set can be fragmented, decomposed, reacted, derivatized, or otherwise modified or altered to distinguish the different reporter signals in the set. Preferably, the reporter signals are fragmented to yield fragments of similar charge but different mass. The reporter signals can also be fragmented to yield fragments of different charge and mass. Such changes allow each reporter signal in a set to be distinguished by the different mass-to-charge ratios of the fragments of the reporter signals. This is possible since, although the unfragmented reporter signals in a set are isobaric, the fragments of the different reporter signals are not. Thus, a key feature of the disclosed reporter signals is that the reporter signals have a similarity of properties while the modified reporter signals are distinguishable.

Differential distribution of mass in the fragments of the reporter signals can be accomplished in a number of ways. For example, reporter signals of the same nominal structure (for example, peptides having the same amino acid sequence), can be made with different distributions of heavy isotopes, such as deuterium ($^2H$), tritium ($^3H$) $^{17}O$, $^{18}O$, $^{13}C$, or $^{14}C$; stable isotopes are preferred. All reporter signals in the set would have the same number of a given heavy isotope, but the distribution of these would differ for different reporter signals. An example of such a set of reporter signals is A*G*SLDPAGSLR, A*GSLDPAG*SLR, and AGSLDPA*G*SLR (SEQ ID NO:2), where the asterisk indicates at least one heavy isotope substituted amino acid. For a singly charged parent ion and, following fragmentation at the scissile DP bond, one predominantly charged daughter, there are three distinguishable primary daughter ions, PAGSLR$^+$, PAG*SLR$^+$, PA*G*SLR$^+$ (amino acids 6–11 of SEQ ID NO:2).

Similarly, reporter signals of the same general structure (for example, peptides having the same amino acid sequence), can be made with different distributions of modifications or substituent groups, such as methylation, phosphorylation, sulphation, and use of seleno-methionine for methionine. All reporter signals in the set would have the same number of a given modification, but the distribution of these would differ for different reporter signals. An example of such a set of reporter signals is AGS*M*LDPAGSMLR, AGS*MLDPAGSM*LR, and AGS*MLDPAGS*M*LR (SEQ ID NO:3), where S* indicates phosphoserine rather than serine, and, M* indicates seleno-methionine rather than methionine. For a singly charged parent ion and, following fragmentation at the scissile DP bond, one predominantly charged daughter, there are three distinguishable primary daughter ions, PAGSMLR$^+$, PAGSM*LR$^+$, PAGS*M*LR$^+$ (amino acids 7–13 of SEQ ID NO:3).

Reporter signals of the same nominal composition (for example, made up of the same amino acids), can be made with different ordering of the subunits or components of the reporter signal. All reporter signals in the set would have the same number of subunits or components, but the distribution of these would be different for different reporter signals. An example of such a set of reporter signals is AGSLADPGSLR (SEQ ID NO:4), ALSLADPGSGR (SEQ ID NO:5), ALSLGDPASGR (SEQ ID NO:6). For a singly charged parent ion and, following fragmentation at the scissile DP bond, one predominantly charged daughter, there are three distinguishable primary daughter ions, PGSLR$^+$ (amino acids 7–11 of SEQ ID NO:4), PGSGR$^+$ (amino acids 7–11 of SEQ ID NO:5), PASGR$^+$ (amino acids 7–11 of SEQ ID NO:6).

Reporter signals having the same nominal composition (for example, made up of the same amino acids), can be made with a labile or scissile bond at a different location in the reporter signal. All reporter signals in the set would have the same number and order of subunits or components. Where the labile or scissile bond is present between particular subunits or components, the order of subunits or components in the reporter signal can be the same except for the subunits or components creating the labile or scissile bond. Reporter signal peptides used in reporter signal fusions preferably use this form of differential mass distribution. An example of such a set of reporter signals is AGSLADPGSLR (SEQ ID NO:4), AGSDPLAGSLR (SEQ ID NO:7), ADPGSLAGSLR (SEQ ID NO:8). For a singly charged parent ion and, following fragmentation at the scissile DP bond, one predominantly charged daughter, there are three distinguishable primary daughter ions, PGSLR$^+$ (amino acids 7–11 of SEQ ID NO:4), PLAGSLR$^+$ (amino acids 5–11 of SEQ ID NO:7), PGSLAGSLR$^+$ (amino acids 3–11 of SEQ ID NO:8).

Each of these modes can be combined with one or more of the other modes to produce differential distribution of mass in the fragments of the reporter signals. For example, different distributions of heavy isotopes can be used in reporter signals where a labile or scissile bond is placed in different locations. Different mass distribution can be accomplished in other ways. For example, reporter signals can have a variety of modifications introduced at different positions. Some examples of useful modifications include acetylation, methylation, phosphorylation, selenomethionine rather than methionine, sulphation. Similar principles can be used to distribute charge differentially in reporter signals. Differential distribution of mass and charge can be used together in sets of reporter signals.

Reporter signals can also contain combinations of scissile bonds and labile bonds. This allows more combinations of distinguishable signals or to facilitate detection. For example, labile bonds may be used to release the isobaric fragments, and the scissile bonds used to decode the proteins.

Selenium substitution can be used to alter the mass of reporter signals. Selenium can substitute for sulfur in methionine, resulting in the modified amino acid selenomethionine. Selenium is approximately forty seven mass units larger than sulfur. Mass spectrometry may be used to identify peptides or proteins incorporating selenomethionine and methionine at a particular ratio. Small proteins and peptides with known selenium/sulfur ratio are preferably produced by chemical synthesis incorporating selenomethionine and methionine at the desired ratio. Larger proteins or peptides may be by produced from an *E. coli* expression system, or any other expression system that inserts selenomethionine and methionine at the desired ratio (Hendrickson et al., *Selenomethionyl proteins produced for analysis by multi-wavelength anomalous diffraction (MAD): a vehicle for direct determination of three-dimensional structure.* Embo J, 9(5):1665–72 (1990), Cowie and Cohen, *Biosynthesis by Escherichia coli of active altered proteins containing selenium instead of sulfur.* Biochimica et Biophysica Acta, 26:252–261 (1957), and Oikawa et al., *Metalloselenonein, the selenium analogue of metallothionein: synthesis and characterization of its complex with copper ions.* Proc Natl Acad Sci USA, 88(8):3057–9 (1991).

Some forms of reporter signals can include one or more affinity tags. Such affinity tags can allow the detection, separation, sorting, or other manipulation of the labeled proteins, reporter signals, or reporter signal fragments based on the affinity tag. Such affinity tags are separate from and in addition to (not the basis of) the common properties of a set of reporter signals that allows separation of reporter signals from other molecules. Rather, such affinity tags serve the different purpose of allowing manipulation of a sample prior to or as a part of the disclosed method, not the means to separate reporter signals based on the common property. Reporter signals can have none, one, or more than one affinity tag. Where a reporter signal has multiple affinity tags, the tags on a given reporter signal can all be the same or can be a combination of different affinity tags. Affinity tags also can be used to distribute mass and/or charge differentially on reporter tags following the principles described above and elsewhere herein. Affinity tags can be used with reporter signals in a manner similar to the use of affinity labels as described in PCT Application WO 00/11208.

Peptide-DNA conjugates (Olejnik et al., *Nucleic Acids Res.*, 27(23):4626–31 (1999)), synthesis of PNA-DNA constructs, and special nucleotides such as the photocleavable universal nucleotides of WO 00/04036 can be used as reporter signals in the disclosed method. Useful photocleavable linkages are also described by Marriott and Ottl, *Synthesis and applications of heterobifunctional photocleavable cross-linking reagents*, Methods Enzymol. 291:155–75 (1998).

Photocleavable bonds and linkages are useful in (and for use with) reporter signals because it allows precise and controlled fragmentation of the reporter signals (for subsequent detection) and precise and controlled release of reporter signals from analytes (or other intermediary molecules) to which they are attached. A variety of photocleavable bonds and linkages are known and can be adapted for use in and with reporter signals. Recently, photocleavable amino acids have become commercially available. For example, an Fmoc protected photocleavable slightly modified phenylalanine (Fmoc-D,L-βPhe(2-NO$_2$)) is available (Catalog Number 0011-F; Innovachem, Tucson, Ariz.). The introduction of the nitro group into the phenylalanine ring causes the amino acid to fragment under exposure to UV light (at a wavelength of approximately 350 nm). The nitrogen laser emits light at approximately 337 nm and can be used for fragmentation. The wavelength used will not cause significant damage to the rest of the peptide.

Fmoc synthesis is a common technique for peptide synthesis and Fmoc-derivative photocleavable amino acids can be incorporated into peptides using this technique. Although photocleavable amino acids are usable in and with any reporter signal, they are particularly useful in peptide reporter signals.

Use of photocleavable bonds and linkages in and with reporter signals can be illustrated with the following examples. Materials on a blank plastic substrate (for example, a Compact Disk (CD)) may be directly measured from that surface using a MALDI source ion trap. For example, a thin section of tissue sample, flash frozen, could be applied to the CD surface. A reporter molecule (for example, an antibody with a reporter signal attached via a photocleavable linkage) can be applied to the tissue surface. Recognition of specific components within the tissue allows for some of the antibody/reporter signal conjugates to associate (excess conjugate is removed during subsequent wash steps). The reporter signal then can be released from the antibody by applying a UV light and detected directly using the MALDI ion trap instrument. For example, a peptide of sequence CF*XXXXXDPXXXXXR (SEQ ID NO:24) (which contains a reporter signal) can be attached to an antibody using a disulfide bond linkage method. Exposure to the UV source of a MALDI laser will cleave the peptide at the modified phenylalanine, F*, releasing the XXXXXD-PXXXXXR reporter signal (amino acids 3–15 of SEQ ID NO:24). The reporter signal subsequently can be fragmented at the DP bond and the charged fragment detected as described elsewhere herein.

Another example of the use of photocleavable linkages with reporter signals involves DNA-peptide chimeras used as reporter molecules. Such reporter molecules are useful as probes to detect particular nucleic acid sequences. In a DNA-peptide chimera (or PNA-peptide chimera), the peptide portion can be or include a reporter signal. Placement of a photocleavable phenylalanine, for example, near the DNA peptide junction of the reporter molecule allows for the release of the reporter signal from the reporter molecule by UV light. The released reporter signal can be detected directly or fragmented and detected as described elsewhere herein. Similarly to the case of the antibody-peptide reporter molecule described above, the DNA-peptide chimera can be associated with a nucleic acid molecule present on the surface of a substrate such as a CD and the reporter signal released using the UV source of a MALDI laser.

A photocleavable linkage also can be incorporated into a reporter signal and used for fragmentation of the reporter signal in the disclosed methods. For example, a photocleavable amino acid (such as the photocleavable phenylalanine) can be incorporated at any desired position in a peptide reporter signal. A reporter signal such as XXXXXXF*XXXXXR containing photocleavable phenylalanine (F*) that is photocleavable. The reporter signal can then be fragmented using the appropriate wavelength of light and the charged fragment detected. When ionizing the reporter signal (from a surface, for example) for detection, a MALDI laser that does not cause significant photocleavage (for example, Er:YAG at 2.94 µm) can be used for ionization and a second laser (for example, Nitrogen at 337 nm) can be used to fragment the reporter signal. In this case XXXXXXFXXXXXR⁺ would be photocleaved to yield XXXXXR⁺. The second laser may intersect the reporter signal ion packet at any location. Modification to the vacuum system of a mass spectrometer for this purpose is straightforward.

The use of photocleavable linkages in reporter signals is particularly useful when the analyte (or other component) to which the reporter signal is attached could fragment at a scissile bond in a collision cell. For example, in reporter signal fusions, a protein fragment/reporter signal polypeptide could be generated that contained a scissile bond in both the protein fragment portion and the reporter signal portion. An example would be XXXXXXXXDPXXX (XXXXXXXDPXXXXXXXR)XXXX (SEQ ID NO:25), where the sequence in parenthesis indicate the reporter signal portion and the DP dipeptides contain scissile bonds. Fragmenting this polypeptide in a collision cell could result in fragmentation at either or both of the DP bonds, thus complicating the fragment spectrum. Use of a photocleavable linkage (such as a photocleavable amino acid) in the reporter signal portion would allow specific photocleavage of the reporter signal during analysis. For example, an analogous polypeptide XXXXXXXXDPXXX (XXXXXXXF*XXXXXXXR)XXXX (SEQ ID NO:26) would allow specific photocleavage a the F* position of the reporter signal.

Multiple photocleavable bonds and/or linkages can be used in or with the same reporter signals or reporter signal conjugates (such as reporter molecules or reporter signal fusions) to achieve a variety of effects. For example, different photocleavable linkages that are cleaved by different wavelengths of light can be used in different parts of reporter signals or reporter signal conjugates to be cleaved at different stages of the method. Different fragmentation wavelengths allow sequential processing which enables, for example, the combinations of the release and fragmentation methods.

As an example, a peptide containing two photocleavable amino acids, Z (cleavage wavelength in the infrared) and F* (photocleavable phenylalanine, cleavage wavelength in UV) can be constructed of the form XZXXXXXXXF*XXXXXXR where the amino terminus can be attached to an analyte or other molecule utilizing known chemistry. The result is a reporter signal/analyte conjugate (or, alternatively, a reporter molecule). The reporter signal can be released from the conjugate by exposing the conjugate to an appropriate wavelength of light (infrared in this example), thus cleaving the bond at Z. Once the parent ion is selected and stored in the ion trap, the reporter signal can be fragmented by exposing it to an appropriate wavelength of light (UV in this example) to produce the daughter ion (XXXXXXR⁺) which can be detected and quantitated.

Reporter signal calibrators are a special form of reporter signal characterized by their use in reporter signal calibration. Reporter signal calibrators can be any form of reporter signal, as described above and elsewhere herein, but are used as separate molecules that are not physically associated with analytes being assessed. Thus, reporter signal calibrators need not (and preferably do not) have reactive groups for coupling to analytes and need not be (and preferably are not) associated with specific binding molecules or other molecules or components described herein as being associated with reporter signals.

Reporter signal calibrators preferably share one or more common properties with one or more analytes. Reporter signal calibrators and analytes that share one or more common properties are referred to as a reporter signal calibrator/analyte set. When only one analyte and one reporter signal calibrator share the common property they also can be referred to as a reporter signal calibrator/analyte pair. Reporter signal calibrators and analytes in a reporter signal calibrator/analyte set are said to be matching. The common property allows a reporter signal calibrator and its matching analyte to be distinguished and/or separated from other molecules lacking one or more of the properties. Preferably, the reporter signal calibrators and analytes in a set have the same mass-to-charge ratio (m/z). That is, the matching reporter signal calibrators and analytes in a set are isobaric. This allows the reporter signal calibrators and analytes to be separated precisely from other molecules based on mass-to-charge ratio. Reporter signal calibrators can be fragmented, decomposed, reacted, derivatized, or otherwise modified or altered to distinguish the altered reporter signal calibrators from their matching analytes. The analytes can also be fragmented. Preferably, the reporter signal calibrators are fragmented to yield fragments of similar charge but different mass. The reporter signal calibrators can also be fragmented to yield fragments of different charge and mass. Such changes allow the reporter signal calibrator to be distinguished from its matching analyte (and other analytes and/or reporter signal calibrators that are members of the same set, if any) by the different mass-to-charge ratio of the fragment of the reporter signal calibrator. This is possible since, although the unfragmented reporter signal calibrator(s) and analyte(s) in a set are isobaric, the fragments of the reporter signal calibrator(s) are not. Thus, a key feature of the disclosed reporter signal calibrators is that the reporter signal calibrators have a similarity of properties with their matching analytes while the modified reporter signal calibrators are distinguishable from their matching analytes.

Preferred analytes for use with reporter signal calibrators are proteins, peptides, and/or protein fragments (collectively referred to for convenience as proteins). Reporter signal calibrators and proteins that share one or more common properties are referred to as a reporter signal calibrator/protein set. When only one protein and one reporter signal calibrator share the common property they also can be referred to as a reporter signal calibrator/protein pair. Reporter signal calibrators and proteins in a reporter signal calibrator/analyte set are said to be matching.

As described elsewhere herein, reporter signal calibrators can be used as standards for assessing the presence and amount of analytes in samples. For this purpose, a reporter signal calibrator designed for each analyte to be assessed can be mixed with the sample to be analyzed. Analytes and their matching reporter signal calibrators are then processed together to result in detection of both analytes and reporter signal calibrators (preferably in their altered forms). The amount of reporter signal calibrator or altered reporter signal calibrator detected provides a standard (since the amount of reporter signal calibrator added can be known) against which the amount of analyte or altered analyte detected can be compared. This allows the amount of analyte present in the sample to be accurately gauged.

B. Analytes

The disclosed methods make use of analytes generally as objects of detection, measurement and/or analysis. Analytes can be any molecule or portion of a molecule that is to be detected, measured, or otherwise analyzed. An analyte need not be a physically separate molecule, but may be a part of a larger molecule. Analytes include biological molecules, organic molecules, chemicals, compositions, and any other molecule or structure to which the disclosed method can be adapted. It should be understood that different forms of the disclosed method are more suitable for some types of analytes than other forms of the method. Analytes are also referred to as target molecules.

Preferred analytes are biological molecules. Biological molecules include but are not limited to proteins, peptides, enzymes, amino acid modifications, protein domains, protein motifs, nucleic acid molecules, nucleic acid sequences, DNA, RNA, mRNA, cDNA, metabolites, carbohydrates, and nucleic acid motifs. As used herein, "biological molecule" and "biomolecule" refer to any molecule or portion of a molecule or multi-molecular assembly or composition, that has a biological origin, is related to a molecule or portion of a molecule or multi-molecular assembly or composition that has a biological origin. Biomolecules can be completely artificial molecules that are related to molecules of biological origin.

Although reference is made above and elsewhere herein to detection of a "protein" or "proteins," the disclosed method and compositions encompass proteins, peptides, and fragments of proteins or peptides. Thus, reference to a protein herein is intended to refer to proteins, peptides, and fragments of proteins or peptides unless the context clearly indicates otherwise.

C. Analyte Samples

Any sample from any source can be used with the disclosed method. In general, analyte samples should be samples that contain, or may contain, analytes. Examples of suitable analyte samples include cell samples, tissue samples, cell extracts, components or fractions purified from another sample, environmental samples, culture samples, tissue samples, bodily fluids, and biopsy samples. Numerous other sources of samples are known or can be developed and any can be used with the disclosed method. Preferred analyte samples for use with the disclosed method are samples of cells and tissues. Analyte samples can be complex, simple, or anywhere in between. For example, an analyte sample may include a complex mixture of biological molecules (a tissue sample, for example), an analyte sample may be a highly purified protein preparation, or a single type of molecule.

D. Protein Samples

Any sample from any source can be used with the disclosed method. In general, protein samples should be samples that contain, or may contain, protein molecules. Examples of suitable protein samples include cell samples, tissue samples, cell extracts, components or fractions purified from another sample, environmental samples, biofilm samples, culture samples, tissue samples, bodily fluids, and biopsy samples. Numerous other sources of samples are known or can be developed and any can be used with the disclosed method. Preferred protein samples for use with the disclosed method are samples of cells and tissues. Protein samples can be complex, simple, or anywhere in between. For example, a protein sample may include a complex mixture of proteins (a tissue sample, for example), a protein sample may be a highly purified protein preparation, or a single type of protein.

E. Reporter Molecules

Reporter molecules are molecules that combine a reporter signal with a specific binding molecule or decoding tag. Preferably, the reporter signal and specific binding molecule or decoding tag are covalently coupled or tethered to each other. As used herein, molecules are coupled when they are covalent joined, directly or indirectly. One form of indirect coupling is via a linker molecule. The reporter signal can be coupled to the specific binding molecule or decoding tag by any of several established coupling reactions. For example, Hendrickson et al., *Nucleic Acids Res.*, 23(3):522–529 (1995) describes a suitable method for coupling oligonucleotides to antibodies.

One form of reporter molecule has a peptide nucleic acid as the decoding tag and a reporter signal peptide as the reporter signal. The peptide nucleic acid can associate with, for example, an oligonucleotide coding tag, thus associating the reporter signal peptide with the coding tag. As described elsewhere herein, coding tags can be used to labeled analytes and other molecules.

As used herein, a molecule is said to be tethered to another molecule when a loop of (or from) one of the molecules passes through a loop of (or from) the other molecule. The two molecules are not covalently coupled when they are tethered. Tethering can be visualized by the analogy of a closed loop of string passing through the hole in the handle of a mug. In general, tethering is designed to allow one or both of the molecules to rotate freely around the loop.

F. Specific Binding Molecules

A specific binding molecule is a molecule that interacts specifically with a particular molecule or moiety. The molecule or moiety that interacts specifically with a specific binding molecule is referred to herein as an analyte, such as an analyte. Preferred analytes are analytes. It is to be understood that the term analyte refers to both separate molecules and to portions of such molecules, such as an epitope of a protein, that interacts specifically with a specific binding molecule. Antibodies, either member of a receptor/ligand pair, synthetic polyamides (Dervan and Burli, *Sequence-specific DNA recognition by polyamides*. Curr Opin Chem Biol, 3(6):688–93 (1999); Wemmer and Dervan, *Targeting the minor groove of DNA*. Curr Opin Struct Biol, 7(3):355–61 (1997)), nucleic acid probes, and other molecules with specific binding affinities are examples of specific binding molecules, useful as the affinity portion of a reporter binding molecule.

A specific binding molecule that interacts specifically with a particular analyte is said to be specific for that analyte. For example, where the specific binding molecule is an antibody that associates with a particular antigen, the specific binding molecule is said to be specific for that antigen. The antigen is the analyte. A reporter molecule containing the specific binding molecule can also be referred to as being specific for a particular analyte. Specific binding molecules preferably are antibodies, ligands, binding proteins, receptor proteins, haptens, aptamers, carbohydrates, synthetic polyamides, peptide nucleic acids, or oligonucleotides. Preferred binding proteins are DNA binding proteins. Preferred DNA binding proteins are zinc finger motifs, leucine zipper motifs, helix-turn-helix motifs. These motifs can be combined in the same specific binding molecule.

Antibodies useful as the affinity portion of reporter binding agents, can be obtained commercially or produced using well established methods. For example, Johnstone and Thorpe, *Immunochemistry In Practice* (Blackwell Scientific Publications, Oxford, England, 1987) on pages 30–85, describe general methods useful for producing both polyclonal and monoclonal antibodies. The entire book describes many general techniques and principles for the use of antibodies in assay systems.

Properties of zinc fingers, zinc finger motifs, and their interactions, are described by Nardelli et al., *Zinc finger-DNA recognition: analysis of base specificity by site-directed mutagenesis*. Nucleic Acids Res, 20(16):4137–44 (1992), Jamieson et al., *In vitro selection of zinc fingers with* altered DNA-binding specificity. Biochemistry, 33(19):5689–95 (1994), Chandrasegaran and Smith, *Chimeric restriction enzymes: what is next?* Biol Chem, 380(7–8):841–8 (1999), and Smith et al., *A detailed study of the substrate specificity of a chimeric restriction enzyme.* Nucleic Acids Res, 27(2):674–81 (1999).

One form of specific binding molecule is an oligonucleotide or oligonucleotide derivative. Such specific binding molecules are designed for and used to detect specific nucleic acid sequences. Thus, the analyte for oligonucleotide specific binding molecules are nucleic acid sequences. The analyte can be a nucleotide sequence within a larger nucleic acid molecule. An oligonucleotide specific binding molecule can be any length that supports specific and stable hybridization between the reporter binding probe and the analyte. For this purpose, a length of 10 to 40 nucleotides is preferred, with an oligonucleotide specific binding molecule 16 to 25 nucleotides long being most preferred. It is preferred that the oligonucleotide specific binding molecule is peptide nucleic acid. Peptide nucleic acid forms a stable hybrid with DNA. This allows a peptide nucleic acid specific binding molecule to remain firmly adhered to the target sequence during subsequent amplification and detection operations.

This useful effect can also be obtained with oligonucleotide specific binding molecules by making use of the triple helix chemical bonding technology described by Gasparro et al., *Nucleic Acids Res.,* 22(14):2845–2852 (1994). Briefly, the oligonucleotide specific binding molecule is designed to form a triple helix when hybridized to a target sequence. This is accomplished generally as known, preferably by selecting either a primarily homopurine or primarily homopyrimidine target sequence. The matching oligonucleotide sequence which constitutes the specific binding molecule will be complementary to the selected target sequence and thus be primarily homopyrimidine or primarily homopurine, respectively. The specific binding molecule (corresponding to the triple helix probe described by Gasparro et al.) contains a chemically linked psoralen derivative. Upon hybridization of the specific binding molecule to a target sequence, a triple helix forms. By exposing the triple helix to low wavelength ultraviolet radiation, the psoralen derivative mediates cross-linking of the probe to the target sequence.

G. Reporter Signal Fusions

Reporter signal fusions are reporter signal peptides joined with a protein or peptide of interest in a single amino acid segment (that is, a fusion protein). Such fusions of proteins and peptides of interest with reporter signal peptides can be expressed as a fusion protein or peptide from a nucleic acid molecule encoding the amino acid segment that constitutes the fusion. A reporter signal fusion nucleic acid molecule or reporter signal nucleic acid segment refers to a nucleic acid molecule or nucleic acid sequence, respectively, that encodes a reporter signal fusion. Although reference is made above and elsewhere herein to detection of, and fusion with, a "protein" or "proteins," the disclosed reporter signal fusions encompass fusions with proteins, peptides, and fragments of proteins or peptides. Thus, reference to a protein herein is intended to refer to proteins, peptides, and fragments of proteins or peptides unless the context clearly indicates otherwise.

As used herein "reporter signal fusion" refers to a protein, peptide, or fragment of a protein or peptide to which a reporter signal peptide is fused (that is, joined by peptide bond(s) in the same polypeptide chain) unless the context clearly indicates otherwise. The reporter signal peptide and the protein of interest involved in a reporter signal fusion need not be directly fused. That is, other amino acids, amino acid sequences, and/or peptide elements can intervene. For example, an epitope tag, if present, can be located between the protein of interest and the reporter signal peptide in a reporter signal fusion. The reporter signal peptide(s) can be fused to a protein in any arrangement, such as at the N-terminal end of the protein, at the C-terminal end of the protein, in or at domain junctions, or at any other appropriate location in the protein. In some forms of the method, it is desirable that the protein remain functional. In such cases, terminal fusions or inter-domain fusions are preferably. Those of skill in the art of protein fusions generally know how to design fusions where the protein of interest remains functional. In other embodiments, it is not necessary that the protein remain functional in which case the reporter signal peptide and protein can have any desired structural organization.

A given reporter signal fusion can include one or more reporter signal peptides and one or more proteins or peptides of interest. In addition, reporter signal fusions can include one or more amino acids, amino acid sequences, and/or peptide elements. The disclosed reporter signal fusions comprise a single, contiguous polypeptide chain. Thus, although multiple amino acid segments can be part of the same contiguous polypeptide chain, all of the components (that is, the reporter signal peptide(s) and protein(s) and peptide(s) of interest) of a given amino acid segment are part of the same contiguous polypeptide chain.

Reporter signal fusions can be produced by expression from nucleic acid molecules encoding the fusions. Thus, the disclosed fusions generally can be designed by designing nucleic acid segments that encode amino acid segments where the amino acid segments comprise a reporter signal peptide and a protein or peptide of interest. A given nucleic acid molecule can comprise one or more nucleic acid segments. A given nucleic acid segment can encode one or more amino acid segments. A given amino acid segment can include one or more reporter signal peptides and one or more proteins or peptides of interest. The disclosed amino acid segments consist of a single, contiguous polypeptide chain. Thus, although multiple amino acid segments can be part of the same contiguous polypeptide chain, all of the components (that is, the reporter signal peptide(s) and protein(s) and peptide(s) of interest) of a given amino acid segment are part of the same contiguous polypeptide chain.

Reporter signal fusions can include other components besides a protein of interest and a reporter signal peptide. For example, reporter signal fusions can include epitope tags or flag peptides (see, for example, Groth et al. (2000) A phage integrase directs efficient site-specific integration in human cells. Proc Natl Acad Sci USA 97:5995–6000). Epitope tags and flag peptides can serve as tags by which reporter signal fusions can be separated, distinguished, associated, and/or bound. The use of epitope tags and flag peptides generally is known and can be adapted for use in the disclosed reporter signal fusions.

Reporter signal peptides can be fragmented, decomposed, reacted, derivatized, or otherwise modified, preferably in a characteristic way. This allows a protein to which the reporter signal peptide is fused to be identified by detection of one or more of the products of the reporter signal fusion following fragmentation, decomposition, reaction, derivatization, or other modification of the reporter signal peptide. The protein can also be identified by the correlated detection of the reporter signal fusion and one or more of the products of the reporter signal fusion following fragmentation, decomposition, reaction, derivatization, or other modification of the reporter signal peptide. The alteration of the reporter signal peptide will alter the reporter signal fusion in a characteristic and detectable way. Together, the detection of a characteristic reporter signal fusion and a characteristic product of (that is, altered form of) the reporter signal fusion can uniquely identify the protein (although the altered form alone can be detected, if desired). In this way, expression of one or more proteins can be detected, either alone or together (for example, in a multiplex assay). Further, expression of one or more proteins in one or more samples can be detected in a multiplex manner. Preferably, for mass spectrometry reporter signals, the reporter signal peptides are fragmented to yield fragments of similar charge but different mass.

Preferably, the reporter signal peptides are designed to be fragmented to yield fragments of similar charge but different mass. This allows each reporter signal fusion (and/or each reporter signal peptide) in a set to be distinguished by the different mass-to-charge ratios of the fragments of (that is, altered forms of) the reporter signal peptides. This is possible since the fragments of the different reporter signal peptides (or the fragments of the reporter signal fusions) can be designed to have different mass-to-charge ratios. In the disclosed method, this allows each reporter signal fusion to be distinguished by the mass-to-charge ratios of the reporter signal fusions after fragmentation of the reporter signal peptide.

Alteration of reporter signals peptides in reporter signal fusions can produce a variety of altered compositions. Any or all of these altered forms can be detected. For example, the altered form of the reporter signal peptide can be detected, the altered form of the amino acid segment (which contains the reporter signal peptide) can be detected, the altered form of a subsegment of the amino acid segment can be detected, or a combination of these can be detected. Where the reporter signal peptide is altered by fragmentation, the result generally will be a fragment of the reporter signal peptide and an altered form of the amino acid segment containing the protein or peptide of interest and a portion of the reporter signal peptide (that is, the portion not in the reporter signal peptide fragment).

The protein or peptide of interest also can be fragmented. The result would be a subsegment of the amino acid segment. The amino acid subsegment would contain the reporter signal peptide and a portion of the protein or peptide of interest. When the reporter signal peptide in an amino acid subsegment is altered (which can occur before, during, or after fragmentation of the amino acid segment), the result is an altered form of the amino acid subsegment (and an altered form of the reporter signal peptide). This altered form of amino acid subsegment can be detected. Where the reporter signal peptide is altered by fragmentation, the result generally will be a fragment of the reporter signal peptide and an altered form of (that is, fragment of) the amino acid subsegment. In this case, the altered form of the amino acid subsegment, which is also referred to herein as a reporter signal fusion fragment, will contain a portion of the protein or peptide of interest and a portion of the reporter signal peptide (that is, the portion not in the reporter signal peptide fragment).

As with reporter signals generally, reporter signal fusions (also referred to as amino acid segments), reporter signal fusion fragments (also referred to as subsegments of the reporter signal fusions), or reporter signal peptides can be used in sets where the reporter signal fusions, reporter signal fusion fragments, or reporter signal peptides in a set can have one or more common properties that allow the reporter signal fusions, reporter signal fusion fragments, or reporter signal peptides to be separated or distinguished from molecules lacking the common property. In the case of reporter signal fusions, amino acid segments and amino acid subsegments can be used in sets where the amino acid segments and amino acid subsegments in a set can have one or more common properties that allow the amino acid segments and amino acid subsegments, respectively, to be separated or distinguished from molecules lacking the common property. In general, the component(s) of the reporter signal fusions having common properties can depend on the component(s) to be detected and/or the mode of the method being used.

A variety of different properties can be used as the common physical property used to separate reporter signal fusions, reporter signal fusion fragments, and/or reporter signal peptides from other molecules lacking the common property. For example, physical properties useful as common properties include mass-to-charge ratio, mass, charge, isoelectric point, hydrophobicity, chromatography characteristics, and density. It is preferred that the physical property shared by reporter signal fusions, reporter signal fusion fragments, or reporter signal peptides in a set (and used to distinguish or separate the reporter signal fusions, reporter signal fusion fragments, or reporter signal peptides from other molecules) is an overall property of the reporter signal fusions, reporter signal fusion fragments, or reporter signal peptides (for example, overall mass, overall charge, isoelectric point, overall hydrophobicity, etc.) rather than the mere presence of a feature or moiety (for example, an affinity tag, such as biotin). Such properties are referred to herein as "overall" properties (and thus, reporter signal fusions, reporter signal fusion fragments, or reporter signal peptides in a set would be referred to as sharing a "common overall property"). It should be understood that reporter signal fusions, reporter signal fusion fragments, or reporter signal peptides can have features and moieties, such as affinity tags, and that such features and moieties can contribute to the common overall property (by contributing mass, for example). However, such limited and isolated features and moieties would not serve as the sole basis of the common overall property.

It is preferred that the common property of reporter signal fusions, reporter signal fusion fragments, or reporter signal peptides is not an affinity tag. Nevertheless, even in such a case, reporter signal fusions, reporter signal fusion fragments, or reporter signal peptides that otherwise have a common property may also include an affinity tag—and in fact may all share the same affinity tag—so long as another common property is present that can be (and, in some embodiments of the disclosed method, is) used to separate reporter signal fusions, reporter signal fusion fragments, or reporter signal peptides sharing the common property from other molecules lacking the common property. With this in mind, it is preferred that, if chromatography or other separation techniques are used to separate reporter signal fusions, reporter signal fusion fragments, or reporter signal peptides based on the common property, the affinity be based on an overall physical property of the reporter signal fusions, reporter signal fusion fragments, or reporter signal peptides and not on the presence of, for example, a feature or moiety such as an affinity tag. As used herein, a common property is a property shared by a set of components (such as reporter signal fusions, reporter signal fusion fragments, or reporter signal peptides). That is, the components have the property "in common." It should be understood that reporter signal fusions, reporter signal fusion fragments, or reporter signal peptides in a set may have numerous properties in common. However, as used herein, the common properties of reporter signal fusions, reporter signal fusion fragments, or reporter signal peptides referred to are only those used in the disclosed method to distinguish and/or separate the reporter signal fusions, reporter signal fusion fragments, or reporter signal peptides sharing the common property from molecules that lack the common property.

In preferred embodiments, reporter signal peptides, reporter signal fusions (or amino acid segments), nucleic acid segments encoding reporter signal fusions, and/or nucleic acid molecules comprising nucleic acid segments encoding reporter signal fusions are used in sets where the reporter signal peptides, the reporter signal fusions, and/or subsegments of the reporter signal fusions constituting or present in the set have similar properties (such as similar mass-to-charge ratios). The similar properties allow the reporter signals, the reporter signal fusions, or subsegments of the reporter signal fusions to be distinguished and/or separated from other molecules lacking one or more of the properties. Preferably, the reporter signals, the reporter signal fusions, or subsegments of the reporter signal fusions constituting or present in a set have the same mass-to-charge ratio (m/z). That is, the reporter signals, the reporter signal fusions, or subsegments of the reporter signal fusions in a set are isobaric. This allows the reporter signals, the reporter signal fusions, or subsegments of the reporter signal fusions to be separated precisely from other molecules based on mass-to-charge ratio. The result of the filtering is a huge increase in the signal to noise ratio (S/N) for the system, allowing more sensitive and accurate detection.

Sets of reporter signal fusions (also referred to as amino acid segments), reporter signal fusion fragments (also referred to as subsegments of the reporter signal fusions or amino acid subsegments), reporter signal peptides, nucleic acid segments encoding reporter signal fusions, or nucleic acid molecules comprising nucleic acid segments encoding reporter signal fusions can have any number of reporter signal fusions, reporter signal fusion fragments, reporter signal peptides, nucleic acid segments encoding reporter signal fusions, or nucleic acid molecules comprising nucleic acid segments encoding reporter signal fusions. For example, sets of reporter signal fusions, reporter signal fusion fragments, reporter signal peptides, nucleic acid segments encoding reporter signal fusions, or nucleic acid molecules comprising nucleic acid segments encoding reporter signal fusions can have one, two or more, three or more, four or more, five or more, six or more, seven or more, eight or more, nine or more, ten or more, twenty or more, thirty or more, forty or more, fifty or more, sixty or more, seventy or more, eighty or more, ninety or more, one hundred or more, two hundred or more, three hundred or more, four hundred or more, or five hundred or more different reporter signal fusions, reporter signal fusion fragments, reporter signal peptides, nucleic acid segments encoding reporter signal fusions, or nucleic acid molecules comprising nucleic acid segments encoding reporter signal fusions. Although specific numbers of reporter signal fusions, reporter signal fusion fragments, reporter signal peptides, nucleic acid segments encoding reporter signal fusions, and nucleic acid molecules comprising nucleic acid segments encoding reporter signal fusions, and specific endpoints for ranges of the number of reporter signal fusions, reporter signal fusion fragments, reporter signal peptides, nucleic acid segments encoding reporter signal fusions, and nucleic acid molecules comprising nucleic acid segments encoding reporter signal fusions, are recited, each and every specific number of reporter signal fusions, reporter signal fusion fragments, reporter signal peptides, nucleic acid segments encoding reporter signal fusions, and nucleic acid molecules comprising nucleic acid segments encoding reporter signal fusions, and each and every specific endpoint of ranges of numbers of reporter signal fusions, reporter signal fusion fragments, reporter signal peptides, nucleic acid segments encoding reporter signal fusions, and nucleic acid molecules comprising nucleic acid segments encoding reporter signal fusions, are specifically contemplated, although not explicitly listed, and each and every specific number of reporter signal fusions, reporter signal fusion fragments, reporter signal peptides, nucleic acid segments encoding reporter signal fusions, and nucleic acid molecules comprising nucleic acid segments encoding reporter signal fusions, and each and every specific endpoint of ranges of numbers of reporter signal fusions, reporter signal fusion fragments, reporter signal peptides, nucleic acid segments encoding reporter signal fusions, and nucleic acid molecules comprising nucleic acid segments encoding reporter signal fusions, are hereby specifically described.

The reporter signal fusions are preferably detected using mass spectrometry which allows sensitive distinctions between molecules based on their mass-to-charge ratios. A set of isobaric reporter signal peptides or reporter signal fusions can be used for multiplex labeling and/or detection of the expression of many genes, proteins, vectors, expression constructs, cells, cell lines, and organisms since the reporter signal peptide fragments can be designed to have a large range of masses, with each mass individually distinguishable upon detection. Where the same gene, protein, vectors, expression construct, cell, cell line, or organism (or the same type of gene, protein, vector, expression construct, cell, cell line, or organism) is labeled with a set of reporter signal fusions that are isobaric or that include isobaric reporter signal peptides (by, for example, "labeling" the same gene, protein, vector, expression construct, cell, cell line, or organism in different samples), the set of reporter signal fusions or reporter signal peptides that results will also be isobaric. Fragmentation of the reporter signal peptides will split the set of reporter signal peptides into individually detectable reporter signal fusion fragments and reporter signal peptide fragments of characteristically different mass.

Reporter signal fusions can be expressed in any suitable manner. For example, nucleic acid sequences and nucleic acid segments encoding reporter signal fusions can be expressed in vitro, in cells, and/or in cells in organism. Many techniques and systems for expression of nucleic acid sequences and proteins are known and can be used with the disclosed reporter signal fusions. For example, many expression sequences, vector systems, transformation and transfection techniques, and transgenic organism production methods are known and can be used with the disclosed reporter signal peptide method and compositions. Systems are known for integration of nucleic acid constructs into chromosomes of cells and organisms (see, for example, Groth et al. (2000) A phage integrase directs efficient site-specific integration in human cells. Proc Natl Acad Sci USA 97:5995–6000; Hong et al. (2001) Development of two bacterial artificial chromosome shuttle vectors for a recombination-based cloning and regulated expression of large genes in mammalian cells. Analytical Biochemistry 291:142–148) which can be used with the disclosed nucleic acid molecules and segments encoding reporter signal fusions or to form nucleic acid segment encoding reporter signal fusions.

As used herein, an expression sample is a sample that contains, or might contain, one or more reporter signal fusions expressed from a nucleic acid molecule. An expression sample to be analyzed can be subjected to fractionation or separation to reduce the complexity of the samples. Fragmentation and fractionation can also be used together in the same assay. Such fragmentation and fractionation can simplify and extend the analysis of the expression.

Nucleic acid molecules encoding reporter signal fusions can be used in sets where the reporter signal peptides in the reporter signal fusions encoded by a set of nucleic acid molecules can have one or more common properties that allow the reporter signal peptides to be separated or distinguished from molecules lacking the common property. Similarly, nucleic acid molecules encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid molecules encoding amino acid segments can be used in sets where the amino acid segments encoded by a set of nucleic acid molecules can have one or more common properties that allow the amino acid segments to be separated or distinguished from molecules lacking the common property.

Nucleic acid segments (which, generally, are part of nucleic acid molecules) encoding reporter signal fusions can be used in sets where the reporter signal peptides in the reporter signal fusions encoded by a set of nucleic acid segments can have one or more common properties that allow the reporter signal peptides to be separated or distinguished from molecules lacking the common property. Similarly, nucleic acid segments encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid segments encoding amino acid segments can be used in sets where the amino acid segments encoded by a set of nucleic acid molecules can have one or more common properties that allow the amino acid segments to be separated or distinguished from molecules lacking the common property. Other relationships between members of the sets of nucleic acid molecules, nucleic acid segments, amino acid segments, reporter signal peptides, and proteins of interest are contemplated.

Reporter signal fusions allow sensitive and multiplex detection of expression of particular proteins and peptides of interest, and/or of the genes, vectors, and expression constructs encoding the proteins and peptides of interest. The disclosed reporter signal fusions can also be used for any purpose including as a source of reporter signals for other forms of the disclosed method and compositions.

H. Reporter Signal/Analyte Conjugates

Compositions where reporter signals are associated with, incorporated into, or otherwise linked to the analytes are referred to as reporter signal/analyte conjugates. Such conjugates include reporter signals associated with analytes, such as a reporter signal probe hybridized to a nucleic acid sequence; reporter signals covalently coupled to analytes, such as reporter signals linked to proteins via a linking group; and reporter signals incorporated into analytes, such as fusions between a protein of interest and a peptide reporter signal.

Reporter signal/analyte conjugates can be altered, generally through alteration of the reporter signal portion of the conjugate, such that the altered forms of different reporter signals, altered forms of different reporter signal/analyte conjugates, or both, can be distinguished from each other. Where the reporter signal or reporter signal/analyte conjugate is altered by fragmentation, any, some, or all of the fragments can be distinguished from each other, depending on the embodiment. For example, where reporter signal/analyte conjugates are fragmented into two parts (with the break point in the reporter signal portion), either the reporter signal fragment, the reporter signal/analyte fragment, or both can be distinguished.

Sets of reporter signal/analyte conjugates can be used where two or more of the reporter signal/analyte conjugates in a set have one or more common properties that allow the reporter signal/analyte conjugates having the common property to be distinguished and/or separated from other molecules lacking the common property. In still other embodiments, analytes can be fragmented (prior to or following conjugation) to produce reporter signal/analyte fragment conjugates (which can be referred to as fragment conjugates). In such cases, sets of fragment conjugates can be used where two or more of the fragment conjugates in a set have one or more common properties that allow the fragment conjugates having the common property to be distinguished and/or separated from other molecules lacking the common property. It should be understood that fragmented analytes can be considered analytes in their own right. In this light, reference to fragmented analytes is made for convenience and clarity in describing certain embodiments and to allow reference to both the base analyte and the fragmented analyte.

Sets of reporter signal/analyte conjugates or reporter signal/analyte fragment conjugates (fragment conjugates) can have any number of reporter signal/analyte conjugates or reporter signal/analyte fragment conjugates. For example, sets of reporter signal/analyte conjugates or reporter signal/analyte fragment conjugates can have one, two or more, three or more, four or more, five or more, six or more, seven or more, eight or more, nine or more, ten or more, twenty or more, thirty or more, forty or more, fifty or more, sixty or more, seventy or more, eighty or more, ninety or more, one hundred or more, two hundred or more, three hundred or more, four hundred or more, or five hundred or more different reporter signal/analyte conjugates or reporter signal/analyte fragment conjugates. Although specific numbers of reporter signal/analyte conjugates and reporter signal/analyte fragment conjugates, and specific endpoints for ranges of the number of reporter signal/analyte conjugates and reporter signal/analyte fragment conjugates, are recited, each and every specific number of reporter signal/analyte conjugates and reporter signal/analyte fragment conjugates, and each and every specific endpoint of ranges of numbers of reporter signal/analyte conjugates and reporter signal/analyte fragment conjugates, are specifically contemplated, although not explicitly listed, and each and every specific number of reporter signal/analyte conjugates and reporter signal/analyte fragment conjugates, and each and every specific endpoint of ranges of numbers of reporter signal/analyte conjugates and reporter signal/analyte fragment conjugates, are hereby specifically described.

As indicated above, reporter signals conjugated with analytes can be altered while in the conjugate and distinguished. Conjugated reporter signals can also be dissociated or separated, in whole or in part, from the conjugated analytes prior to their alteration. Where the reporter signals are dissociated (in whole or in part) from the analytes, the method can be performed such that the fact of association between the analyte and reporter signal is part of the information obtained when the reporter signal is detected. In other words, the fact that the reporter signal may be dissociated from the analyte for detection does not obscure the information that the detected reporter signal was associated with the analyte.

As used herein, reporter signal conjugate refers both to reporter signal/analyte conjugates and to other components of the disclosed method such as reporter molecules.

As with reporter signals generally, reporter signal/analyte conjugates and reporter signal/analyte fragment conjugates can be used in sets where the reporter signal/analyte conjugates or fragment conjugates in a set can have one or more common properties that allow the reporter signal/analyte conjugates or fragment conjugates to be separated or distinguished from molecules lacking the common property. As with reporter signals generally, a variety of different properties can be used as the common physical property used to separate reporter signal/analyte conjugates or fragment conjugates from other molecules lacking the common property. For example, physical properties useful as common properties include mass-to-charge ratio, mass, charge, isoelectric point, hydrophobicity, chromatography characteristics, and density. It is preferred that the physical property shared by reporter signal/analyte conjugates or fragment conjugates in a set (and used to distinguish or separate the reporter signal/analyte conjugates or fragment conjugates from other molecules) is an overall property of the reporter signal/analyte conjugates or fragment conjugates (for example, overall mass, overall charge, isoelectric point, overall hydrophobicity, etc.) rather than the mere presence of a feature or moiety (for example, an affinity tag, such as biotin). Such properties are referred to herein as "overall" properties (and thus, reporter signal/analyte conjugates or fragment conjugates in a set would be referred to as sharing a "common overall property"). It should be understood that reporter signal/analyte conjugates or fragment conjugates can have features and moieties, such as affinity tags, and that such features and moieties can contribute to the common overall property (by contributing mass, for example). However, such limited and isolated features and moieties would not serve as the sole basis of the common overall property.

It is preferred that the common property of reporter signal/analyte conjugates or fragment conjugates is not an affinity tag. Nevertheless, even in such a case, reporter signal/analyte conjugates or fragment conjugates that otherwise have a common property may also include an affinity tag—and in fact may all share the same affinity tag—so long as another common property is present that can be (and, in some embodiments of the disclosed method, is) used to separate reporter signal/analyte conjugates or fragment conjugates sharing the common property from other molecules lacking the common property. With this in mind, it is preferred that, if chromatography or other separation techniques are used to separate reporter signal/analyte conjugates or fragment conjugates based on the common property, the affinity be based on an overall physical property of the reporter signal/analyte conjugates or fragment conjugates and not on the presence of, for example, a feature or moiety such as an affinity tag. As used herein, a common property is a property shared by a set of components (such as reporter signal/analyte conjugates or fragment conjugates). That is, the components have the property "in common." It should be understood that reporter signal/analyte conjugates or fragment conjugates in a set may have numerous properties in common. However, as used herein, the common properties of reporter signal/analyte conjugates or fragment conjugates referred to are only those used in the disclosed method to distinguish and/or separate the reporter signal/analyte conjugates or fragment conjugates sharing the common property from molecules that lack the common property.

I. Capture Arrays

A capture array (also referred to herein as an array) includes a plurality of capture tags immobilized on a solid-state substrate, preferably at identified or predetermined locations on the solid-state substrate. In this context, plurality of capture tags refers to a multiple capture tags each having a different structure. Preferably, each predetermined location on the array (referred to herein as an array element) has one type of capture tag (that is, all the capture tags at that location have the same structure). Each location will have multiple copies of the capture tag. The spatial separation of capture tags of different structure in the array allows separate detection and identification of analytes that become associated with the capture tags. If a decoding tag is detected at a given location in a capture array, it indicates that the analyte corresponding to that array element was present in the target sample.

Solid-state substrates for use in capture arrays can include any solid material to which capture tags can be coupled, directly or indirectly. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, disks, compact disks, fibers, optical fibers, woven fibers, shaped polymers, particles and microparticles. A preferred form for a solid-state substrate is a compact disk.

Although preferred, it is not required that a given capture array be a single unit or structure. The set of capture tags may be distributed over any number of solid supports. For example, at one extreme, each capture tag may be immobilized in a separate reaction tube or container. Arrays may be constructed upon non permeable or permeable supports of a wide variety of support compositions such as those described above. The array spot sizes and density of spot packing vary over a tremendous range depending upon the process(es) and material(s) used.

Methods for immobilizing antibodies and other proteins to substrates are well established. Immobilization can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in *Protein immobilization: fundamentals and applications*, Richard F. Taylor, ed. (M. Dekker, New York, 1991), Johnstone and Thorpe, *Immunochemistry In Practice* (Blackwell Scientific Publications, Oxford, England, 1987) pages 209–216 and 241–242, and *Immobilized Affinity Ligands*, Craig T. Hermanson et al., eds. (Academic Press, New York, 1992). Antibodies can be attached to a substrate by chemically cross-linking a free amino group on the antibody to reactive side groups present within the substrate. For example, antibodies may be chemically cross-linked to a substrate that contains free amino or carboxyl groups using glutaraldehyde or carbodiimides as cross-linker agents. In this method, aqueous solutions containing free antibodies are incubated with the solid-state substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art.

Methods for immobilization of oligonucleotides to solid-state substrates are well established. Oligonucleotide capture tags can be coupled to substrates using established coupling methods. For example, suitable attachment methods are described by Pease et al., *Proc. Natl. Acad. Sci. USA* 91(11):5022–5026 (1994), Khrapko et al., *Mol Biol (Mosk) (USSR)* 25:718–730 (1991), U.S. Pat. No. 5,871,928 to Fodor et al., U.S. Pat. No. 5,654,413 to Brenner, U.S. Pat. No. 5,429,807, and U.S. Pat. No. 5,599,695 to Pease et al. A method for immobilization of 3'-amine oligonucleotides on casein-coated slides is described by Stimpson et al., *Proc. Natl. Acad. Sci. USA* 92:6379–6383 (1995). A preferred method of attaching oligonucleotides to solid-state substrates is described by Guo et al., *Nucleic Acids Res.* 22:5456–5465 (1994).

Planar array technology has been utilized for many years (Shalon, D, S.J. Smith, and P. O. Brown, *A DNA microarray system for analyzing complex DNA samples using two-color fluorescent probe hybridization.* Genome Res, 1996.6(7): p. 639–45, Singh-Gasson, S., et al., *Maskless fabrication of light-directed oligonucleotide microarrays using a digital micromirror array.* Nat Biotechnol, 1999.17(10): p. 974–8, Southern, E. M., U. Maskos, and J. K. Elder, *Analyzing and comparing nucleic acid sequences by hybridization to arrays of oligonucleotides: evaluation using experimental models.* Genomics, 1992. 13(4): p. 1008–17, Nizetic, D, et al., *Construction, arraying, and high-density screening of large insert libraries of human chromosomes X and 21: their potential use as reference libraries.* Proc Natl Acad Sci USA, 1991. 88(8): p. 3233–7, Van Oss, C. J., R. J. Good, and M. K. Chaudhury, *Mechanism of DNA (Southern) and protein (Western) blotting on cellulose nitrate and other membranes.* J Chromatogr, 1987. 391(1): p. 53–65, Ramsay, G., *DNA chips: state-of-the art.* Nat Biotechnol, 1998. 16(1): p. 40–4, Schena, M., et al., *Parallel human genome analysis: microarray-based expression monitoring of 1000 genes.* Proc Natl Acad Sci USA, 1996. 93(20): p. 10614–9, Lipshutz, R. J., et al., *High density synthetic oligonucleotide arrays.* Nat Genet, 1999. 21(1 Suppl): p. 20–4, Pease, A. C., et al., *Light-generated oligonucleotide arrays for rapid DNA sequence analysis.* Proc Natl Acad Sci USA, 1994. 91(11): p. 5022–6, Maier, E., et al., *Application of robotic technology to automated sequence fingerprint analysis by oligonucleotide hybridisation.* J Biotechnol, 1994. 35(2–3): p. 191–203, Vasiliskov, A. V., et al., *Fabrication of microarray of gel-immobilized compounds on a chip by copolymerization.* Biotechniques, 1999. 27(3): p. 592–4, 596–8, 600 passim, and Yershov, G., et al., *DNA analysis and diagnostics on oligonucleotide microchips.* Proc Natl Acad Sci USA, 1996. 93(10): p. 4913–8).

Oligonucleotide capture tags in arrays can also be designed to have similar hybrid stability. This would make hybridization of fragments to such capture tags more efficient and reduce the incidence of mismatch hybridization. The hybrid stability of oligonucleotide capture tags can be calculated using known formulas and principles of thermodynamics (see, for example, Santa Lucia et al., *Biochemistry* 35:3555–3562 (1996); Freier et al., *Proc. Natl. Acad. Sci. USA* 83:9373–9377 (1986); Breslauer et al., *Proc. Natl. Acad. Sci. USA* 83:3746–3750 (1986)). The hybrid stability of the oligonucleotide capture tags can be made more similar (a process that can be referred to as smoothing the hybrid stabilities) by, for example, chemically modifying the capture tags (Nguyen et al., *Nucleic Acids Res.* 25(15) :3059–3065 (1997); Hohsisel, *Nucleic Acids Res.* 24(3) :430–432 (1996)). Hybrid stability can also be smoothed by carrying out the hybridization under specialized conditions (Nguyen et al., *Nucleic Acids Res.* 27(6):1492–1498 (1999); Wood et al., *Proc. Natl. Acad. Sci.* USA 82(6):1585–1588 (1985)).

Another means of smoothing hybrid stability of the oligonucleotide capture tags is to vary the length of the capture tags. This would allow adjustment of the hybrid stability of each capture tag so that all of the capture tags had similar hybrid stabilities (to the extent possible). Since the addition or deletion of a single nucleotide from a capture tag will change the hybrid stability of the capture tag by a fixed increment, it is understood that the hybrid stabilities of the capture tags in a capture array will not be equal. For this reason, similarity of hybrid stability as used herein refers to any increase in the similarity of the hybrid stabilities of the capture tags (or, put another way, any reduction in the differences in hybrid stabilities of the capture tags).

The efficiency of hybridization and ligation of oligonucleotide capture tags to sample fragments can also be improved by grouping capture tags of similar hybrid stability in sections or segments of a capture array that can be subjected to different hybridization conditions. In this way, the hybridization conditions can be optimized for particular classes of capture tags.

J. Capture Tags

A capture tag is any compound that can be used to capture or separate compounds or complexes having the capture tag. Preferably, a capture tag is a compound that interacts specifically with a particular molecule or moiety. Preferably, the molecule or moiety that interacts specifically with a capture tag is an analyte. It is to be understood that the term analyte refers to both separate molecules and to portions of such molecules, such as an epitope of a protein, that interacts specifically with a capture tag. Antibodies, either member of a receptor/ligand pair, synthetic polyamides (Dervan and Burli, *Sequence-specific DNA recognition by polyamides.* Curr Opin Chem Biol, 3(6):688–93 (1999); Wemmer and Dervan, *Targeting the minor groove of DNA.* Curr Opin Struct Biol, 7(3):355–61 (1997)), nucleic acid probes, and other molecules with specific binding affinities are examples of capture tags.

A capture tag that interacts specifically with a particular analyte is said to be specific for that analyte. For example, where the capture tag is an antibody that associates with a particular antigen, the capture tag is said to be specific for that antigen. The antigen is the analyte. Capture tags preferably are antibodies, ligands, binding proteins, receptor proteins, haptens, aptamers, carbohydrates, synthetic polyamides, peptide nucleic acids, or oligonucleotides. Preferred binding proteins are DNA binding proteins. Preferred DNA binding proteins are zinc finger motifs, leucine zipper motifs, helix-turn-helix motifs. These motifs can be combined in the same capture tag.

Antibodies useful as the affinity portion of reporter binding agents, can be obtained commercially or produced using well established methods. For example, Johnstone and Thorpe, *Immunochemistry In Practice* (Blackwell Scientific Publications, Oxford, England, 1987) on pages 30–85, describe general methods useful for producing both polyclonal and monoclonal antibodies. The entire book describes many general techniques and principles for the use of antibodies in assay systems.

Properties of zinc fingers, zinc finger motifs, and their interactions, are described by Nardelli et al., *Zinc finger-DNA recognition: analysis of base specificity by site-directed mutagenesis*. Nucleic Acids Res, 20(16):4137–44 (1992), Jamieson et al., *In vitro selection of zinc fingers with altered DNA-binding specificity*. Biochemistry, 33(19):5689–95 (1994), Chandrasegaran and Smith, *Chimeric restriction enzymes: what is next?* Biol Chem, 380(7–8):841–8 (1999), and Smith et al., *A detailed study of the substrate specificity of a chimeric restriction enzyme*. Nucleic Acids Res, 27(2):674–81 (1999).

One form of capture tag is an oligonucleotide or oligonucleotide derivative. Such capture tags are designed for and used to detect specific nucleic acid sequences. Thus, the analyte for oligonucleotide capture tags are nucleic acid sequences. The analyte can be a nucleotide sequence within a larger nucleic acid molecule. An oligonucleotide capture tag can be any length that supports specific and stable hybridization between the capture tag and the analyte. For this purpose, a length of 10 to 40 nucleotides is preferred, with an oligonucleotide capture tag 16 to 25 nucleotides long being most preferred. It is preferred that the oligonucleotide capture tag is peptide nucleic acid. Peptide nucleic acid forms a stable hybrid with DNA. This allows a peptide nucleic acid capture tag to remain firmly adhered to the target sequence during subsequent amplification and detection operations.

This useful effect can also be obtained with oligonucleotide capture tags by making use of the triple helix chemical bonding technology described by Gasparro et al., *Nucleic Acids Res.*, 22(14):2845–2852 (1994). Briefly, the oligonucleotide capture tag is designed to form a triple helix when hybridized to a target sequence. This is accomplished generally as known, preferably by selecting either a primarily homopurine or primarily homopyrimidine target sequence. The matching oligonucleotide sequence which constitutes the capture tag will be complementary to the selected target sequence and thus be primarily homopyrimidine or primarily homopurine, respectively. The capture tag (corresponding to the triple helix probe described by Gasparro et al.) contains a chemically linked psoralen derivative. Upon hybridization of the capture tag to a target sequence, a triple helix forms. By exposing the triple helix to low wavelength ultraviolet radiation, the psoralen derivative mediates cross-linking of the probe to the target sequence.

K. Sample Arrays

A sample array includes a plurality of samples (for example, expression samples, tissue samples, protein samples) immobilized on a solid-state substrate, preferably at identified or predetermined locations on the solid-state substrate. Preferably, each predetermined location on the sample array (referred to herein as an sample array element) has one type of sample. The spatial separation of different samples in the sample array allows separate detection and identification of reporter signals (or reporter molecules or coding tags) that become associated with the samples. If a reporter signal is detected at a given location in a sample array, it indicates that the analyte corresponding to that reporter signal was present in the sample corresponding to that sample array element.

Solid-state substrates for use in sample arrays can include any solid material to which samples can be adhered, directly or indirectly. This includes materials such as acrylamide, cellulose, nitrocellulose, glass, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Solid-state substrates can have any useful form including thin films or membranes, beads, bottles, dishes, disks, compact disks, fibers, optical fibers, woven fibers, shaped polymers, particles and microparticles. A preferred form for a solid-state substrate is a compact disk.

Although preferred, it is not required that a given sample array be a single unit or structure. The set of samples may be distributed over any number of solid supports. For example, at one extreme, each sample may be immobilized in a separate reaction tube or container. Sample arrays may be constructed upon non permeable or permeable supports of a wide variety of support compositions such as those described above. The array spot sizes and density of spot packing vary over a tremendous range depending upon the process(es) and material(s) used. Methods for adhering or immobilizing samples and sample components to substrates are well established.

A preferred form of sample array is a tissue arrays, where there are small tissue samples on a substrate. Such tissue microarrays exist, and are used, for example, in a cohort to study breast cancer. The disclosed method can be used, for example, to probe multiple analytes in multiple samples. Sample arrays can be, for example, labeled with different reporter signals, the whole support then introduced into source region of a mass spec, and sampled by MALDI.

L. Decoding Tags

Decoding tags are any molecule or moiety that can be associated with coding tags, directly or indirectly. Decoding tags are associated with reporter signals (making up a reporter molecule) to allow indirect association of the reporter signals with an analyte. Decoding tags preferably are oligonucleotides, carbohydrates, synthetic polyamides, peptide nucleic acids, antibodies, ligands, proteins, haptens, zinc fingers, aptamers, or mass labels.

Preferred decoding tags are molecules capable of hybridizing specifically to an oligonucleotide coding tag. Most preferred are peptide nucleic acid decoding tags. Oligonucleotide or peptide nucleic acid decoding tags can have any arbitrary sequence. The only requirement is hybridization to coding tags. The decoding tags can each be any length that supports specific and stable hybridization between the coding tags and the decoding tags. For this purpose, a length of 10 to 35 nucleotides is preferred, with a decoding tag 15 to 20 nucleotides long being most preferred.

Reporter molecules containing decoding tags preferably are capable of being released by matrix-assisted laser desorption-ionization (MALDI) in order to be separated and identified by time-of-flight (TOF) mass spectroscopy, or by another detection technique. A decoding tag may be any oligomeric molecule that can hybridize to a coding tag. For example, a decoding tag can be a DNA oligonucleotide, an RNA oligonucleotide, or a peptide nucleic acid (PNA) molecule. Preferred decoding tags are PNA molecules.

M. Coding Tags

Coding tags are molecules or moieties with which decoding tags can associate. Coding tags can be any type of molecule or moiety that can serve as a target for decoding tag association. Preferred coding tags are oligomers, oligonucleotides, or nucleic acid sequences. Coding tags can also be a member of a binding pair, such as streptavidin or biotin, where its cognate decoding tag is the other member of the binding pair. Coding tags can also be designed to associate directly with some types of reporter signals. For example, oligonucleotide coding tags can be designed to interact directly with peptide nucleic acid reporter signals (which are reporter signals composed of peptide nucleic acid).

The oligomeric base sequences of oligomeric coding tags can include RNA, DNA, modified RNA or DNA, modified backbone nucleotide-like oligomers such as peptide nucleic acid, methylphosphonate DNA, and 2'-O-methyl RNA or DNA. Oligomeric or oligonucleotide coding tags can have any arbitrary sequence. The only requirement is association with decoding tags (preferably by hybridization). In the disclosed method, multiple coding tags can become associated with a single analyte. The context of these multiple coding tags depends upon the technique used for signal amplification. Thus, where branched DNA is used, the branched DNA molecule includes the multiple coding tags on the branches. Where oligonucleotide dendrimers are used, the coding tags are on the dendrimer arms. Where rolling circle replication is used, multiple coding tags result from the tandem repeats of complement of the amplification target circle sequence (which includes at least one complement of the coding tag sequence). In this case, the coding tags are tandemly repeated in the tandem sequence DNA.

Oligonucleotide coding tags can each be any length that supports specific and stable hybridization between the coding tags and the decoding tags. For this purpose, a length of 10 to 35 nucleotides is preferred, with a coding tag 15 to 20 nucleotides long being most preferred.

The branched DNA for use in the disclosed method is generally known (Urdea, Biotechnology 12:926–928 (1994), and Horn et al., Nucleic Acids Res 23:4835–4841 (1997)). As used herein, the tail of a branched DNA molecule refers to the portion of a branched DNA molecule that is designed to interact with the analyte. The tail is a specific binding molecule. In general, each branched DNA molecule should have only one tail. The branches of the branched DNA (also referred to herein as the arms of the branched DNA) contain coding tag sequences. Oligonucleotide dendrimers (or dendrimeric DNA) are also generally known (Shchepinov et al., Nucleic Acids Res. 25:4447–4454 (1997), and Orentas et al., J. Virol. Methods 77:153–163 (1999)). As used herein, the tail of an oligonucleotide dendrimer refers to the portion of a dendrimer that is designed to interact with the analyte. In general, each dendrimer should have only one tail. The dendrimeric strands of the dendrimer are referred to herein as the arms of the oligonucleotide dendrimer and contain coding tag sequences.

Coding tags can be coupled (directly or via a linker or spacer) to analytes or other molecules to be labeled. Coding tags can also be associated with analytes and other molecules to be labeled. For this purpose, coding molecules are preferred. Coding molecules are molecules that can interact with an analyte and with a decoding tag. Coding molecules include a specific binding molecule and a coding tag. Specific binding molecules are described above.

N. Reporter Carriers and Coding Carriers

Reporter carriers are associations of one or more specific binding molecules, a carrier, and a plurality of reporter signals. Reporter carriers are used in the disclosed method to associate a large number of reporter signals with an analyte. Coding carriers are associations of one or more specific binding molecules, a carrier, and a plurality of coding tags. Coding carriers are used in the disclosed method to associate a large number of coding tags with an analyte. The carrier can be any molecule or structure that facilitates association of many reporter signals with a specific binding molecule. Examples include liposomes, microparticles, nanoparticles, virons, phagmids, and branched polymer structures. A general class of carriers are structures and materials designed for drug delivery. Many such carriers are known. Liposomes are a preferred form of carrier.

Liposomes are artificial structures primarily composed of phospholipid bilayers. Cholesterol and fatty acids may also be included in the bilayer construction. In some forms of the disclosed method, liposomes serve as carriers for arbitrary reporter signals or coding tags. By combining liposome reporter carriers, loaded with arbitrary signals or tags, with methods capable of separating a very large multiplicity of signals and tags, it becomes possible to perform highly multiplexed assays.

Liposomes, preferably unilamellar vesicles, are made using established procedures that result in the loading of the interior compartment with a very large number (several thousand) of reporter signals or coding tag molecules, where the chemical nature of these molecules is well suited for detection by a preselected detection method. One specific type of reporter signal or coding tag preferably is used for each specific type of liposome carrier.

Each specific type of liposome reporter or coding carrier is associated with a specific binding molecule. The association may be direct or indirect. An example of a direct association is a liposome containing covalently coupled antibodies on the surface of the phospholipid bilayer. An alternative, indirect association composition is a liposome containing covalently coupled DNA oligonucleotides of arbitrary sequence on its surface; these oligonucleotides are designed to recognize, by base complementarity, specific reporter molecules. The reporter molecule may comprise an antibody-DNA covalent complex, whereby the DNA portion of this complex can hybridize specifically with the complementary sequence on a liposome reporter carrier. In this fashion, the liposome reporter carrier becomes a generic reagent, which may be associated indirectly with any desired binding molecule.

The use of liposome reporter carriers can be illustrated with the following example.

1. Liposomes (preferably unilamellar vesicles with an average diameter of 150 to 300 nanometers) are prepared using the extrusion method (Hope et al., Biochimica et Biophysica Acta, 812:55–65 (1985); MacDonald et al., Biochimica et Biophysica Acta, 1061:297–303 (1991)). Other methods for liposome preparation may be used as well.

2. A solution of an oligopeptide, at a concentration 400 micromolar, is used during the preparation of the liposomes, such that the inner volume of the liposomes is loaded with this specific oligopeptide, which will serve to identify a specific analyte of interest. A liposome with an internal diameter of 200 nanometers will contain, on the average, 960 molecules of the oligopeptide. Three separate preparations of liposomes are extruded, each loaded with a different oligopeptide. The oligopeptides are chosen such that they have the same mass-to-charge ratio but will break into fragments with different mass-to-charge ratios such that they will be readily separable by mass spectrometry.

3. The outer surface of the three liposome preparations is conjugated with specific antibodies, as follows: a) the first liposome preparation is reacted with an antibody specific for the p53 tumor suppressor; b) the second liposome preparation is reacted with an antibody specific for the Bcl-2 oncoprotein; c) the third liposome preparation is reacted with an antibody specific or the Her2/neu membrane receptor. Coupling reactions are performed using standard procedures for the covalent coupling of antibodies to molecules harboring reactive amino groups (Hendrickson et al., *Nucleic Acids Research*, 23:522–529 (1995); Hermanson, Bioconjugate techniques, Academic Press, pp.528–569 (1996); Scheffold et al., *Nature Medicine* 1:107–110 (2000)). In the case of the liposomes, the reactive amino groups are those present in the phosphatidyl ethanolamine moieties of the liposomes.

4. A glass slide bearing a standard formaldehyde-fixed histological section is contacted with a mixture of all three liposome preparations, suspended in a buffer containing 30 mM Tris-HCl, pH 7.6, 100 mM Sodium Chloride, 1 mM EDTA, 0.1% Bovine serum albumin, in order to allow association of the liposomes with the corresponding protein antigens present in the fixed tissue. After a one hour incubation, the slides are washed twice, for 5 minutes, with the same buffer (30 mM Tris-HCl, pH 7.6, 100 mM Sodium Chloride, 1 mM EDTA, 0.1% Bovine serum albumin). The slides are dried with a stream of air.

5. The slides are coated with a thin layer of matrix solution consisting of 10 mg/ml alpha-cyano-4-hydroxycinnamic acid, 0.1% trifluoroacetic acid in a 50:50 mixture of acetonitrile in water. The slides are dried with a stream of air.

6. The slide is placed on the surface of a MALDI plate, and introduced in a mass spectrometer such as that described in Loboda et al., *Design and Performance of a MALDI-QqTOF Mass Spectrometer*, in 47th ASMS Conference, Dallas, Tex. (1999), Loboda et al., *Rapid Comm. Mass Spectrom.* 14(12):1047–1057 (2000), Shevchenko et al., *Anal. Chem.*, 72: 2132–2142 (2000), and Krutchinsky et al., *J. Am. Soc. Mass Spectrom.*, 11(6):493–504 (2000).

7. Mass spectra are obtained from defined positions on the slide surface. The relative amount of each of the three peaks of reporter signal polypeptides is used to determine the relative ratios of the antigens detected by the liposome-detector complexes.

The liposome carrier method is not limited to the detection of analytes on histological sections. Cells obtained by sorting may also be used for analysis in the disclosed method (Scheffold, A., Assenmacher, M., Reiners-Schramm, L., Lauster, R., and Radbruch, A., 2000, Nature Medicine 1:107–110).

O. Labeled Proteins

Labeled proteins are proteins or peptides to which one or more reporter signals are attached. Preferably, the reporter signal and the protein or peptide are covalently coupled or tethered to each other. As used herein, molecules are coupled when they are covalent joined, directly or indirectly. One form of indirect coupling is via a linker molecule. The reporter signal can be coupled to the protein or peptide by any suitable coupling reactions. For example, reporter signals can be covalently coupled to proteins through a sulfur—sulfur bond between a cysteine on the protein and a cysteine on the reporter signal. Many other chemistries and techniques for coupling compounds to proteins are known and can be used to couple reporter signals to proteins. For example, coupling can be made using thiols, epoxides, nitriles for thiols, NHS esters, isothiocyantes, isothiocyanates for amines, amines, and alcohols for carboxylic acids. Proteins and peptides can also be labeled in vivo.

As used herein, "labeled protein" refers to both proteins and peptides to which one or more reporter signals are attached. The term labeled protein refers both to proteins and peptides attached to intact (for example, unfragmented) reporter signals and to proteins and peptides attached to modified (for example, fragmented) reporter signals. The latter form of labeled proteins are referred to as fragmented labeled proteins. Although the protein portion of a labeled protein can be fragmented (for example, by protease digestion), the term fragmented labeled protein refers to a labeled protein where the reporter signal has been fragmented. Isobaric labeled proteins are proteins or peptides of the same type that are labeled with isobaric reporter signals such that a set of the proteins has the same mass-to-charge ratio.

P. Labeled Analytes

Labeled analytes are analytes to which one or more reporter signals are attached. Preferably, the reporter signal and the analyte are covalently coupled or tethered to each other. As used herein, molecules are coupled when they are covalent joined, directly or indirectly. One form of indirect coupling is via a linker molecule. The reporter signal can be coupled to the analyte by any suitable coupling reactions. Many chemistries and techniques for coupling compounds are known and can be used to couple reporter signals to analytes. For example, coupling can be made using thiols, epoxides, nitrites for thiols, NHS esters, isothiocyantes, isothiocyanates for amines, amines, and alcohols for carboxylic acids.

As used herein, "labeled analyte" refers to analytes to which one or more reporter signals are attached. The term labeled analyte refers both to analytes attached to intact (for example, unfragmented) reporter signals and to analytes attached to modified (for example, fragmented) reporter signals. The latter form of labeled proteins are referred to as fragmented labeled analytes. Although the analyte portion of a labeled analyte can be fragmented, the term fragmented labeled analyte refers to a labeled analyte where the reporter signal has been fragmented. Isobaric labeled analytes are analytes of the same type that are labeled with isobaric reporter signals such that a set of the analytes has the same mass-to-charge ratio.

Q. Affinity Tags

An affinity tag is any compound that can be used to separate compounds or complexes having the affinity tag from those that do not. Preferably, an affinity tag is a compound, such as a ligand or hapten, that associates or interacts with another compound, such as ligand-binding molecule or an antibody. It is also preferred that such interaction between the affinity tag and the capturing component be a specific interaction, such as between a hapten and an antibody or a ligand and a ligand-binding molecule. Affinity tags preferably are antibodies, ligands, binding proteins, receptor proteins, haptens, aptamers, carbohydrates, synthetic polyamides, or oligonucleotides. Preferred binding proteins are DNA binding proteins. Preferred DNA binding proteins are zinc finger motifs, leucine zipper motifs, helix-turn-helix motifs. These motifs can be combined in the same specific binding molecule.

Affinity tags, described in the context of nucleic acid probes, are described by Syvnen et al., *Nucleic Acids Res.*, 14:5037 (1986). Preferred affinity tags include biotin, which can be incorporated into nucleic acids. In the disclosed method, affinity tags incorporated into reporter signals can allow the reporter signals to be captured by, adhered to, or coupled to a substrate. Such capture allows separation of reporter signals from other molecules, simplified washing and handling of reporter signals, and allows automation of all or part of the method.

Zinc fingers can also be used as affinity tags. Properties of zinc fingers, zinc finger motifs, and their interactions, are described by Nardelli et al., *Zinc finger-DNA recognition: analysis of base specificity by site-directed mutagenesis.* Nucleic Acids Res, 20(16):4137–44 (1992), Jamieson et al., *In vitro selection of zinc fingers with altered DNA-binding specificity.* Biochemistry, 33(19):5689–95 (1994), Chandrasegaran, S. and J. Smith, *Chimeric restriction enzymes: what is next?* Biol Chem, 380(7–8):841–8 (1999), and Smith et al., *A detailed study of the substrate specificity of a chimeric restriction enzyme.* Nucleic Acids Res, 27(2): 674–81 (1999).

Capturing reporter signals on a substrate, if desired, may be accomplished in several ways. In one embodiment, affinity docks are adhered or coupled to the substrate. Affinity docks are compounds or moieties that mediate adherence of a reporter signal by associating or interacting with an affinity tag on the reporter signal. Affinity docks immobilized on a substrate allow capture of the reporter signals on the substrate. Such capture provides a convenient means of washing away molecules that might interfere with subsequent steps. Captured reporter signals can also be released from the substrate. This can be accomplished by dissociating the affinity tag or by breaking a photocleavable linkage between the reporter signal and the substrate.

Substrates for use in the disclosed method can include any solid material to which reporter signals can be adhered or coupled. Examples of substrates include, but are not limited to, materials such as acrylamide, cellulose, nitrocellulose, glass, silicon, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, polypropylfumerate, collagen, glycosaminoglycans, and polyamino acids. Substrates can have any useful form including thin films or membranes, beads, bottles, dishes, fibers, optical fibers, woven fibers, shaped polymers, particles, compact disks, and microparticles.

R. Vectors and Expression Sequences

Gene transfer can be obtained using direct transfer of genetic material, in but not limited to, plasmids, viral vectors, viral nucleic acids, phage nucleic acids, phages, cosmids, and artificial chromosomes, or via transfer of genetic material in cells or carriers such as cationic liposomes. Such methods are well known in the art and readily adaptable for use in the method described herein. Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83–88, (1993)). Appropriate means for transfection, including viral vectors, chemical transfectants, or physico-mechanical methods such as electroporation and direct diffusion of DNA, are described by, for example, Wolff, J. A., et al., Science, 247, 1465–1468, (1990); and Wolff, J. A. Nature, 352, 815–818, (1991).

As used herein, plasmid or viral vectors are agents that transport the gene into the cell without degradation and include a promoter yielding expression of the gene in the cells into which it is delivered. In a preferred embodiment vectors are derived from either a virus or a retrovirus. Preferred viral vectors are Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Preferred retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors have higher transaction (ability to introduce genes) abilities than do most chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

1. Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In Microbiology-1985, American Society for Microbiology, pp. 229–232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (Science 260:926–932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol and env genes which are involved in the making of the protein coat. It is the gag, pol and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

2. Adenoviral Vectors

The construction of replication-defective adenoviruses has been described (Berkner et al., J. Virology 61:1213–1220 (1987); Massie et al., Mol. Cell. Biol. 6:2872–2883 (1986); Haj-Ahmad et al., J. Virology 57:267–274 (1986); Davidson et al., J. Virology 61:1226–1239 (1987); Zhang "Generation and identification of recombinant adenovirus by liposome-mediated transfection and PCR analysis" BioTechniques 15:868–872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, J. Clin. Invest. 92:1580–1586 (1993); Kirshenbaum, J. Clin. Invest. 92:381–387 (1993); Roessler, J. Clin. Invest. 92:1085–1092 (1993); Moullier, Nature Genetics 4:154–159 (1993); La Salle, Science 259:988–990 (1993); Gomez-Foix, J. Biol. Chem. 267:25129–25134 (1992); Rich, Human Gene Therapy 4:461–476 (1993); Zabner, Nature Genetics 6:75–83 (1994); Guzman, Circulation Research 73:1201–1207 (1993); Bout, Human Gene Therapy 5:3–10 (1994); Zabner, Cell 75:207–216 (1993); Caillaud, Eur. J. Neuroscience 5:1287–1291 (1993); and Ragot, J. Gen. Virology 74:501–507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, Virology 40:462–477 (1970); Brown and Burlingham, J. Virology 12:386–396 (1973); Svensson and Persson, J. Virology 55:442–449 (1985); Seth, et al., J. Virol. 51:650–655 (1984); Seth, et al., Mol. Cell. Biol. 4:1528–1533 (1984); Varga et al., J. Virology 65:6061–6070 (1991); Wickham et al., Cell 73:309–319 (1993)).

A preferred viral vector is one based on an adenovirus which has had the E1 gene removed and these virons are generated in a cell line such as the human 293 cell line. In another preferred embodiment both the E1 and E3 genes are removed from the adenovirus genome.

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

3. Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., Nature, 273: 113 (1978)). The immediate early promoter of the human cytomegalovirus is conveniently obtained as a HindIII E restriction fragment (Greenway, P. J. et al., Gene 18: 355–360 (1982)). Of course, promoters from the host cell or related species also are useful herein.

Enhancer generally refers to a sequence of DNA that functions at no fixed distance from the transcription start site and can be either 5' (Laimins, L. et al., Proc. Natl. Acad. Sci. 78: 993 (1981)) or 3' (Lusky, M. L., et al., Mol. Cell Bio. 3: 1108 (1983)) to the transcription unit. Furthermore, enhancers can be within an intron (Banerji, J. L. et al., Cell 33: 729 (1983)) as well as within the coding sequence itself (Osborne, T. F., et al., Mol. Cell Bio. 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, α-fetoprotein and insulin), typically one will use an enhancer from a eukaryotic cell virus. Preferred examples are the SV40 enhancer on the late side of the replication origin (bp 100–270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

It is preferred that the promoter and/or enhancer region act as a constitutive promoter and/or enhancer to maximize expression of the region of the transcription unit to be transcribed. It is further preferred that the promoter and/or enhancer region be active in all eukaryotic cell types. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contain a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In a preferred embodiment of the transcription unit, the polyadenylation region is derived from the SV40 early polyadenylation signal and consists of about 400 bases. It is also preferred that the transcribed units contain other standard sequences alone or in combination with the above sequences improve expression from, or stability of, the construct.

4. Markers

The viral vectors can include nucleic acid sequence encoding a marker product. This marker product is used to determine if the gene has been delivered to the cell and once delivered is being expressed. Preferred marker genes are the *E. Coli* lacZ gene which encodes β-galactosidase and green fluorescent protein. In some embodiments the marker may be a selectable marker. Examples of suitable selectable markers for mammalian cells are dihydrofolate reductase (DBFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR$^-$ cells and mouse LTK$^-$ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., J. Molec. Appl. Genet. 1: 327 (1982)), mycophenolic acid, (Mulligan, R. C. and Berg, P. Science 209: 1422 (1980)) or hygromycin, (Sugden, B. et al., Mol. Cell. Biol. 5: 410–413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

Forms and Embodiments of the Disclosed Materials

A. Reporter Molecule Labeling

Disclosed are sets of reporter signals comprising a plurality of reporter signals, wherein the reporter signals have a common property, wherein the common property allows the reporter signals to be distinguished and/or separated from molecules lacking the common property, wherein the reporter signals can be altered, wherein the altered forms of each reporter signal can be distinguished from every other altered form of reporter signal.

Disclosed are sets of reporter signals, wherein the reporter signals comprise peptides, wherein the peptides have the same mass-to-charge ratio.

Also disclosed are sets wherein the common property is mass-to-charge ratio, wherein the reporter signals are altered by altering their mass, wherein the altered forms of the reporter signals can be distinguished via differences in the mass-to-charge ratio of the altered forms of reporter signals and sets wherein the mass of the reporter signals is altered by fragmentation.

In addition, sets wherein the set comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signals are also disclosed and sets wherein the set comprises ten or more different reporter signals.

Disclosed are sets of wherein the reporter signals are peptides, oligonucleotides, carbohydrates, polymers, oligopeptides, or peptide nucleic acids.

Also disclosed are sets wherein the reporter signals are associated with, or coupled to, specific binding molecules, wherein each reporter signal is associated with, or coupled to, a different specific binding molecule.

Also disclosed are sets wherein the reporter signals are associated with, or coupled to, decoding tags, wherein each reporter signal is associated with, or coupled to, a different decoding tag.

Also disclosed are sets wherein the peptides have the same amino acid composition.

Also disclosed are sets wherein the peptides have the same amino acid sequence.

Further disclosed are sets wherein each peptide contains a different distribution of heavy isotopes.

Further disclosed are sets wherein each peptide has a different amino acid sequence.

Also disclosed are sets wherein each peptide has a labile or scissile bond in a different location.

Disclosed are kits comprising (a) a set of reporter molecules, wherein each reporter molecule comprises a reporter signal and a decoding tag, wherein the reporter signals have a common property, wherein the common property allows the reporter signals to be distinguished and/or separated from molecules lacking the common property, wherein the reporter signals can be altered, wherein the altered forms of each reporter signal can be distinguished from every other altered form of reporter signal, wherein each different reporter molecule comprises a different decoding tag and a different reporter signal, (b) a set of coding molecules, wherein each coding molecule comprises a specific binding molecule and a coding tag, wherein each specific binding molecule can interact specifically with a different analyte, wherein each coding tag can interact specifically with a different decoding tag.

B. Reporter Signal Protein Labeling

Disclosed are sets of labeled proteins wherein each labeled protein comprises a protein or peptide and a reporter signal attached to the protein or peptide, wherein the reporter signals have a common property, wherein the common property allows the labeled proteins comprising the same protein or peptide to be distinguished and/or separated from molecules lacking the common property, wherein the reporter signals can be altered, wherein the altered forms of each reporter signal can be distinguished from every other altered form of reporter signal, wherein alteration of the reporter signals alters the labeled proteins, wherein altered forms of each labeled protein can be distinguished from every other altered form of labeled protein.

Disclosed are sets of labeled proteins wherein each labeled protein comprises a protein or peptide and a reporter signal attached to the protein or peptide, wherein the labeled proteins have a common property, wherein the common property allows the labeled proteins comprising the same protein or peptide to be distinguished and/or separated from molecules lacking the common property, wherein the reporter signals can be altered, wherein the altered forms of each reporter signal can be distinguished from every other altered form of reporter signal, wherein alteration of the reporter signals alters the labeled proteins, wherein altered forms of each labeled protein can be distinguished from every other altered form of labeled protein.

Disclosed are sets of labeled proteins wherein each labeled protein comprises a protein or peptide and a reporter signal attached to the protein or peptide, wherein the reporter signals can be altered, wherein the altered forms of each reporter signal can be distinguished from every other altered form of reporter signal, wherein alteration of the reporter signals alters the labeled proteins, wherein altered forms of each labeled protein can be distinguished from every other altered form of labeled protein.

Disclosed are sets of labeled proteins wherein each labeled protein comprises a protein or peptide and a reporter signal attached to the protein or peptide, wherein the reporter signals have a common property, wherein the common property allows the labeled proteins comprising the same protein or peptide to be distinguished and/or separated from molecules lacking the common property.

Also disclosed are sets wherein the common property is mass-to-charge ratio, wherein the reporter signals are altered by altering their mass, wherein the altered forms of the labeled proteins can be distinguished via differences in the mass-to-charge ratio of the altered forms of reporter signals and sets wherein the mass of the reporter signals is altered by fragmentation.

Further disclosed are sets wherein alteration of the reporter signals also alters their charge.

Also disclosed are sets wherein the common property is mass-to-charge ratio, wherein the reporter signals are altered by altering their charge, wherein the altered forms of the labeled proteins can be distinguished via differences in the mass-to-charge ratio of the altered forms of reporter signals.

Further disclosed are sets wherein the set comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signals.

Disclosed are sets wherein the set comprises ten or more different reporter signals and sets wherein the reporter signals are peptides, oligonucleotides, carbohydrates, polymers, oligopeptides, or peptide nucleic acids.

In addition, disclosed are sets wherein the reporter signals are coupled to the proteins or peptides.

Disclosed are sets wherein the common property allows the labeled proteins to be distinguished and/or separated from molecules lacking the common property.

Also disclosed are sets wherein the common property is one or more affinity tags associated with the reporter signals and sets wherein one or more affinity tags are associated with the reporter signals.

Disclosed are sets of labeled proteins wherein each labeled protein comprises a protein or a peptide and a reporter signal attached to the protein or peptide, wherein the reporter signals comprise peptides, wherein the reporter signal peptides have the same mass-to-charge ratio.

Also disclosed are sets wherein the reporter signal peptides have the same amino acid composition and sets wherein the reporter signal peptides have the same amino acid sequence.

Disclosed are sets wherein each reporter signal peptide contains a different distribution of heavy isotopes and sets wherein each reporter signal peptide contains a different distribution of substituent groups.

Disclosed are sets wherein each reporter signal peptide has a different amino acid sequence and sets wherein each reporter signal peptide has a labile or scissile bond in a different location.

Disclosed are sets wherein one or more affinity tags are associated with the reporter signals.

Disclosed are kits comprising a set of reporter molecules, wherein each reporter molecule comprises a reporter signal and a coupling tag, wherein the reporter signals have a common property, wherein the common property allows the reporter signals to be distinguished and/or separated from molecules lacking the common property, wherein the reporter signals can be altered, wherein the altered forms of each reporter signal can be distinguished from every other altered form of reporter signal, wherein each different reporter molecule comprises a different coupling tag and a different reporter signal.

Disclosed are labeled proteins wherein the labeled protein comprises a protein or peptide and a reporter signal attached to the protein or peptide, wherein the labeled protein has a common property, wherein the common property allows the labeled protein to be distinguished and/or separated from molecules lacking the common property, wherein the reporter signal can be altered, wherein alteration of the reporter signals alters the labeled protein, wherein altered form of the labeled protein can be distinguished from the unaltered form of labeled protein.

C. Reporter Signal Calibrators

Disclosed are sets of reporter signal calibrators, wherein each reporter signal calibrator shares a common property with a target protein fragment in a set of target protein fragments, wherein the common property allows the target protein fragments and reporter signal calibrators having the common property to be distinguished and/or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators can be altered, wherein the altered form of each reporter signal calibrator can be distinguished from the altered form of the target protein fragment with which the reporter signal calibrator shares a common property.

Also disclosed are sets wherein the set includes a predetermined amount of each reporter signal calibrator and sets wherein the amount of at least two of the reporter signal calibrators is different.

Disclosed are sets wherein the relative amount each reporter signal calibrator is based on the relative amount of each corresponding target protein fragment expected to be in the protein sample.

Also disclosed are sets wherein the amount of each of the reporter signal calibrators is the same.

Disclosed are sets wherein the target protein fragments and reporter signal calibrators can be altered by fragmentation and sets wherein the target protein fragments and reporter signal calibrators can be altered by cleavage at a photocleavable amino acid.

Disclosed are sets wherein the target protein fragments and reporter signal calibrators can be fragmented in a collision cell and sets wherein the target protein fragments can be fragmented at an asparagine-proline bond.

Also disclosed are sets wherein the target protein fragments are produced by protease digestion of the protein sample and sets wherein the target protein fragments are produced by digestion of the protein sample with a serine protease.

Also disclosed are sets wherein the serine protease is trypsin and sets wherein the target protein fragments are produced by cleavage at a photocleavable amino acid.

Disclosed are sets wherein the common property is mass-to-charge ratio, wherein the target protein fragments and reporter signal calibrators can be altered by altering their mass, their charge, or their mass and charge, wherein the altered forms of the target protein fragments and reporter signal calibrators can be distinguished via differences in the mass-to-charge ratio of the altered forms of the target protein fragments and reporter signal calibrators.

Also disclosed are sets wherein the set of reporter signal calibrators comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal calibrators.

Disclosed are sets wherein the set of reporter signal calibrators comprises ten or more different reporter signal calibrators and sets wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

Disclosed are sets wherein the reporter signal calibrators comprise peptides, wherein the peptides have the same mass-to-charge ratio as the corresponding target protein fragments.

Also disclosed are sets wherein the peptides have the same amino acid composition as the corresponding target protein fragments.

Also disclosed are sets wherein the peptides have the same amino acid sequence as the corresponding target protein fragments.

In addition, sets are disclosed wherein each peptide has a different amino acid sequence than the corresponding target protein fragment.

Furthermore, sets are disclosed wherein each peptide has a labile or scissile bond in a different location.

Disclosed are sets wherein the reporter signal calibrators are peptides, oligonucleotides, carbohydrates, polymers, oligopeptides, or peptide nucleic acids and sets wherein at least one of the target protein fragments comprises at least one modified amino acid.

Also disclosed are sets wherein the modified amino acid is a phosphorylated amino acid, an acylated amino acid, or a glycosylated amino acid.

Also disclosed are sets wherein at least one of the target protein fragments is the same as the target protein fragment comprising the modified amino acid except for the modified amino acid.

Disclosed are kits for producing a protein signature, the kit comprising (a) a set of reporter signal calibrators, wherein each reporter signal calibrator shares a common property with a target protein fragment in a set of target protein fragments, wherein the common property allows the target protein fragments and reporter signal calibrators having the common property to be distinguished and/or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators can be altered, wherein the altered form of each reporter signal calibrator can be distinguished from the altered form of the target protein fragment with which the reporter signal calibrator shares a common property, (b) one or more reagents for treating a protein sample to produce protein fragments.

Also disclosed are kits wherein the set of reporter signal calibrators includes a predetermined amount of each reporter signal calibrator.

Also disclosed are kits wherein the amount of at least two of the reporter signal calibrators is different and kits wherein the relative amount each reporter signal calibrator is based on the relative amount of each corresponding target protein fragment expected to be in the protein sample.

Disclosed are kits wherein the amount of each of the reporter signal calibrators is the same and kits wherein the target protein fragments and reporter signal calibrators can be altered by fragmentation.

Also disclosed are kits wherein the target protein fragments and reporter signal calibrators can be altered by cleavage at a photocleavable amino acid and kits wherein the target protein fragments and reporter signal calibrators can be fragmented in a collision cell.

Disclosed are kits wherein the target protein fragments can be fragmented at an asparagine-proline bond and kits wherein the target protein fragments are produced by protease digestion of the protein sample.

Disclosed are kits wherein the target protein fragments are produced by digestion of the protein sample with a serine protease and kits wherein the serine protease is trypsin.

Disclosed are kits wherein the target protein fragments are produced by cleavage at a photocleavable amino acid.

Also disclosed are kits wherein the common property is mass-to-charge ratio, wherein the target protein fragments and reporter signal calibrators can be altered by altering their mass, their charge, or their mass and charge, wherein the altered forms of the target protein fragments and reporter signal calibrators can be distinguished via differences in the mass-to-charge ratio of the altered forms of the target protein fragments and reporter signal calibrators.

Disclosed are kits wherein the set of reporter signal calibrators comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal calibrators.

Also disclosed are kits wherein the set of reporter signal calibrators comprises ten or more different reporter signal calibrators.

Disclosed are kits wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

Also disclosed are kits wherein the reporter signal calibrators comprise peptides, wherein the peptides have the same mass-to-charge ratio as the corresponding target protein fragments.

Disclosed are kits wherein the peptides have the same amino acid composition as the corresponding target protein fragments and kits wherein the peptides have the same amino acid sequence as the corresponding target protein fragments and kits wherein each peptide has a different amino acid sequence than the corresponding target protein fragment.

Disclosed are kits wherein each peptide has a labile or scissile bond in a different location.

Also disclosed are kits wherein the reporter signal calibrators are peptides, oligonucleotides, carbohydrates, polymers, oligopeptides, or peptide nucleic acids.

Disclosed are kits wherein at least one of the target protein fragments comprises at least one modified amino acid and disclosed are kits wherein the modified amino acid is a phosphorylated amino acid, an acylated amino acid, or a glycosylated amino acid.

Also disclosed are kits wherein at least one of the target protein fragments is the same as the target protein fragment comprising the modified amino acid except for the modified amino acid.

Disclosed are mixtures comprising a set of reporter signal calibrators and a set of target protein fragments, wherein each reporter signal calibrator shares a common property with a target protein fragment in the set of target protein fragments, wherein the common property allows the target protein fragments and reporter signal calibrators having the common property to be distinguished and/or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators can be altered, wherein the altered form of each reporter signal calibrator can be distinguished from the altered form of the target protein fragment with which the reporter signal calibrator shares a common property.

Also disclosed are mixtures wherein the set of reporter signal calibrators includes a predetermined amount of each reporter signal calibrator.

Also disclosed are mixtures wherein the amount of at least two of the reporter signal calibrators is different and mixtures wherein the relative amount each reporter signal calibrator is based on the relative amount of each corresponding target protein fragment expected to be in the protein sample.

Disclosed are mixtures wherein the amount of each of the reporter signal calibrators is the same and mixtures wherein the target protein fragments and reporter signal calibrators can be altered by fragmentation.

Disclosed are mixtures wherein the target protein fragments and reporter signal calibrators can be altered by cleavage at a photocleavable amino acid.

Also disclosed are mixtures wherein the target protein fragments and reporter signal calibrators can be fragmented in a collision cell.

Disclosed are mixtures wherein the target protein fragments can be fragmented at an asparagine-proline bond and mixtures wherein the target protein fragments are produced by protease digestion of the protein sample and mixtures wherein the target protein fragments are produced by digestion of the protein sample with a serine protease and mixtures wherein the serine protease is trypsin.

Disclosed are mixtures wherein the target protein fragments are produced by cleavage at a photocleavable amino acid and mixtures wherein the common property is mass-to-charge ratio, wherein the target protein fragments and reporter signal calibrators can be altered by altering their mass, their charge, or their mass and charge, wherein the altered forms of the target protein fragments and reporter signal calibrators can be distinguished via differences in the mass-to-charge ratio of the altered forms of the target protein fragments and reporter signal calibrators.

Disclosed are mixtures wherein the set of reporter signal calibrators comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal calibrators.

Also disclosed are mixtures wherein the set of reporter signal calibrators comprises ten or more different reporter signal calibrators and mixtures wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

Disclosed are mixtures wherein the reporter signal calibrators comprise peptides, wherein the peptides have the same mass-to-charge ratio as the corresponding target protein fragments and mixtures wherein the peptides have the same amino acid composition as the corresponding target protein fragments.

Disclosed are mixtures wherein the peptides have the same amino acid sequence as the corresponding target protein fragments and mixtures wherein each peptide has a different amino acid sequence than the corresponding target protein fragment.

Disclosed are mixtures wherein each peptide has a labile or scissile bond in a different location.

Disclosed are mixtures wherein the reporter signal calibrators are peptides, oligonucleotides, carbohydrates, polymers, oligopeptides, or peptide nucleic acids.

Also disclosed are mixtures wherein at least one of the target protein fragments comprises at least one modified amino acid and mixtures wherein the modified amino acid is a phosphorylated amino acid, an acylated amino acid, or a glycosylated amino acid and mixtures wherein at least one of the target protein fragments is the same as the target protein fragment comprising the modified amino acid except for the modified amino acid.

Disclosed are sets of target protein fragments, wherein each target protein fragment shares a common property with a reporter signal calibrator in a set of reporter signal calibrators, wherein the common property allows the target protein fragments and reporter signal calibrators having the common property to be distinguished and/or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators can be altered, wherein the altered form of each reporter signal calibrator can be distinguished from the altered form of the target protein fragment with which the reporter signal calibrator shares a common property.

Also disclosed are sets wherein the set of reporter signal calibrators includes a predetermined amount of each reporter signal calibrator.

Disclosed are sets wherein the amount of at least two of the reporter signal calibrators is different and sets wherein the relative amount each reporter signal calibrator is based on the relative amount of each corresponding target protein fragment expected to be in the protein sample.

Disclosed are sets wherein the amount of each of the reporter signal calibrators is the same and sets wherein the target protein fragments and reporter signal calibrators can be altered by fragmentation.

Disclosed are sets wherein the target protein fragments and reporter signal calibrators can be altered by cleavage at a photocleavable amino acid and sets wherein the target protein fragments and reporter signal calibrators can be fragmented in a collision cell.

Disclosed are sets wherein the target protein fragments can be fragmented at an asparagine-proline bond.

Also disclosed are sets wherein the target protein fragments are produced by protease digestion of the protein sample.

Also disclosed are sets wherein the target protein fragments are produced by digestion of the protein sample with a serine protease and sets wherein the serine protease is trypsin and sets wherein the target protein fragments are produced by cleavage at a photocleavable amino acid.

Disclosed are sets wherein the common property is mass-to-charge ratio, wherein the target protein fragments and reporter signal calibrators can be altered by altering their mass, their charge, or their mass and charge, wherein the altered forms of the target protein fragments and reporter signal calibrators can be distinguished via differences in the mass-to-charge ratio of the altered forms of the target protein fragments and reporter signal calibrators.

Also disclosed are sets wherein the set of reporter signal calibrators comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal calibrators.

Also disclosed are sets wherein the set of reporter signal calibrators comprises ten or more different reporter signal calibrators.

Also disclosed are sets wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

Disclosed are sets wherein the reporter signal calibrators comprise peptides, wherein the peptides have the same mass-to-charge ratio as the corresponding target protein fragments.

Also disclosed are sets wherein the peptides have the same amino acid composition as the corresponding target protein fragments.

Disclosed are sets wherein the peptides have the same amino acid sequence as the corresponding target protein fragments and sets wherein each peptide has a different amino acid sequence than the corresponding target protein fragment.

Also disclosed are sets wherein each peptide has a labile or scissile bond in a different location.

Disclosed are sets wherein the reporter signal calibrators are peptides, oligonucleotides, carbohydrates, polymers, oligopeptides, or peptide nucleic acids.

Also disclosed are sets wherein at least one of the target protein fragments comprises at least one modified amino acid.

Also disclosed are sets wherein the modified amino acid is a phosphorylated amino acid, an acylated amino acid, or a glycosylated amino acid.

Disclosed are sets wherein at least one of the target protein fragments is the same as the target protein fragment comprising the modified amino acid except for the modified amino acid.

Disclosed are sets of reporter signal calibrators, wherein each reporter signal calibrator shares a common property with a target protein fragment in a set of target protein fragments, wherein the common property allows each of the target protein fragments and reporter signal calibrators having the common property to be distinguished and/or separated from molecules lacking the common property, wherein the target protein fragment and reporter signal calibrator that share a common property correspond to each other, wherein each of the target protein fragments can be altered, wherein the altered forms of each target protein fragment can be distinguished from every other altered form of target protein fragment, wherein each of the reporter signal calibrators can be altered, wherein the altered form of each reporter signal calibrator can be distinguished from the altered form of the target protein fragment with which the reporter signal calibrator shares a common property.

Disclosed are kits for producing a protein signature, the kit comprising (a) a set of reporter signal calibrators, wherein each reporter signal calibrator shares a common property with a target protein fragment in a set of target protein fragments, wherein the common property allows each of the target protein fragments and reporter signal calibrators having the common property to be distinguished and/or separated from molecules lacking the common property, wherein the target protein fragment and reporter signal calibrator that share a common property correspond to each other, wherein each of the target protein fragments can be altered, wherein the altered forms of each target protein fragment can be distinguished from every other altered form of target protein fragment, wherein each of the reporter signal calibrators can be altered, wherein the altered form of each reporter signal calibrator can be distinguished from the altered form of the target protein fragment with which the reporter signal calibrator shares a common property, (b) one or more reagents for treating a protein sample to produce protein fragments.

Disclosed are mixtures comprising a set of reporter signal calibrators and a set of target protein fragments, wherein each reporter signal calibrator shares a common property with a target protein fragment in the set of target protein fragments, wherein the common property allows each of the target protein fragments and reporter signal calibrators having the common property to be distinguished and/or separated from molecules lacking the common property, wherein the target protein fragment and reporter signal calibrator that share a common property correspond to each other, wherein each of the target protein fragments can be altered, wherein the altered forms of each target protein fragment can be distinguished from every other altered form of target protein fragment, wherein each of the reporter signal calibrators can be altered, wherein the altered form of each reporter signal calibrator can be distinguished from the altered form of the target protein fragment with which the reporter signal calibrator shares a common property.

Also disclosed are sets of target protein fragments, wherein each target protein fragment shares a common property with a reporter signal calibrator in a set of reporter signal calibrators, wherein the common property allows each of the target protein fragments and reporter signal calibrators having the common property to be distinguished and/or separated from molecules lacking the common property, wherein the target protein fragment and reporter signal calibrator that share a common property correspond to each other, wherein each of the target protein fragments can be altered, wherein the altered forms of each target protein fragment can be distinguished from every other altered form of target protein fragment, wherein each of the reporter signal calibrators can be altered, wherein the altered form of each reporter signal calibrator can be distinguished from the altered form of the target protein fragment with which the reporter signal calibrator shares a common property.

D. Reporter Signal Fusions

Disclosed are sets of nucleic acid molecules wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Also disclosed are sets wherein each nucleic acid molecule further comprises expression sequences, wherein the expression sequences are operably linked to the nucleotide segment such that the amino acid segment can be expressed.

Also disclosed are sets wherein the expression sequences comprise translation expression sequences and sets wherein the expression sequences further comprise transcription expression sequences.

Disclosed are sets wherein the amino acid segment can be expressed in vitro and sets wherein the amino acid segment can be expressed in vivo and sets wherein the amino acid segment can be expressed in cell culture.

Also disclosed are sets wherein the expression sequences of each nucleic acid molecule are different and sets wherein the different expression sequences are differently regulated and sets wherein the expression sequences are similarly regulated and sets wherein a plurality of the expression sequences are expression sequences of, or derived from, genes expressed as part of the same expression cascade and sets wherein the expression sequences of each nucleic acid molecule are the same and sets wherein the expression sequences are similarly regulated and sets wherein the expression sequences of at least two nucleic acid molecules are different and sets wherein the expression sequences of at least two nucleic acid molecules are the same.

Disclosed are sets wherein each nucleic acid molecule further comprises replication sequences, wherein the replication sequences allow replication of the nucleic acid molecules.

Disclosed are sets wherein the nucleic acid molecules can be replicated in vitro and sets wherein the nucleic acid molecules can be replicated in vivo and sets wherein the nucleic acid molecules can be replicated in cell culture.

Disclosed are sets wherein each nucleic acid molecule further comprises integration sequences, wherein the integration sequences allow integration of the nucleic acid molecules into other nucleic acids.

Also disclosed are sets wherein the nucleic acid molecules can be integrated into a chromosome and sets wherein the nucleic acid molecules can be integrated into a chromosome at a predetermined location.

Also disclosed are sets wherein the nucleic acids molecules are produced by replicating nucleic acids in one or more nucleic acid samples.

Also disclosed are sets wherein the nucleic acids are replicated using pairs of primers, wherein each of the first primers in the primer pairs used to produce the nucleic acid molecules comprises a nucleotide sequence encoding the reporter signal peptide and sets wherein each first primer further comprises expression sequences and sets wherein the nucleotide sequence of each first primer also encodes an epitope tag.

Disclosed are sets wherein each amino acid segment further comprises an epitope tag and sets wherein the epitope tag of each amino acid segment is different and sets wherein the epitope tag of each amino acid segment is the same and sets wherein the epitope tag of at least two amino acid segments are different and sets wherein the epitope tag of at least two amino acid segments are the same.

Disclosed are sets wherein the reporter signal peptide of each amino acid segment is different and sets wherein the reporter signal peptide of each amino acid segment is the same and sets wherein the reporter signal peptide of at least two amino acid segments are different and sets wherein the reporter signal peptide of at least two amino acid segments are the same.

Disclosed are sets wherein the nucleic acid molecules are in cells and sets wherein each nucleic acid molecule is in a different cell and sets wherein each nucleic acid molecule is in the same cell and sets wherein each nucleic acid molecule further comprises expression sequences, wherein the expression sequences are operably linked to the nucleotide segment such that the amino acid segment can be expressed and sets wherein the expression sequences of each nucleic acid molecule are different and sets wherein the expression sequences are similarly regulated and sets wherein a plurality of the expression sequences are expression sequences of, or derived from, genes expressed as part of the same expression cascade.

Disclosed are sets wherein the nucleic acid molecules are integrated into a chromosome of the cell.

Also disclosed are sets wherein the nucleic acid molecules are integrated into the chromosome at a predetermined location.

Disclosed are sets wherein the chromosome is an artificial chromosome.

Disclosed are sets wherein the nucleic acid molecules are, or are integrated into, a plasmid.

Also disclosed are sets wherein the cells are in cell lines.

Also disclosed are sets wherein each nucleic acid molecule is in a different cell line and sets wherein each nucleic acid molecule is in the same cell line.

Disclosed are sets wherein the nucleic acid molecules are in organisms and sets wherein each nucleic acid molecule is in a different organism and sets wherein each nucleic acid molecule is in the same organism and sets wherein each nucleic acid molecule further comprises expression sequences, wherein the expression sequences are operably linked to the nucleotide segment such that the amino acid segment can be expressed and sets wherein the expression sequences of each nucleic acid molecule are different and sets wherein the expression sequences are similarly regulated and sets wherein a plurality of the expression sequences are expression sequences of, or derived from, genes expressed as part of the same expression cascade.

Also disclosed are sets wherein the nucleic acid molecules are integrated into a chromosome of the organism.

Disclosed are sets wherein the nucleic acid molecules are integrated into the chromosome at a predetermined location.

Also disclosed are sets wherein the chromosome is an artificial chromosome.

Disclosed are sets wherein the nucleic acid molecules are, or are integrated into, a plasmid.

Also disclosed are sets wherein each nucleic acid molecule is in a different organism and sets wherein each nucleic acid molecule is in the same organism and sets wherein the nucleic acid molecules are in cells of an organism and sets wherein the nucleic acid molecules are in substantially all of the cells of the organism and sets wherein the nucleic acid molecules are in some of the cells of the organism.

Disclosed are sets wherein the amino acid segments are expressed in substantially all of the cells of the organism and sets wherein the amino acid segments are expressed in some of the cells of the organism.

Disclosed are sets wherein the protein or peptide of interest of each amino acid segment is different and sets wherein the protein or peptide of interest of each amino acid segment is the same and sets wherein the protein or peptide of interest of at least two amino acid segments are different and sets wherein the protein or peptide of interest of at least two amino acid segments are the same and sets wherein the proteins or peptides of interest are related and sets wherein the proteins or peptides of interest are proteins produced in the same cascade and sets wherein the proteins or peptides of interest are proteins expressed under the same conditions and sets wherein the proteins or peptides of interest are proteins associated with the same disease and sets wherein the proteins or peptides of interest are proteins associated with the same cell type and sets wherein the proteins or peptides of interest are proteins associated with the same tissue type and sets wherein the proteins or peptides of interest are proteins in the same enzymatic pathway.

Disclosed are sets wherein the nucleotide segment encodes a plurality of amino acid segments each comprising a reporter signal peptide and a protein or peptide of interest and sets wherein the protein or peptide of interest of at least two of the amino acid segments in one of the nucleotide segments are different and sets wherein the protein or peptide of interest of the amino acid segments in one of the nucleotide segments are different and sets wherein the protein or peptide of interest of at least two of the amino acid segments in each of the nucleotide segments are different and sets wherein the protein or peptide of interest of the amino acid segments in each of the nucleotide segments are different.

Disclosed are sets wherein the set consists of a single nucleic acid molecule and sets wherein the set consists of a single nucleic acid molecule, wherein the nucleic acid molecule comprises a plurality of nucleotide segments each encoding an amino acid segment and sets wherein the amino acid segment comprises a cleavage site near the junction between the reporter signal peptide and the protein or peptide of interest and sets wherein the cleavage site is a trypsin cleavage site and sets wherein the cleavage site is at the junction between the reporter signal peptide and the protein or peptide of interest.

Disclosed are sets wherein each amino acid segment further comprises a self-cleaving segment.

Disclosed are sets wherein the self-cleaving segment is between the reporter signal peptide and the protein or peptide of interest.

Disclosed are sets wherein the self-cleaving segment is an intein segment.

Disclosed are sets of nucleic acid molecules wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein alteration of the reporter signal peptides alters the amino acid segments, wherein the altered form of each amino acid segment can be distinguished from the altered forms of the other amino acid segments.

Disclosed are sets of nucleic acid molecules wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished and/or separated from molecules lacking the common property, wherein the reporter signal peptides can be altered, wherein the altered form of each reporter signal peptide can be distinguished from the altered forms of the other reporter signal peptides.

Disclosed are sets of nucleic acid molecules wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished and/or separated from molecules lacking the common property, wherein the reporter signal peptides can be altered, wherein alteration of the reporter signal peptides alters the amino acid segments, wherein the altered form of each amino acid segment can be distinguished from the altered forms of the other amino acid segments.

Disclosed are sets of nucleic acid molecules wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished and/or separated from molecules lacking the common property, wherein the reporter signal peptides can be altered, wherein the altered form of each reporter signal peptide can be distinguished from the altered forms of the other reporter signal peptides.

Disclosed are sets of nucleic acid molecules wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished and/or separated from molecules lacking the common property, wherein the reporter signal peptides can be altered, wherein alteration of the reporter signal peptides alters the amino acid subsegments, wherein the altered form of each amino acid subsegment can be distinguished from the altered forms of the other amino acid subsegments.

Disclosed are sets of amino acid segments wherein each amino acid segment comprises a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Also disclosed are sets wherein the amino acid segment is a protein or peptide and sets wherein the set consists of a single amino acid segment, wherein the amino acid segment comprises a plurality of reporter signal peptides.

Also disclosed cells comprising a set of nucleic acid molecules wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Disclosed are sets of cells wherein each cell comprises a nucleic acid molecule wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Also disclosed are sets wherein each cell further comprises additional nucleic acid molecules and sets wherein the set consists of a single cell, wherein the cell comprises a plurality of nucleic acid molecules and sets wherein the set consists of a single cell, wherein the cell comprises a set of nucleic acid molecules, wherein the set of nucleic acid molecules consists of a single nucleic acid molecule, wherein the nucleic acid molecule encodes a plurality of nucleic acid segments.

Disclosed are organisms comprising a set of nucleic acid molecules wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Disclosed are sets of organisms each organism comprises a nucleic acid molecule wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides.

Also disclosed are sets wherein each organism further comprises additional nucleic acid molecules and sets wherein the set consists of a single organism, wherein the organism comprises a plurality of nucleic acid molecules and sets wherein the set consists of a single organism, wherein the organism comprises a set of nucleic acid molecules, wherein the set of nucleic acid molecules consists of a single nucleic acid molecule, wherein the nucleic acid molecule encodes a plurality of nucleic acid segments.

Method

The disclosed methods are useful for sensitive detection of one or multiple analytes. In general, the methods involve the use of special label components, referred to as reporter signals, that can be associated with, incorporated into, or otherwise linked to the analytes, or that can be used merely in conjunction with analytes, with no significant association between the analytes and reporter signals. In some embodiments of the methods, the reporter signals (or derivatives of the reporter signals) are detected, thus indicating the presence of the associated analytes. In other embodiments, the analyte (or derivatives of the analytes) are detected along with the reporter signals (or derivatives of the reporter signals).

In some embodiments of the methods, the reporter signals can be altered such that the altered forms of different reporter signals can be distinguished from each other. Reporter signal/analyte conjugates can be altered, generally through alteration of the reporter signal portion of the conjugate, such that the altered forms of different reporter signals, altered forms of different reporter signal/analyte conjugates, or both, can be distinguished from each other. Where the reporter signal or reporter signal/analyte conjugate is altered by fragmentation, any, some, or all of the fragments can be distinguished from each other, depending on the embodiment. For example, where reporter signals fragmented into two parts, either or both parts of the reporter signals can be distinguished. Where reporter signal/analyte conjugates are fragmented into two parts (with the break point in the reporter signal portion), either the reporter signal fragment, the reporter signal/analyte fragment, or both can be distinguished. In some embodiments, only one part of a fragmented reporter signal will be detected and so only this part of the reported signals need be distinguished.

In some embodiments of the methods, sets of reporter signals can be used where two or more of the reporter signals in a set have one or more common properties that allow the reporter signals having the common property to be distinguished and/or separated from other molecules lacking the common property. In other embodiments, sets of reporter signal/analyte conjugates can be used where two or more of the reporter signal/analyte conjugates in a set have one or more common properties that allow the reporter signal/analyte conjugates having the common property to be distinguished and/or separated form other molecules lacking the common property. In still other embodiments, analytes can be fragmented (prior to or following conjugation) to produce reporter signal/analyte fragment conjugates (which can be referred to as fragment conjugates). In such cases, sets of fragment conjugates can be used where two or more of the fragment conjugates in a set have one or more common properties that allow the fragment conjugates having the common property to be distinguished and/or separated from other molecules lacking the common property.

As indicated above, reporter signals conjugated with analytes can be altered while in the conjugate and distinguished. Conjugated reporter signals can also be dissociated or separated, in whole or in part, from the conjugated analytes prior to their alteration. Where the reporter signals are dissociated (in whole or in part) from the analytes, the method can be performed such that the fact of association between the analyte and reporter signal is part of the information obtained when the reporter signal is detected. In other words, the fact that the reporter signal may be dissociated from the analyte for detection does not obscure the information that the detected reporter signal was associated with the analyte.

Reporter signals can also be in conjunction with analytes (such as in mixtures of reporter signals and analytes), where no significant physical association between the reporter signals and analytes occurs; or alone, where no analyte is present. In such cases, where reporter signals are not or are no longer associated with analytes, sets of reporter signals can be used where two or more of the reporter signals in a set have one or more common properties that allow the reporter signals having the common property to be distinguished and/or separated from other molecules lacking the common property.

In preferred embodiments, the disclosed methods involves two basic steps. A filtering, selection, or separation step to separate reporter signals from other molecules that may be present, and a detection step that distinguishes different reporter signals. The reporter signals preferably are distinguished and/or separated from other molecules based on some common property shared by the reporter signals but not present in most (or, preferably, all) other molecules present. The separated reporter signals are then treated and/or detected such that the different reporter signals are distinguishable. Useful forms of the disclosed method involve association of reporter signals with analytes of interest. Detection of the reporter signals results in detection of the corresponding analytes. Thus, the disclosed method is a general technique for labeling and detection of analytes.

A preferred form of the disclosed method involves filtering of isobaric reporter signals from other molecules based on mass-to-charge ratio, fragmentation of the reporter signals to produce fragments having different masses, and detection of the different fragments based on their mass-to-charge ratios. The method is best carried out using a tandem mass spectrometer. There are two types of tandem mass spectrometers, as well as hybrids and combinations of these types: "tandem in space" spectrometers and "tandem in time" spectrometers. Tandem in space spectrometers utilize spatially ordered elements and act upon the ions in turn as the ions pass through each element. Tandem in time spectrometers utilize temporally ordered manipulations on the ions as the ions are contained in a space. In a tandem in space class of instrument, the isobaric reporter signals are first passed through a filtering quadrupole, the reporter signals are fragmented (preferably in a collision cell), and the fragments are distinguished and detected in a time-of-flight (TOF) stage. In such an instrument the sample is ionized in the source (for example, in a MALDI) to produce charged ions. It is preferred that the ionization conditions are such that primarily a singly charged parent ion is produced. A first quadrupole, Q0, is operated in radio frequency (RF) mode only and acts as an ion guide for all charged particles. The second quadrupole, Q1, is operated in RF+DC mode to pass only a narrow range of mass-to-charge ratios (that includes the mass-to-charge ratio of the reporter signals). This quadrupole selects the mass-to-charge ratio of interest. Quadrupole Q2, surrounded by a collision cell, is operated in RF only mode and acts as ion guide. The collision cell surrounding Q2 can be filled to appropriate pressure with a gas to fracture the input ions by collisionally induced dissociation. The collision gas preferably is chemically inert, but reactive gases can also be used. Preferred molecular systems utilize reporter signals that contain scissile bonds, labile bonds, or combinations, such that these bonds will be preferentially fractured in the Q2 collision cell.

The same sample can be analyzed both with and without fragmentation (by operating with and without collision gas), and the results compared to detect shifts in mass-to-charge ratio. Both the unfragmented and fragmented results should give diagnostic peaks, with the combination of peaks both with and without fragmentation confirming the reporter signal (and analyte) involved. Such distinctions are accomplished by using appropriate sets of isobaric reporter signals and allows large scale multiplexing in the detection of analytes.

The disclosed method is particularly well suited to the use of a MALDI-QqTOF mass spectrometer. The method enables highly multiplexed analyte detection, and very high sensitivity. Preferred tandem mass spectrometers are described by Loboda et al., *Design and Performance of a MALDI-QqTOF Mass Spectrometer*, in *47th ASMS Conference*, Dallas, Tx. (1999), Loboda et al., *Rapid Comm. Mass Spectrom.* 14(12):1047–1057 (2000), Shevchenko et al., *Anal. Chem.*, 72: 2132–2142 (2000), and Krutchinsky et al., *J. Am. Soc. Mass Spectrom.*, 11(6):493–504 (2000). In such an instrument the sample is ionized in the source (MALDI, for example) to produce charged ions; it is preferred that the ionization conditions are such that primarily a singly charged parent ion is produced. First and third quadrupoles, Q0 and Q2, will be operated in RF only mode and will act as ion guides for all charged particles, second quadrupole Q1 will be operated in RF+DC mode to pass only a particular mass-to-charge (or, in practice, a narrow mass-to-charge range). This quadrupole selects the mass-to-charge ratio, (m/z), of interest. The collision cell surrounding Q2 can be filled to appropriate pressure with a gas to fracture the input ions by collisionally induced dissociation (normally the collision gas is chemically inert, but reactive gases are contemplated). Preferred molecular systems utilize reporter signals that contain scissile bonds, labile bonds, or combinations, and these bonds will be preferentially fractured in the Q2 collision cell.

A MALDI source is preferred for the disclosed method because it facilitates the multiplexed analysis of samples from heterogeneous environments such as arrays, beads, microfabricated devices, tissue samples, and the like. An example of such an instrument is described by Qin et al., *A practical ion trap mass spectrometer for the analysis of peptides by matrix-assisted laser desorption/ionization.*, Anal. Chem., 68:1784–1791 (1996). For homogeneous assays electrospray ionization (ESI) sources will work very well. Electrospray ionization source instruments interfaced to LC systems are commercially available (for example, QSTAR from PE-SCIEX, Q-TOF from Micromass). It is of note that the ESI sources are operated such that they tend to produce multiply charged ions, doubly charged ions would be most common for ions in the disclosed method. Such doubly charged ions are well known in the art and present no limitation to the disclosed method. TOF analyzers and quadrupole analyzers are preferred detectors over sector analyzers. Tandem in time ion trap systems such as Fourier Transform Ion Cyclotron Resonance (FT-ICR) mass spectrometers also may be used with the disclosed method.

A number of elements contribute to the sensitivity of the disclosed method. The filter quadrupole, Q1, selects a narrow mass-to-charge ratio and discriminates against other mass-to-charge ions, significantly decreasing background from non germane ions. For example, for a sample containing a distribution of mass-to-charges of width 3000 Da, a mass-to-charge transmission window of 2 Da applied to this distribution can improve the signal to noise by at least a factor of 3000/2=1500. Once the parent ion is selected by quadrupole Q1, fragmentation of the parent ion, preferably into a single charged daughter ion, has the advantage over systems which fragment the parent into a number of daughter ions. For example, a parent fragmented into 20 daughter ions will yield signals that are on average $\frac{1}{20}^{th}$ the intensity of the parent ions. For a parent to single daughter system there will not be this signal dilution.

This preferred system for use with the disclosed method has a high duty cycle, and as such good statistics can be collected quickly. For the case where a single set of isobaric parents is used, the multiplexed detection is accomplished without having to scan the filter quadrupole (although such a scan is useful for single pass analysis of a complex protein sample with multiple labeled proteins). Electrospray sources can operate continuously, MALDI sources can operate at several kHz, quadrupoles operate continuously, and time of flight analyzers can capture the entire mass-to-charge region of interest at several kHz repetition rate. Thus, the overall system can acquire thousands of measurements per second. For throughput advantage in a multiplexed assay the time of flight analyzer has an advantage over a quadruple analyzer for the final stage because the time of flight analyzer detects all fragment ions in the same acquisition rather than requiring scanning (or stepping) over the ions with a quadrupole analyzer.

Instrumental improvements including addition of laser ports along the flight path to allow intersection of the proteins with additional laser(s) open additional fragmentation avenues through photochemical and photophysical processes (for example, selective bond cleavage, selective ionization). Use of lasers to fragment the proteins after the filter stage will enable the use of the very high throughput TOF—TOF instruments (50 kHz to 100 kHz systems).

The disclosed method is compatible with techniques involving cleavage, treatment, or fragmentation of a bulk sample in order to simplify the sample prior to introduction into the first stage of a multistage detection system. The disclosed method is also compatible with any desired sample, including raw extracts and fractionated samples.

A. Reporter Molecule Labeling

In one form of the disclosed method, referred to as reporter molecule labeling, reporter signals are associated with analytes to be detected and/or quantitated. For example, a reporter signal can be associated with a specific binding molecule that interacts with the analyte of interest. Such a combination is referred to as a reporter molecule. The specific binding molecule in the reporter molecule interacts with the analyte thus associating the reporter signal with the analyte. Alternatively, a reporter signal can be associated with an analyte indirectly. In this mode, a "coding" molecule containing a specific binding molecule and a coding tag is associated with the analyte (via the specific binding molecule). Alternatively, a coding tag can be coupled or directly associated with the analyte. Then a reporter signal associated with a decoding tag (such a combination is another form of reporter molecule) is associated with the coding molecule through an interaction between the coding tag and the decoding tag. An example of this interaction is hybridization where the coding and decoding tags are complementary nucleic acid sequences. The result is an indirect association of the reporter signal with the analyte. This mode has the advantage that all of the interactions of the reporter signals with the coding molecule can be made chemically and physically similar by using the same types of coding tags and decoding tags for all of the coding molecules and reporter molecules in a set.

The disclosed method increases the sensitivity and accuracy of detection of an analyte of interest. Preferred forms of the disclosed method make use of multistage detection systems to increase the resolution of the detection of molecules having very similar properties. The method involves at least two stages. The first stage is filtration or selection that allows passage or selection of reporter signals (that is, a subset of the molecules present), based upon intrinsic properties of the reporter signals, and discrimination against all other molecules. The subsequent stage(s) further separate (s) and/or detect(s) the reporter signals which were filtered in the first stage. A key facet of this method is that a multiplexed set of reporter signals will be selected by the filter and subsequently cleaved, decomposed, reacted, or otherwise modified to realize the identities and/or quantities of the reporter signals in further stages. There is a correspondence between the specific binding molecule and the detected daughter fragment.

B. Reporter Signal Labeling

Another form of the disclosed method, referred to as reporter signal labeling, involves detection of analytes by detecting a reporter signal, labeled analyte, or both; or by distinguishing different reporter signals, different labeled analytes, or both. Detection of the reporter signals results in detection of the corresponding labeled analytes (where the analytes are labeled with the reporter signals). Detection of the labeled analytes results in detection of the corresponding analytes. Thus, reporter signal labeling is a general technique for labeling, detection, and quantitation of analytes.

In one embodiment, the disclosed method can involve two basic steps. A filtering, selection, or separation step to separate labeled analytes from other molecules that may be present, and a detection step that detects a reporter signal, labeled analyte, or both; or that distinguishes different reporter signals, different labeled analytes, or both. The labeled analytes preferably are distinguished and/or separated from other molecules based on some common property shared by the attached reporter signals but not present in most (or, preferably, all) other molecules present. The labeled analytes can also be distinguished and/or separated from other molecules based on a common property of the labeled analyte as a whole, such as the mass-to-charge ratio of the labeled analyte. The separated labeled analytes are then treated and/or detected in such a way that the different reporter signals, different labeled analytes, or both, are distinguishable.

Reporter signals can be coupled or directly associated with an analyte. For example, a reporter signal can be coupled to an analyte via reactive groups, or a reporter molecule (composed of a specific binding molecule and a reporter signal) can be associated with an analyte. Alternatively, a reporter signal can be associated with an analyte indirectly. In this mode, a "coding" molecule containing a specific binding molecule and a coding tag can be associated with the analyte (via the specific binding molecule). Alternatively, a coding tag can be coupled or directly associated with the analyte. Then a reporter signal associated with a decoding tag (such a combination is another form of reporter molecule) is associated with the coding molecule through an interaction between the coding tag and the decoding tag. An example of this interaction is hybridization where the coding and decoding tags are complementary nucleic acid sequences. The result is an indirect association of the reporter signal with the analyte. This mode has the advantage that all of the interactions of the reporter signals with the coding molecule can be made chemically and physically similar by using the same types of coding tags and decoding tags for all of the coding molecules and reporter molecules in a set.

Reporter signals, or constructs containing reporters signals, also can be attached or coupled to analytes by ligation. Methods for ligation of nucleic acids are well known (see, for example, Sambrook et al. Molecular Cloning: A Laboratory Manual, second edition, 1989, Cold Spring Harbor Laboratory Press, New York.), and efficient protein ligation is known (see, for example, Dawson et al., "Synthesis of proteins by native chemical ligation" Science 266, 776–9 (1994); Hackeng et al., "Chemical synthesis and spontaneous folding of a multidomain protein: anticoagulant microprotein S" Proc Natl Acad Sci USA 97:14074–8 (2000); Dawson et al., "Synthesis of Native Proteins by Chemical Ligation" Ann. Rev. Biochem. 69:923–960 (2000); U.S. Pat. No. 6,184,344; PCT Publication WO 98/28434).

The disclosed method can be used in many modes. For example, the disclosed method can be used to detect a specific analyte (in a specific sample or in multiple samples) or multiple analytes (in a single sample or multiple samples). In each case, the analyte(s) to be detected can be separated either from other, unlabeled analytes or from other molecules lacking a property of the labeled analyte(s) to be detected. For example, analytes in a sample can be generally labeled with reporter signals and some analytes can be separated on the basis of some property of the analytes. For example, the separated analytes could have a certain mass-to-charge ratio (separation based on mass-to-charge ratio will select both labeled and unlabeled analytes having the selected mass-to-charge ratio). As another example, all of the labeled analytes can be distinguished and/or separated from unlabeled molecules based on a feature of the reporter signal such as an affinity tag. Where different affinity tags are used, some labeled analytes can be distinguished and/or separated from others.

In one mode of the disclosed method, multiple analytes in multiple samples are labeled where all of the analytes in a given sample are labeled with the same reporter signal. That is, the reporter signal is used as a general label of the analytes in a sample. Each sample, however, uses a different reporter signal. This allows samples as a whole to be compared with each other. By additionally separating or distinguishing different analytes in the samples, one can easily analyze many analytes in many samples in a single assay. For example, proteins in multiple samples can be labeled with reporter signals as described above, and the samples mixed together. If some or all of the various labeled proteins are separated by, for example, association of the proteins with antibodies on an array, the presence and amount of a given protein in each of the samples can be determined by identifying the reporter signals present at each array element. If the protein corresponding to a given array element was present in a particular sample, then some of the protein associated with that array element will be labeled with the reporter signal used to label that particular sample. Detection of that reporter signal will indicate this. This same relationship holds true for all of the other samples. Further, the amount of reporter signal detected can indicate the amount of a given protein in a given sample, and the simultaneous quantitation of protein in multiple samples can provide a particularly accurate comparison of the levels of the proteins in the various samples.

Optionally, the selection step can be preceded by fractionation step where a subset of analytes, including the analytes that are, or will be, labeled, are separated from other components in a sample. Such a step, although not necessary, can improve the selection step by reducing the number of extraneous molecules present.

A preferred form of the disclosed method involves filtering of isobaric labeled analytes from other molecules based on mass-to-charge ratio, fragmentation of the reporter signals to produce fragments having different mass-to-charge ratios, and detection of the different fragments based on their mass-to-charge ratios. The different fragments will include the fragment of the reporter signal and the fragmented labeled analyte (made up of the analyte and the remaining part of the reporter signal). Either or both may be detected and will be characteristic of the initial labeled analyte. The method is best carried out using a tandem mass spectrometer. In such an instrument the isobaric reporter signals are first filtered, then reporter signals are fragmented (preferably by collision), and the fragments are distinguished and detected.

A preferred form of the disclosed method involves detection of labeled analytes in two or more samples in the same assay. This allows simple and consistent detection of differences between the analytes in the samples. Differential detection is accomplished by labeling the analytes in each sample with a different reporter signal. Preferably, the different reporter signals used for the different samples will make up an isobaric set. In this way, the same labeled analyte in each sample will have the same mass-to-charge ratio as that labeled analyte in a different sample. Upon fragmentation of the reporter signals, however, each of the fragmented labeled analytes in the different samples will have a different mass-to-charge ratio and thus each can be separately detected. All can be detected in the same measurement. This is a tremendous advantage in both time and quality of the data. For example, since the samples are assayed in a single run, there is no need to correct or normalize the results of different samples assayed in different runs. This allows accurate comparisons of the relative amounts of the same analyte in different samples since that are measured in the same run. There would be no differences to cause inconsistency between the samples.

A preferred use for this multiple sample mode of the disclosed method is the analysis of a time series of samples. Such series are useful for detecting changes in a sample or reaction over time. For example, changes in analyte levels in a cell culture over time after addition of a test compound can be assessed. In this mode, different time point samples are labeled with different reporter signals, preferably making up an isobaric set. In this way, the same labeled analyte for each time point will have the same mass-to-charge ratio as that labeled analyte from a different time point. Upon fragmentation of the reporter signals, however, each of the fragmented labeled analytes from the different time points will have a different mass-to-charge ratio and thus each can be separately detected.

The disclosed method can also be used to gather and catalog information about unknown analytes. This analyte discovery mode can easily link the presence or pattern of analytes with their analysis. For example, a sample of labeled analytes can be compared to analytes in one or more other samples. Analytes that appear in one or some samples but not others can be analyzed using conventional techniques. The object analytes will be distinguishable from others by virtue of the disclosed labeling, detection, and quantitation. This mode of the method is preferably carried out using mass spectrometry.

The disclosed method increases the sensitivity and accuracy of detection of analytes of interest. Preferred forms of the disclosed method make use of multistage detection systems to increase the resolution of the detection of molecules having very similar properties. The method can involve at least two stages. The first stage is filtration or selection that allows passage or selection of labeled analytes (that is, a subset of the molecules present), based upon intrinsic properties of the reporter signals (and the attached analytes), and discrimination against all other molecules. The subsequent stage(s) further separate(s) and/or detect(s) the labeled analytes that were filtered in the first stage. A key facet of this method is that a multiplexed set of labeled analytes will be selected by the filter and the attached reporter signals subsequently will be cleaved, decomposed, reacted, or otherwise modified to realize the identities and/or quantities of the fragmented reporter signals and/or the fragmented labeled analytes in further stages. There is a correspondence between the reporter signal and the detected daughter fragment(s).

In some embodiments, the disclosed method allows a complex sample of analytes to be quickly and easily cataloged in a reproducible manner. Such a catalog can be compared with other, similarly prepared catalogs of other analyte samples to allow convenient detection of differences between the samples. The catalogs, which incorporate a significant amount of information about the analyte samples, can serve as fingerprints of the samples which can be used both for detection of related analyte samples and comparison of analyte samples. For example, the presence or identity of specific organisms can be detected by producing a catalog of analytes of the test organism and comparing the resulting catalog with reference catalogs prepared from known organisms. Changes and differences in analyte patterns can also be detected by preparing catalogs of analytes from different cell samples and comparing the catalogs. Comparison of analyte catalogs produced with the disclosed method is facilitated by the fine resolution that can be provided with, for example, mass spectrometry.

Each labeled analyte processed in the disclosed method will result in a signal based on the characteristics of the labeled analyte (for example, the mass-to-charge ratio). A complex analyte sample can produce a unique pattern of signals. It is this pattern that can allow unique cataloging of analyte samples and sensitive and powerful comparisons of the patterns of signals produced from different analyte samples.

The presence, amount, presence and amount, or absence of different labeled analytes forms a pattern of signals that provides a signature or fingerprint of the analytes, and thus of the analyte sample based on the presence or absence of specific analytes or analyte fragments in the sample. For this reason, cataloging of this pattern of signals (that is, the pattern of the presence, amount, presence and amount, or absence of labeled analytes) is an embodiment of the disclosed method that is of particular interest.

Catalogs can be made up of, or be referred to, as, for example, a pattern of labeled analytes, a pattern of the presence of labeled analytes, a catalog of labeled analytes, or a catalog of analytes in a sample. The information in the catalog is preferably in the form of mass-to-charge information or compositional information. Catalogs can also contain or be made up of other information derived from the information generated in the disclosed method (for example, the identity of the analytes detected), and can be combined with information obtained or generated from any other source. The informational nature of catalogs produced using the disclosed method lends itself to combination and/or analysis using known bioinformatics systems and methods.

Such catalogs of analyte samples can be compared to a similar catalog derived from any other sample to detect similarities and differences in the samples (which is indicative of similarities and differences in the analytes in the samples). For example, a catalog of a first analyte sample can be compared to a catalog of a sample from the same type of organism as the first analyte sample, a sample from the same type of tissue as the first analyte sample, a sample from the same organism as the first analyte sample, a sample obtained from the same source but at time different from that of the first analyte sample, a sample from an organism different from that of the first analyte sample, a sample from a type of tissue different from that of the first analyte sample, a sample from a strain of organism different from that of the first analyte sample, a sample from a species of organism different from that of the first analyte sample, or a sample from a type of organism different from that of the first analyte sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same analyte, or the same analyte sample. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or $E.$ $coli$ and Salmonella. A different type of tissue refers to tissues of different types such as liver and kidney, or skin and brain. A different strain or species of organism refers to organisms differing in their species or strain designation as those terms are understood in the art.

When comparing catalogs of analytes obtained from related samples, it is possible to identify the presence of a subset of correlated pairs of labeled analytes and their altered forms. The disclosed method can be used to detect the original labeled analytes (and determine characteristics of them) and the altered form of the labeled analytes. This pair of detected analytes will be characteristic of the analyte that is labeled and the specific reporter signal used (although not necessarily unique).

1. Reporter Signal Protein Labeling

One form of reporter signal labeling, referred to as reporter signal protein labeling, involves detection of proteins by detecting a reporter signal, labeled protein, or both; or by distinguishing different reporter signals, different labeled proteins, or both. Detection of the reporter signals results in detection of the corresponding labeled proteins. Detection of the labeled proteins results in detection of the corresponding proteins. Thus, the disclosed method is a general technique for labeling, detection, and quantitation of proteins.

In one embodiment, the disclosed method can involve two basic steps. A filtering, selection, or separation step to separate labeled proteins from other molecules that may be present, and a detection step that detects a reporter signal, labeled protein, or both; or that distinguishes different reporter signals, different labeled proteins, or both. The labeled proteins preferably are distinguished and/or separated from other molecules based on some common property shared by the attached reporter signals but not present in most (or, preferably, all) other molecules present. The labeled proteins can also be distinguished and/or separated from other molecules based on a common property of the labeled protein as a whole, such as the mass-to-charge ratio of the labeled protein. The separated labeled proteins are then treated and/or detected in such a way that the different reporter signals, different labeled proteins, or both, are distinguishable.

The disclosed method can be used in many modes. For example, the disclosed method can be used to detect a specific protein (in a specific sample or in multiple samples) or multiple proteins (in a single sample or multiple samples). In each case, the protein(s) to be detected can be separated either from other, unlabeled proteins or from other molecules lacking a property of the labeled protein(s) to be detected. For example, proteins in a sample can be generally labeled with reporter signals and some proteins can be separated on the basis of some property of the proteins. For example, the separated proteins could have a certain mass-to-charge ratio (separation based on mass-to-charge ratio will select both labeled and unlabeled proteins having the selected mass-to-charge ratio). As another example, all of the labeled proteins can be distinguished and/or separated from unlabeled molecules based on a feature of the reporter signal such as an affinity tag. Where different affinity tags are used, some labeled proteins can be distinguished and/or separated from others.

Optionally, the selection step can be preceded by fractionation step where a subset of proteins, including the proteins that are, or will be, labeled, are separated from other components in a sample. For example, proteins having an SH2 domain can be separated from other proteins in a cell sample prior to the selection step. Such a step, although not necessary, can improve the selection step by reducing the number of extraneous molecules present.

A preferred form of the disclosed method involves filtering of isobaric labeled proteins from other molecules based on mass-to-charge ratio, fragmentation of the reporter signals to produce fragments having different mass-to-charge ratios, and detection of the different fragments based on their mass-to-charge ratios. The different fragments will include the fragment of the reporter signal and the fragmented labeled protein (made up of the protein and the remaining part of the reporter signal). Either or both may be detected and will be characteristic of the initial labeled protein. The method is best carried out using a tandem mass spectrometer. In such an instrument the isobaric reporter signals are first filtered, then reporter signals are fragmented (preferably by collision), and the fragments are distinguished and detected.

The same sample can be analyzed both with and without fragmentation (by operating with and without collision gas), and the results compared to detect shifts in mass-to-charge ratio. Both the unfragmented and fragmented results should give diagnostic peaks, with the combination of peaks both with and without fragmentation confirming the identity of the protein (and reporter signal) involved. Such distinctions are accomplished by using appropriate sets of isobaric reporter signals and allows large scale multiplexing in the detection of proteins.

A preferred form of the disclosed method involves detection of labeled proteins in two or more samples in the same assay. This allows simple and consistent detection of differences between the proteins in the samples. Differential detection is accomplished by labeling the proteins in each sample with a different reporter signal. Preferably, the different reporter signals used for the different samples will make up an isobaric set. In this way, the same labeled protein in each sample will have the same mass-to-charge ratio as that labeled protein in a different sample. Upon fragmentation of the reporter signals, however, each of the fragmented labeled proteins in the different samples will have a different mass-to-charge ratio and thus each can be separately detected. All can be detected in the same measurement. This is a tremendous advantage in both time and quality of the data. For example, since the samples are assayed in a single run, there is no need to correct or normalize the results of different samples assayed in different runs. This allows accurate comparisons of the relative amounts of the same protein or peptide in different samples since that are measured in the same run. There would be no differences to cause inconsistency between the samples.

A preferred use for this multiple sample mode of the disclosed method is the analysis of a time series of samples. Such series are useful for detecting changes in a sample or reaction over time. For example, changes in expressed proteins in a cell culture over time after addition of a test compound can be assessed. In this mode, different time point samples are labeled with different reporter signals, preferably making up an isobaric set. In this way, the same labeled protein for each time point will have the same mass-to-charge ratio as that labeled protein from a different time point. Upon fragmentation of the reporter signals, however, each of the fragmented labeled proteins from the different time points will have a different mass-to-charge ratio and thus each can be separately detected.

The disclosed method can also be used to gather and catalog information about unknown proteins. This protein discovery mode can easily link the presence or pattern of proteins with their analysis. For example, a sample of labeled proteins can be compared to proteins in one or more other samples. Proteins that appear in one or some samples but not others can be analyzed for composition and/or sequence using conventional techniques. The object proteins will be distinguishable from others by virtue of the disclosed labeling, detection, and quantitation. This mode of the disclosed method is especially useful as an aid to functional genomics or proteomics since proteins discovered to differ between samples can be characterized. This mode of the method is preferably carried out using mass spectrometry.

The disclosed method increases the sensitivity and accuracy of detection of proteins of interest. Preferred forms of the disclosed method make use of multistage detection systems to increase the resolution of the detection of molecules having very similar properties. The method involves at least two stages. The first stage is filtration or selection that allows passage or selection of labeled proteins (that is, a subset of the molecules present), based upon intrinsic properties of the reporter signals (and the attached proteins), and discrimination against all other molecules. The subsequent stage(s) further separate(s) and/or detect(s) the labeled proteins that were filtered in the first stage. A key facet of this method is that a multiplexed set of labeled proteins will be selected by the filter and the attached reporter signals subsequently will be cleaved, decomposed, reacted, or otherwise modified to realize the identities and/or quantities of the fragmented reporter signals and/or the fragmented labeled proteins in further stages. There is a correspondence between the reporter signal and the detected daughter fragment(s).

In some embodiments, the disclosed method allows a complex sample of proteins and/or peptides to be quickly and easily cataloged in a reproducible manner. Such a catalog can be compared with other, similarly prepared catalogs of other protein samples to allow convenient detection of differences between the samples. The catalogs, which incorporate a significant amount of information about the protein samples, can serve as fingerprints of the samples which can be used both for detection of related protein samples and comparison of protein samples. For example, the presence or identity of specific organisms can be detected by producing a catalog of proteins and/or peptides of the test organism and comparing the resulting catalog with reference catalogs prepared from known organisms. Changes and differences in protein expression patterns can also be detected by preparing catalogs of proteins from different cell samples and comparing the catalogs. Comparison of protein catalogs produced with the disclosed method is facilitated by the fine resolution that can be provided with, for example, mass spectrometry.

Each labeled protein processed in the disclosed method will result in a signal based on the characteristics of the labeled protein (for example, the mass-to-charge ratio). A complex protein sample can produce a unique pattern of signals. It is this pattern that can allow unique cataloging of protein samples and sensitive and powerful comparisons of the patterns of signals produced from different protein samples.

The presence, amount, presence and amount, or absence of different labeled proteins forms a pattern of signals that provides a signature or fingerprint of the proteins, and thus of the protein sample based on the presence or absence of specific proteins, peptides or protein fragments in the sample. For this reason, cataloging of this pattern of signals (that is, the pattern of the presence, amount, presence and amount, or absence of labeled proteins) is an embodiment of the disclosed method that is of particular interest.

Catalogs can be made up of, or be referred to, as, for example, a pattern of labeled proteins, a pattern of the presence of labeled proteins, a catalog of labeled proteins, a catalog of proteins in a sample, or a catalog of amino acid sequences in a sample. The information in the catalog is preferably in the form of mass-to-charge information, compositional information (that is, the composition of amino acids) or, more preferably, in the form of amino acid sequences. Catalogs can also contain or be made up of other information derived from the information generated in the disclosed method (for example, the identity of the proteins detected), and can be combined with information obtained or generated from any other source. The informational nature of catalogs produced using the disclosed method lends itself to combination and/or analysis using known bioinformatics systems and methods.

Such catalogs of protein samples can be compared to a similar catalog derived from any other sample to detect similarities and differences in the samples (which is indicative of similarities and differences in the proteins in the samples). For example, a catalog of a first protein sample can be compared to a catalog of a sample from the same type of organism as the first protein sample, a sample from the same type of tissue as the first protein sample, a sample from the same organism as the first protein sample, a sample obtained from the same source but at time different from that of the first protein sample, a sample from an organism different from that of the first protein sample, a sample from a type of tissue different from that of the first protein sample, a sample from a strain of organism different from that of the first protein sample, a sample from a species of organism different from that of the first protein sample, or a sample from a type of organism different from that of the first protein sample.

When comparing catalogs of proteins obtained from related samples, it is possible to identify the presence of a subset of correlated pairs of labeled proteins and their altered forms. The disclosed method can be used to detect the original labeled proteins (and determine characteristics of them) and the altered form of the labeled proteins. This pair of detected proteins will be characteristic of the protein that is labeled and the specific reporter signal used (although not necessarily unique).

C. Reporter Signal Calibration

In another form of the method, referred to as reporter signal calibration (RSC), a form of reporter signals referred to as reporter signal calibrators are mixed with analytes or analyte fragments, the reporter signal calibrators and the analytes or analyte fragments are altered, and the altered forms of the reporter signal calibrators and altered forms of the analytes or analyte fragments are detected. Reporter signal calibrators are useful as standards for assessing the amount of analytes present. That is, one can add a known amount of a reporter signal calibrator in order to assess the amount of analyte present comparing the amount of altered analyte or analyte fragment detected with the amount of altered reporter signal calibrator detected and calibrating these amounts with the known amount of reporter signal calibrator added (and thus the predicted amount of altered reporter signal calibrator).

The disclosed reporter signal calibration method generates, with high sensitivity, unique analyte signatures related to the relative abundance of different analytes in tissue, microorganisms, or any other biological sample. The disclosed method allows one, for example, to define the status of a cell or tissue by identifying and measuring the relative concentrations of a small but highly informative subset of analytes. Such as measurement is known as an analyte signature. Analyte signatures are useful, for example, in the diagnosis, grading, and staging of cancer, in drug screening, and in toxicity testing.

In some embodiments, each analyte or analyte fragment can share one or more common properties with at least one reporter signal calibrator such that the reporter signal calibrators and analytes or analyte fragments having the common property can be distinguished and/or separated from other molecules lacking the common property.

In some embodiments, reporter signal calibrators and analytes and analyte fragments can be altered such that the altered form of an analyte or analyte fragment can be distinguished from the altered form of the reporter signal calibrator with which the analyte or analyte fragment shares a common property. In some embodiments, the altered forms of different reporter signal calibrators can be distinguished from each other. In some embodiments, the altered forms of different analytes or analyte fragments can be distinguished from each other.

In some embodiments of reporter signal calibration, the analyte or analyte fragment is not altered and so the altered reporter signal calibrators and the analytes or analyte fragments are detected. In this case, the analyte or analyte fragment can be distinguished from the altered form of the reporter signal calibrator with which the analyte or analyte fragment shares a common property.

In some embodiments the analyte or analyte fragment may be a reporter signal or a fragment of a reporter signal. In this case, the reporter signal calibrators can serve as calibrators for the amount of reporter signal detected.

Reporter signal calibration is preferably used in connection with proteins and peptides (as the analytes). This form of reporter signal calibration is referred to as reporter signal protein calibration. Reporter signal protein calibration is useful, for example, for producing protein signatures of protein samples. As used herein, a protein signature is the presence, absence, amount, or presence and amount of a set of proteins or protein surrogates.

In some embodiments of reporter signal protein calibration, the presence of labile, scissile, or cleavable bonds in the proteins to be detected can be exploited. Peptides, proteins, or protein fragments (collectively referred to, for convenience, as protein fragments in the remaining description) containing such bonds can be altered by fragmentation at the bond. In this way, reporter signal calibrators having a common property (such as mass-to-charge ratio) with the protein fragments can be used and the altered forms of the reporter signal calibrators and the altered (that is, fragmented) forms of the protein fragments can be detected and distinguished. In this regard, although the protein fragments share a common property with their matching reporter signal calibrators, the altered forms of the reporter signal calibrators and altered forms of protein fragments can be distinguished (because, for example, the altered forms have different properties, such as different mass-to-charge ratios).

The disclosed reporter signal protein calibration method generates, with high sensitivity, unique protein signatures related to the relative abundance of different proteins in tissue, microorganisms, or any other biological sample. The disclosed method allows one, for example, to define the status of a cell or tissue by identifying and measuring the relative concentrations of a small but highly informative subset of proteins. Such as measurement is known as a protein signature. Protein signatures are useful, for example, in the diagnosis, grading, and staging of cancer, in drug screening, and in toxicity testing.

As an example of reporter signal protein calibration, a protein sample of interest can be digested with a serine protease, preferably trypsin. The digest generates a complex mixture of protein fragments. Among these protein fragments, there will exist a subset (approximately one protein fragment among every 400) that contains the dipeptide Asp-Pro. This dipeptide sequence is uniquely sensitive to fragmentation during mass spectrometry, an thus produces a high yield of ions in fragmentation mode. Since the human proteome consists of at least 2,000,000 distinct tryptic peptides, the number of protein fragments containing the Asp-Pro sequence is of the order of 5,000. Since some of these may exist as phosphopeptides or other modified forms, the number may be even higher. This number is sufficiently high to permit the selection of a subset (perhaps 50 to 100 or so) of fragmentable protein fragments that is suitable for generating a highly informative protein signature. Peptides that contain the Asp-Pro dipeptide sequence, peptides that contain amino acids that are modified by phosphorylation inside the cell, or peptides that contain an internal methionine are particularly preferred for use in reporter signal calibration. Alternatively, tryptic peptides terminating in arginine may be modified by reaction with acetylacetone (pentane-2,4-dione) to increase the frequency of fragment ions (Dikler et al., J Mass Spectrom 32:1337–49 (1997)). Selection of the subsets of protein fragments can be performed using bioinformatics in order to maximize the information content of the protein signatures.

For this form of reporter signal calibration, the protein digest can be mixed with a specially designed set of reporter signal calibrators, and then can be analyzed using tandem mass spectrometry. In the case of a tandem in space instrument (for example, Q-Tof™ from Micromass), using first quadrupole settings for single-ion filtering (defined by the molecular mass of each unique fragment, which can be obtained from sequence data), followed by a collision stage for ion fragmentation, and finally TOF spectrometry of the peptide fragments (generated by cleavage at fragile bonds, such as Asp-Pro, bonds involving a phosphorylated amino-acid, or bonds adjacent to an oxidized amino-acid such as methionine sulfoxide, Smith et al., Free Radic Res. 26:103–11 (1997)) that arise from the original single-ion. In the second stage, signal to noise of the TOF measurement is much larger than in a conventional MS experiment. In general, one reporter signal calibrator can be used for each protein fragment in the sample that will be used to make up the protein signature (such protein fragments are referred to as signature protein fragments), and each is designed to fragment in an easily detectable pattern of masses, distinct from the fragment masses of the unfragmented signature protein fragments. The quadrupole filtering settings are then varied in sequence over a range of values (fifty, for example), corresponding to the masses of each of the protein fragments previously chosen to comprise the protein signature (that is, the signature protein fragments). At each filtered mass setting, there will be two types of signals detectable by TOF after fragmentation, one set derived from the tryptic peptide (that is, the original protein fragment), and another set corresponding to the reporter signal calibrator. The reporter signal calibrator permits one to calculate relative abundance for each of the signature protein fragments. These relative abundance ratios, determined for a given sample, constitute the protein signature. The detection limit of the tandem mass spectrometer in MS/MS mode, is remarkably good, perhaps of the order of 500 molecules of peptide. This level of detection is approximately 1,000 times better than that for MALDI-TOF mass spectrometry, and should permit the generation of protein signatures from single cells.

As can be seen, for this form of reporter signal calibration, the availability of the sequence of the entire human genome, as well as the genomes of many other organisms, can facilitate the identification of protein fragments that are unique in the context of all known proteins. That is, the sequence information can be used to identify peptides that will be generated in a protein signature and guide selection of reporter signal calibrators.

D. Reporter Signal Fusions

In another form of the disclosed method, referred to as reporter signal fusions (RSF), reporter signal peptides are joined with a protein or peptide of interest in a single amino acid segment, and the reporter signal peptide, reporter signal fusion, altered forms of the reporter signal peptide, and/or altered forms of the reporter signal fusion can be detected.

The disclosed method provides sensitive monitoring and detection of the proteins and peptides to which reporter signal peptides are fused. In particular, the method provides sensitive and multiplex detection of expression of particular proteins and peptides of interest, and/or of the genes, vectors, and expression constructs encoding the proteins and peptides of interest.

The disclosed method can use cells, cell lines, and organisms that have particular protein(s), gene(s), vector(s), and/ or expression sequence(s) labeled (that is, associated with or involved in) reporter signal fusions. For example, a set of nucleic acid constructs, each encoding a reporter signal fusion with a different reporter signal peptide, can be used to uniquely label a set of cells, cell lines, and/or organisms. Processing, in the disclosed method, of a sample from any of the labeled sources can result in a unique altered form of the reporter signal peptide (or the amino acid segment or an amino acid subsegment) for each of the possible sources that can be distinguished from the other altered forms. Detection of a particular altered form identifies the source from which it came. As a more specific example, a genetically modified plant line (for example, a Roundup resistant corn line) into which a nucleic acid construct encoding a reporter signal fusion has been introduced can be identified by detecting the reporter signal fusion.

The disclosed method can also be used to assess the state and/or expression of particular pathways, regulatory cascades, and other suites of genes, proteins, vectors, and/or expressions sequences. By using reporter signal fusions to "label" such pathways, cascades, etc. within the same cell, cell line, or organism, or across a set of cells, cell lines, or organisms, the pathways, cascades and other systems can be assessed in a single assay and/or compared across cells, cell lines, or organisms. For example, nucleic acid segments encoding reporter signal fusions can be associated with endogenous expression sequences of interest, endogenous genes of interest, exogenous expression sequences of interest, exogenous genes of interest, or a combination, and the expression of the genes and/or expression sequences assessed by detecting the reporter signal peptides and/or reporter signal fusions. Many other modes of the method are possible, a number of which are described in the illustrations below. In particular, the disclosed reporter signal fusions can be used in the disclosed method for purposes analogous to any purpose that green fluorescent protein and green fluorescent protein fusions are used. However, the disclosed method can make use of reporter signal fusions in many more ways and for more useful purposes than green fluorescent protein at least because of the ability to multiplex the disclosed reporter signal fusions.

Nucleic acid sequences encoding reporter signal peptides can be engineered into particular exons of a gene. This would be the normal situation when the gene encoding the protein to be fused contains introns, although sequence encoding a reporter signal peptide can be split between different exons to be spliced together. Placement of nucleic acid sequences encoding reporter signal peptides into particular exons is useful for monitoring and analyzing alternative splicing of RNA. The appearance of a reporter signal peptide in the final protein indicates that the exon encoding the reporter signal peptide was spliced into the mRNA.

The disclosed method can provide sensitive detection of one or multiple proteins (that is, proteins to which reporter signal peptides are fused). In the method, proteins fused with reporter signal peptides are analyzed using the reporter signal peptides to distinguish the reporter signal fusions. Detection of the reporter signal peptides indicates the presence of the corresponding protein(s). The detected protein(s) can then be analyzed using known techniques. The reporter signal fusions provide a unique protein/label composition that can specifically identify the protein(s). This is accomplished through the use of the specialized reporter signal peptides as the labels.

In the method, reporter signal fusions can be fragmented, such as by protease digestion, prior to analysis. An expression sample to be analyzed can also be subjected to fractionation or separation to reduce the complexity of the samples. Fragmentation and fractionation can also be used together in the same assay. Such fragmentation and fractionation can simplify and extend the analysis of the expression.

In the method, reporter signal peptides can be fragmented, decomposed, reacted, derivatized, or otherwise modified, preferably in a characteristic way. This allows a protein to which the reporter signal peptide is fused to be identified by detection of one or more of the products of the reporter signal fusion following fragmentation, decomposition, reaction, derivatization, or other modification of the reporter signal peptide. The protein can also be identified by the correlated detection of the reporter signal fusion and one or more of the products of the reporter signal fusion following fragmentation, decomposition, reaction, derivatization, or other modification of the reporter signal peptide. The alteration of the reporter signal peptide will alter the reporter signal fusion in a characteristic and detectable way. Together, the detection of a characteristic reporter signal fusion and a characteristic product of (that is, altered form of) the reporter signal fusion can uniquely identify the protein (although the altered form alone can be detected, if desired). In this way, using the disclosed method, expression of one or more proteins can be detected, either alone or together (for example, in a multiplex assay). Further, expression of one or more proteins in one or more samples can be detected in a multiplex manner. Preferably, for mass spectrometry reporter signals, the reporter signal peptides are fragmented to yield fragments of similar charge but different mass.

Preferably, the reporter signal peptides are fragmented to yield fragments of similar charge but different mass. This allows each reporter signal fusion (and/or each reporter signal peptide) in a set to be distinguished by the different mass-to-charge ratios of the fragments of (that is, altered forms of) the reporter signal peptides. This is possible since the fragments of the different reporter signal peptides (or the fragments of the reporter signal fusions) can be designed to have different mass-to-charge ratios. In the disclosed method, this allows each reporter signal fusion to be distinguished by the mass-to-charge ratios of the reporter signal fusions after fragmentation of the reporter signal peptide.

Alteration of reporter signals peptides in reporter signal fusions can produce a variety of altered compositions. Any or all of these altered forms can be detected. For example, the altered form of the reporter signal peptide can be detected, the altered form of the amino acid segment (which contains the reporter signal peptide) can be detected, the altered form of a subsegment of the amino acid segment can be detected, or a combination of these can be detected. Where the reporter signal peptide is altered by fragmentation, the result generally will be a fragment of the reporter signal peptide and an altered form of the amino acid segment containing the protein or peptide of interest and a portion of the reporter signal peptide (that is, the portion not in the reporter signal peptide fragment).

The protein or peptide of interest also can be fragmented. The result would be a subsegment of the amino acid segment. The amino acid subsegment would contain the reporter signal peptide and a portion of the protein or peptide of interest. When the reporter signal peptide in an amino acid subsegment is altered (which can occur before, during, or after fragmentation of the amino acid segment), the result is an altered form of the amino acid subsegment (and an altered form of the reporter signal peptide). This altered form of amino acid subsegment can be detected. Where the reporter signal peptide is altered by fragmentation, the result generally will be a fragment of the reporter signal peptide and an altered form of (that is, fragment of) the amino acid subsegment. In this case, the altered form of the amino acid subsegment will contain a portion of the protein or peptide of interest and a portion of the reporter signal peptide (that is, the portion not in the reporter signal peptide fragment).

Cells, cell lines, organisms, and expression of genes and proteins can be detected using the disclosed reporter signal fusions in a variety of ways. For example, the protein and attached reporter signal peptide can be detected together, one or more peptides of the protein and the attached reporter signal peptide(s) can be detected together, the fragments of the reporter signal peptide can be detected, or a combination. Preferred detection involves detection of the reporter signal fusion both before and after fragmentation of the reporter signal peptide.

A preferred form of the disclosed method involves correlated detection of the reporter signal peptides both before and after fragmentation of the reporter signal peptide. This allows genes, proteins, vectors, and expression constructs "labeled" with a reporter signal peptide to be detected and identified via the change in the reporter signal fusion and/or reporter signal peptide. That is, the nature of the reporter signal fusion or reporter signal peptide detected (non-fragmented versus fragmented) identifies the gene, protein, vector, or nucleic acid construct from which it was derived. Where the reporter signal fusions and reporter signal peptides are detected by mass-to-charge ratio, the change in mass-to-charge ratio between fragmented and non-fragmented samples provides the basis for comparison. Such mass-to-charge ratio detection is preferably accomplished with mass spectrometry.

As an example, a fusion between a protein of interest and a reporter signal peptide designed as a mass spectrometry label can be expressed. The reporter signal fusion can be subjected to tryptic digest followed by mass spectrometry of the resulting materials. A peak corresponding to the tryptic fragment containing the reporter signal peptide will be detected. Fragmentation of the reporter signal peptide in a collision cell in the mass spectrometer would result in a shift in the peak corresponding to the loss of a portion of the attached reporter signal peptide, the appearance of a peak corresponding to the lost fragment, or a combination of both events. Significantly, the shift observed will depend on which reporter signal peptide is fused to the protein since different reporter signal peptides will, by design, produce fragments with different mass-to-charge ratios. The combination event of detection of the parent mass-to-charge (with no collision gas) and the mass-to-charge corresponding to the loss of the fragment from the reporter signal peptide (with collision gas) indicates a reporter signal fusion (thus indicating expression of the reporter signal fusion and of the gene, vector, or construct encoding it).

A powerful form of the disclosed method is use of reporter signal fusions to assay multiple samples (for example, time series assays or other comparative analyses). Knowledge of the temporal response of a biological system following perturbation is a very powerful process in the pursuit of understanding the system. To follow the temporal response a sample of the system is obtained (for example, cells from a cell culture, mice initially synchronized and sacrificed) at determined times following the perturbation. Knowledge of spatial protein profiles (for example, relative position within a tissue section) is a very powerful process in the pursuit of understanding the biological system.

The reporter signal fusions are preferably detected using mass spectrometry which allows sensitive distinctions between molecules based on their mass-to-charge ratios. A set of isobaric reporter signal peptides or reporter signal fusions can be used for multiplex labeling and/or detection of the expression of many genes, proteins, vectors, expression constructs, cells, cell lines, and organisms since the reporter signal peptide fragments can be designed to have a large range of masses, with each mass individually distinguishable upon detection. Where the same gene, protein, vectors, expression construct, cell, cell line, or organism (or the same type of gene, protein, vector, expression construct, cell, cell line, or organism) is labeled with a set of reporter signal fusions that are isobaric or that include isobaric reporter signal peptides (by, for example, "labeling" the same gene, protein, vector, expression construct, cell, cell line, or organism in different samples), the set of reporter signal fusions or reporter signal peptides that results will also be isobaric. Fragmentation of the reporter signal peptides will split the set of reporter signal peptides into individually detectable reporter signal fusion fragments and reporter signal peptide fragments of characteristically different mass.

A preferred form of the disclosed method involves filtering of isobaric reporter signal fusions or reporter signal peptides from other molecules based on mass-to-charge ratio, fragmentation of the reporter signal peptides to produce fragments having different masses, and detection of the different fragments based on their mass-to-charge ratios. The method is best carried out using a tandem mass spectrometer as described elsewhere herein.

Nucleic acid sequences and segments encoding reporter signal fusions can be expressed in any suitable manner. For example, the disclosed nucleic acid sequences and nucleic acid segments can be expressed in vitro, in cells, and/or in cells in organism. Many techniques and systems for expression of nucleic acid sequences and proteins are known and can be used with the disclosed reporter signal fusions. For example, many expression sequences, vector systems, transformation and transfection techniques, and transgenic organism production methods are known and can be used with the disclosed reporter signal peptide method and compositions.

For example, kits for the in vitro transcription/translation of DNA constructs containing promoters and nucleic acid sequence to be transcribed and translated are known (for example, PROTEINscript-PRO™ from Ambion, Inc. Austin Tex.; Wilkinson (1999) "Cell-Free And Happy: In Vitro Translation And Transcription/Translation Systems", The Scientist 13[13]:15, Jun. 21, 1999). Such constructs can be used in the genomic DNA of an organism, in a plasmid or other vector that may be transfected into an organism, or in in vitro systems. For example, constructs containing a promoter sequence and a nucleic acid sequence that, following transcription and translation, results in production of green fluorescence protein or luciferase as a reporter/marker in in vivo systems are known (for example, Sawin and Nurse, "Identification of fission yeast nuclear markers using random polypeptide fusions with green fluorescent protein." Proc Natl Acad Sci USA 93(26):15146–51 (1996); Chatterjee et al., "In vivo analysis of nuclear protein traffic in mammalian cells." Exp Cell Res 236(1):346–50 (1997); Patterson et al., "Quantitative imaging of TATA-binding protein in living yeast cells." Yeast 14(9):813–25 (1998); Dhandayuthapani et al., "Green fluorescent protein as a marker for gene expression and cell biology of mycobacterial interactions with macrophages." Mol Microbiol 17(5):901–12 (1995); Kremer et al., "Green fluorescent protein as a new expression marker in mycobacteria." Mol Microbiol 17(5):913–22 (1995); Reiländer et al., "Functional expression of the Aequorea victoria green fluorescent protein in insect cells using the baculovirus expression system." Biochem Biophys Res Commun 219(1):14–20 (1996); Mankertz et al., "Expression from the human occludin promoter is affected by tumor necrosis factor alpha and interferon gamma" J Cell Sci, 113:2085–90 (2000); White et al., "Real-time analysis of the transcriptional regulation of HIV and hCMV promoters in single mammalian cells" J Cell Sci, 108:441–55 (1995)). Green fluorescence protein, or variants, have been shown to be stably incorporated and not interfere with the organism—generally GFP is larger relative to the disclosed reporter signal peptides (GFP from Aequorea Victoria is 238 amino acids in size; NCBI GI:606384), and thus the reporter signal peptides are less likely to disrupt an expression system to which they are added.

Techniques are known for modifying promoter regions such that the endogenous promoter is replaced with a promoter-reporter construct, for example, where the reporter is green fluorescent protein (Patterson et al., "Quantitative imaging of TATA-binding protein in living yeast cells." Yeast 14(9): 813–25 (1998)) or luciferase. Transcription factor concentrations are followed by monitoring the GFP or luciferase. These techniques can be used with the disclosed reporter signal fusions and reporter signal fusion constructs. Techniques are also known for targeted knock-in of nucleic acid sequences into a gene of interest, typically under control of the endogenous promoter. Such techniques, which can be used with the disclosed method and compositions, have been used to introduce reporter/markers of the transcription and translation of the gene where then nucleic acid was inserted. The same techniques can be used to place the disclosed reporter signal fusions under control of endogenous expression sequences. Alternately, non-targeted knock-ins (techniques for which are also known) can be used to follow the level or activity of transcription factors.

As with reporter signals generally, reporter signal peptides can be used in sets where the reporter signal peptides in a set can have one or more common properties that allow the reporter signal peptides to be separated or distinguished from molecules lacking the common property. In the case of reporter signal fusions, amino acid segments and amino acid subsegments can be used in sets where the amino acid segments and amino acid subsegments in a set can have one or more common properties that allow the amino acid segments and amino acid subsegments, respectively, to be separated or distinguished from molecules lacking the common property. In general, the component(s) of the reporter signal fusions having common properties can depend on the component(s) to be detected and/or the mode of the method being used.

Nucleic acid molecules encoding reporter signal fusions can be used in sets where the reporter signal peptides in the reporter signal fusions encoded by a set of nucleic acid molecules can have one or more common properties that allow the reporter signal peptides to be separated or distinguished from molecules lacking the common property. Similarly, nucleic acid molecules encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid molecules encoding amino acid segments can be used in sets where the amino acid segments encoded by a set of nucleic acid molecules can have one or more common properties that allow the amino acid segments to be separated or distinguished from molecules lacking the common property.

Nucleic acid segments (which, generally, are part of nucleic acid molecules) encoding reporter signal fusions can be used in sets where the reporter signal peptides in the reporter signal fusions encoded by a set of nucleic acid segments can have one or more common properties that allow the reporter signal peptides to be separated or distinguished from molecules lacking the common property. Similarly, nucleic acid segments encoding amino acid segments can be used in sets where the reporter signal peptides in the amino acid segments encoded by a set of nucleic acid molecules can have one or more common properties that allow the reporter signal peptides to be separated or distinguished from molecules lacking the common property. Nucleic acid segments encoding amino acid segments can be used in sets where the amino acid segments encoded by a set of nucleic acid molecules can have one or more common properties that allow the amino acid segments to be separated or distinguished from molecules lacking the common property. Other relationships between members of the sets of nucleic acid molecules, nucleic acid segments, amino acid segments, reporter signal peptides, and proteins of interest are contemplated.

Reporter signal fusions can include other components besides a protein of interest and a reporter signal peptide. For example, reporter signal fusions can include epitope tags or flag peptides. Epitope tags and flag peptides can serve as tags by which reporter signal fusions can be separated, distinguished, associated, and/or bound. The use of epitope tags and flag peptides generally is known and can be adapted for use in the disclosed reporter signal fusions.

In preferred embodiments, reporter signal peptides, reporter signal fusions (or amino acid segments), nucleic acid segments encoding reporter signal fusion, and/or nucleic acid molecules comprising nucleic acid segments encoding reporter signal fusions are used in sets where the reporter signal peptides, the reporter signal fusions, and/or subsegments of the reporter signal fusions constituting or present in the set have similar properties (such as similar mass-to-charge ratios). The similar properties allow the reporter signals, the reporter signal fusions, or subsegments of the reporter signal fusions to be distinguished and/or separated from other molecules lacking one or more of the properties. Preferably, the reporter signals, the reporter signal fusions, or subsegments of the reporter signal fusions constituting or present in a set have the same mass-to-charge ratio (m/z). That is, the reporter signals, the reporter signal fusions, or subsegments of the reporter signal fusions in a set are isobaric. This allows the reporter signals, the reporter signal fusions, or subsegments of the reporter signal fusions to be separated precisely from other molecules based on mass-to-charge ratio. The result of the filtering is a huge increase in the signal to noise ratio (S/N) for the system, allowing more sensitive and accurate detection.

Preferred reporter signal peptides for use in reporter signal fusions used in or associated with different genes, proteins, vectors, constructs, cells, cell lines, or organisms would be those using differentially distributed mass. In particular, the use of alternative amino acid sequences using the same amino acid composition is preferred.

Although reference is made above and elsewhere herein to detection of and fusion with, a "protein" or "proteins," the disclosed method can involve proteins, peptides, and fragments of proteins or peptides. Thus, reference to a protein herein is intended to refer to proteins, peptides, and fragments of proteins or peptides unless the context clearly indicates otherwise. As used herein "reporter signal fusion" refers to a protein, peptide, or fragment of a protein or peptide to which a reporter signal peptide is fused (that is, joined by peptide bond(s) in the same polypeptide chain) unless the context clearly indicates otherwise. The reporter signal peptide(s) can be fused to a protein in any arrangement, such as at the N-terminal end of the protein, at the C-terminal end of the protein, in or at domain junctions, or at any other appropriate location in the protein. In some forms of the method, it is desirable that the protein remain functional. In such cases, terminal fusions or inter-domain fusions are preferably. Those of skill in the art of protein fusions generally know how to design fusions where the protein of interest remains functional. In other embodiments, it is not necessary that the protein remain functional in which case the reporter signal peptide and protein can have any desired structural organization.

The reporter signal fusions can be produced by expression from nucleic acid molecules encoding the fusions. Thus, the disclosed fusions generally can be designed by designing nucleic acid segments that encode amino acid segments where the amino acid segments comprise a reporter signal peptide and a protein or peptide of interest. A given nucleic acid molecule can comprise one or more nucleic acid segments. A given nucleic acid segment can encode one or more amino acid segments. A given amino acid segment can include one or more reporter signal peptides and one or more proteins or peptides of interest. The disclosed amino acid segments consist of a single, contiguous polypeptide chain. Thus, although multiple amino acid segments can be part of the same contiguous polypeptide chain, all of the components (that is, the reporter signal peptide(s) and protein(s) and peptide(s) of interest) of a given amino acid segment are part of the same contiguous polypeptide chain.

Reporter signal fusions can be used to monitor and analyze alternative RNA splicing. A central problem in translating the information in the genome to protein expression is an understanding of mRNA alternative processing, and the generation of protein isoforms via alternative exon utilization (Black, "Protein diversity from alternative splicing: a challenge for bioinformatics and post-genome biology" Cell 103:367–70 (2000)). Many examples of the use of alternative pre-mRNA splicing to generate protein isoform diversity exist, such as in the control of erythroid differentiation (see, for example, Hou and Conboy, "Regulation of alternative pre-mRNA splicing during erythroid differentiation" Curr Opin Hematol 8:74–9 (2001)). Often the detection of complex, alternatively spliced protein isoforms is a difficult task, since exons may be as small as 6 amino acids in protein of over 2000 amino acids (see, for example, Cianci et al., "Brain and muscle express a unique alternative transcript of all spectrin" Biochem 38:15721–15730 (1999)).

Exon utilization and processing information can be obtained by insertion of a nucleic acid sequence encoding a reporter signal into the exon sequence of interest (thus forming a nucleic acid segment that encodes a reporter signal fusion). The insertions can be made, for example, into genomic DNA, appropriate mini-gene constructs, or non-endogenous pre-mRNA introduced into the cell. Use of a set of reporter signals allows the multiplexed readout of all exons of a translated protein at one time. The use of mini-gene constructs or constructs incorporating short exogenous open-reading frame DNA sequences into exons, and the incorporation of foreign DNA in association with functional intron splice elements are developed technologies that can be used for incorporation of reporter signals (see, for example, Gee et al., "Alternative splicing of protein 4.1R exon 16: ordered excision of flanking introns ensures proper splice site choice" Blood 95:692–9 (2000); Kikumori et al., "Promiscuity of pre-mRNA spliceosome-mediated trans splicing: a problem for gene therapy?" Hum Gene Ther 12:1429–41 (2001); Malik et al., "Effects of a second intron on recombinant MFG retroviral vector" Arch Virol 146:601–9 (2001); Virts and Raschke, "The role of intron sequences in high level expression from CD45 cDNA constructs" J Biol Chem 276:19913–20 (2001)). Detection of the reporter signals, the amounts of the reporter signals, and the knowledge of which reporter signal correlates with which exon, provides information about exon usage and alternative splicing.

The disclosed reporter signal fusions also can be used in the detection and analysis of protein interactions with other proteins and molecules. For example. interaction traps for protein—protein interactions include the well known yeast two-hybrid (Fields and Song. "A novel genetic system to detect protein—protein interactions" Nature 340:245–6 (1989); Uetz et al., "A comprehensive analysis of protein—protein interactions in Saccharomyces cerevisiae" Nature 403:623–7 (2000)) and related systems (Ausubel et al., Current Protocols in Molecular Biology, John Wiley & Sons, Inc., 2001; Van Criekinge and Beyaert, "Yeast two-hybrid: state of the art" Biological Procedures Online, 2(1), 1999). Incorporation of nucleic acid sequence encoding a peptide reporter signal can be introduced into these systems, for example at a terminus of the ordinarily used LacZ selection region (LacZ selection is described in, for example, Sambrook et al., Molecular Cloning: A Laboratory Manual, second edition, 1989, Cold Spring Harbor Laboratory Press, New York). A set of such incorporated sequences (for example, in a set of such plasmids, where each plasmid has a reporter signal coding sequence and the LacZ functionality), allows the unambiguous detection of many interactions simultaneously rather (as many different interactions as reporter signals used).

In another mode of reporter signal fusions, a nucleic acid sequence encoding a reporter signal could be added to sequence encoding the constant (C) region of T cell and B cell receptors. The reporter signal would appear in T or B cell receptors when that C region is spliced to a J region following transcription.

In another mode of reporter signal fusions, referred to as reporter signal presentation, the presentation of specific antigenic peptides by major histocompatibility (MHC) and non-major histocompatibility molecules can be detected and analyzed. It is well known that protein antigens are processed by antigen presenting cells and that small peptides, typically 8–12 amino acids are presented by Class I and Class II MHC molecules for recognition by T cells. The study of specific T cell/peptide-MHC complexes is technically challenging due various labeling requirements (either radioactive or fluorescence) and the common reliance on antibody reagents that recognize specific receptors and/or peptide-MHC complexes.

There is a need to be able to further expand our knowledge of antigen processing and antigen presentation. Reporter signals that have been engineered into specific protein antigens could provide novel insight into this process and enable new experimental approaches. For instance, consider two viral or bacterial proteins, protein A and protein B, that differ by only a few amino acids. It would be useful to know if they are processed and presented to immune cells (for example, T cells) with the same efficiency. By engineering reporter signals into protein A and engineered protein B to antigen presenting cells, one could test for the presence of the different reporter signals presented on and thus determine if the proteins are efficiently processed and presented. The presence of reporter signal A (present in protein A) but not reporter signal B (present in protein B), indicates that protein A is processed and that protein B is not. The lack of antigen processing of protein B may then be an explanation of why a virus or bacteria escapes immune surveillance by the immune system. Antigenic peptides are characterized by conserved anchor residues near both the amino and carboxy ends, with more heterogeneity tolerated in the middle. This middle heterogeneity is thus a preferred site for addition of a reporter signal peptide.

E. Rearranging Reporter Signals

Another embodiment of the disclosed method and compositions, referred to as rearranging reporter signals, enables one to detect the occurrence of specific gene rearrangement events, their protein products, and specific cell populations bearing those receptors. Rearranging reporter signals will also allow one to follow the progression or development of certain receptors and cells or populations of cells by monitoring the presence and/or absence of a reporter signal. Design considerations for rearranged reporter signals are analogous to those required for reporter signal fusions as described elsewhere herein.

Most embodiments of the disclosed method involve intact reporter signals that are associated with analytes in various ways. Rearranging reporter signals make use of processes, such as biological processes, to form reporter signals by specific rearrangement of the reporter signal pieces or rearrangement of nucleic acid segments encoding only portions of reporter signals. One form of rearranging reporter signals utilizes endogenous biological systems, such as the variable-diversity-joining (V-D-J) gene rearrangement machinery present in the mammalian immune system. In this system, short stretches of germline DNA (the V, D & J gene fragments) that are not contiguous, are brought together (recombined) prior to serving as a template for transcription. Gene rearrangement occurs in white blood cells such as T and B lymphocytes and is a key mechanism for generating diversity of T cell and B cell antigen receptors. Theoretically, billions of different receptors can be generated. This level of complexity makes it difficult to detect the presence of rare rearrangement events, or receptors. PCR based assays and flow cytometry approaches are now used to study receptor diversity. However, PCR approaches are laborious and do not provide any information on the status of expressed protein. Flow cytometry approaches have limited multiplexing capabilities due to emission spectra overlap of the fluorescent probes used.

If one desired to test for 50–100 T cell or B cell receptors, one would need to make use of a similar number of antibodies to those receptors, something that in practice is not done. Therefore, there is a real need for methods that would allow highly sensitive and specific detection of specific receptors in a highly complex pool of receptors. The ability to highly multiplex this approach would enable currently unattainable experimental approaches. The disclosed reporter signal technology allows large scale multiplexing of signals for detection.

As an example of rearranging reporter signals, transgenic mice can be generated in which nucleic acid sequences encoding reporter signals have been engineered into the mouse germline. Methods for doing this are well known in the art and include using standard molecular biology methods to engineer rearranging reporter signal into, for example, yeast or bacterial artificial chromosomes (YACs or BACs) and then using these constructs to generate transgenic mice.

As an example of the use of immunoglobulin rearrangement for rearranging reporter signals, part of a reporter signal could be encoded on the D region and another part of the reporter signal could be encoded on the J region. Upon a rearrangement event that joined the D and J regions encoding these "partial" reporter signals, a coding sequence for a "complete" reporter signal would be generated. Following transcription and translation, the reporter signal would be encoded within the protein product. The reporter signal could then be detected as described elsewhere herein. In the absence of a rearrangement event that joins the engineered D and J region, no reporter signal would be detected. By including sequences encoding parts of a variety of reporter signals with different D and J regions, a variety of different reporter signals can be generated by rearrangement, a different, and diagnostic, reporter signal for each of the different possible rearrangements. This system also could be extended to include, for example, reporter signals split among three or more gene regions (for example, V-D-J, V-D-D-J, etc) with the result that multiple rearrangement events would produce the reporter signal. In this mode, the combinations of rearrangements of the reporter signal parts can give rise to an large number of different reporter signals, each characterized by the specific reporter signal parts rearranged to form the reporter signal.

Transgenic mice carrying rearranging reporter signals would enable one to address questions that would otherwise be very difficult or impossible to address. For instance, one could dissect what specific T and B cell receptors (out of the thousands or millions possible) respond to specific stimuli or what cell types are present at certain stages of development.

F. Lipid Reporter Signals

The disclosed method and compositions also can be used to monitor lipid composition, distribution, and processing. Lipids are hydrophobic biomolecules that have high solubility in organic solvents. They have a variety of biological roles that make them valuable targets for monitoring. As a nutritional source, lipids (together with carbohydrates) constitute an important source of cellular energy and metabolic intermediates needed for cell signaling and other processes. Lipids processed for energy conversion typically pass through a variety of enzymatic pathways, generating many intermediates. A summary of these cycles is available in most modern biochemistry texts (see, for example, Stryer, 1995). Monitoring the processing of acyl chain intermediates as they are metabolized is an important tool in lipid and cell biological research, as well as for the clinical detection of biochemical diseases such as medium-chain acyl-CoA dehydrogenase deficiencies (see, for example, Zschocke et al., "Molecular and functional characterization of mild MCAD deficiency.", Hum Genet 108:404–8 (2001)). Incorporating reporter signals into, or associating reporter signals with, lipids can improve methods of detecting lipids (such as Andresen et al., "Medium-chain acyl-CoA dehydrogenase (MCAD) mutations identified by MS/MS-based prospective screening of newborns differ from those observed in patients with clinical symptoms: identification and characterization of a new, prevalent mutation that results in mild MCAD deficiency" Am J Hum Genet 68:1408–18. (2001)) by allowing, for example, more rapid and multiplex detection of processed acyl chain intermediates.

In another role, lipids function as the most fundamental and defining component of all biological membranes. The three major types of membrane lipids are phospholipids, glycolipids, and cholesterol. The most abundant of these are the phospholipids, derived either from glycerol or sphingosine. Those based on glycerol typically contain two esterified long-chain fatty acids (14 to 24 carbons) and a phosphorylated alcohol or sugar. Phospholipids based on sphingosine contain a single fatty acid. Collectively these lipids contribute to the structure and fluidity of biological membranes. Cyclic changes in their processing, particularly of acidic glycophosolipids such as phosphatidyl inositol 4,5-phosphate, also regulate a wide variety of cellular processes (see, for example, Cantrell, "Phosphoinositide 3-kinase signaling pathways" J Cell Sci 114:1439–45 (2001); Payrastre et al., "Phosphoinositides: key players in cell signaling, in time and space" Cell Signal 13:377–87 (2001)). Thus, by incorporating reporter signals into, or associating reporter signals with, the acyl chains of such molecules, the subsequent incorporation of such reporter molecules into either in vitro assays such as those used for enzyme determinations or in vivo assays, allows one to rapidly follow the segregation of these lipids into distinct cellular compartments (for example, golgi versus plasma membrane (see, for example, Godi et al., "ARF mediates recruitment of PtdIns-4-OH kinase-beta and stimulates synthesis of PtdIns(4,5)P2 on the Golgi complex" Nat Cell Biol 1:280–7 (1999)), and their processing via metabolic and signaling pathways such as those cited above.

It is known that exogenous lipid labels can be incorporated readily into biological systems, and the disclosed reporter signals also can be incorporated into such systems. For example, spin-labeled acyl fatty acids and phospholipids have been incorporated into the membranes of phospholipid vesicles and cells (see, for example, Kornberg and McConnell, "Inside-outside transitions of phospholipids in vesicle membranes" Biochemistry 10:1111–20 (1971); Kornberg and McConnell, "Lateral diffusion of phospholipids in a vesicle membrane" Proc Natl Acad Sci USA 68:2564–8 (1971); Arora et al., "Selectivity of lipid-protein interactions with trypsinized Na, K-ATPase studied by spin-label EPR" Biochim Biophys Acta 1371:163–7 (1998); Alonso et al., "Lipid chain dynamics in stratum corneum studied by spin label electron paramagnetic resonance" Chem Phys Lipids 104:101–11 (2000)).

Triglycerides, or the acyl chain of sphinoglipids or glycolipids, and cholesterol, may be synthesized to include a reporter signal. An example of such a reporter signal would be a lipid made from an aliphatic chain with a carboxylic acid with a photocleavable bond. Examples of photocleavable bonds are described by Glatthar and Geise, Org. Lett, 2:2315–2317 (2000); Guillier et al., Chem. Rev. 100:2091–2157 (2000); Wierenga, U.S. Pat. No. 4,086,254; and elsewhere here. A set of reporter signals may be prepared by locating the cleavable bond at different locations within an aliphatic chain (thus resulting in fragments of different mass when the bond is cleaved). The aliphatic chain with a photocleavable bond constitutes the reporter signal. Such synthetic reporter molecules can be incorporated into synthetic triglycerides by, for example, a dehydration reaction. Once formed, a set of these synthetic triglycerides can be introduced into biological systems of interest, such as those described above. Reporter signals can be recovered from the biological system of interest for detection and quantitation by, for example, extraction of the lipid into chloroform and release of reporter signals from the trigyceride using a lipase or hydrolysis reaction.

Forms and Embodiments of the Disclosed Methods

A. Reporter Molecule Labeling

Disclosed are methods comprising (a) separating a set of reporter signals, where each reporter signal has a common property, from molecules lacking the common property, (b) altering the reporter signals, (c) detecting and distinguishing the altered forms the reporter signals from each other.

Also disclosed are methods wherein the common property is mass-to-charge ratio, wherein the reporter signals are altered by altering their mass, wherein the altered forms of the reporter signals are distinguished via differences in the mass-to-charge ratio of the altered forms of reporter signals.

Also disclosed are methods wherein the mass of the reporter signals is altered by fragmentation.

Also disclosed are methods wherein the set of reporter signals comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signals.

Also disclosed are methods wherein the set of reporter signals comprises ten or more different reporter signals.

Also disclosed are methods wherein the reporter signals are peptides, oligonucleotides, carbohydrates, polymers, oligopeptides, or peptide nucleic acids.

Also disclosed are methods wherein the reporter signals are associated with, or coupled to, specific binding molecules, wherein each reporter signal is associated with, or coupled to, a different specific binding molecule.

Also disclosed are methods wherein the reporter signals are associated with, or coupled to, decoding tags, wherein each reporter signal is associated with, or coupled to, a different decoding tag.

Also disclosed are methods further comprising, prior to step (a), associating the reporter signals with one or more analytes, wherein each reporter signal is associated with, or coupled to, a different specific binding molecule, wherein each specific binding molecule can interact specifically with a different one of the analytes, wherein the reporter signals are associated with the analytes via interaction of the specific binding molecules with the analytes.

Also disclosed are methods wherein steps (a) through (c) are repeated one or more times using a different set of reporter signals each time.

Also disclosed are methods wherein, prior to step (a), the different sets of reporter signals are associated with different samples.

Also disclosed are methods wherein the different sets of reporter signals each comprise the same reporter signals.

Also disclosed are methods wherein the sets of reporter signals each contain a single reporter signal.

Also disclosed are methods wherein not all of the reporter signals in the set are distinguished and/or separated from molecules lacking the common property, not all of the reporter signals are altered, and not all of the altered forms of the reporter signals are detected at the same time.

Also disclosed are methods wherein all of the reporter signals in the set are distinguished and/or separated from molecules lacking the common property, all of the reporter signals are altered, and all of the altered forms of the reporter signals are detected at different times.

Also disclosed are methods wherein steps (a) through (c) are performed separately for each reporter signal.

Also disclosed are methods wherein the reporter signals comprise peptides, wherein the peptides have the same mass-to-charge ratio and methods wherein the peptides have the same amino acid composition and methods wherein the peptides have the same amino acid sequence and methods wherein each peptide contains a different distribution of heavy isotopes and methods wherein each peptide has a different amino acid sequence and methods wherein each peptide has a labile or scissile bond in a different location.

Disclosed are methods comprising (a) separating one or more reporter signals, where each reporter signal has a common property, from molecules lacking the common property in each of a plurality of samples, (b) altering the reporter signals, (c) detecting and distinguishing the altered forms the reporter signals from each other.

Also disclosed are methods wherein the common property is mass-to-charge ratio, wherein the reporter signals are altered by altering their mass, wherein the altered forms of the reporter signals are distinguished via differences in the mass-to-charge ratio of the altered forms of reporter signals.

Also disclosed are methods wherein the mass of the reporter signals is altered by fragmentation.

Also disclosed are methods wherein the reporter signals are associated with, or coupled to, specific binding molecules, wherein each reporter signal is associated with, or coupled to, a different specific binding molecule.

Also disclosed are methods wherein the reporter signals are associated with, or coupled to, decoding tags, wherein each reporter signal is associated with, or coupled to, a different decoding tag.

Also disclosed are methods further comprising, prior to step (a), associating the reporter signals with one or more analytes, wherein each reporter signal is associated with, or coupled to, a different specific binding molecule, wherein each specific binding molecule can interact specifically with a different one of the analytes, wherein the reporter signals are associated with the analytes via interaction of the specific binding molecules with the analytes.

Also disclosed are methods wherein steps (a) through (c) are repeated one or more times using a different set of one or more reporter signals each time and methods wherein, prior to step (a), the different sets of reporter signals are associated with different samples and methods wherein the different sets of reporter signals each comprise the same reporter signals and methods wherein the sets of reporter signals each contain a single reporter signal.

Also disclosed are methods wherein not all of the reporter signals are distinguished and/or separated from molecules lacking the common property, not all of the reporter signals are altered, and not all of the altered forms of the reporter signals are detected at the same time.

Also disclosed are methods wherein all of the reporter signals are distinguished and/or separated from molecules lacking the common property, all of the reporter signals are altered, and all of the altered forms of the reporter signals are detected at different times.

Also disclosed are methods wherein steps (a) through (c) are performed separately for each sample.

B. Reporter Signal Protein Labeling

Also disclosed are methods comprising (a) separating a set of labeled proteins, wherein each labeled protein comprises a protein or peptide and a reporter signal attached to the protein or peptide, wherein each reporter signal has a common property, wherein the common property allows the labeled proteins comprising the same protein or peptide to be distinguished and/or separated from molecules lacking the common property, (b) altering the reporter signals, thereby altering the labeled proteins, (c) detecting and distinguishing the altered forms of the labeled proteins from each other.

Also disclosed are methods wherein the common property is mass-to-charge ratio, wherein the reporter signals are altered by altering their mass, wherein the altered forms of the labeled proteins are distinguished via differences in the mass-to-charge ratio of the altered forms of the labeled proteins.

Also disclosed are methods wherein the mass of the reporter signals is altered by fragmentation.

Also disclosed are methods wherein alteration of the reporter signals also alters their charge.

Also disclosed are methods wherein the common property is mass-to-charge ratio, wherein the reporter signals are altered by altering their charge, wherein the altered forms of the labeled proteins can be distinguished via differences in the mass-to-charge ratio of the altered forms of reporter signals.

Also disclosed are methods wherein the set of labeled proteins comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signals.

Also disclosed are methods wherein the set of labeled proteins comprises ten or more different reporter signals.

Also disclosed are methods wherein the reporter signals are peptides, oligonucleotides, carbohydrates, polymers, oligopeptides, or peptide nucleic acids.

Also disclosed are methods wherein the reporter signals are coupled to the proteins or peptides.

Also disclosed are methods wherein steps (a) through (c) are performed separately for each labeled protein.

Also disclosed are methods further comprising, prior to step (a), attaching the reporter signals to one or more proteins, one or more peptides, or one or more proteins and peptides.

Also disclosed are methods wherein steps are repeated one or more times using a different set of reporter signals each time.

Also disclosed are methods wherein, prior to step (a), the different sets of reporter signals are attached to proteins or peptides in different samples.

Also disclosed are methods wherein the different sets of reporter signals each comprise the same reporter signals.

Also disclosed are methods wherein the sets of reporter signals each contain a single reporter signal.

Also disclosed are methods wherein not all of the labeled proteins in the set are distinguished and/or separated from molecules lacking the common property, not all of the reporter signals are altered, and not all of the altered forms of the labeled proteins are detected at the same time.

Also disclosed are methods wherein all of the labeled proteins in the set are distinguished and/or separated from molecules lacking the common property, all of the reporter signals are altered, and all of the altered forms of the labeled proteins are detected at different times.

Also disclosed are methods wherein steps (a) through (c) are performed separately for each reporter signal.

Also disclosed are methods wherein the common property is one or more affinity tags associated with the reporter signals.

Also disclosed are methods wherein one or more affinity tags are associated with the reporter signals.

Also disclosed are methods wherein the collection of altered forms of the labeled proteins detected constitutes a catalog of proteins.

Also disclosed are methods comprising (a) separating one or more labeled proteins, wherein each labeled protein comprises a protein or peptide and a reporter signal attached to the protein or peptide, wherein each reporter signal has a common property, wherein the common property allows the labeled proteins comprising the same protein or peptide to be distinguished and/or separated from molecules lacking the common property in each of one or more samples, (b) altering the reporter signals, thereby altering the labeled proteins, (c) detecting and distinguishing the altered forms the labeled proteins from each other.

Also disclosed are methods wherein the common property is mass-to-charge ratio, wherein the reporter signals are altered by altering their mass, wherein the altered forms of the labeled proteins are distinguished via differences in the mass-to-charge ratio of the altered forms of labeled proteins.

Also disclosed are methods wherein the mass of the reporter signals is altered by fragmentation.

Also disclosed are methods wherein alteration of the reporter signals also alters their charge.

Also disclosed are methods wherein the common property is mass-to-charge ratio, wherein the reporter signals are altered by altering their charge, wherein the altered forms of the labeled proteins can be distinguished via differences in the mass-to-charge ratio of the altered forms of reporter signals.

Also disclosed are methods wherein the reporter signals are coupled to the proteins or peptides.

Also disclosed are methods further comprising, prior to step (a), attaching the reporter signals to one or more proteins, one or more peptides, or one or more proteins and peptides.

Also disclosed are methods wherein steps are repeated one or more times using a different set of one or more reporter signals each time.

Also disclosed are methods wherein, prior to step (a), the different sets of reporter signals are attached to proteins or peptides in different samples.

Also disclosed are methods wherein the different sets of reporter signals each comprise the same reporter signals.

Also disclosed are methods wherein the sets of reporter signals each contain a single reporter signal.

Also disclosed are methods wherein not all of the labeled proteins are distinguished and/or separated from molecules lacking the common property, not all of the reporter signals are altered, and not all of the altered forms of the labeled proteins are not detected at the same time.

Also disclosed are methods wherein all of the labeled proteins are distinguished and/or separated from molecules lacking the common property, all of the reporter signals are altered, and all of the altered forms of the labeled proteins are detected at different times.

Also disclosed are methods wherein steps (a) through (c) are performed separately for each sample and methods wherein the different samples are from the same protein sample and methods wherein the different samples are obtained at different times and methods wherein the different samples are from the same type of organism and methods wherein the different samples are from the same type of tissue and methods wherein the different samples are from the same organism and methods wherein the different samples are obtained at different times. Also disclosed are methods wherein the different samples are from different organisms. Also disclosed are methods wherein the different samples are from different types of tissues.

Also disclosed are methods wherein the different samples are from different species of organisms.

Also disclosed are methods wherein the different samples are from different strains of organisms.

Also disclosed are methods wherein the different samples are from different cellular compartments.

Also disclosed are methods further comprising identifying or preparing proteins or peptides corresponding the proteins or peptides present in one sample but not present in another sample.

Also disclosed are methods further comprising determining the relative amount of proteins or peptides in the different samples.

Also disclosed are methods wherein the common property is one or more affinity tags associated with the reporter signals.

Also disclosed are methods wherein one or more affinity tags are associated with the reporter signals.

Also disclosed are methods wherein the pattern of the presence, amount, presence and amount, or absence of labeled proteins in one of the samples constitutes a catalog of proteins in the sample.

Also disclosed are methods wherein the pattern of the presence, amount, presence and amount, or absence of labeled proteins in a second one of the samples constitutes a catalog of proteins in the second sample, wherein the catalog of proteins in the first sample is a first catalog and the catalog of proteins in the second sample is a second catalog, the method further comprising comparing the first catalog and the second catalog.

Also disclosed are methods wherein each labeled protein comprises a protein or a peptide and a reporter signal attached to the protein or peptide, wherein the reporter signals comprise peptides, wherein the reporter signal peptides have the same mass-to-charge ratio.

Also disclosed are methods wherein the reporter signal peptides have the same amino acid composition.

Also disclosed are methods wherein the reporter signal peptides have the same amino acid sequence.

Also disclosed are methods wherein each reporter signal peptide contains a different distribution of heavy isotopes.

Also disclosed are methods wherein each reporter signal peptide contains a different distribution of substituent groups.

Also disclosed are methods wherein each reporter signal peptide has a different amino acid sequence.

Also disclosed are methods wherein each reporter signal peptide has a labile or scissile bond in a different location.

Also disclosed are methods wherein one or more affinity tags are associated with the reporter signals.

Disclosed are methods comprising (a) separating a set of labeled proteins, wherein each labeled protein comprises a protein or peptide and a reporter signal attached to the protein or peptide, wherein each labeled protein has a common property, wherein the common property allows the labeled proteins comprising the same protein or peptide to be distinguished and/or separated from molecules lacking the common property, (b) altering the reporter signals, thereby altering the labeled proteins, (c) detecting and distinguishing the altered forms of the labeled proteins from each other.

Disclosed are methods comprising (a) altering labeled proteins, wherein each labeled protein comprises a protein or peptide and a reporter signal attached to the protein or peptide, wherein the labeled proteins are altered by altering the reporter signals, (b) detecting and distinguishing the altered forms of the labeled proteins from each other.

Disclosed are methods of detecting a protein or peptide, the method comprising (a) altering a labeled protein, wherein the labeled protein comprises a protein or peptide and a reporter signal attached to the protein or peptide, wherein the labeled protein is altered by altering the reporter signal, (b) detecting and distinguishing the altered form of the labeled protein from the unaltered form of labeled protein.

Also disclosed are methods further comprising, detecting the unaltered form of labeled protein.

Disclosed are methods of detecting a protein, the methods comprising, detecting a labeled protein, wherein the labeled protein comprises a protein or peptide and a reporter signal attached to the protein or peptide, wherein the labeled protein is altered by altering the reporter signal, detecting an altered form of the labeled protein, wherein the labeled protein is altered by altering the reporter signal, and identifying the protein based on the characteristics of the labeled protein and altered form of the labeled protein.

Also disclosed are methods wherein the labeled protein and altered form of the labeled protein are detected by detecting the mass-to-charge ratio of the labeled protein and the mass-to-charge ratio of the altered form of the labeled protein or the mass-to-charge ratio of the altered form of the reporter signal.

Disclosed are methods comprising (a) separating one or more labeled proteins from other molecules, wherein the labeled proteins are derived from one or more samples, wherein each labeled protein comprises a protein or peptide and a reporter signal attached to the protein or peptide, (b) altering the reporter signals, thereby altering the labeled proteins, (c) detecting and distinguishing the altered forms the labeled proteins from each other.

Also disclosed are methods further comprising, prior to step (a), associating one or more reporter signals with one or more proteins, one or more peptides, or one or more proteins and peptides from each of the one or more samples.

Also disclosed are methods wherein steps are repeated one or more times using a different set of one or more reporter signals each time.

Also disclosed are methods wherein, prior to step (a), the different sets of reporter signals are attached to proteins or peptides in different samples.

Also disclosed are methods wherein the different sets of reporter signals each comprise the same reporter signals.

Also disclosed are methods wherein each reporter signal or each labeled protein has a common property, wherein the common property allows the labeled proteins comprising the same protein or peptide to be distinguished and/or separated from molecules lacking the common property.

Also disclosed are methods wherein the one or more labeled proteins are derived from a single sample.

Also disclosed are methods wherein a single labeled protein is distinguished and/or separated from other molecules.

Also disclosed are methods wherein a plurality of labeled proteins are distinguished and/or separated from other molecules.

Also disclosed are methods wherein the detected altered forms of the labeled proteins constitute a catalog of proteins in the sample.

Also disclosed are methods wherein one or more labeled proteins are derived from each of a plurality of samples.

Also disclosed are methods wherein a single labeled protein derived from each of the samples is distinguished and/or separated from other molecules.

Also disclosed are methods wherein a plurality of labeled proteins derived from each of the samples are distinguished and/or separated from other molecules.

Also disclosed are methods wherein the detected altered forms of the labeled proteins derived from each sample constitute a catalog of proteins in the sample.

Disclosed are catalogs of proteins and peptides comprising, proteins and peptides in a sample detected by (a) separating one or more labeled proteins from other molecules, wherein the labeled proteins are derived from the sample, wherein each labeled protein comprises a protein or peptide and a reporter signal attached to the protein or peptide, (b) altering the reporter signals, thereby altering the labeled proteins, (c) detecting and distinguishing the altered forms the labeled proteins from each other.

Also disclosed are catalogs of proteins and peptides comprising, proteins and peptides in one or more samples detected by (a) separating one or more labeled proteins from other molecules, wherein the labeled proteins are derived from the one or more samples, wherein each labeled protein comprises a protein or peptide and a reporter signal attached to the protein or peptide, (b) altering the reporter signals, thereby altering the labeled proteins, (c) detecting and distinguishing the altered forms the labeled proteins from each other.

C. Reporter Signal Calibration

Disclosed are methods method of producing a protein signature, the method comprising (a) treating a protein sample to produce protein fragments, wherein the protein fragments comprise a set of target protein fragments, wherein the target protein fragments can be altered, wherein the altered forms of the target protein fragments can be distinguished from the other altered forms of the target protein fragments, (b) mixing the target protein fragments with a set of reporter signal calibrators, wherein each target protein fragment shares a common property with at least one of the reporter signal calibrators, wherein the common property allows the target protein fragments and reporter signal calibrators having the common property to be distinguished and/or separated from molecules lacking the common property, wherein the target protein fragment and reporter signal calibrator that share a common property correspond to each other, wherein the reporter signal calibrators can be altered, wherein the altered form of each reporter signal calibrator can be distinguished from the altered form of the target protein fragment with which the reporter signal calibrator shares a common property, (c) separating the target protein fragments and reporter signal calibrators from other molecules based on the common properties of the target protein fragments and reporter signal calibrators, (d) altering the target protein fragments and reporter signal calibrators, (e) detecting the altered forms of the target protein fragments and reporter signal calibrators, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

Also disclosed are methods wherein steps (d) and (e) are performed simultaneously.

Also disclosed are methods wherein the altered forms of the target protein fragments are detecting using mass spectrometry.

Also disclosed are methods wherein steps (c), (d), and (e) are performed with a tandem mass spectrometer.

Also disclosed are methods wherein the tandem mass spectrometer comprises a first stage and a last stage, wherein step (c) is performed using the first stage of the tandem mass spectrometer to select ions in a narrow mass-to-charge range, wherein step (d) is performed by collision with a gas, and wherein step (e) is performed using the final stage of the tandem mass spectrometer.

Also disclosed are methods where the first stage of the tandem mass spectrometer is a quadrupole mass filter and methods where the final stage of the tandem mass spectrometer is a time of flight analyzer and methods wherein the final stage of the tandem mass spectrometer is a time of flight analyzer.

Also disclosed are methods wherein the mass-to-charge range is varied to cover the mass-to-charge ratio of each of the target protein fragments.

Also disclosed are methods wherein a predetermined amount of each reporter signal calibrator is mixed with the target protein fragments, wherein the amount of each altered form of reporter signal calibrator detected provides a standard for assessing the amount of the altered form of the corresponding target protein fragment.

Also disclosed are methods wherein the amount of at least two of the reporter signal calibrators is different.

Also disclosed are methods wherein the relative amount each reporter signal calibrator is based on the relative amount of each corresponding target protein fragment expected to be in the protein sample.

Also disclosed are methods wherein the amount of each of the reporter signal calibrators is the same.

Also disclosed are methods wherein the target protein fragments and reporter signal calibrators are altered by fragmentation.

Also disclosed are methods wherein the target protein fragments and reporter signal calibrators are altered by cleavage at a photocleavable amino acid.

Also disclosed are methods wherein the target protein fragments and reporter signal calibrators are fragmented in a collision cell.

Also disclosed are methods wherein the target protein fragments are fragmented at an asparagine-proline bond.

Also disclosed are methods wherein the protein fragments are produced by protease digestion of the protein sample.

Also disclosed are methods wherein the protein fragments are produced by digestion of the protein sample with a serine protease.

Also disclosed are methods wherein the serine protease is trypsin.

Also disclosed are methods wherein the protein fragments are produced by digestion of the protein sample with Factor Xa or Enterokinase.

Also disclosed are methods wherein the protein fragments are produced by cleavage at a photocleavable amino acid.

Also disclosed are methods wherein the common property is mass-to-charge ratio, wherein the target protein fragments and reporter signal calibrators are altered by altering their mass, their charge, or their mass and charge, wherein the altered forms of the target protein fragments and reporter signal calibrators can be distinguished via differences in the mass-to-charge ratio of the altered forms of the target protein fragments and reporter signal calibrators.

Also disclosed are methods wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

Also disclosed are methods wherein the set of target protein fragments comprises ten or more different target protein fragments.

Also disclosed are methods wherein the set of reporter signal calibrators comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal calibrators.

Also disclosed are methods wherein the reporter signal calibrators comprise peptides, wherein the peptides have the same mass-to-charge ratio as the corresponding target protein fragments.

Also disclosed are methods wherein the peptides have the same amino acid composition as the corresponding target protein fragments and methods wherein the peptides have the same amino acid sequence as the corresponding target protein fragments and methods wherein each peptide has a different amino acid sequence than the corresponding target protein fragment and methods wherein each peptide has a labile or scissile bond in a different location.

Also disclosed are methods wherein the reporter signal calibrators are peptides, oligonucleotides, carbohydrates, polymers, oligopeptides, or peptide nucleic acids.

Also disclosed are methods further comprising comparing the protein signature to one or more other protein signatures.

Also disclosed are methods wherein at least one of the target protein fragments comprises at least one modified amino acid.

Also disclosed are methods wherein the modified amino acid is a phosphorylated amino acid, an acylated amino acid, or a glycosylated amino acid.

Also disclosed are methods wherein at least one of the target protein fragments is the same as the target protein fragment comprising the modified amino acid except for the modified amino acid.

Also disclosed are methods further comprising performing steps (a) through (e) on a plurality of protein samples.

Also disclosed are methods further comprising identifying differences between the protein signatures produced from the protein samples.

Also disclosed are methods further comprising performing steps (a) through (e) on a control protein sample, identifying differences between the protein signatures produced from the protein samples and the control protein sample.

Also disclosed are methods wherein the differences are differences in the presence, amount, presence and amount, or absence of target protein fragments in the protein samples and the control protein sample.

Also disclosed are methods wherein the steps (a) through (e) are performed on a control protein sample and a tester protein sample, wherein the tester protein sample, or the source of the tester protein sample, is treated, prior to step (a), so as to destroy, disrupt or eliminate one or more protein molecules in the tester protein sample, wherein the target protein fragments corresponding to the destroyed, disrupted, or eliminated protein molecules will be produced from the control protein sample but not the tester protein sample.

Also disclosed are methods wherein the tester protein sample is treated so as to destroy, disrupt or eliminate one or more protein molecules in the tester protein sample.

Also disclosed are methods wherein one or more protein molecules in the tester sample are eliminated by separating the one or more protein molecules from the tester protein sample.

Also disclosed are methods wherein the one or more protein molecules are separated by affinity separation.

Also disclosed are methods wherein the source of the tester protein sample is treated so as to destroy, disrupt or eliminate one or more protein molecules in the tester protein sample.

Also disclosed are methods wherein the treatment of the source is accomplished by exposing cells from which the tester sample will be derived with a compound, composition, or condition that will reduce or eliminate expression of one or more genes.

Also disclosed are methods further comprising identifying differences in the target protein fragments in the control protein sample and tester protein sample.

Also disclosed are methods further comprising identifying differences between the target protein fragments in the protein samples.

Also disclosed are methods wherein the plurality of protein samples are produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

Also disclosed are methods wherein the protein samples are different fractions or samples produced by the same separation procedure.

Also disclosed are methods further comprising performing steps (a) through (e) on a second protein sample.

Also disclosed are methods wherein the second protein sample is a sample from the same type of organism as the first protein sample.

Also disclosed are methods wherein the second protein sample is a sample from the same type of tissue as the first protein sample.

Also disclosed are methods wherein the second protein sample is a sample from the same organism as the first protein sample.

Also disclosed are methods wherein the second protein sample is obtained at a different time than the first protein sample.

Also disclosed are methods wherein the second protein sample is a sample from a different organism than the first protein sample.

Also disclosed are methods wherein the second protein sample is a sample from a different type of tissue than the first protein sample.

Also disclosed are methods wherein the second protein sample is a sample from a different species of organism than the first protein sample.

Also disclosed are methods wherein the second protein sample is a sample from a different strain of organism than the first protein sample.

Also disclosed are methods wherein the second protein sample is a sample from a different cellular compartment than the first protein sample.

Also disclosed are methods further comprising producing a second protein signature from a second protein sample and comparing the first protein signature and second protein signature, wherein differences in the first and second protein signatures indicate differences in source or condition of the source of the first and second protein samples.

Also disclosed are methods further comprising producing a second protein signature from a second protein sample and comparing the first protein signature and second protein signature, wherein differences in the first and second protein signatures indicate differences in protein modification of the first and second protein samples.

Also disclosed are methods wherein the second protein sample is a sample from the same type of cells as the first protein sample except that the cells from which the first protein sample is derived are modification-deficient relative to the cells from which the second protein sample is derived.

Also disclosed are methods wherein the second protein sample is a sample from a different type of cells than the first protein sample, and wherein the cells from which the first protein sample is derived are modification-deficient relative to the cells from which the second protein sample is derived.

Also disclosed are methods wherein the protein sample is derived from one or more cells.

Also disclosed are methods wherein the protein signature indicates the physiological state of the cells.

Also disclosed are methods wherein the protein signature indicates the effect of a treatment of the cells.

Also disclosed are methods wherein the cells are derived from an organism, wherein the cells are treated by treating the organism.

Also disclosed are methods wherein the organism is treated by administering a compound to the organism.

Also disclosed are methods wherein the organism is human.

Also disclosed are methods wherein the protein sample is produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

Also disclosed are methods wherein the set of reporter signal calibrators consists of a single reporter signal calibrator.

Also disclosed are methods wherein the protein signature of the protein sample represents the presence, absence, amount, or presence and amount of the target protein fragment in the protein sample that corresponds to the reporter signal calibrator.

Disclosed are methods of producing a protein signature, the method comprising detecting altered forms of target protein fragments and reporter signal calibrators, wherein the altered forms of the target protein fragments can be distinguished from the other altered forms of the target protein fragments, wherein each target protein fragment shares a common property with at least one of the reporter signal calibrators, wherein the common property allows the target protein fragments and reporter signal calibrators having the common property to be distinguished and/or separated from molecules lacking the common property, wherein the target protein fragment and reporter signal calibrator that share a common property correspond to each other, wherein the altered form of each reporter signal calibrator can be distinguished from the altered form of the target protein fragment with which the reporter signal calibrator shares a common property, wherein the presence, absence, amount, or presence and amount of the altered forms of the target protein fragments indicates the presence, absence, amount, or presence and amount in a protein sample of the target protein fragments from which the altered forms of the target protein fragments are derived, wherein the presence, absence, amount, or presence and amount of the target protein fragments in the protein sample constitutes a protein signature of the protein sample.

Also disclosed are methods wherein the target protein fragments and reporter signal calibrators are distinguished and/or separated from other molecules based on the common properties of the target protein fragments and reporter signal calibrators.

Also disclosed are methods wherein the target protein fragments and reporter signal calibrators are altered following separation.

Also disclosed are methods wherein the target protein fragments are produced by treating the protein sample.

Disclosed are methods of producing a protein signature, the method comprising (a) treating a protein sample to produce protein fragments, wherein the protein fragments comprise a set of target protein fragments, wherein the target protein fragments can be altered, wherein the altered forms of the target protein fragments can be distinguished from the other altered forms of the target protein fragments, (b) separating the target protein fragments from other protein fragments in the protein sample, (c) altering the target protein fragments, (d) detecting the altered forms of the target protein fragments, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

Also disclosed are methods further comprising, prior to or simultaneous with step (b), mixing the target protein fragments with a set of reporter signal calibrators, wherein each target protein fragment shares a common property with at least one of the reporter signal calibrators, wherein the common property allows the target protein fragments and reporter signal calibrators having the common property to be distinguished and/or separated from molecules lacking the common property, wherein the reporter signal calibrators can be altered, wherein the altered form of each reporter signal calibrator can be distinguished from the altered form of the target protein fragment with which the reporter signal calibrator shares a common property.

Disclosed is a method of producing a protein signature, the method comprising (a) separating a plurality of target protein fragments from other protein fragments in a protein sample, (b) altering the target protein fragments, (c) detecting the altered forms of the target protein fragments, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

Disclosed are methods of analyzing a protein sample, the method comprising (a) mixing a protein sample with a predetermined amount of a reporter signal calibrator, wherein the protein sample has a known amount of protein, wherein the protein sample comprises a target protein fragment, wherein the target protein fragment can be altered, wherein the reporter signal calibrator can be altered, wherein the altered form of the reporter signal calibrator can be distinguished from the altered form of the target protein fragment, (b) altering the target protein fragment and reporter signal calibrator, (c) detecting the altered forms of the target protein fragment and reporter signal calibrator.

Also disclosed are methods further comprising determining the ratio of the amount of the target protein fragment and the amount of the reporter signal calibrator detected, and comparing the determined ratio with the predicted ratio of the amount of the target protein fragment and the amount of the reporter signal calibrator, wherein the predicted ratio is based on the predicted amount of target protein fragment in the protein sample and the predetermined amount of reporter signal calibrator, wherein the predicted amount of target protein fragment is the amount of target protein fragment the protein sample would have if the known amount of protein in the protein sample consisted of the target protein fragment, wherein the difference between the determined ratio and the predicted ratio is a measure of the purity of the protein sample for the target protein fragment, wherein the closer the determined ratio is to the predicted ratio, the purer the protein sample.

Disclosed are methods of analyzing a protein sample, the method comprising (a) treating a protein sample to produce protein fragments, wherein the protein sample has a known amount of protein, wherein the protein sample comprises a target protein, wherein the protein fragments comprise a target protein fragment derived from the target protein, (b) mixing the protein sample with a predetermined amount of a reporter signal calibrator, wherein the target protein fragment can be altered, wherein the reporter signal calibrator can be altered, wherein the altered form of the reporter signal calibrator can be distinguished from the altered form of the target protein fragment, (b) altering the target protein fragment and reporter signal calibrator, (c) detecting the altered forms of the target protein fragment and reporter signal calibrator.

Also disclosed are methods further comprising determining the ratio of the amount of the target protein fragment and the amount of the reporter signal calibrator detected, and comparing the determined ratio with the predicted ratio of the amount of the target protein fragment and the amount of the reporter signal calibrator, wherein the predicted ratio is based on the predicted amount of target protein fragment in the protein sample and the predetermined amount of reporter signal calibrator, wherein the predicted amount of target protein fragment is the amount of target protein fragment the protein sample would have if the known amount of protein in the protein sample consisted of the target protein, wherein the difference between the determined ratio and the predicted ratio is a measure of the purity of the protein sample for the target protein, wherein the closer the determined ratio is to the predicted ratio, the purer the protein sample.

Disclosed are methods of producing a protein signature, the method comprising (a) treating a protein sample to produce protein fragments, wherein the protein fragments comprise a set of target protein fragments, wherein each of the target protein fragments can be altered, wherein the altered forms of each target protein fragment can be distinguished from every other altered form of target protein fragment, (b) mixing the target protein fragments with a set of reporter signal calibrators, wherein each target protein fragment shares a common property with at least one of the reporter signal calibrators, wherein the common property allows each of the target protein fragments and reporter signal calibrators having the common property to be distinguished and/or separated from molecules lacking the common property, wherein the target protein fragment and reporter signal calibrator that share a common property correspond to each other, wherein each of the reporter signal calibrators can be altered, wherein the altered form of each reporter signal calibrator can be distinguished from the altered form of the target protein fragment with which the reporter signal calibrator shares a common property, (c) separating the target protein fragments and reporter signal calibrators from other molecules based on the common properties of the target protein fragments and reporter signal calibrators, (d) altering the target protein fragments and reporter signal calibrators, (e) detecting the altered forms of the target protein fragments and reporter signal calibrators, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

Disclosed are methods of producing a protein signature, the method comprising detecting altered forms of target protein fragments and reporter signal calibrators, wherein the altered forms of each target protein fragment can be distinguished from every other altered form of target protein fragment, wherein each target protein fragment shares a common property with at least one of the reporter signal calibrators, wherein the common property allows each of the target protein fragments and reporter signal calibrators having the common property to be distinguished and/or separated from molecules lacking the common property, wherein the target protein fragment and reporter signal calibrator that share a common property correspond to each other, wherein the altered form of each reporter signal calibrator can be distinguished from the altered form of the target protein fragment with which the reporter signal calibrator shares a common property, wherein the presence, absence, amount, or presence and amount of the altered forms of the target protein fragments indicates the presence, absence, amount, or presence and amount in a protein sample of the target protein fragments from which the altered forms of the target protein fragments are derived, wherein the presence, absence, amount, or presence and amount of the target protein fragments in the protein sample constitutes a protein signature of the protein sample.

Disclosed are methods of producing a protein signature, the method comprising (a) treating a protein sample to produce protein fragments, wherein the protein fragments comprise a set of target protein fragments, wherein each of the target protein fragments can be altered, wherein the altered forms of each target protein fragment can be distinguished from every other altered form of target protein fragment, (b) separating the target protein fragments from other protein fragments in the protein sample, (c) altering the target protein fragments, (d) detecting the altered forms of the target protein fragments, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

Also disclosed are methods further comprising, prior to or simultaneous with step (b), mixing the target protein fragments with a set of reporter signal calibrators, wherein each target protein fragment shares a common property with at least one of the reporter signal calibrators, wherein the common property allows each of the target protein fragments and reporter signal calibrators having the common property to be distinguished and/or separated from molecules lacking the common property, wherein each of the reporter signal calibrators can be altered, wherein the altered form of each reporter signal calibrator can be distinguished from the altered form of the target protein fragment with which the reporter signal calibrator shares a common property.

D. Reporter Signal Fusions

Disclosed are methods of detecting expression, the method comprising detecting a target altered reporter signal peptide derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates expression of the amino acid segment that comprises the reporter signal peptide from which the target altered reporter signal peptide is derived.

Also disclosed are methods further comprising determining the amount of the target altered reporter signal peptide detected, wherein the amount of the target altered reporter signal peptide indicates the amount present in the one or more expression samples of the amino acid segment that comprises the reporter signal peptide from which the target altered reporter signal peptide is derived.

Also disclosed are methods wherein the amount of the amino acid segment present is proportional to the amount of the target altered reporter signal peptide detected.

Also disclosed are methods further comprising detecting a plurality of the altered reporter signal peptides, wherein detection of each altered reporter signal peptide indicates expression of the amino acid segment that comprises the reporter signal peptide from which that altered reporter signal peptide is derived.

Also disclosed are methods further comprising determining the amount of the altered reporter signal peptides detected, wherein the amount of each altered reporter signal peptide indicates the amount present in the one or more expression samples of the amino acid segment that comprises the reporter signal peptide from which that altered reporter signal peptide is derived.

Also disclosed are methods wherein the amount of the amino acid segment present is proportional to the amount of the altered reporter signal peptide detected.

Also disclosed are methods wherein the presence, absence, amount, or presence and amount of the altered forms of the reporter signal peptides indicates the presence, absence, amount, or presence and amount in the expression sample of the reporter signal peptides from which the altered forms of the reporter signal peptides are derived, wherein the presence, absence, amount, or presence and amount of the reporter signal peptides in the expression sample constitutes a protein signature of the expression sample.

Also disclosed are methods wherein the altered forms of the reporter signal peptides are detecting using mass spectrometry.

Also disclosed are methods wherein the altered forms of the reporter signal peptides are detected with a tandem mass spectrometer.

Also disclosed are methods wherein the mass spectrometer includes a quadrupole set for single-ion filtering, a collision cell, and a time-of-flight spectrometer.

Also disclosed are methods wherein the reporter signal peptides are altered by fragmentation.

Also disclosed are methods wherein the reporter signal peptides are altered by cleavage at a photocleavable amino acid.

Also disclosed are methods wherein the reporter signal peptides are fragmented in a collision cell.

Also disclosed are methods wherein the reporter signal peptides are fragmented at an asparagine-proline bond, a methionine, or a phosphorylated amino acid.

Also disclosed are methods wherein the common property is mass-to-charge ratio, wherein the reporter signal peptides are altered by altering their mass, their charge, or their mass and charge, wherein the altered forms of the reporter signal peptides can be distinguished via differences in the mass-to-charge ratio of the altered forms of the reporter signal peptides.

Also disclosed are methods wherein there are two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal peptides.

Also disclosed are methods wherein there are ten or more different reporter signal peptides.

Also disclosed are methods wherein each peptide has a labile or scissile bond in a different location.

Also disclosed are methods further comprising comparing the protein signature to one or more other protein signatures.

Also disclosed are methods wherein the detected altered reporter signal peptides are derived from a plurality of expression samples.

Also disclosed are methods wherein some of the detected altered reporter signal peptides derived from a control expression sample, identifying differences between the protein signatures produced from the expression samples and the control expression sample.

Also disclosed are methods wherein the differences are differences in the presence, amount, presence and amount, or absence of reporter signal peptides in the expression samples and the control expression sample.

Also disclosed are methods wherein the plurality of expression samples comprises a control expression sample and a tester expression sample, wherein the tester expression sample, or the source of the tester expression sample, is treated so as to destroy, disrupt or eliminate one or more of the amino acid segments in the tester expression sample, wherein the reporter signal peptides corresponding to the destroyed, disrupted, or eliminated amino acid segments will be produced from the control expression sample but not the tester expression sample.

Also disclosed are methods wherein the tester expression sample is treated so as to destroy, disrupt or eliminate one or more of the amino acid segments in the tester expression sample.

Also disclosed are methods wherein one or more of the amino acid segments in the tester sample are eliminated by separating the one or more of the amino acid segments from the tester expression sample.

Also disclosed are methods wherein the one or more of the amino acid segments are separated by affinity separation.

Also disclosed are methods wherein the source of the tester expression sample is treated so as to destroy, disrupt or eliminate one or more of the amino acid segments in the tester expression sample.

Also disclosed are methods wherein the treatment of the source is accomplished by exposing cells from which the tester sample will be derived with a compound, composition, or condition that will reduce or eliminate expression of one or more of the nucleotide segments.

Also disclosed are methods further comprising identifying differences in the reporter signal peptides in the control expression sample and tester expression sample.

Also disclosed are methods further comprising identifying differences between the reporter signal peptides in the expression samples.

Also disclosed are methods wherein at least two of the expression samples, or the sources of the at least two expression samples, are subjected to different conditions.

Also disclosed are methods wherein the sources of the expression samples are cells.

Also disclosed are methods wherein differences in the protein signatures of the at least two expression samples indicate the effect of the different conditions.

Also disclosed are methods wherein the different conditions are exposure to different compounds.

Also disclosed are methods wherein the different conditions are exposure to a compound and no exposure to the compound.

Also disclosed are methods further comprising producing a second protein signature from a second expression sample and comparing the first protein signature and second protein signature, wherein differences in the first and second protein signatures indicate differences in source or condition of the source of the first and second expression samples.

Also disclosed are methods further comprising producing a second protein signature from a second expression sample and comparing the first protein signature and second protein signature, wherein differences in the first and second protein signatures indicate differences in protein modification of the first and second expression samples.

Also disclosed are methods wherein the second expression sample is a sample from the same type of cells as the first expression sample except that the cells from which the first expression sample is derived are modification-deficient relative to the cells from which the second expression sample is derived.

Also disclosed are methods wherein the second expression sample is a sample from a different type of cells than the first expression sample, and wherein the cells from which the first expression sample is derived are modification-deficient relative to the cells from which the second expression sample is derived.

Also disclosed are methods wherein the expression sample is derived from one or more cells.

Also disclosed are methods wherein the protein signature indicates the physiological state of the cells.

Also disclosed are methods wherein the protein signature indicates the effect of a treatment of the cells.

Also disclosed are methods wherein the cells are derived from an organism, wherein the cells are treated by treating the organism.

Also disclosed are methods wherein the organism is treated by administering a compound to the organism.

Also disclosed are methods wherein the organism is human.

Also disclosed are methods wherein altered reporter signal peptides are detected in a first and a second expression sample.

Also disclosed are methods wherein the second expression sample is a sample from the same type of organism as the first expression sample.

Also disclosed are methods wherein the second expression sample is a sample from the same type of tissue as the first expression sample.

Also disclosed are methods wherein the second expression sample is a sample from the same organism as the first expression sample.

Also disclosed are methods wherein the second expression sample is obtained at a different time than the first expression sample.

Also disclosed are methods wherein the second expression sample is a sample from a different organism than the first expression sample.

Also disclosed are methods wherein the second expression sample is a sample from a different type of tissue than the first expression sample.

Also disclosed are methods wherein the second expression sample is a sample from a different species of organism than the first expression sample.

Also disclosed are methods wherein the second expression sample is a sample from a different strain of organism than the first expression sample.

Also disclosed are methods wherein the second expression sample is a sample from a different cellular compartment than the first expression sample.

Also disclosed are methods further comprising altering the reporter signal peptides.

Also disclosed are methods wherein the reporter signal peptides are altered by fragmentation.

Also disclosed are methods wherein the reporter signal peptides are altered by cleavage at a photocleavable amino acid.

Also disclosed are methods wherein the reporter signal peptides are fragmented in a collision cell.

Also disclosed are methods wherein the reporter signal peptides are fragmented at an asparagine-proline bond, a methionine, or a phosphorylated amino acid.

Also disclosed are methods further comprising separating the reporter signal peptides from the expression samples.

Also disclosed are methods wherein the reporter signal peptides are distinguished and/or separated from the expression samples based on the common property.

Also disclosed are methods further comprising cleaving the reporter signal peptides from the proteins or peptides of interest.

Also disclosed are methods wherein the reporter signal peptides are distinguished and/or separated from the proteins or peptides of interest based on the common property.

Also disclosed are methods further comprising cleaving the amino acid segments into a reporter signal peptide portion and a protein portion.

Also disclosed are methods further comprising mixing two or more of the expression samples together.

Also disclosed are methods further comprising mixing two or more amino acid segments together, wherein the mixed amino acid segments were derived from two or more different expression samples.

Also disclosed are methods wherein expression of the amino acid segment that comprises the reporter signal peptide from which the target altered reporter signal peptide is derived identifies the expression sample from which the target altered reporter signal peptide is derived.

Also disclosed are methods wherein the expression samples are derived from one or more cells, wherein expression of the amino acid segment that comprises the reporter signal peptide from which the target altered reporter signal peptide is derived identifies the cell from which the identified expression sample is derived.

Also disclosed are methods wherein the expression samples are derived from one or more organisms, wherein expression of the amino acid segment that comprises the reporter signal peptide from which the target altered reporter signal peptide is derived identifies the organism from which the identified expression sample is derived.

Also disclosed are methods wherein the expression samples are derived from one or more tissues, wherein expression of the amino acid segment that comprises the reporter signal peptide from which the target altered reporter signal peptide is derived identifies the tissue from which the identified expression sample is derived.

Also disclosed are methods wherein the expression samples are derived from one or more cell lines, wherein expression of the amino acid segment that comprises the reporter signal peptide from which the target altered reporter signal peptide is derived identifies the cell line from which the identified expression sample is derived.

Also disclosed are methods wherein each nucleic acid molecule further comprises expression sequences, wherein the expression sequences are operably linked to the nucleotide segment such that the amino acid segment is expressed.

Also disclosed are methods wherein the expression sequences comprise translation expression sequences.

Also disclosed are methods wherein the expression sequences further comprise transcription expression sequences.

Also disclosed are methods wherein the amino acid segment is expressed in vitro.

Also disclosed are methods wherein the amino acid segment is expressed in vivo.

Also disclosed are methods wherein the amino acid segment is expressed in cell culture.

Also disclosed are methods wherein the expression sequences of each nucleic acid molecule are different.

Also disclosed are methods wherein the different expression sequences are differently regulated.

Also disclosed are methods wherein the expression sequences are similarly regulated.

Also disclosed are methods wherein a plurality of the expression sequences are expression sequences of, or derived from, genes expressed as part of the same expression cascade.

Also disclosed are methods wherein the expression sequences of each nucleic acid molecule are the same.

Also disclosed are methods wherein the expression sequences are similarly regulated.

Also disclosed are methods wherein the expression sequences of at least two nucleic acid molecules are different.

Also disclosed are methods wherein the expression sequences of at least two nucleic acid molecules are the same.

Also disclosed are methods wherein expression of the amino acid segment is induced.

Also disclosed are methods wherein each nucleic acid molecule further comprises replication sequences, wherein the replication sequences mediate replication of the nucleic acid molecules.

Also disclosed are methods wherein the nucleic acid molecules are replicated in vitro.

Also disclosed are methods wherein the nucleic acid molecules are replicated in vivo.

Also disclosed are methods wherein the nucleic acid molecules are replicated in cell culture.

Also disclosed are methods wherein each nucleic acid molecule further comprises integration sequences, wherein the integration sequences mediate integration of the nucleic acid molecules into other nucleic acids.

Also disclosed are methods wherein the nucleic acid molecules are integrated into a chromosome.

Also disclosed are methods wherein the nucleic acid molecules are integrated into a chromosome at a predetermined location.

Also disclosed are methods wherein the nucleic acids molecules are produced by replicating nucleic acids in one or more nucleic acid samples.

Also disclosed are methods wherein the nucleic acids are replicated using pairs of primers, wherein each of the first primers in the primer pairs used to produce the nucleic acid molecules comprises a nucleotide sequence encoding the reporter signal peptide.

Also disclosed are methods wherein each first primer further comprises expression sequences.

Also disclosed are methods wherein the nucleotide sequence of each first primer also encodes an epitope tag.

Also disclosed are methods wherein each amino acid segment further comprises an epitope tag.

Also disclosed are methods wherein the epitope tag of each amino acid segment is different.

Also disclosed are methods wherein the epitope tag of each amino acid segment is the same.

Also disclosed are methods wherein the epitope tag of at least two amino acid segments are different.

Also disclosed are methods wherein the epitope tag of at least two amino acid segments are the same.

Also disclosed are methods wherein the amino acid segments are distinguished and/or separated from the one or more expression samples via the epitope tags.

Also disclosed are methods wherein the reporter signal peptide of each amino acid segment is different.

Also disclosed are methods wherein the reporter signal peptide of each amino acid segment is the same.

Also disclosed are methods wherein the reporter signal peptide of at least two amino acid segments are different.

Also disclosed are methods wherein the reporter signal peptide of at least two amino acid segments are the same.

Also disclosed are methods wherein the nucleic acid molecules are in cells.

Also disclosed are methods wherein each nucleic acid molecule is in a different cell.

Also disclosed are methods wherein each nucleic acid molecule is in the same cell.

Also disclosed are methods wherein each nucleic acid molecule further comprises expression sequences, wherein the expression sequences are operably linked to the nucleotide segment such that the amino acid segment can be expressed.

Also disclosed are methods wherein the expression sequences of each nucleic acid molecule are different.

Also disclosed are methods wherein the expression sequences are similarly regulated.

Also disclosed are methods wherein a plurality of the expression sequences are expression sequences of, or derived from, genes expressed as part of the same expression cascade.

Also disclosed are methods wherein the nucleic acid molecules are integrated into a chromosome of the cell.

Also disclosed are methods wherein the nucleic acid molecules are integrated into the chromosome at a predetermined location.

Also disclosed are methods wherein the chromosome is an artificial chromosome.

Also disclosed are methods wherein the nucleic acid molecules are, or are integrated into, a plasmid.

Also disclosed are methods wherein the cells are in cell lines.

Also disclosed are methods wherein each nucleic acid molecule is in a different cell line.

408H. The method of claim 408F wherein each nucleic acid molecule is in the same cell line.

Also disclosed are methods wherein the expression samples are produced from the cells.

Also disclosed are methods wherein each expression sample is produced from cells from a cell sample, wherein each expression sample is produced from a different cell sample.

Also disclosed are methods wherein each cell sample is subjected to different conditions.

Also disclosed are methods wherein each cell sample is brought into contact with a different test compound.

Also disclosed are methods wherein each cell sample is cultured under different conditions.

Also disclosed are methods wherein each cell sample is derived from a different organism.

Also disclosed are methods wherein each cell sample is derived from a different tissue.

Also disclosed are methods wherein each cell sample is taken from the same source at different times.

Also disclosed are methods wherein the expression samples are produced by lysing the cells.

Also disclosed are methods wherein the nucleic acid molecules are in organisms.

Also disclosed are methods wherein each nucleic acid molecule is in a different organism.

Also disclosed are methods wherein each nucleic acid molecule is in the same organism.

Also disclosed are methods wherein each nucleic acid molecule further comprises expression sequences, wherein the expression sequences are operably linked to the nucleotide segment such that the amino acid segment can be expressed.

Also disclosed are methods wherein the expression sequences of each nucleic acid molecule are different.

Also disclosed are methods wherein the expression sequences are similarly regulated.

Also disclosed are methods wherein a plurality of the expression sequences are expression sequences of, or derived from, genes expressed as part of the same expression cascade.

Also disclosed are methods wherein the nucleic acid molecules are integrated into a chromosome of the organism.

Also disclosed are methods wherein the nucleic acid molecules are integrated into the chromosome at a predetermined location.

Also disclosed are methods wherein the chromosome is an artificial chromosome.

Also disclosed are methods wherein the nucleic acid molecules are, or are integrated into, a plasmid.

Also disclosed are methods wherein each nucleic acid molecule is in a different organism.

Also disclosed are methods wherein each nucleic acid molecule is in the same organism.

Also disclosed are methods wherein the nucleic acid molecules are in cells of an organism.

Also disclosed are methods wherein the nucleic acid molecules are in substantially all of the cells of the organism.

Also disclosed are methods wherein the nucleic acid molecules are in some of the cells of the organism.

Also disclosed are methods wherein the amino acid segments are expressed in substantially all of the cells of the organism.

Also disclosed are methods wherein the amino acid segments are expressed in some of the cells of the organism.

Also disclosed are methods wherein the protein or peptide of interest of each amino acid segment is different.

Also disclosed are methods wherein the protein or peptide of interest of each amino acid segment is the same.

Also disclosed are methods wherein the protein or peptide of interest of at least two amino acid segments are different.

Also disclosed are methods wherein the protein or peptide of interest of at least two amino acid segments are the same.

Also disclosed are methods wherein the proteins or peptides of interest are related.

Also disclosed are methods wherein the proteins or peptides of interest are proteins produced in the same cascade.

Also disclosed are methods wherein the proteins or peptides of interest are proteins expressed under the same conditions.

Also disclosed are methods wherein the proteins or peptides of interest are proteins associated with the same disease.

Also disclosed are methods wherein the proteins or peptides of interest are proteins associated with the same cell type.

Also disclosed are methods wherein the proteins or peptides of interest are proteins associated with the same tissue type.

Also disclosed are methods wherein the proteins or peptides of interest are proteins in the same enzymatic pathway.

Also disclosed are methods wherein the nucleotide segment encodes a plurality of amino acid segments each comprising a reporter signal peptide and a protein or peptide of interest.

Also disclosed are methods wherein the protein or peptide of interest of at least two of the amino acid segments in one of the nucleotide segments are different.

Also disclosed are methods wherein the protein or peptide of interest of the amino acid segments in one of the nucleotide segments are different.

Also disclosed are methods wherein the protein or peptide of interest of at least two of the amino acid segments in each of the nucleotide segments are different.

Also disclosed are methods wherein the protein or peptide of interest of the amino acid segments in each of the nucleotide segments are different.

Also disclosed are methods wherein the set consists of a single nucleic acid molecule.

Also disclosed are methods wherein the set consists of a single nucleic acid molecule, wherein the nucleic acid molecule comprises a plurality of nucleotide segments each encoding an amino acid segment.

Also disclosed are methods wherein the amino acid segment comprises a cleavage site near the junction between the reporter signal peptide and the protein or peptide of interest.

Also disclosed are methods wherein the cleavage site is cleaved.

Also disclosed are methods wherein the reporter signal peptide is distinguished and/or separated from the peptide or protein of interest.

Also disclosed are methods wherein the cleavage site is a trypsin cleavage site.

Also disclosed are methods wherein the cleavage site is at the junction between the reporter signal peptide and the protein or peptide of interest.

Also disclosed are methods wherein each amino acid segment further comprises a self-cleaving segment.

Also disclosed are methods wherein the self-cleaving segment is between the reporter signal peptide and the protein or peptide of interest.

Also disclosed are methods wherein the self-cleaving segment cleaves the amino acid segment.

Also disclosed are methods wherein the reporter signal peptide is distinguished and/or separated from the peptide or protein of interest.

Also disclosed are methods wherein the self-cleaving segment is an intein segment.

Also disclosed are methods wherein a plurality of different altered reporter signal peptides are detected, wherein detection of each altered reporter signal peptide indicates expression of the amino acid segment that comprises the reporter signal peptide from which that altered reporter signal peptide is derived.

Also disclosed are methods wherein different expression samples comprise different nucleic acid molecules, wherein detection of each altered reporter signal peptide indicates expression in the expression sample that comprises the nucleic acid molecule that comprises the nucleotide segment encoding the amino acid segment that comprises the reporter signal peptide from which that altered reporter signal peptide is derived.

Also disclosed are methods wherein there are a plurality of different expression samples, wherein each different expression sample comprises different nucleic acid molecules, wherein detection of an altered reporter signal peptide indicates expression in the expression sample that comprises the nucleic acid molecule that comprises the nucleotide segment encoding the amino acid segment that comprises the reporter signal peptide from which the detected altered reporter signal peptide is derived.

Disclosed are methods of detecting expression, the method comprising detecting a target altered reporter signal peptide derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates expression of the nucleotide segment encoding the amino acid segment that comprises the reporter signal peptide from which the target altered reporter signal peptide is derived.

Also disclosed are methods further comprising determining the amount of the target altered reporter signal peptide detected, wherein the amount of the target altered reporter signal peptide indicates the amount present in the one or more expression samples of the nucleotide segment that comprises the reporter signal peptide from which the target altered reporter signal peptide is derived.

Also disclosed are methods wherein the amount of the nucleotide segment present is proportional to the amount of the target altered reporter signal peptide detected.

Also disclosed are methods further comprising detecting a plurality of the altered reporter signal peptides, wherein detection of each altered reporter signal peptide indicates expression of the nucleotide segment that comprises the reporter signal peptide from which that altered reporter signal peptide is derived.

Also disclosed are methods further comprising determining the amount of the altered reporter signal peptides detected, wherein the amount of each altered reporter signal peptide indicates the amount present in the one or more expression samples of the nucleotide segment that comprises the reporter signal peptide from which that altered reporter signal peptide is derived.

Also disclosed are methods wherein the amount of the nucleotide segment present is proportional to the amount of the altered reporter signal peptide detected.

Disclosed are methods of detecting expression, the method comprising detecting a target altered amino acid segment derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished and/or separated from molecules lacking the common property, wherein the reporter signal peptides can be altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates expression of the amino acid segment from which the target altered amino acid segment is derived.

Disclosed are methods of detecting expression, the method comprising detecting an altered amino acid subsegment derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished and/or separated from molecules lacking the common property, wherein the reporter signal peptides can be altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates expression of the amino acid segment from which the target altered amino acid subsegment is derived.

Disclosed are methods of detecting cells, the method comprising detecting a target altered reporter signal peptide derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell from which the target altered reporter signal peptide is derived.

Also disclosed are methods wherein each cell is engineered to contain at least one of the nucleic acid molecules, wherein the reporter signal peptide of the amino acid segment encoded by the nucleotide segment of the nucleic acid molecule in each cell is different.

Also disclosed are methods wherein each cell having a trait of interest comprises the same reporter signal peptide.

Also disclosed are methods wherein the trait of interest is a heterologous gene.

Also disclosed are methods wherein the heterologous gene comprises the nucleic acid molecule.

Also disclosed are methods wherein the heterologous gene encodes the amino acid segment.

Also disclosed are methods wherein a plurality of different altered reporter signal peptides are detected, wherein detection of each altered reporter signal peptide indicates the presence of the cell from which that altered reporter signal peptide is derived.

Also disclosed are methods wherein different cells comprise different nucleic acid molecules, wherein detection of each altered reporter signal peptide indicates the presence of the cell that comprises the nucleic acid molecule that comprises the nucleotide segment encoding the amino acid segment that comprises the reporter signal peptide from which that altered reporter signal peptide is derived.

Also disclosed are methods wherein there are a plurality of different cells, wherein each different cell comprises different nucleic acid molecules, wherein detection of an altered reporter signal peptide indicates the presence of the cell that comprises the nucleic acid molecule that comprises the nucleotide segment encoding the amino acid segment that comprises the reporter signal peptide from which the detected altered reporter signal peptide is derived.

Disclosed are methods of detecting cell samples, the method comprising detecting a target altered reporter signal peptide derived from one or more cell samples, wherein the one or more cell samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell sample from which the target altered reporter signal peptide is derived.

Also disclosed are methods wherein a plurality of different altered reporter signal peptides are detected, wherein detection of each altered reporter signal peptide indicates the presence of the cell sample from which that altered reporter signal peptide is derived.

Also disclosed are methods wherein different cell samples comprise different nucleic acid molecules, wherein detection of each altered reporter signal peptide indicates the presence of the cell sample that comprises the nucleic acid molecule that comprises the nucleotide segment encoding the amino acid segment that comprises the reporter signal peptide from which that altered reporter signal peptide is derived.

Also disclosed are methods wherein there are a plurality of different cell samples, wherein each different cell sample comprises different nucleic acid molecules, wherein detection of an altered reporter signal peptide indicates the presence of the cell sample that comprises the nucleic acid molecule that comprises the nucleotide segment encoding the amino acid segment that comprises the reporter signal peptide from which the detected altered reporter signal peptide is derived.

Disclosed are methods of detecting cells, the method comprising detecting a target altered reporter signal peptide derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell from which the target altered reporter signal peptide is derived.

Disclosed are methods of detecting cells, the method comprising detecting a target altered amino acid segment derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished and/or separated from molecules lacking the common property, wherein the reporter signal peptides can be altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates the presence of the cell from which the target altered amino acid segment is derived.

Disclosed are methods of detecting cells, the method comprising detecting an altered amino acid subsegment derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished and/or separated from molecules lacking the common property, wherein the reporter signal peptides can be altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates the presence of the cell from which the target altered amino acid subsegment is derived.

Disclosed are methods of detecting organisms, the method comprising detecting a target altered reporter signal peptide derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the organism from which the target altered reporter signal peptide is derived.

Also disclosed are methods wherein each organism is engineered to contain at least one of the nucleic acid molecules, wherein the reporter signal peptide of the amino acid segment encoded by the nucleotide segment of the nucleic acid molecule in each organism is different.

Also disclosed are methods wherein each organism having a trait of interest comprises the same reporter signal peptide.

Also disclosed are methods wherein the trait of interest is a transgene and methods wherein the transgene gene comprises the nucleic acid molecule and methods wherein the transgene gene encodes the amino acid segment.

Also disclosed are methods wherein a plurality of different altered reporter signal peptides are detected, wherein detection of each altered reporter signal peptide indicates the presence of the organism from which that altered reporter signal peptide is derived.

Also disclosed are methods wherein different organisms comprise different nucleic acid molecules, wherein detection of each altered reporter signal peptide indicates the presence of the organism that comprises the nucleic acid molecule that comprises the nucleotide segment encoding the amino acid segment that comprises the reporter signal peptide from which that altered reporter signal peptide is derived.

Also disclosed are methods wherein there are a plurality of different organisms, wherein each different organism comprises different nucleic acid molecules, wherein detection of an altered reporter signal peptide indicates the presence of the organism that comprises the nucleic acid molecule that comprises the nucleotide segment encoding the amino acid segment that comprises the reporter signal peptide from which the detected altered reporter signal peptide is derived.

Disclosed are methods of detecting organisms, the method comprising detecting a target altered reporter signal peptide derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished and/or separated from molecules lacking the common property, wherein the reporter signal peptides can be altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the organism from which the target altered reporter signal peptide is derived.

Disclosed are methods of detecting organisms, the method comprising detecting a target altered amino acid segment derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished and/or separated from molecules lacking the common property, wherein the reporter signal peptides can be altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates the presence of the organism from which the target altered amino acid segment is derived.

Disclosed are methods of detecting organisms, the method comprising detecting an altered amino acid subsegment derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished and/or separated from molecules lacking the common property, wherein the reporter signal peptides can be altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates the presence of the organism from which the target altered amino acid subsegment is derived.

Illustrations

The disclosed methods can be further understood by way of the following illustrations which involve examples of the disclosed methods. The illustrations are not intended to limit the scope of the method in any way.

A. Illustration 1: Heavy Isotopes

This illustration makes use of peptide reporter signals having the same mass, that fragment at certain peptide bonds, and that use heavy isotopes to distribute mass differently in different reporter signals. For example, it has been demonstrated, in ion traps, that peptides containing arginine will preferentially fragment at the C-termini of aspartic acid or glutamic acid residues, and, proline containing peptides will fragment at the N-termini of the proline residues (Qin and Chait, Int. *J. Mass Spectrom.* (Netherlands), 190–191:313–20 (1999)). DP (aspartic acid (D) and proline (P)) amino acid sequences can be used in the disclosed reporter signals resulting in collisionally induced fragmentation at the scissile bond between the aspartic acid and proline.

The singly charged ion of an exemplary peptide, AGSLDPAGSLR (SEQ ID NO:2), will fragment between the 'D' and 'P' in the collision cell of the mass spectrometer. Utilizing natural abundance isotopes the singly charged parent ion will have an average nominal (m/z)=1043 amu, and the possible resultant daughter ions AGSLD$^+$ (amino acids 1–5 of SEQ ID NO:2) and PAGSLR$^+$ (amino acids 6–11 of SEQ ID NO:2) have average nominal (m/z) of 461 and 600 amu, respectively. As a practical matter, fragmentation will typically yield one dominant daughter ion, say PAGSLR$^+$ (amino acids 6–11 of SEQ ID NO:2) in this case. For this illustration consider only one charged daughter from the population of singly charged parent. Note that, without loss of generality or applicability, the branching ratio into these daughter ion channels may be other than 100% into the PAGSLR$^+$ (amino acids 6–11 of SEQ ID NO:2) daughter fragment.

Standard synthetic methods can be utilized to construct such peptides. In this illustration of reporter molecules consider isotopically labeled amino acids (for example, A vs. A*, where A has a $CH_3$ and A* has a $CD_3$ side chain). There are four possibilities for the synthetic peptide, with their nominal (m/z) indicated in parentheses: AGSLDPAGSLR (1043), A*GSLDPAGSLR (1046), AGSLDPA*GSLR (1046), A*GSLDPA*GSLR (1049) (SEQ ID NO:2). For this example consider the two monolabeled peptides A*GSLDPAGSLR, AGSLDPA*GSLR (SEQ ID NO:2), which have a common nominal mass-to-charge of 1046.

As a simple demonstration of a preferred mode of the disclosed method consider a solution containing the two synthetic peptides. This solution could have been collected following any number of biological experiments and, in general because of processing, would contain many additional components.

The solution containing A*GSIDPAGSLR and AGSLDPA*GSLR (SEQ ID NO:2) is mixed with a suitable matrix solution for performing analysis by mass spectrometry. Suitable matrices, including sinapic acid, 4-hydroxy-α-cyanocinamic acid or 2,5-dihydroxybenzoic acid, are known in the art.

The resulting solution is spotted onto the MALDI target and allowed to crystallize.

The target is inserted into the source of the mass spectrometer. Utilizing the laser impinging on the sample spot on the MALDI target, many ions are introduced into the first quadrupole, Q0. Among the species introduced into Q0 are predominantly singly charged species (A*GSLDPAGSLR+, AGSLDPA*GSLR+; SEQ ID NO:2), various fragmentation ions, neutral matrix, matrix ions and multimers as known in the art. Neutral particles will pass out of Q0 without being guided into the second quadrupole, Q1.

Ions introduced into Q0 are guided into the higher vacuum region containing Q1.

Quadrupole Q1 is set to pass ions with the mass-to-charge ratio of 1046 into the third quadrupole, Q2 (recall A*GSLDPAGSLR and AGSLDPA*GSLR (SEQ ID NO:2) have the same mass-to-charge; "isobaric" in the parlance of mass spectrometry). Ions with mass-to-charge ratios different from 1046 will follow trajectories that do not exit Q1 on the Q1–Q2 axis, and are effectively discarded. This yields a huge increase in the signal to noise for the system, on the order of 100–1000 fold improvement over systems which do not have this mass filtering.

The collision cell surrounding Q2 is filled with a chemically inert gas at an appropriate pressure to cause preferential cleavage of the DP scissile bond of the peptide ions, typically a few milliTorr of nitrogen. As discussed above, the fragmentation of the singly charged parent ion is expected to yield predominantly one daughter ion. In this case each of the isobaric parents (SEQ ID NO:2) will yield correlated, unique daughters (amino acids 1–5 and 6–11 of SEQ ID NO:2):
A*GSLDPAGSLR+→A*GSLD+PAGSLR+ (m/z 600)
AGSLDPA*GSLR+→AGSLD+PA*GSLR+ (m/z 603)

The resolution of the mass spectrometers as discussed here is on the order of 5000 to 10000, and thus the 3 amu difference is readily attained at these (m/z).

The ions exiting Q2 enter the time-of-flight (TOF) section of the instrument. A transient electric field gradient is applied and the positively charged ions are accelerated toward the reflectron and ultimately to the detector. The ions are all accelerated through the same electric field gradient (the reflectron will compensate for a small perturbation in this assertion, as is known in the art) and thus will all have the same kinetic energy imparted to them. Because the kinetic energy is the same for all ions, and the masses of the ions are different, the time it takes for the ions to reach the detector will be different: heavier ions will arrive later than lighter ions.

The resulting mass spectrum reflects the relative amount of the two analytes (for example, peptides) in the original sample.

This scheme can be extended to more analytes (for example, peptides). The most basic extension for a panel of isobaric detectors based upon the above peptide, utilizing X/X* differences, would be as shown in Table 2. The asterisk indicates heavy isotope labeled amino acids. This set assumes that the non-labeled to labeled mass change $\{(m/z)_x{}^* - (m/z)_x\}$ for each residue is the same. For the general case where $\{(m/z)_x{}^* - (m/z)_x\}$ is not the same for all the residues there are more combinations for a given peptide which can be resolved by the mass spectrometer. The parent molecule is SEQ ID NO:2 and the primary daughter is amino acids 6–11 of SEQ ID NO:2.

TABLE 2

| Parent | Primary Daughter |
| --- | --- |
| A*G*S*L*DPAGSLR | PAGSLR |
| AG*S*L*DPA*GSLR | PA*GSLR |

TABLE 2-continued

| Parent | Primary Daughter |
| --- | --- |
| AGS*L*DPA*G*SLR | PA*G*SLR |
| AGSL*DPA*G*S*LR | PA*G*S*LR |
| AGSLDPA*G*S*L*R | PA*G*S*L*R |

The synthesis of specific isotope labeled amino acids would facilitate rapidly increased panel size. For example, synthesis of unique alanines with $CH_3$, $CH_2D$, $CHD_2$, $CD_3$ side chains could be used to yield a significant panel size with a small peptide.

This mode of the disclosed method has the desirable property that all the detected ions originate from a very similar chemical environment (only differing by the location of a few neutrons) and will thus behave identically (for all practical purposes) when processed in the MALDI source and in the collision cell. Of particular note is the case where one of the isobaric reporter signal molecules is added as a quantitation standard to the isobaric detector molecules used for the assay. Quantitation of the entire set of detector molecules used in the assay is straightforward and quantitative. For the case where the molecules are essentially identical except for the isotopic enrichment all the isobars in a set will behave identically through the processing.

B. Illustration 2: Labile Bond, One Daughter Ion

This illustration makes use of peptide reporter signals having the same mass that fragment at a labile bond, where the labile bond is placed in different locations in the different reporter signals. In this illustration, the parent ion produces a single daughter. An example of synthesis of peptides with labile bonds at defined positions between amino acids is disclosed by WO 97/11958. Analogous chemistry may be utilized to produce peptides with labile bonds between amino acids for use in the disclosed method and compositions. For example, consider a pair of peptide molecules of the form GSWFSGMCAR (SEQ ID NO:12):

Peptide A: GSWFSG#MCAR

Peptide B: GSWF#SGMCAR where the symbol # indicates the location of the labile bond. Note that the peptide sequence does not have to be conserved for this method, the only requirement is that the molecular mass of the peptides be the same.

For simplicity consider a solution containing the two aforementioned synthetic peptides with labile bonds, A and B. This solution could have been collected following any number of biological experiments and, in general, because of processing, would contain many additional components.

The solution containing A and B is mixed with a suitable matrix solution for performing analysis by mass spectrometry. Suitable matrices, including sinapic acid, 4-hydroxy-α-cyanocinamic acid or 2,5-dihydroxybenzoic acid, are known in the art.

The resulting solution is spotted onto the MALDI target and allowed to crystallize.

The target is inserted into the source of the mass spectrometer.

Utilizing the laser impinging on the sample spot on the MALDI target, many ions are introduced into the first quadrupole, Q0. Among the species introduced into Q0 are predominantly singly charged species (A+, B+), various fragmentation ions, neutral matrix, matrix ions and multimers as known in the art. Neutral particles will pass out of Q0 without being guided into Q1.

Ions introduced into Q0 are guided into the higher vacuum region containing Q1.

Quadrupole Q1 is set to pass ions with the mass-to-charge ratio of $(m/z)_A$ and $(m/z)_B$ (recall $(m/z)_A=(m/z)_B$; "isobaric" in the parlance of mass spectrometry). Ions with mass-to-charge ratios different from $(m/z)_A$ and $(m/z)_B$ will follow trajectories that do not exit Q1 on the Q1–Q2 axis, and are effectively discarded. This yields a huge increase in the signal to noise for the system, on the order of 100–1000 fold improvement over systems which do not have this mass filtering.

The collision cell surrounding Q2 is filled with a chemically inert gas at an appropriate pressure to cause preferential cleavage of the labile bond of the peptide ions $A^+$ and $B^+$, typically a few milliTorr of nitrogen. Considering only fragmentation at the labile bond, and the operation of Q2 in RF only mode, there will be four possible ions which can emerge from Q2 into the TOF section. As discussed above, depending upon the thermodynamics and kinetics, it is common that one of the daughters for each parent will be more likely to take the charge than the other daughter. For the majority of cases there will be one predominant daughter ion. The primary fragmentation will be (SEQ ID NO:12 into amino acids 1–6 and 7–10 of SEQ ID NO:12 and SEQ ID NO: 12 into amino acids 1–4 and 5–10 of SEQ ID NO:12):
GSWFSG#MCAR$^+$→GSWFSG+MCAR$^+$
GSWF#SGMCAR$^+$→GSWF+SGMCAR$^+$ The ions exiting Q2 enter the time-of-flight, TOF, section of the instrument. A transient electric field gradient is applied and the positively charged ions are accelerated toward the reflectron and ultimately to the detector. The ions are all accelerated through the same electric field gradient (the reflectron will compensate for a small perturbation in this assertion, as is known in the art) and thus will all have the same kinetic energy imparted to them. Because the kinetic energy is the same for all ions, and the masses of the ions are different, the time it takes for the ions to reach the detector will be different: heavier ions will arrive later than lighter ions.

The resulting mass spectrum shows the relative amount of the two reporter signals in the original sample.

A standard, with the same mass as the peptides (say GSW#FSGMCAR; SEQ ID NO: 12), could have been added to facilitate quantitative results. In order to extract quantitative results the relative efficiencies of the isobaric detector molecule under consideration should be calibrated; a straightforward process.

C. Illustration 3: Labile Bond, Two Daughter Ions

This illustration makes use of peptide reporter signals having the same mass that fragment at a labile bond, where the labile bond is placed in different locations in the different reporter signals. In this illustration, the parent ion branches into two daughters. Consider the peptides as described in Illustration 2 (SEQ ID NO: 12):
Peptide A: GSWFSG#MCAR
Peptide B: GSWF#SGMCAR
where the symbol # indicates the location of the labile bond. Note that the peptide sequence does not have to be conserved for this method, the only requirement is that the molecular mass of the reporter molecule peptides be nominally the same.

For simplicity consider a solution containing the two aforementioned synthetic peptides with labile bonds, A and B. This solution could have been collected following any number of biological experiments and, in general, because of processing, would contain many additional components.

The solution containing A and B is mixed with a suitable matrix solution for performing analysis by mass spectrometry. Suitable matrices, including sinapic acid, 4-hydroxy-α-cyanocinamic acid or 2,5-dihydroxybenzoic acid, are known in the art.

The resulting solution is spotted onto the MALDI target and allowed to crystallize.

The target is inserted into the source of the mass spectrometer.

Utilizing the laser impinging on the sample spot on the MALDI target, many ions are introduced into the first quadrupole, Q0. Among the species introduced into Q0 are predominantly singly charged species ($A^+$, $B^+$), various fragmentation ions, neutral matrix, matrix ions and multimers as known in the art. Neutral particles will pass out of Q0 without being guided into Q1.

Ions introduced into Q0 are guided into the higher vacuum region containing Q1.

Quadrupole Q1 is set to pass ions with the mass-to-charge ratio of $(m/z)_A$ and $(m/z)_B$ (recall $(m/z)_A=(m/z)_B$; "isobaric" in the parlance of mass spectrometry). Ions with mass-to-charge ratios different from $(m/z)_A$ and $(m/z)_B$ will follow trajectories that do not exit Q1 on the Q1–Q2 axis, and are effectively discarded. This yields a huge increase in the signal to noise for the system, on the order of 100–1000 fold improvement over systems which do not have this mass filtering.

The collision cell surrounding Q2 is filled with a chemically inert gas at an appropriate pressure to cause preferential cleavage of the labile bond of the peptide ions $A^+$ and $B^+$, typically a few milliTorr of nitrogen. Considering only fragmentation at the labile bond, and the operation of Q2 in RF only mode, there will be four possible ions which can emerge from Q2 into the TOF section. As discussed above for the majority of cases there will be a predominant daughter ion. The fragmentation of the population of singly charged parent ions into the daughter may be as follows (these branching ratios would be empirically determined) (SEQ ID NO: 12 into amino acids 1–6 and 7–10 of SEQ ID NO: 12 and SEQ ID NO:12 into amino acids 1–4 and 5–10 of SEQ ID NO: 12):
GSWFSG#MCAR$^+$→GSWFSG+MCAR$^+$(A1: 50%)
→GSWFSG$^+$+MCAR (A2: 50%)
GSWF#SGMCAR$^+$+→GSWF+SGMCAR$^+$(B 1: 50%)
→GSWF$^+$SGMCAR (B2: 50%)

The branching ratios as noted here would yield a mass spectrum as shown schematically in FIG. 2. The spectrum indicates there is twice as much B as A in the original sample. In the case of very low pressure in the collision cell the parent ions will pass through Q2 without fragmenting (FIG. 2A), with gas in the collision cell the peptides will fragment at the labile bonds (FIG. 2B). Note the correlation (intensities are the same, and the sum of the masses is equal to the parent ion mass-to-charge) of the $A^+$ daughters and the $B^+$ daughters.

The ions exiting Q2 enter the time-of-flight, TOF, section of the instrument. A transient electric field gradient is applied and the positively charged ions are accelerated toward the reflectron and ultimately to the detector. The ions are all accelerated through the same electric field gradient (the reflectron will compensate for a small perturbation in this assertion, as is known in the art) and thus will all have the same kinetic energy imparted to them. Because the kinetic energy is the same for all ions, and the masses of the ions are different, the time it takes for the ions to reach the detector will be different: heavier ions will arrive later than lighter ions.

The resulting mass spectrum shows the relative amount of the two analytes (for example, peptides) in the original sample. The daughter ion signals will be correlated with each other at known branching ratio and known parent ion (m/z), and thus there is increased confidence in the measurement of the analytes.

A standard, with the same mass as the analytes (say GSW#FSGMCAR; SEQ ID NO: 12), could have been added to facilitate quantitative results. In order to extract quantitative results the relative efficiencies of the isobars under consideration should be calibrated.

D Illustration 4: Scissile Bond

This illustration makes use of peptide reporter signals having the same mass that fragment at certain peptide bonds, where the bond is placed in different locations in the different reporter signals. As discussed above, DP containing amino acid sequence will fragment between the aspartic acid and proline in a collision cell. A set of peptides that may be useful for the disclosed method may be:

Peptide C: YFMTSGCDPGGR (SEQ ID NO: 13)
Peptide D: YFMTSGDPCGGR (SEQ ID NO:14)
Peptide E: YFMTSDPGCGGR (SEQ ID NO: 15)
Peptide F: YFMTDPSGCGGR (SEQ ID NO:16)
Peptide G: YFMDPTSGCGGR (SEQ ID NO: 17)

For simplicity consider a solution containing these synthetic peptides. This solution could have been collected following any number of biological experiments and, in general, because of processing would contain many additional components.

The solution containing C, D, E, F, G is mixed with a suitable matrix solution for performing analysis by mass spectrometry. Suitable matrices, including sinapic acid, 4-hydroxy-α-cyanocinamic acid or 2,5-dihydroxybenzoic acid, are known in the art.

The resulting solution is spotted onto the MALDI target and allowed to crystallize.

The target is inserted into the source of the mass spectrometer.

Utilizing the laser impinging on the spot on the MALDI target, many ions are introduced into the first quadrupole, Q0. Among the species introduced into Q0 are $C^+$, $D^+$, $E^+$, $F^+$, $G^+$, various fragmentation ions, matrix ions and multimers as known in the art. Neutral particles will pass out of Q0 without being guided into Q1. Ions introduced into Q0 are guided into the higher vacuum region containing Q1.

Quadrupole Q1 is set to pass ions with the mass-to-charge ratio of $(m/z)_C$, $(m/z)_D$, $(m/z)_E$, $(m/z)_F$, $(m/z)_G$ (they have the same molecular weight "isobaric"). Ions with mass-to-charge ratios different from $(m/z)_C$, $(m/z)_D$, $(m/z)_E$, $(m/z)_F$, $(m/z)_G$ will follow trajectories which will not exit Q1 on the Q1–Q2 axis, and are effectively discarded. This yields a huge increase in the signal to noise for the system, on the order of 100–1000 fold improvement over systems which do not have this mass filtering.

The collision cell surrounding Q2 is filled with a chemically inert gas at an appropriate pressure to cause scission of the D-P bond, typically a few milliTorr of nitrogen. Considering only fragmentation at the DP bond, and total retention of the charge by the C termini fragments, and the operation of Q2 in RF only mode, there will be five possible ions which can emerge from Q2 into the TOF section.

C1$^+$: PGGR$^+$ (amino acids 9–12 of SEQ ID NO: 13)
D1$^+$: PCGGR$^+$ (amino acids 8–12 of SEQ ID NO: 14)
E1$^+$: PGCGGR$^+$ (amino acids 7–12 of SEQ ID NO:15)
F1$^+$: PSGCGGR$^+$ (amino acids 6–12 of SEQ ID NO:16)
G1$^+$: PTSGCGGR$^+$ (amino acids 5–12 of SEQ ID NO: 17)

The ions exiting Q2 enter the time-of-flight, TOF, section of the instrument. A transient electric field gradient is applied and the positively charged ions are accelerated toward the reflectron and ultimately to the detector. The ions are all accelerated through the same electric field gradient (the reflectron will compensate for a small perturbation in this assertion, as is known in the art) and thus will all have the same kinetic energy imparted to them. Because the kinetic energy is the same for all ions, and the masses of the ions are different, the time it takes for the ions to reach the detector will be different: heavier ions will arrive later than light ions.

The resulting mass spectrum will indicate the relative amount of the analytes (for example, peptides) in the original sample.

A standard with the same mass as the analytes could have been added to facilitate quantitative results. In order to extract quantitative results the relative efficiencies of molecules under consideration should be determined to be used in calibration; a straightforward process.

E. Illustration 5: Pre Treatment Direct Readout

This illustration involves release of the reporter signal from a specific binding molecule prior to the first quadrupole of the instrument. The specific binding molecule may be a DNA, a PNA, an antibody, or any other moiety with high specificity and affinity. The reporter signal is attached to the specific binding molecule through an interaction which can be selectively broken through the use of, for example, restriction enzymes, photocleavable nucleotides (WO 00/04036), photocleavable linkages (Olejnik et al., *Nucleic Acids Res.*, 27(23):4626–31 (1999)), and biotin-advidin like interactions (Niemeyer et al., *Nucleic Acids Res.*, 22(25): 5530–9 (1994), Sano et al., *Science*, 258(5079):120–2 (1992)).

An exemplary set of constructs might have the general form $N_j$-$X_k$, where the nucleotides are indicated by N and are PNA, the amino acids are indicated by X, the dash indicates the transition from PNA to peptide through a photocleavable linkage, and 'j' and 'k' are independent integers. Two members of such an exemplary set are (SEQ ID NO:18; peptide portion):

H: ACGGCGACGTGGCTAATC-A*G*S*L*A*G*S*L*DPAGSLAGSLR

I: CGAGAGCTAGCTATATGC-AG*S*L*A*G*S*L*DPA*GSLAGSLR where the asterisk indicates a heavy amino acid as described in Illustration 1. The PNA will direct specific molecular recognition such that 'H' will recognize GATTAGC-CACGTCGCCGT (SEQ ID NO: 19) and 'I' will recognize GCATATAGCTAGCTCTCG (SEQ ID NO:20). Processing in an analogous fashion to the above illustrations, the photocleavable linkage will be broken by the MALDI laser pulse and the peptide isobar signal molecules will be selected by the Q1 mass filter, and one will detect PAGSLAGSLR$^+$ and PA*GSLAGSLR$^+$ (amino acids 10 to 19 of SEQ ID NO:18) for 'H' and 'I' reporter molecules respectively.

Design of DNA-peptide constructs where an internal restriction site is engineered into the DNA strand would enable a DNA specific binding molecule and a peptide reporter signal. Endonucleases Hha I, HinP1 I and Mn1 I are known to have significant single strand activity (NEB catalog). A prototypical reporter molecule, utilizing Hha I (GCG^C), could have the form (SEQ ID NO:21, DNA portion; SEQ ID NO:18, peptide portion)

GACGACGGCGACGTGGC<u>TGCGC</u>-A*G*S*L*A*G* S*L*DPAGSLAGSLR where GACGACGGCGACGTG-GCT (nucleotides 1 to 18 of SEQ ID NO:21) represents the specific binding molecule, GCGC is the recognition site for Hha I, and the dash represents the transition from DNA to peptide. For this mode of the disclosed method, the set of molecules would all share the underlined sequence adjacent to the transition to the peptide. Pretreatment with Hha I will cleave the all molecules containing GCGC leaving the 3' cytosine nucleotide attached to the peptide.

In an analogous manner, because one has freedom over the peptide sequence, one can make use of the huge body of literature in the art for specific cleavage of peptides to specifically cleave the reporter molecule within the peptide moiety. Examples of such specific cleavage systems include thrombin (cleaves between Arg and Gly), trypsin (cleaves C-terminus of Arg or Lys), endoprotease Glu-C (cleavages C-terminus of Asp or Glu), and the general classes known as oligopeptidases or endoproteases.

F. Illustration 6: Indirect Readout

In a preferred embodiment of the disclosed method, a reporter molecule containing a decoding tag is used to specifically recognize a coding molecule. As an example consider a coding molecule which has the recognition sequence as shown for 'H' in Illustration 5 (SEQ ID NO:22 and SEQ ID NO:23) ACGGCGACGTGGCTAATC-spacer-CGTCATCGTAG
where the specific binding molecule will recognize and associate with GATTAGCCACGTCGCCGT (SEQ ID NO: 19), -spacer-is a convenient spacer moiety such as PEG, and, CGTCATCGTAG (SEQ ID NO:23) represents a coding tag. The reporter molecule is of the form $N_j$-$X_k$, where the nucleotides are indicated by N and are PNA, the amino acids are indicated by X, the dash indicates the transition from PNA to peptide (optionally through a cleavable linkage), and 'j' and 'k' are independent integers. An example is (SEQ ID NO: 18, peptide portion) CTACGATGACG-A*G*S*L*A*G*S*L*DPAGSLAGSLR The PNA, which is the decoding tag, will recognize and specifically associate with the CGTCATCGTAG (SEQ ID NO:23) coding tag of the coding molecule selectively broken the filter quadrupole, Q1, would be tuned to the mass-to-charge of the peptide ion.

A set of molecules for multiplex assay only requires the reporter molecule to have a common mass among the set (or a common mass among the set of peptides, in the case of the selective bond breakage between the PNA and the peptide). A common mass for the reporter molecule is easily attained simply by utilizing alternate sequence of the PNA preserving the composition of the PNA (that is, same number of A, C, G, T residues in all instances) in combination with the peptide isobar detector molecules as described in Illustration 1.

A clear advantage of this mode of the disclosed method is the ability to separately optimize the specific binding molecule and the reporter signal of the reporter molecules. A minor constraint on the coding tag of the coding molecule is that among a set the A, C, G, T content must remain fixed.

G. Illustration 7: Detection of SH2 and SH3 Domains in Proteins of a Single Sample This illustration involves detection of individual SH2 and SH3 domains in particular proteins. The SH2 and SH3 domains of proteins are of considerable interest in the field of proteomics, and of particular relevance in the field of oncology. Consider a sample containing two known proteins that each contain both the SH2 and SH3 domains: human

```
ACGGCGACGTGGCTAATC-spacer-CGTCATCGTAG (SEQ ID NO:22 and SEQ ID NO:23)
                  GCAGTAGCATC
                  |
                  A*G*S*L*A*G*S*L*DPAGSLAGSLR (SEQ ID NO:18)
```

During processing as described above, the reporter molecule ion may be selected by the filter quadrupole, Q1, and read out through the daughter fragments. In the optional case where the link between the PNA and the peptide may be c-src and v-src. A capture moiety that recognizes these domains (such as an antibody) can be used to select proteins containing these domains from a sample. A pair of such protein sequences is shown below.

```
          c-src (NCBI reference GI:11433119; SEQ ID NO:9)

MSAIQAAWPS GTECIAKYNF HGTAEQDLPF CKGDVLTIVA VTKDPNWYKA KNKVGREGII
          PANYVQKREG VKAGTKLSLM PWFHGKITRE QAERLLYPPE TGLFLVREST NYPGDYTLCV
          SCDGKVEHYR IMYHASKLSI DEEVYFENLM QLVEHYTSDA DGLCTRLIKP KVMEGTVAAQ
          DEFYRSGWAL NMKELKLLQT IGKGEFGDVM LGDYRGNKVA VKCIKNDATA QAFLAEASVM
          TQLRHSNLVQ LLGVIVEEKG GLYIVTEYMA KGSLVDYLRS RGRSVLGGDC LLKFSLDVCE
          AMEYLEGNNF VHRDLAARNV LVSEDNVAKV SDFGLTKEAS TPRTRASCQS SGQPLRP v-src (NCBI reference GI:11421794; SEQ ID NO:10)

MGSNKSKPKD ASQRRRSLEP AENVHGAGGG AFPASQTPSK PASADGHRGP SAAFAPAAAE
          PKLFGGFNSS DTVTSPQRAG PLAGGVTTFV ALYDYESRTE TDLSFKKGER LQIVNNTEGD
          WWLAHSLSTG QTGYIPSNYV APSDSIQAEE WYFGKITRRE SERLLLNAEN PRGTFLVRES
          ETTKGAYCLS VSDFDNAKGL NVKHYKIRKL DSGGFYITSR TQFNSLQOLV AYYSKHADGL
          CHRLTTVCPT SKPQTQGLAK DAWEIPRESL RLEVKLGQGC FGEVWMGTWN GTTRVAIKTL
          KPGTMSPEAF LQEAQVMKKL RHEKLVQLYA VVSEEPIYIV TEYMSKGSLL DFLKGETGKY
          LRLPQLVDMA AQIASGMAYV ERMNYVHRDL RAANILVGEN LVCKVADFGL ARLIEDNEYT
          ARQGAKFPIK WTAPEAALYG RFTIKSDVWS FGILLTELTT KGRVPYPGMV NREVLDQVER
          GYRMPCPPEC PESLHDLMCQ CWRKEPEERP TFEYLQAFLE DYFTSTEPQY QPGENL
```

The SH3 and SH2 domains are indicated in double underline and single underline respectively. Cysteine residues are indicated in bold. These can be labeled by covalent sulfur—sulfur bridges. Tryptic digest of the c-src and v-src proteins results in the fragments shown in Table 3.

Consider a reporter signal of composition CGAGSD-PLAGSLR (m/z=1203; SEQ ID NO: 11) and labeling of the cysteine residues of the c-src and v-src proteins with this reporter signal through formation of covalent bond between the sulfur groups of the cysteine of the protein and the sulfur groups of cysteine of the reporter signal. Table 3 shows the masses of the unlabeled, labeled and altered fragments.

In this illustration, the reporter signals are peptides that have been designed to have a preferred fragmentation site. Peptides containing arginine will preferentially fragment at the C-termini of aspartic acid or glutamic acid residues, and, proline containing peptides will fragment at the N-termini of the proline residues (Qin and Chait, Int. J. Mass Spectrom. (Netherlands), 190–191:313–20 (1999)). Thus, DP (aspartic acid (D) and proline (P)) amino acid sequences are used in the reporter signals resulting in collisionally induced fragmentation at the scissile bond between the aspartic acid and proline.

The existence of reporter signals are clearly seen by the parent ion mass-to-charge shift of a multiple of the PLAGSLR (amino acids 7–13 of SEQ ID NO:11) units upon fragmentation at the scissile bonds, or in some cases (as determined by the molecular dissociation kinetics, dynamics and thermodynamics) a PLAGSLR$^+$ (amino acids 7–13 of SEQ ID NO:11) will be directly observed. For example, the labeled protein C(CGAGSDPLAGSLR)IK (amino acids 223–225 of SEQ ID NO:9 and SEQ ID NO:11), shown in row 5 in Table 3, would be selected in the first quadrupole at 1563 amu, and would fragment to yield 851 amu (and possibly 712 amu for PLAGSLR$^+$; amino acids 7–13 of SEQ ID NO:11). In contrast, unlabeled fragments of the same nominal mass (there are none in this illustration) would be selected by the first quadrupole but would not exhibit the 712 amu shift nor the 712 amu peak. This yields an exceptional discrimination against unlabelled fragments. A representation of the mass spectrum is shown in FIG. 1.

For an unknown fragment, or to confirm a known fragment, determined to contain the label, the sequence can be obtained using standard MS/MS peptide sequencing techniques without further processing.

This illustration demonstrates a simple case of detection of a pair of known proteins using the method (via detection

| Source | | Fragment | Unlabeled mass (amu) | Labeled mass (amu) | Labeled mass after PLAGSLR fragment loss (amu) |
|---|---|---|---|---|---|
| c-src, | SH3 domain | MSAIQAAWPSGTECIAK | 1763 | 2964 | 2252 |
| c-src, | SH3 domain | YNFHGTAEQDLPFCK | 1769 | 2972 | 2260 |
| c-src, | SH2 domain | ESTNYPGDYTLCVSCDGK | 1951 | 4353 | 2929 |
| c-src, | SH2 domain | LSIDEEVYFENLMQLVEHYTSDADGLCTR | 389 | 1590 | 878 |
| c-src | | CIK | 362 | 1563 | 851 |
| c-src | | SVLGGDCLLK | 1003 | 2504 | 1792 |
| c-src | | FSLDVCEAMEYLEGNNFVHR | 2372 | 2573 | 1861 |
| c-src | | ASCQSSGQPLR | 1230 | 2731 | 2019 |
| v-src, | SH2 domain | GAYCLSVSDFDNAK | 1489 | 2690 | 1978 |
| v-src, | SH2 domain | HADGLCHR | 907 | 2108 | 1396 |
| v-src | | LTTVCPTSKPQTQGLAK | 1772 | 2973 | 2261 |
| v-src | | LGQGCFGEVWMGTWNGTTR | 2099 | 3300 | 2588 |
| v-src | | AANILVGENLVCK | 1343 | 2544 | 1832 |
| v-src | | MPCPPECPESLHDLMCQCWR | 2374 | 7178 | 4330 |

Table 3. Fragments resulting from tryptic digest of CGAGSDPLAGSLR (SEQ ID NO: 11) labeled src proteins. The fragments are, from top to bottom, amino acids 1–17 of SEQ ID NO:9, amino acids 18–32 of SEQ ID NO:9, amino acids 108–125 of SEQ ID NO:9, amino acids 138–166 of SEQ ID NO:9, amino acids 223–225 of SEQ ID NO:9, amino acids 284–293 of SEQ ID NO:9, amino acids 294–313 of SEQ ID NO:9, amino acids 346–357 of SEQ ID NO:9, amino acids 185–198 of SEQ ID NO:10, amino acids 236–243 of SEQ ID NO:10, amino acids 244–260 of SEQ ID NO:10, amino acids 276–294 of SEQ ID NO:10, amino acids 392–404 of SEQ ID NO:10, amino acids 484–503 of SEQ ID NO:10. Also shown is the resulting mass of the labeled fragment after loss of the PLAGSLR fragment (amino acids 7–13 of SEQ ID NO:11).

Tryptic digests of the proteins are introduced into a mass spectrometer. Ions corresponding to the masses in the labeled mass column of Table 3 are selected and fragmented in the collision cell, subsequently analyzed in the TOF. The collision energy and collision gas density are tuned such that the primary fragmentation is the scissile bond between aspartic acid (D) and proline (P).

of particular fragments of the proteins). This method is extensible to a large number of proteins, known and/or unknown, in a complex mixture. The combination event of the parent signal and the fragmentation ion(s) provides an enormous discrimination against the "background".

If further fractionation is desired automated industrial systems, such as HPLC or capillary electrophoresis, may be inserted in front of the mass spectrometer to increase the discrimination further. Fractionation systems may be used in tandem arrangement (for example, LC/LC). In the fields of protein discovery and functional genomics, biological fractionation may be employed using interactions of interest, for example a functionally related system such as an affinity partner for the SH2 and SH3 domains to capture the families.

H. Illustration 8: Protein Profiling of SH2 and SH3 Domains in Proteins of a Multiple Samples Consider the protein c-src as described in Illustration 7 and its tryptic fragments as described in Table 3.

The temporal protein expression of c-src produced by a stimulus applied to stable Jurkat T cells (see, for example, Brdicka et al., Phosphoprotein associated with glycosphingolipid-enriched microdomains (PAG), a novel ubiquitously expressed transmembrane adaptor protein, associates with the protein tyrosine kinase csk and is involved in regulation of T cell activation. J Exp Med,. 191:1591–604 (2000)) can be followed by collecting sample cells at defined time following the stimulus and lysing the cells. The SH2 and SH3 domain containing proteins (including c-src) may be captured at this point in the procedure. Each lysate is then labeled with a different reporter signal from Table 1 and the proteins are digested with trypsin.

Consider the specific example of the c-src tryptic fragment CIK shown in row 5 in Table 3. For fixed times of 0, 1, 2, 3 and 4 hours the lysates are labeled with CG*G*G*G*DPGGGGR, CG*G*G*GDPGGGG*R, CG*G*GGDPGGG*G*R, CG*GGGDPGG*G*G*R, and GGGGDPG*G*G*G*R (SEQ ID NO:1), respectively that will yield PGGGGR$^+$, PGGGG*R$^+$, PGGG*G*R$^+$, PGG*G*G*R$^+$, and PG*G*G*G*R$^+$ (amino acids 7 to 12 of SEQ ID NO: 1) respectively upon collisional fragmentation. Five time point measurements are obtained in a single measurement by introducing the labeled protein mixture into the mass spectrometer, setting the first filter to pass the isobaric set of labeled proteins (at mass-to-charge corresponding to C(CG*G*G*G*DPGGGGR)IK; SEQ ID NO:1), fragmenting the reporter signal and measuring the reporter signals at m/z=499, 500, 501, 502, 503 in order to detect fragments having the characteristic mass-to-charge ratio for each of the time points (0, 1, 2, 3 and 4 hours, respectively).

Other labeled proteins of interest are selected with the filter and quantitated in similar fashion.

I. Illustration 9: Protein Fragment Detection with Reporter Signal Calibrators

This illustration involves detection of protein fragments using reporter signal calibrators.

1. A suspension containing 1000 cells is centrifuged to get a cell pellet.
2. The cells are lysed using detergent.
3. The lysate is digested with trypsin.
4. Optionally, the protein digest is oxidized with hydrogen peroxide or derivatized with acetylacetone.
5. The material placed in a tandem mass spectrometer, ionized, selected by a mass-to-charge filter, fragmented, mass analyzed, and detected, in order to measure the signals from unique fragile tryptic peptides and the corresponding reporter signal calibrator standard designed for each unique tryptic peptide.
6. Mass spectrometry detection is repeated with different, specific filtering settings for 50 different peptide mass/charge ratios suitable for each signature tryptic peptide and its corresponding reporter signal calibrator peptide.
7. Data is collected as a catalog of 50×2 independent measurements, constituting the peptide signature.

J. Illustration 10: Reporter Signal Fusions, Expressed From Plasmid Vectors, With Epitope Tags This illustration provides an example of, and an example of the use of, a set of simple expression vectors encoding an amino acid segment that includes an epitope tag that is the same in all the vectors, and that includes a reporter signal peptide that is different in all the vectors of the set of vectors. The reporter signal peptides can be cleaved from the amino acid segment with trypsin. All of the reporter signal peptides have the same mass-to-charge ratio, but, when fragmented, produce fragments that have different mass-to-charge ratios.

1. A set of different DNA plasmid vectors is constructed containing the following elements:
    (a) a common origin of replication and a common antibiotic selectable marker,
    (b) an inducible promoter (for this illustration, the promoter could be the same for all plasmids or different for each plasmid), and
    (c) a nucleic acid segment encoding an amino acid segment (the reporter signal fusion) where the amino acid segment includes:
        (1) a protein of interest to be expressed under the control of (that is, operably linked to) the promoter (for this illustration, the protein could be different for each plasmid or could be the same for all plasmids),
        (2) a common epitope tag, such as a flag peptide, and
        (3) a reporter signal peptide that can be released from the amino acid segment upon trypsin digestion (for this illustration, each plasmid encodes a different reporter signal peptide where each reporter signal peptide belongs to the same isobaric set of reporter signal peptides).
2. Each plasmid vector is introduced individually into transformation-competent cells.
3. Transformed cells are grown under the antibiotic selection.
4. The inducible promoter is induced by its appropriate activator compound.
5. The expressed amino acid segments (that is, reporter signal fusions) are measured as follows:
    (a) the cells, harboring different expression vectors, are mixed in a single vessel,
    (b) the mixture of cells is lysed to release all proteins,
    (c) an antibody specific for the epitope tag is used to purify (separate) the reporter signal fusion(s) from the lysate,
    (d) the epitope tag-purified reporter signal fusion is digested with trypsin,
    (e) the tryptic peptides are combined with matrix and analyzed by MALDI-tandem mass spectrometry where the amount of each different reporter signal is measured.

K. Illustration 11: Reporter Signal Fusions, Expressed From Plasmid Vectors, With Cis-Cleavable Linkage This illustration provides an example of, and an example of the use of, a set of expression vectors encoding reporter signal fusions with a peptide-release mechanism based on activatable self-cleavage proteolytic activity of an intein, or any suitable cis-acting protease. The proteolytic activity serves to control the release of the reporter signal peptide present in the each of the reporter signal fusions.

1. A set of different DNA plasmid vectors is constructed harboring the following sequence elements:
    (a) an origin of replication and an antibiotic selectable marker,
    (b) an inducible promoter, wherein the promoter may be the same for all plasmids, or different for each plasmid,
    (c) a nucleic acid segment encoding an amino acid segment (the reporter signal fusion), to be expressed under the direction of the promoter, where the amino acid segment includes:
        (1) a protein of interest, wherein the protein could be different for each plasmid, or could be the same for all plasmids,
        (2) an intein protein domain located such as to be able to catalyze release of the reporter signal peptide by a cis-cleavage reaction.

(3) a reporter signal peptide belonging to a specific isobaric set of reporter signal peptides, wherein each plasmid encodes a different member of the isobaric set of reporter signal peptides.
2. The plasmid vector is introduced into transformation-competent cells.
3. Transformed cells are grown under the antibiotic selection.
4. The inducible promoter is induced by its appropriate activator compound.
5. The expressed reporter signal fusion is measured as follows:
   (a) the cells are lysed to release internal proteins,
   (b) DTT is added to activate the intein self-cleavage activity (Chong et al. (1998) Utilizing the C-terminal cleavage activity of a protein splicing element to purify recombinant proteins in a single chromatographic step. Nucleic Acids Res 26:5109–5115),
   (c) the released peptides are combined with matrix and analyzed by MALDI-tandem mass spectrometry where the amount of each different reporter signal is measured.

L. Illustration 12: Reporter Signal Fusions, Expressed From BAC Vectors, With Epitope Tags This illustration provides an example of, and an example of the use of, a set of mammalian BAC expression vectors with recombinase sites capable of driving integration in specific gene loci.
1. A set of different BAC vectors derived from pEYMT (Hong et al. (2001) Development of two bacterial artificial chromosome shuttle vectors for a recombination-based cloning and regulated expression of large genes in mammalian cells. Analytical Biochemistry 291:142–148) is constructed. These vectors are capable of shuttling between bacteria, yeast and mammalian cells. The vectors have the following features:
   (a) a common promoter,
   (b) a nucleic acid segment encoding an amino acid segment (the reporter signal fusion), to be expressed under the direction of the promoter, where the amino acid segment includes:
      (1) one of a set of proteins of interest, wherein the protein coding sequence is different for each BAC, or, alternatively, the protein coding sequence is the same for all BACs, but the BACs then are made different by the use of a different promoter in each BAC,
      (2) an epitope tag, such as the flag peptide,
      (3) a reporter signal peptide belonging to a specific isobaric set of reporter signal peptides, whereby the reporter signal fusion is tagged with the epitope tag and a unique reporter signal peptide, whereby the reporter signal peptide may be released by trypsin digestion.
2. Each of the BAC vectors is introduced individually into mouse embryonic stem cells, to achieve integration in genomic DNA. The transformed ES cells are introduced into an embryo, to generate a chimeric animal, containing ES cells in the germline. The progeny of these mice are screened to identify transgenic mice that harbor the integrated reporter signal fusion construct.
3. Tissue is obtained from each transgenic animal, and equal amounts of tissue from several animals is mixed.
4. The mixture of tissues is lysed to release proteins.
5. An antibody specific for the epitope tag (for example, anti-flag antibody) is used to purify the reporter signal fusions.
6. The flag-purified proteins are digested with trypsin.
7. The tryptic peptides are combined with matrix and analyzed by MALDI-tandem mass spectrometry where the amount of each different reporter signal is measured.

M. Illustration 13: Reporter Signal Fusions, Expressed From Plant Vectors, With Epitope Tags and Recombinase Sites This illustration provides an example of, and an example of the use of, a set of plant expression vectors with two directly oriented lox site sites capable of driving integration in a specific recipient gene locus (slightly modified from Vergunst et al. (1998) Site-specific integration of Agrobacterium T-DNA in Arabidopsis thaliana mediated by Cre recombinase. Nucleic Acids Res 26:2729–2734).
1. A set of different Agrobacterium T-DNA vectors is constructed harboring the following sequence elements:
   (a) A Floxed T-DNA recombination cassette, without a promoter (Vergunst et al. (1998) Site-specific integration of Agrobacterium T-DNA in Arabidopsis thaliana mediated by Cre recombinase. Nucleic Acids Res 26:2729–2734), designed to be integrated in the genome of a recipient plant by Cre recombinase-driven integration, with the cassette comprising a nucleic acid segment encoding an amino acid segment (the reporter signal fusion), to be expressed under the direction of the promoter, where the amino acid segment includes:
      (1) a coding sequence for a protein of interest, wherein the protein could be different for each T-DNA, or could be the same for all T-DNAs,
      (2) an epitope tag, such as the flag peptide,
      (3) a reporter signal peptide belonging to a specific isobaric set of reporter signal peptides.
2. The T-DNA plasmid vector is introduced into recipient plants, such plants harboring a chimeric promoter-lox-Cre gene, under the control of a chemically inducible promoter (Kunkel et al. (1999) Inducible isopentenyl transferase as a high-efficiency marker for plant transformation. Nature Biotechnology 17:916–919), designed to receive the recombinant protein cassette of the integrative vector by Credriven recombination. As in the original design of Vergunst and co-workers (1998), site-specific integration simultaneously leads to loss of Cre-expression, making the insertion event irreversible.
3. The expressed, integrated reporter signal fusion is generated under the direction of the chemically inducible promoter present in front of the integrated gene. Expression is measured as follows:
   (a) tissue is obtained from each plant, and equal amounts of tissue from several plants is mixed,
   (b) the mixture of tissues is lysed to release proteins,
   (c) an antibody specific for the epitope tag (i.e., anti-flag) is used to purify the reporter signal fusions,
   (d) the flag-purified proteins are digested with trypsin,
   (e) the tryptic peptides are combined with matrix and analyzed by MALDI-tandem mass spectrometry where the amount of each different reporter signal is measured.

N. Illustration 14: Kit Including Vectors Encoding Reporter Signal Fusions

This illustration provides an example of a kit comprising a set of 2 or more vectors encoding reporter signal fusions. The kit comprises two or more expression vectors, wherein each vector expresses a different reporter signal fusion, wherein all reporter signal peptides in the reporter signal fusions belong to single isobaric set. The kit also can contain reagents needed for use of the vectors, such as
- (a) Reagents for transformation,
- (b) Reagents for inducing release of reporter signal peptides from reporter signal fusions, and
- (c) Reagents for performing mass spectral analysis, such as a matrix optimized for analysis of reporter signal peptides.

O. Illustration 15: Reporter Signal Fusions Encoded by PCR Products

This illustration provides an example of, and an example of the use of, a set of reporter signal fusions designed for expression in a rabbit reticulocyte cell-free system, where the DNA encoding the reporter signal fusion is generated by PCR.

1. PCR primers are designed to amplify a protein sequence of interest, whereby the one of the PCR primers contains a T7 RNA polymerase promoter, and a Kozak translational initiation sequence, positioned correctly in relation to the AUG start codon. The PCR primers also contain sequences coding for a reporter signal peptide, which may be placed at the amino terminus or at the carboxyl terminus of the protein of interest (thus forming a reporter signal fusion). Each reporter signal peptide is designed such as to cleavable from the protein by trypsin digestion.
2. The artificial gene is amplified by PCR, to generate sufficient DNA.
3. The DNA generated by PCR is transcribed in vitro using T7 RNA polymerase.
4. The solution containing the transcribed DNA is added to a rabbit reticulocyte in vitro translation system, to generate the reporter signal fusion product.
5. The in vitro synthesized reporter signal fusion is used with or without purification.
6. The process is repeated for other variants of the protein of interest. In a typical application, as many as 128 different protein variants may be generated by in vitro transcription/translation.

P. Illustration 16: Reporter Signal Fusions Encoded by PCR Products

This illustration provides an example of, and an example of the use of, a set of reporter signal fusions encoding by nucleic acid molecules designed for expression in an E. coli coupled transcription/translation system.

1. PCR primers are designed to amplify a protein sequence of interest, whereby the one of the PCR primers contains a T7 RNA polymerase promoter, and a Shine-Dalgamo translational initiation sequence, positioned correctly in relation to the AUG start codon. The PCR primers also contain sequences coding for a reporter signal peptide, which may be placed at the amino terminus or at the carboxyl terminus of the protein of interest (thus forming a reporter signal fusion). Each reporter signal peptide is designed such as to cleavable from the protein by trypsin digestion.
2. The artificial gene is amplified by PCR, to generate sufficient DNA for use in a coupled in vitro transcription/translation system.
3. The DNA generated by PCR is incubated in the in vitro coupled transcription/translation system, to generate the reporter signal fusion product.
4. The in vitro synthesized reporter signal fusion is used with or without purification.
5. The process is repeated for other variants of the protein of interest. In a typical application, as many as 128 different protein variants may be generated by in vitro transcription/translation.

Q. Illustration 17: Reporter Signal Fusions Expressed in Yeast Cells

This illustration provides an example of, and an example of the use of, a set of 32 yeast strains, each strain harboring a single reporter signal fusion.

A yeast strain (Saccharomyces cerevisiae) is constructed, using homologous recombination targeted to a non-essential gene, whereby a fusion of a candidate therapeutic protein and a reporter signal peptide (belonging to a set of 32 isobaric reporter signal peptides) is placed under the control of a galactose-responsive promoter. Another 31 similar yeast strains are constructed, using the same yeast promoter, whereby the only other difference in the DNA sequence coding for the reporter signal fusion is the use of codons designed to generate one of 31 different reporter signal peptides, completing a set of 32 different promoters and an isobaric set of 32 distinct reporter signal peptides. The yeast strains may be used for any assay where the reporter signal peptides (and/or reporter signal fusions) serve as reporters for the expression of the protein fused to the reporter signal peptide, which in this case is a candidate therapeutic protein.

R. Illustration 18: Reporter Signal Fusions Expressed in Mouse Cells

This illustration provides an example of, and an example of the use of, a set of 32 mouse cell lines, each cell line harboring a single reporter signal fusion.

A mouse cell line is constructed, using an SV40 vector system, whereby a fusion of a candidate therapeutic protein and a reporter signal peptide (belonging to a set of 32 isobaric reporter signal peptides) is placed under the control of a cytokine promoter. Another 31 similar cell lines are constructed, using 31 different cytokine promoters, whereby the only other difference in the DNA sequence coding for the reporter signal fusion is the use of codons designed to generate one of 31 different reporter signal peptides, completing a set of 32 different promoters and an isobaric set of 32 distinct reporter signal peptides. The cell lines may be used for any assay where the reporter signal peptides (and/or reporter signal fusions) serve as reporters for the expression of the protein fused to the reporter signal peptide, which in this case is a candidate therapeutic protein.

S. Illustration 19: Reporter Signal Fusions Expressed Using Promoter of Interest This illustration provides an example of the use of cells that harbor single fusions, as part of a cytokine-STAT5a-responsive promoter. This system can provide a comparison of reporter signal peptides versus a GFP internal standard.

1. An experiment is performed using a set of 96 different reporter signal peptides belonging to a unique mass set (that is, an isobaric set), where each cell line harbors a nucleic acid construct encoding a single reporter signal fusion. The fusion construct contains a cytokine-responsive promoter for the CIS1 protein, which is activated through a STAT5 response (Masumoto et al. (1999) Suppression of STAT5 functions in liver, mammary glands, and T cells in cytokine-inducible, SH2-containing protein 1 transgenic mice. Mol Cell Biol 19:6396–6407), a GFP-encoding sequence and a sequence encoding a reporter signal peptide fused to the GFP.
2. After treatment of 38,400 cell cultures for 6 hours with a set of 38,400 different cytokine-mimic drug candidates from a combinatorial drug library, a subset of 3,840 cell cultures are sampled to obtain values for GFP fluorescence.

3. The cells are pooled in groups of 96.
4. The mixture of cells is lysed to release the GFP fusion proteins.
5. The lysate is digested with trypsin.
6. The tryptic peptides are combined with matrix and analyzed by MALDI-tandem mass spectrometry where the amount of each different reporter signal is measured.

The readout speed of an expensive mass spectrometer is often the rate-limiting factor in proteomic analysis. A key feature of this method is the ability to pool sets of 96 treated cell samples prior to immunoprofiling based on mass spectrometry of reporter signal peptides. A total of 38,400 cell cultures are treated, each with a different drug. The use of pooling different cells harboring one of 96 different reporter signal peptides permits the 38,400 cultures to be analyzed as 400 pooled samples.

The GFP fluorescence values obtained in step 2 for a subset of the samples (3,840 out of 38,400) are compared to the data obtained by mass spectrometry analysis of the reporter signal peptides from the same samples. A good correlation between the fluorescence values and the values obtained by mass spectrometry constitutes a control for the function and utility of an reporter signal fusion-tagged cell line.

T. Illustration 20: Multiple Reporter Signal Fusions Expressed in a Cell

This illustration provides an example of a method for expression profiling of 32 different reporter signal fusions, utilizing cells that harbor multiple reporter signal fusions.

An experiment is performed using a set of 32 different reporter signal peptides belonging to a unique mass set (that is, they are isobaric), where each cell line harbors 32 different reporter signal fusions that are expressed independently, under the control of different promoters. Monitoring the expression of these 32 different proteins serves as a measure of drug toxicity.

Cell cultures are analyzed one at a time:
(a) the cells are lysed to release proteins,
(b) the lysate is digested with trypsin.
(c) the tryptic peptides are combined with matrix and analyzed by MALDI-tandem mass spectrometry where the amount of each different reporter signal is measured.

U. Illustration 21: Multiple Reporter Signal Fusions Expressed in a Mammalian Cell Line This illustration provides an example of, and an example of the use of, a mammalian cell line, designed for use as a microencapsulated producer for heterologous protein delivery, the cell line harboring 12 reporter signal fusions.

A mammalian cell line is constructed, using a BAC homologous recombination vector system (Hong et al. (2001) Development of two bacterial artificial chromosome shuttle vectors for a recombination-based cloning and regulated expression of large genes in mammalian cells. Analytical Biochemistry 291:142–148), whereby a fusion of two candidate therapeutic proteins and two isobaric reporter signal peptides (belonging to a set of 12 isobaric reporter signal peptides) is placed under the control of a tetracycline promoter. Another 10 fusions in 10 genes, coding for different secretory proteins, are constructed in the same cell line, under the control of their own native promoters, whereby the only other difference in the DNA sequence coding for the fusion peptides is the use of codons designed to generate one of 10 different reporter signal peptides. This completes a set of 12 different genes and 12 distinct reporter signal peptides.

The cell line is microencapsulated, and used for heterologous protein delivery in an animal host, or a human patient, where secretion of the therapeutic proteins is induced by tetracycline.

An immunoassay is performed, where specific antibodies are used to capture the 12 reporter signal fusions of interest, whereby the reporter signal peptides (and/or reporter signal fusions) serve as reporters for the expression of each protein fused to one reporter signal peptide, including the two candidate therapeutic proteins. One may thus measure the response of the microencapsulated cells to tetracycline induction, and, simultaneously, the production of other secretory proteins by the microencapsulated cells.

This precise monitoring of protein expression by the microencapsulated cells, using reporter signal fusions, serves to accelerate the dosage optimization, and results in increased therapeutic safety control. Among the additional secretory proteins monitored by the method one may include cytokines or other proteins with mitogenic potential.

V. Illustration 22: Multiple Reporter Signal Fusions Expressed in Multiple Cell Lines This illustration provides an example of, and an example of the use of, a set of six different human cell lines, each cell line harboring ten different reporter signal fusions, whereby all reporter signal peptides belong to the same isobaric set.

Six cell lines are derived from adult stem cells, where each cell line is representative of a different major human haplotype, defined by unique SNP combinations, whereby each of the six haplotypes is representative of an important pharmacogenomic drug response subset of the human population for beta(2)-adrenergic receptor (Drysdale et al. (2000) Complex promoter and coding region beta 2-adrenergic receptor haplotypes alter receptor expression and predict in vivo responsiveness. Proc Natl Acad Sci USA. 97:10483–10488).

A total of six mammalian cell lines are constructed, using a BAC homologous recombination vector system (Hong et al. (2001) Development of two bacterial artificial chromosome shuttle vectors for a recombination-based cloning and regulated expression of large genes in mammalian cells. Analytical Biochemistry 291:142–148), whereby a set of ten fusions in ten different genes, coding for different signal transduction proteins, are constructed in same cell line, under the control of their own native promoters, whereby the only other difference in the DNA sequence coding for the fusion peptides is the use of codons designed to generate only one of ten different reporter signal peptides. This completes a set of ten different genes and ten corresponding, distinct reporter signal fusions for each cell line, whereby each cell line represents a major haplotype of the human beta(2)-adrenergic receptor, and thus sixty different reporter signal fusions are present in the combined set of all six cell lines.

The cell lines may be used for any assay where the set of sixty reporter signal peptides serve as reporters for the expression of the specific proteins fused to each reporter signal peptide in each cell line.

W. Illustration 23: Multiple Reporter Signal Fusions Expressed in Multiple Human Cell Lines This illustration provides an example of, and an example of the use of, a set of six cell lines, where each cell line is representative of a human haplotype, and each cell line harbors multiple reporter signal fusions.

1. An experiment is performed using a set of sixty different reporter signal peptides belonging to a unique mass set (that is, they are isobaric), where each cell line harbors ten reporter signal fusions. The objective of the experiment is to measure the response of the cells to a drug.

2. The cells are pooled in groups of six haplotypes.
3. The mixture of cells is lysed to release proteins.
4. The lysate is digested with trypsin.
5. The tryptic peptides are combined with matrix and analyzed by MALDI-tandem mass spectrometry where the amount of each different reporter signal is measured.

The readout speed of an expensive mass spectrometer is often the rate-limiting factor in proteomic analysis. A key feature of this method is the ability to pool sets of six treated cell samples prior to immunoprofiling based on mass spectrometry of reporter signal peptides. A total of 2,400 cell cultures are treated, each with a different drug. The use of pooling of six different cell lines permits the 2,400 cultures to be analyzed as 400 pooled samples. All 400 samples are deposited on the plate of a mass spectrometer, and analyzed by tandem mass spectrometry. The information for each laser shot consists of the expression levels of sixty different reporter signal fusions.

X. Illustration 24: Kit of Reporter Signal Fusion-Labeled Human Cell Lines

This illustration provides an example of, and an example of the use of, a kit comprising six cell lines, where each cell line is representative of a major human haplotype, and each cell line harbors multiple reporter signal fusions. The kit includes the cell lines, and a set of reporter signal peptide controls designed to be used in experiments that are performed using a set of sixty different reporter signal peptides belonging to a unique mass set, where each cell line harbors ten reporter signal fusions. The objective of the experiment is to the response of the cells to different drugs.

Y. Illustration 25: Reporter Signal Fusion-Labeled Flies

This illustration provides an example of, and an example of the use of, a transgenic fruit fly harboring reporter signal fusions.

A recombinant fly of the species Drosophila melanogaster is constructed, using homologous recombination (Rong & Golic (2001) A targeted gene knockout in Drosophila. Genetics 157:1307–1312), so that a total of 16 genes are modified by addition of sequence encoding reporter signal fusions belonging to a unique mass set (that is, they are isobaric). The 16 recombinant proteins are chosen on the basis of their known function at various levels of different signal transduction pathways, such as ras, myc, etc. The fusion is located at either the carboxyl-terminus or the amino-terminus of each of the proteins, and may optionally be preceded by an epitope tag, such as the flag epitope.

The flies are used for an experiment in which a new genotype is generated by transformation with P-elements harboring members of a recombinant protein library. The objective of performing the transformation is to observe the phenotypes generated by different protein sequences present in the recombinant library.

After transformation, individual flies are processed to extract proteins, the proteins are digested with trypsin, and the reporter signal peptides derived from reporter signal fusions are analyzed by desorption-ionization using a nanostructured silicon film (Hayes et al. (2001) Desorption-ionization mass spectrometry using deposited nanostructured silicon films. Anal. Chem. 73:1292–1295), coupled with collision-induced fragmentation tandem mass spectrometric analysis. The reporter signal peptide profile generates a representation of the relative abundance of the reporter signal fusions in the fly.

Z. Illustration 26: Reporter Signal Fusion-Labeled Mice

This illustration provides an example of, and an example of the use of, transgenic mice harboring reporter signal fusions for signal transduction pathway analysis.

A recombinant mouse of the species Mus musculus is constructed, using homologous recombination in embryonic stem (ES) cells, (Templeton et al. (1997) Efficient gene targeting in mouse embryonic stem cells. Gene Therapy 4:700–709), so that a total of 12 genes are modified by addition of reporter signal fusions belonging to a unique mass set (that is, they are isobaric). The gene fusions are designed by adding the reporter signal peptide at either the amino terminus or the carboxyl-terminus of each of the recombinant proteins of interest. The 12 recombinant proteins are chosen on the basis of their known key functions at various levels of different signal transduction pathways, such as ras, myc, wnt, etc. Some of the fusions may optionally contain an epitope tag, such as the flag epitope, or a GFP fusion. Some of the fusions may involve mouse proteins of unknown function.

Most of the recombinant reporter signal fusions are placed under their normal mouse promoter, while one or a few of the recombinant reporter signal fusions may be under the control of a heterologous promoter, to test a certain experimental hypothesis. For example, an experimental recombinant reporter signal fusion may consist of an interleukin-6 coding sequence, fused to an reporter signal peptide, under the (inappropriate) control of the interleukin-2 promoter.

Mice with normal promoters, as well as the mice with an experimental heterologous promoters linked to reporter signal fusions, are used in a series of experiment in which tumors are induced by a chemical mutagen (2-azoxymethane). After tumors appear, the mice are treated with different candidate anti-tumor drugs.

At different times after drug treatment, tumors are dissected from individual mice, and the tumor tissue is processed to extract proteins. The proteins are digested with trypsin, and the reporter signal peptides derived from reporter signal fusions are analyzed by desorption-ionization using a nanostructured silicon film (Hayes et al. (2001) Desorption-ionization mass spectrometry using deposited nanostructured silicon films. Anal. Chem. 73:1292–1295), coupled with collision-induced fragmentation tandem mass spectrometric analysis. The reporter signal peptide profile generates a representation of the relative abundance of the 12 reporter signal fusions, and this profile serves as an informative measure of multiple pathway responses to the antitumor drug in a normal mouse, or in a mouse with experimental heterologous promoter constructs. The profiles may also provide information regarding the expression of proteins of unknown function.

AA. Illustration 27: Reporter Signal Fusion-Labeled Mice

This illustration provides an example of, and an example of the use of, transgenic mice harboring reporter signal fusions for studying inflammatory responses and Cyclooxygenase 2 (Cox-2) promoter mutants.

A recombinant mouse of the species Mus musculus is constructed, using homologous recombination in embryonic stem (ES) cells, (Templeton et al. (1997) Efficient gene targeting in mouse embryonic stem cells. Gene Therapy 4:700–709), so that a total of ten genes are modified by addition of reporter signal fusions belonging to a unique mass set. The gene fusions are designed by adding the reporter signal peptide at either the amino terminus or the carboxyl-terminus of each of the recombinant proteins of interest. The ten recombinant proteins are chosen on the basis of their known function at various levels of tissue inflammatory responses (such as Cox-2, etc). Some of the fusions may optionally contain an epitope tag, such as the flag epitope, or a GFP fusion. Some of the fusions may involve mouse proteins of unknown function, but which are suspected to have a role in inflammation.

Most of the recombinant reporter signal fusions are placed under their normal mouse promoter, while one or a few of the recombinant reporter signal fusions may be under the control of a mutant promoter, to test a certain experimental hypothesis. For example, an experimental recombinant reporter signal fusion may consist of a Cox-2 coding sequence, fused to an reporter signal peptide, under the control of a reduced transcriptional response Cox-2 mutant promoter.

Mice with normal promoters, as well as the mice with an experimental mutant promoters linked to reporter signal fusions, are used in a series of experiments in which colonic inflammation and colitis is induced by Dextran sulfate, an then the mice are treated with anti-inflammatory drugs.

At different times after drug treatment, colons are dissected from individual mice, and the tissue is processed to extract proteins. The proteins are digested with trypsin, and the reporter signal peptides derived from reporter signal fusions are analyzed by desorption-ionization using a nanostructured silicon film (Hayes et al. (2001) Desorption-ionization mass spectrometry using deposited nanostructured silicon films. Anal. Chem. 73:1292–1295), coupled with collision-induced fragmentation tandem mass spectrometric analysis. The reporter signal peptide profile generates a representation of the relative abundance of the ten reporter signal fusions, and this profile serves as an informative measure of multiple pathway responses to the anti-inflammatory drug in the colon of a normal mouse with colitis, or in a mouse with experimental mutant Cox-2 promoter constructs. The profiles may also provide information regarding the expression of proteins of unknown function.

BB. Illustration 28: Multiple Samples Labeled With Different Reporter Signals

This illustration is an example of multiple sample labeling using reporter signals where each sample is labeled with a different reporter signal.

This illustration involves the use of 384 antibody minicolumns, in order to generate a profile of 384 different protein antigens. Antibodies are covalently coupled to agarose beads using standard water-soluble carbodiimide chemistry. (March et al. (1974) A simplified method for cyanogen bromide activation of agarose for affinity chromatography. Anal Biochem. 60:149–152). The capacity of a small (75 microliter) affinity column with one antibody is equal to approximately $2 \times 10^{11}$ molecules of each protein. If multiplexing of reporter signals is 256×, the maximum protein binding capacity will be approximately $10^8$ molecules. The dynamic range of the assay will thus be 10,000 to 100,000,000 molecules of protein.

1. Prepare 4 sets of 64 reporter signals (for a total of 256), each of the four sets having the same mass.
2. Label each of 256 cell preps by covalent coupling of a unique reporter signal, using standard heterobifunctional reagents such as SATA and SSCP (Pierce Chemicals). Preferred chemistry for this purpose is the use of Sulfo-LS-SPDP (cat #21650 from Pierce; Uto et al., Determination of urinary Tamm-Horsfall protein by ELISA using a maleimide method for enzyme-antibody conjugation, J. Immunol. Methods, 138:87–94 (1991).
3. Associate with affinity column on microtip containing specific antibody.
4. Repeat for 384 antibodies. That is, associate all of the labeled cell preps to each of the 384 columns.
5. Elute from column using photocleavable reporter signal-release-chemistry (Innovachem, Tucson, Ariz.; see, for example, Harth-fritschy and Cantacuzene, Pept. Res. 50:415 (1997)).
6. The reporter signals are combined with matrix and analyzed by MALDI-tandem mass spectrometry where the amount of each different reporter signal is measured, using 4 successive mass-to-charge settings (4×64), one for the mass of each of the four sets.

The number of data points will be 256×384=98,304. Ten runs per day would provide 980,000 data points. This method is easily scalable to 384×10 antibodies=3840 antibodies. For 3840 antibodies, 10 runs per day would give 9,830,400 data points per day.

CC. Illustration 29: Multiple Samples Labeled With Different Reporter Signals

This illustration is an example of multiple sample labeling using reporter signals where each sample is labeled with a different reporter signal. The samples are labeled via a DNA coding tag intermediate.

This illustration involves the use of 384 antibody minicolumns, in order to generate a profile of 384 different protein antigens. Antibodies are covalently coupled to agarose beads using standard water-soluble carbodiimide chemistry. (March et al. (1974) A simplified method for cyanogen bromide activation of agarose for affinity chromatography. Anal Biochem. 60:149–152). The capacity of a small (75 microliter) affinity column with one antibody is equal to approximately $2 \times 10^{11}$ molecules of each protein. If multiplexing of reporter signals is 256×, the maximum protein binding capacity will be approximately $10^8$ molecules. The dynamic range of the assay will thus be 10,000 to 100,000,000 molecules of protein.

Each of the protein preparations is tagged with a unique DNA oligonucleotides (coding tags), wherein a set of 64 different coding tags has the property of not being able to hybridize with each other. The protein preparation is reacted with 2-iminothiolane (Alagon and King, (1980) Activation of polysaccharides with 2-iminothiolane and its uses. Biochemistry. 19:4341–4345) to introduce reactive sulfhydryl groups, if none is present. A DNA oligonucleotide (the coding tag), containing a reactive amino group at one of its termini is reacted with a heterobifunctional cross-linking reagent, such as SULFO-SMCC (Pierce, Inc.). The thiol-containing proteins are incubated together with the activated oligonucleotide, to form a covalent protein-DNA adduct (thus labeling the protein with a coding tag). For most protein molecules, the formation of this covalent adduct will not interfere with the capacity of the protein to associate with its cognate antibody. A total of 64 protein preparations, each harboring covalently coupled unique coding tag sequences, are pooled together before being used for the multiplexed assay.

This example also involves the use of reporter molecules composed of peptide nucleic acid decoding tags and reporter signal peptides. The decoding tags comprise 64 different PNA sequences designed to be incapable of hybridizing to each other and additionally designed to be complementary to each of the 64 aforementioned coding tags used for protein labeling. The length of the PNA portion of the reporter molecule is preferably 9 to 15 bases, and more preferably 10 to 11 bases. The reporter molecules of this example also comprises 64 different sequences of amino acids (the reporter signal peptides) which have the common property of having the same mass, but being cleavable in such a way that they can be separated from each other after collision-induced fragmentation.

1. Label each of 64 cell preps with a unique, non-self hybridizing, DNA oligonucleotide (coding tag), using SULFO-SMCC chemistry as indicated above.

2. Associate with affinity column on microtip containing specific antibody.
3. Repeat for 384 antibodies. That is, associate all of the labeled cell preps to each of the 384 columns.
4. Pass all 64 reporter molecules through columns, to achieve hybridization of PNA to DNA coding tags on proteins.
5. Elute proteins from column using acid matrix.
6. Separate and quantify reporter signals by MALDI-tandem mass spectrometry where the amount of each different reporter signal is measured.

This example can be performed using peptide nucleic acid reporter signals (that is, reporter signals composed of peptide nucleic acid) to associate directly with the coding tags. The reporter signals would comprise 64 different PNA sequences of the same mass, designed to be incapable of hybridizing to each other, and additionally designed to be complementary to each of the 64 aforementioned coding tags used for protein labeling. The reporter signals could be easily dissociated from the coding tags (for detection) since they are only non-covalently associated with the coding tags.

DD. Illustration 30: Multiple Samples Labeled With Different Reporter Signals

This illustration is an example of multiple sample labeling using reporter signals where each sample is labeled with a different reporter signal. The samples are labeled via a DNA coding tag intermediate and the samples are analyzed using an antibody array.

This illustration involves the use of an antibody microarray of 3200 elements, constructed on a solid surface, the surface being compatible with analysis by mass spectrometry.

Each of the protein preparations is tagged with a unique DNA oligonucleotides (coding tags), wherein a set of 16 different oligonucleotides has the property of not being able to hybridize with each other. The protein preparation is reacted with 2-iminothiolane (Alagon and King, (1980) Activation of polysaccharides with 2-iminothiolane and its uses. Biochemistry. 19:4341–4345) to introduce reactive sulfhydryl groups, if none is present. A DNA oligonucleotide (coding tag), containing a reactive amino group at one of its termini is reacted with a heterobifunctional cross-linking reagent, such as SULFO-SMCC (Pierce, Inc.). The thiol-containing proteins are incubated together with the activated oligonucleotide, to form a covalent protein-DNA adduct, thus labeling the proteins with the coding tags. For most protein molecules, the formation of this covalent adduct will not interfere with the capacity of the protein to associate with its cognate antibody. A total of 16 protein preparations, each harboring covalently coupled unique DNA coding tag sequences, are pooled together before being used for the multiplexed assay.

As in Illustration 29, this example also involves the use of PNA-peptide reporter signals reporter molecules. The PNA portions are decoding tags and comprises 16 different PNA sequences, designed to be incapable of hybridizing to each other, and additionally designed to be complementary to sequences in each of the 16 aforementioned DNA tags used for protein labeling. The reporter signal portion of the reporter molecules comprises 16 different sequences of amino acids which have the common property of having the same mass, but being cleavable in such a way that they can be separated from each other after collision-induced fragmentation.

An additional property of the 16 coding tags used for tagging each of the 16 protein samples is that each coding tag is able to associate with eight molecules of the reporter molecule. Each tagged protein in the sample will contain, on the average, one to three DNA coding tags. Thus, each protein will be able to associate with many (8 to 24) reporter molecules. This design results in increased signal intensity of reporter signals in the mass spectrometer.

1. Label each of 16 cell preps with a unique, non-self hybridizing, DNA oligonucleotide (coding tag), using SULFO-SMCC chemistry as indicated above.
2. Place the sample on a microarray containing 3200 immobilized antibodies, the microarray being constructed on the surface of a plate suitable for reading on a mass spectrometer. Incubate for 2 hours at 37° C. Wash the surface to remove un-associated sample.
3. Contact the antibody microarray with a mixture of 16 PNA-peptide reporter signal reporter molecules. Wash to remove excess reporter molecules.
4. Coat the surface with matrix, and load the microarray into a MALDI tandem mass spectrometer.
5. Separate and quantify reporter signals by MALDI-tandem mass spectrometry where the amount of each different reporter signal is measured.

This example can be performed using peptide nucleic acid reporter signals (that is, reporter signals composed of peptide nucleic acid) to associate directly with the coding tags. The reporter signals would comprise 16 different PNA sequences of the same mass, designed to be incapable of hybridizing to each other, and additionally designed to be complementary to each of the 16 aforementioned coding tags used for protein labeling. The reporter signals could be easily dissociated from the coding tags (for detection) since they are only non-covalently associated with the coding tags.

EXAMPLE

An important property of some of the disclosed reporter signals is their use in sets where the reporter signals all have a common property (allowing the reporter signals to be separated from the "junk" based upon this common property) and where the reporter signals can be subsequently altered to allow the detection of the individual members of the set of reporter signals. A number of peptides were synthesized with particular sequences and compositions in order to demonstrate the manipulation and analysis of reporter signals utilizing a tandem mass spectrometer. For this example, a set of reporter signals of common mass but differing sequence was used. The reporter signals were fragmented to reveal a part of the sequence, and the reporter signal fragments were detected. Use of reporter signals having a scissile, -DP-, bond was demonstrated.

The quantification of multiple proteins from a complex mixture has not been adequately performed in the field of proteomics. Singly charged peptides containing a C-terminal arginine in an ion trap will preferentially fragment at the C-termini of aspartic acid or glutamic acid residues, and proline containing peptides will fragment at the N-termini of the proline residues (Qin and Chait, Collision-induced dissociation of singly charged peptide ions in a matrix-assisted laser desorption ionization ion trap mass spectrometer. Int. J. Mass Spectrom. (Netherlands), 190–191:313–20 (1999)). These principles were used in designing an exemplary set of peptide reporter signals making use of a DP amino acid sequence to test the collisional fragmentation at the scissile bond between the aspartic acid and proline.

A Micromass Q-TOF instrument (Micromass Inc., Beverly, Mass.) was used in this example. Peptides for this example were synthesized by Fmoc amino acid synthesis on a Rainin Symphony. The reaction scale was 25 μmol. Crude synthesis products were used in this example. The disclosed method should tolerate dirty samples and complex mixtures.

A. Initial Peptides

Eight peptides that varied in the amino acid sequence and/or incorporated isotopes of specific amino acids were synthesized. These were the reporter signals. Modified amino acids were used to demonstrate differential distribution of mass by differential distribution of heavy isotope in reporter signals (heavy isotope mode), and reporter signals of differing sequence were used to demonstrate differential distribution of mass by differential distribution of individual amino acids in reporter signals (variable sequence mode). Modified protected amino acids containing heavy stable isotopes were obtained from Cambridge Isotopes. The two amino acids used here were 3-$^{13}$C-Ala and 2-$^{13}$C-Gly which are each one Dalton heavier than their natural amino acids. Fmoc protected phosphorylated serine was used to further demonstrate the heavy isotope mode and also demonstrate the use of side chain modified amino acids. These peptides were synthesized with free $NH_2$ and free COOH on N and C termini, respectively, as shown in Table 4.

TABLE 4

| Peptide ID | Peptide | Expected primary charged fragment | Mode (H: Heavy Isotope, S: Scissile Bond, C: Control) |
|---|---|---|---|
| LAT3838 | AGSLDPAGSLR | PAGSLR$^+$ | C |
| LAT3839 | A*G*S*LDPAGSLR | PAGSLR$^+$ | H |
| LAT3840 | A*G*SLDPAGS*LR | PAGS*LR$^+$ | H |
| LAT3841 | A*GSLDPAG*S*LR | PAG*S*LR$^+$ | H |
| LAT3842 | AGSLDPA*G*S*LR | PA*G*S*LR$^+$ | H |
| LAT3843 | AGSLADPGSLR | PGSLR$^+$ | S |
| LAT3844 | AGSDPLAGSLR | PLAGSLR$^+$ | S |
| LAT3845 | ADPGSLAGSLR | PGSLAGSLR$^+$ | S |
| LAT3846 | AGSLAGSLDPR | PR$^+$ | S |

The peptides and primary charge fragments are SEQ ID NO:2 and amino acids 6–11 of SEQ ID NO:2 for LAT3838, LAT3839, LAT3840, LAT3841, and LAT3842; SEQ ID NO:4 and amino acids 7–11 of SEQ ID NO:4 for LAT3843; SEQ ID NO:7 and amino acids 5–11 of SEQ ID NO:7 for LAT3844; SEQ ID NO:8 and amino acids 3–11 of SEQ ID NO:8 for LAT3845; and SEQ ID NO:27 and amino acids 10–11 of SEQ ID NO:27 for LAT3846. In Table 4, an asterisk indicates cold heavy isotope amino acid in the case of gly and ala, phosphoserine in the case of serine. For LAT3839, the fragment is distinguishable from control, but the parent ion is distinguishable. LAT3845 and LAT3846 exhibit an end of peptide effect.

B. Second Peptides

Based upon the results with the first peptides, six additional peptides (to serve as reporter signals) were synthesized to demonstrate further points, including reversing the sequence, adding a terminal cysteine (to facilitate sulfur bridge covalent coupling) and addition of tyrosine (to allow for UV quantitation). These reporter signals are shown in Table 5. The set KER4086-KER4090 contain tryptophan to allow for quantitation using UV absorbance. The peptides and primary charged fragments are SEQ ID NO:28 and amino acids 8–14 of SEQ ID NO:28 for KER4086; SEQ ID NO:29 and amino acids 9–14 of SEQ ID NO:29 for KER4076; SEQ ID NO:30 and amino acids 10–14 of SEQ ID NO:30 for KER4088; SEQ ID NO:31 and amino acids 11–14 of SEQ ID NO:31 for KER4089; SEQ ID NO:32 and amino acids 12–14 of SEQ ID NO:32 for KER4090; and SEQ ID NO:33 and amino acids 1–6 of SEQ ID NO:33 for KER4120.

TABLE 5

| Peptide ID | Peptide | Expected primary charged fragment | Addresses |
|---|---|---|---|
| KER4086 | CGWAGSDPLAGSLR | PLAGSLR$^+$ | UV quantitation |
| KER4087 | CGWAGSLDPAGSLR | PAGSLR$^+$ | UV quantitation |
| KER4088 | CGWAGSLADPGSLR | PGSLR$^+$ | UV quantitation |
| KER4089 | CGWAGSLAGDPSLR | PSLR$^+$ | UV quantitation |
| KER4090 | CGWAGSLAGSDPLR | PLR$^+$ | UV quantitation |
| KER4120 | RLSGADPLSGAWGC | RLSGAD$^+$ | Sequence direction |

C. Instrumentation

The preferred mode for the disclosed method makes use of mass spectrometry. Mass spectrometers consist of three major categories of modules: source, filter/ion guide/analyzer, and detector. Commonly used sources for biological applications include Matrix Assisted Laser Desorption Ionization, MALDI, and Electrospray Ionization, ESI. Detectors on current instrumentation are generally Microchannel Plate, MCP, with a number of other detectors available. Between the source and the detector are any number of filters, ion guides, collision cells, laser excitation regions, mass analyzers, etc.

The class of instrument used in this example is called tandem mass spectrometer. The specific instrument used for these experiments is shown schematically in FIG. 1. A preferred spectrometer would have a MALDI source rather than the ESI source (MALDI tends to product singly charged ions, ESI tens to produce multiply charged ions). The ESI source of the spectrometer used here served to provide a more stringent demonstration of the disclosed method.

D. Results

1. DP Sequence, One Component

The first analysis was conducted using a single peptide (LAT3838) to demonstrate scissile bond cleavage in this instrument. To demonstrate scissile bond cleavage, an approximate 1 mg/ml solution of a single peptide (LAT3838—dissolved in 50% acetonitrile/50% water/0.2% formic acid) was loaded into the mass spectrometer.

Figure 3:
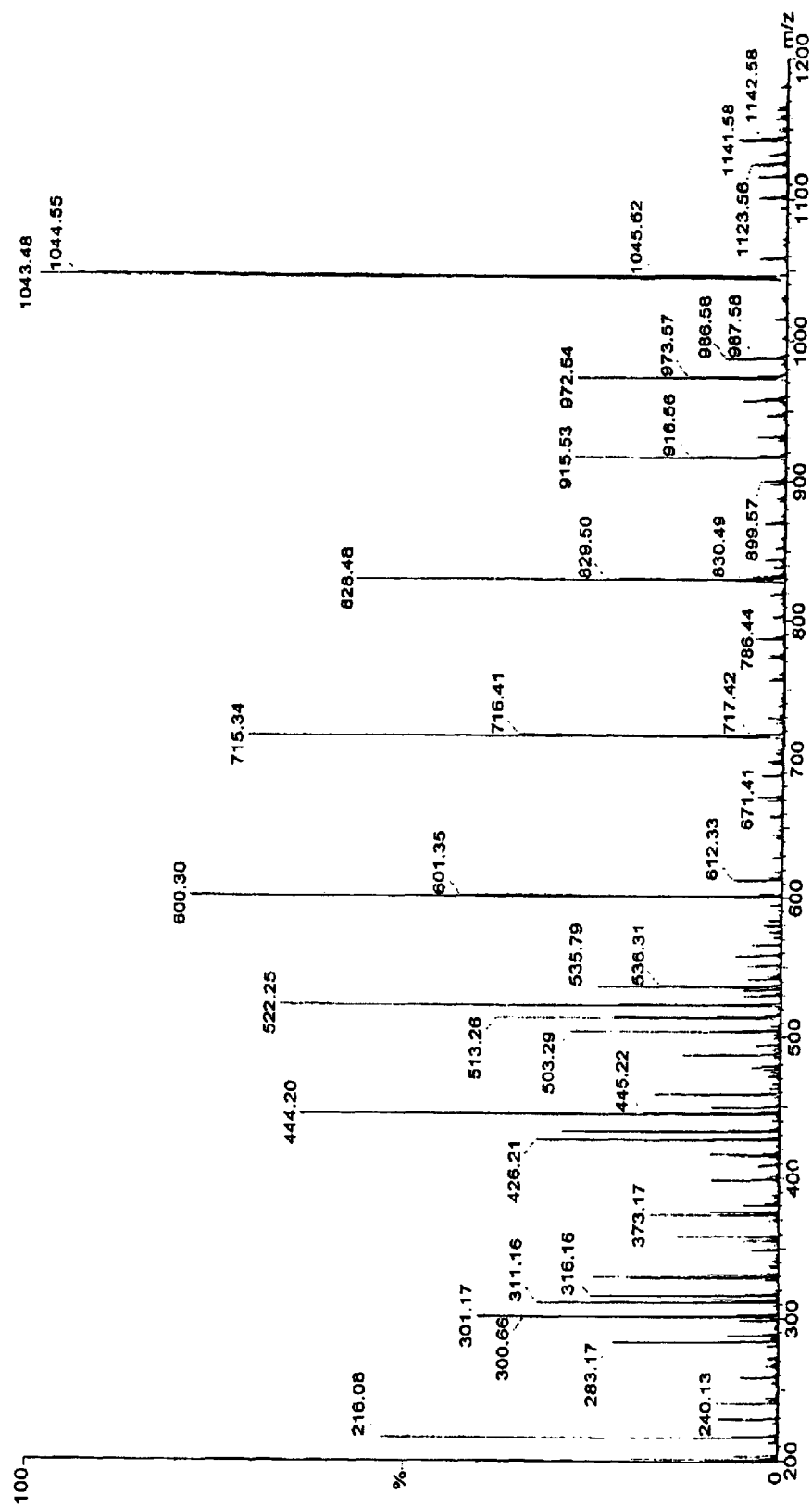
FIG. 3 is an example of an ESI-TOF mass spectrum of an example of a reporter signal peptide (LAT3838 in this case). Most of the complexity of the spectrum comes from fragmentation of the reporter signal peptide in the source.
Figure 4:
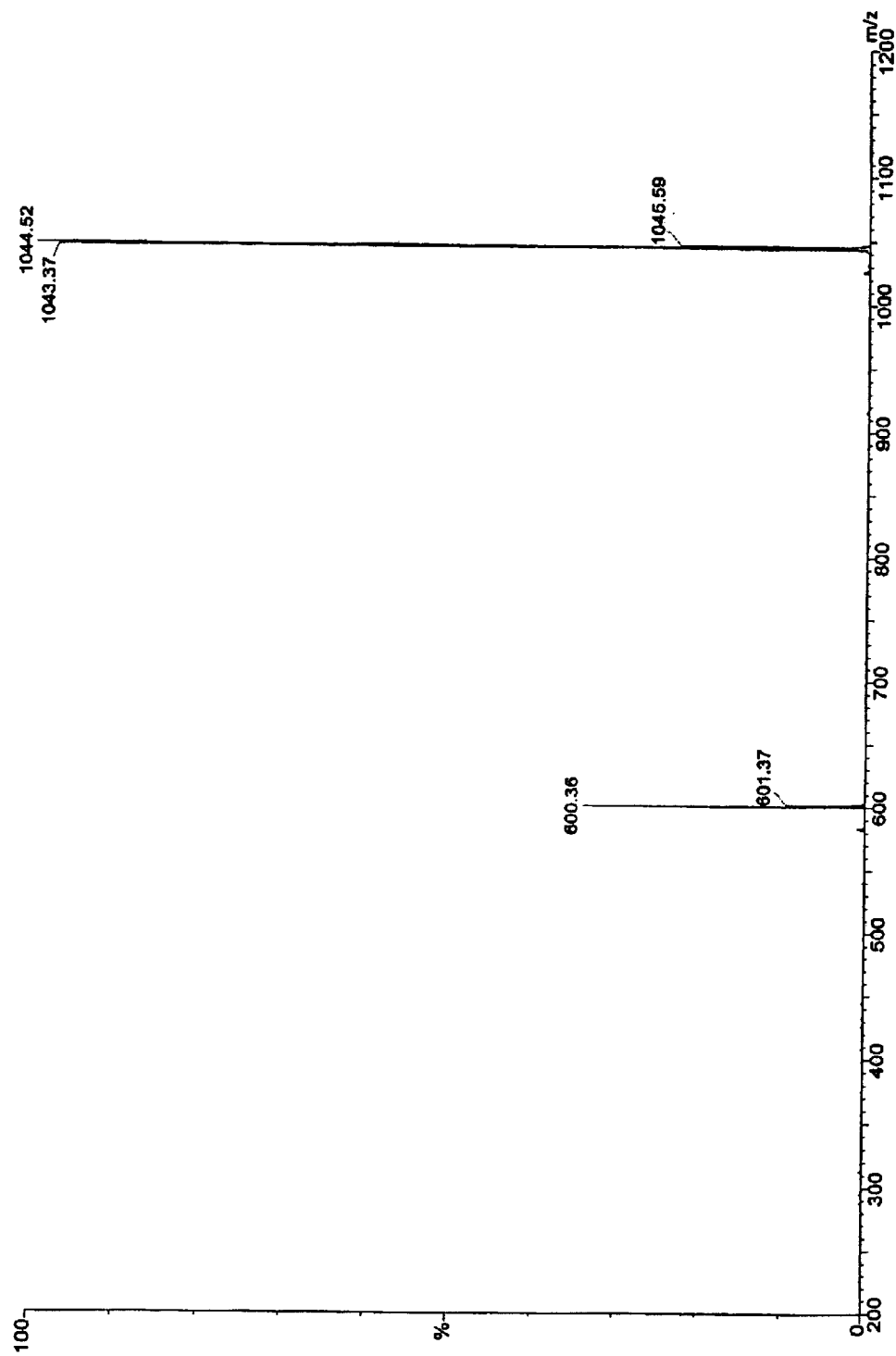
FIG. 4 is an example a spectrum of a selected reporter signal peptide (LAT3838 in this case) following fragmentation. The parent reporter signal was selected at a filter setting of m/z=1044 and altered by fragmented by collision with argon gas at about 20 eV collision energy. The daughter reporter signal peptide fragment at m/z=600 corresponds to the expected PAGSLR$^+$ fragment (amino acids 6–11 of SEQ ID NO:2).

The sequence is AGSLDPAGSLR (SEQ ID NO:2) and was expected to fragment to a single daughter PAGSLR$^+$ (amino acids 6–11 of SEQ ID NO:2). The complex ESI-TOF spectrum of AGSLDPAGSLR (SEQ ID NO:2) is shown in FIG. 3. This spectrum was generated when all peptides (the complete peptide and any fragments) from the ESI source are passed through the first resolving quadrupole, the collision cell, and into the TOF. The daughter ESI-MS/MS spectrum is shown in FIG. 4. To produce this spectrum, the resolving quadrupole operated as a mass filter to select for the parent peptide, allowing it to enter the collision cell while other peptides were not able to pass into the collision cell. Once in the collision cell, fragmentation occurred at the scissile DP bond as expected.

2. DP Sequence, Multiplexed

Figure 5:
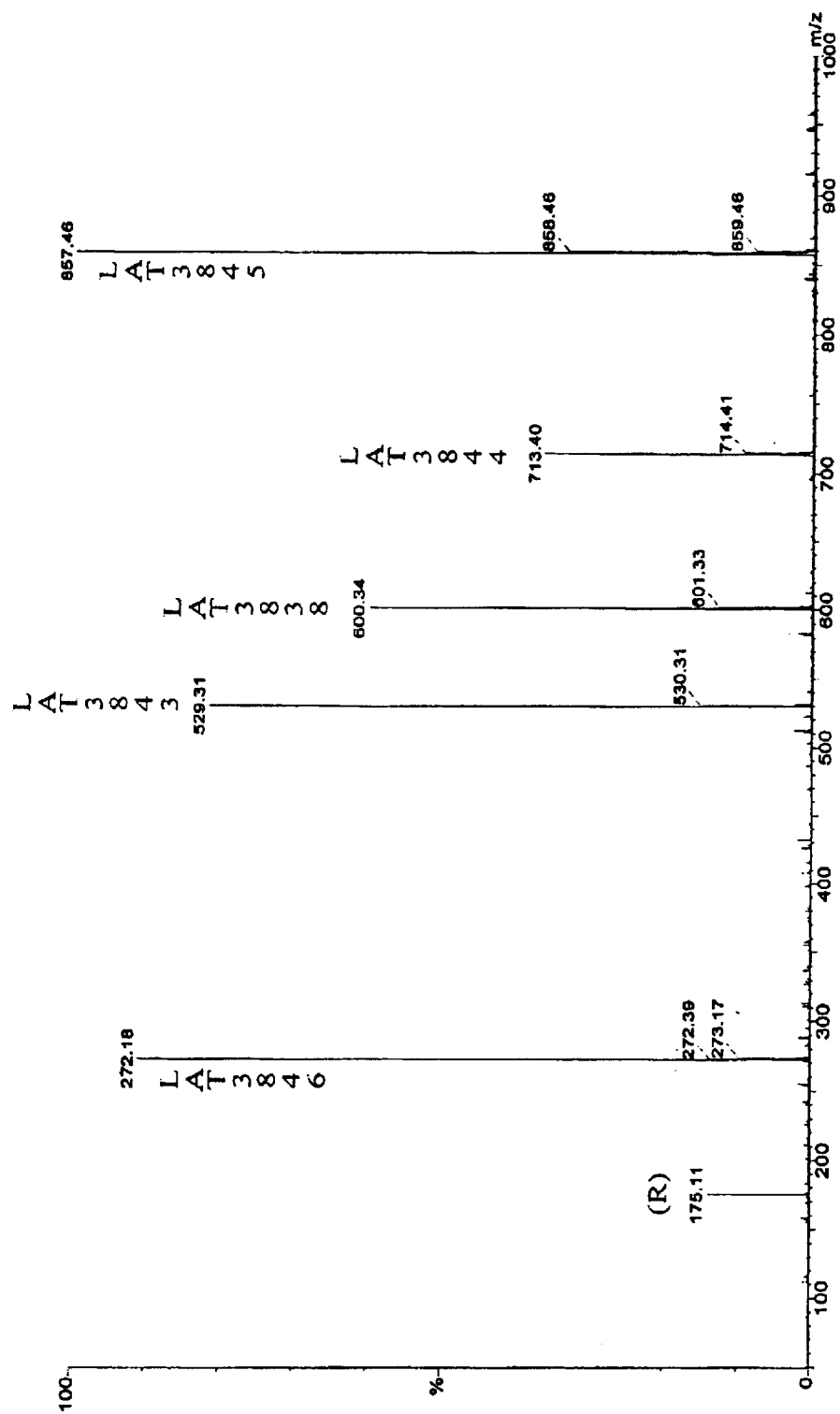
FIG. 5 is an example of a spectrum of the fragmentation products of five reporter signal peptides (LAT3838 and LAT3843 through LAT3856). The peaks corresponding to the reporter signal peptide fragments of each are labeled.

The set of peptides LAT3838 and LAT3843–3846 comprise an isobaric set of reporter signals. That is, all of the reporter signals in this set have the same mass-to-charge ratio. This set was mixed together in approximately equal concentration. 7 mg of each peptide was dissolved in 0.7 ml of 50% acetonitrile/50% water/0.2% formic acid. Dilutions of the stock samples were prepared and a final solution containing 0.1 µg/ml of each peptide was loaded into the mass spectrometer and subjected to ESI-MS/MS analysis. The parent spectrum was comparable to that shown in FIG. 3, the daughter ion spectrum, shown in FIG. 5, exhibits all five reporter signals at approximately equal amounts.

3. Heavy Isotopes i. Phosphate Loss from Phosphorylated Serine

Figure 6:
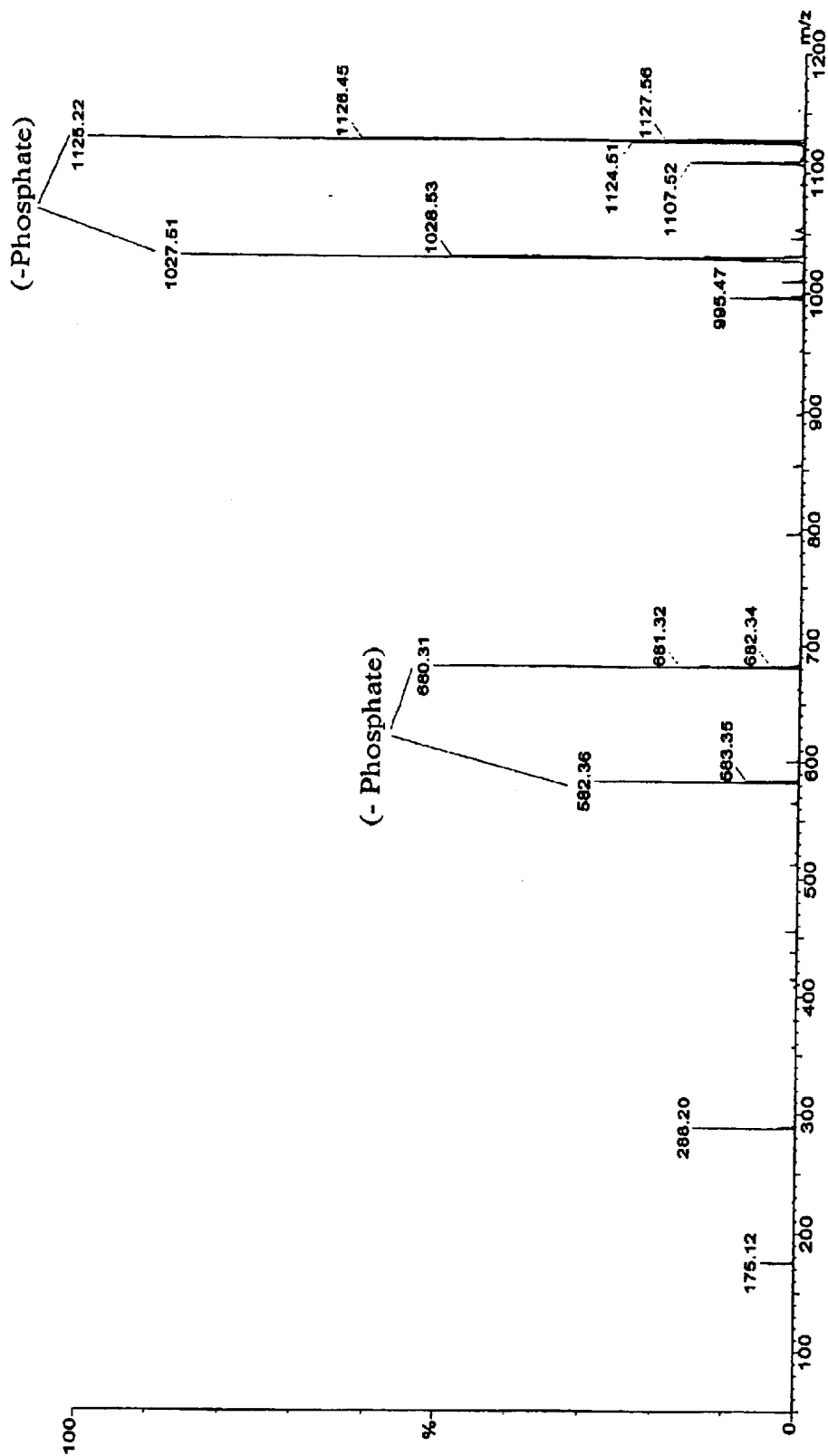
FIG. 6 is an example of a spectrum showing the effect of the loss of a phosphate group from reporter signal peptide fragments.

Spectra clearly show that phosphate loss is common in this system. This provides increased sampling, with two data points generated per reporter signal. A typical example of loss of phosphate from the phosphorylated serine is shown in FIG. 6.

ii. Stable Isotope Amino Acids

The stable isotopes incorporated into the reporter signals differed from the nature forms of the amino acids by 1 Dalton. As a consequence, naturally occurring heavy isotope peaks and the peak from the engineered reporter signals are at the same (degenerate) mass-to-charge. A range of mass-to-charge ratios is preferred for the disclosed method. The resulting traces were analyzed in a straightforward manner (see Table 6). It is clear from Table 6 and FIG. 7 that the "complicated peaks" correspond to three species and there are five measurements—the simultaneous equations can be solved for each fragment. Additionally, the peaks near m/z=582 and the peaks near m/z=680 correspond to the fragment less phosphate and fragment respectively. This information is redundant (assuming the loss of phosphate is a random chance event) and may be used to increase the quantitation confidence.

TABLE 6

| Observed m/z | Species responsible for signal |
| --- | --- |
| 600.34 | $LAT3839_M$ |
| 601.33 | $LAT3839_{M+1}$ |
| 602.34 | $LAT3839_{M+2}$ |
| 680.30 | $LAT3840_M$ |
| 681.32 | $LAT3840_{M+1}$ + $LAT3841_M$ |
| 682.30 | $LAT3840_{M+2}$ + $LAT3841_{M+1}$ + $LAT3842_M$ |
| 683.31 | $LAT3841_{M+2}$ + $LAT3842_{M+1}$ |
| 684.31 | $LAT3842_{M+2}$ |
| 582.33 | $LAT3840_M$ − $H_3PO_4$ |
| 583.33 | $LAT3840_{M+1}$ + $LAT3841_M H_3PO_4$ |
| 584.35 | $LAT3840_{M+2}$ + $LAT3841_{M+1}$ + $LAT3842_M$ − $H_3PO_4$ |
| 585.35 | $LAT3841_{M+2}$ + $LAT3842_{M+1}$ − $H_3PO_4$ |
| 568.35 | $LAT3842_{M+2}$ − $H_3PO_4$ |

Figure 7:
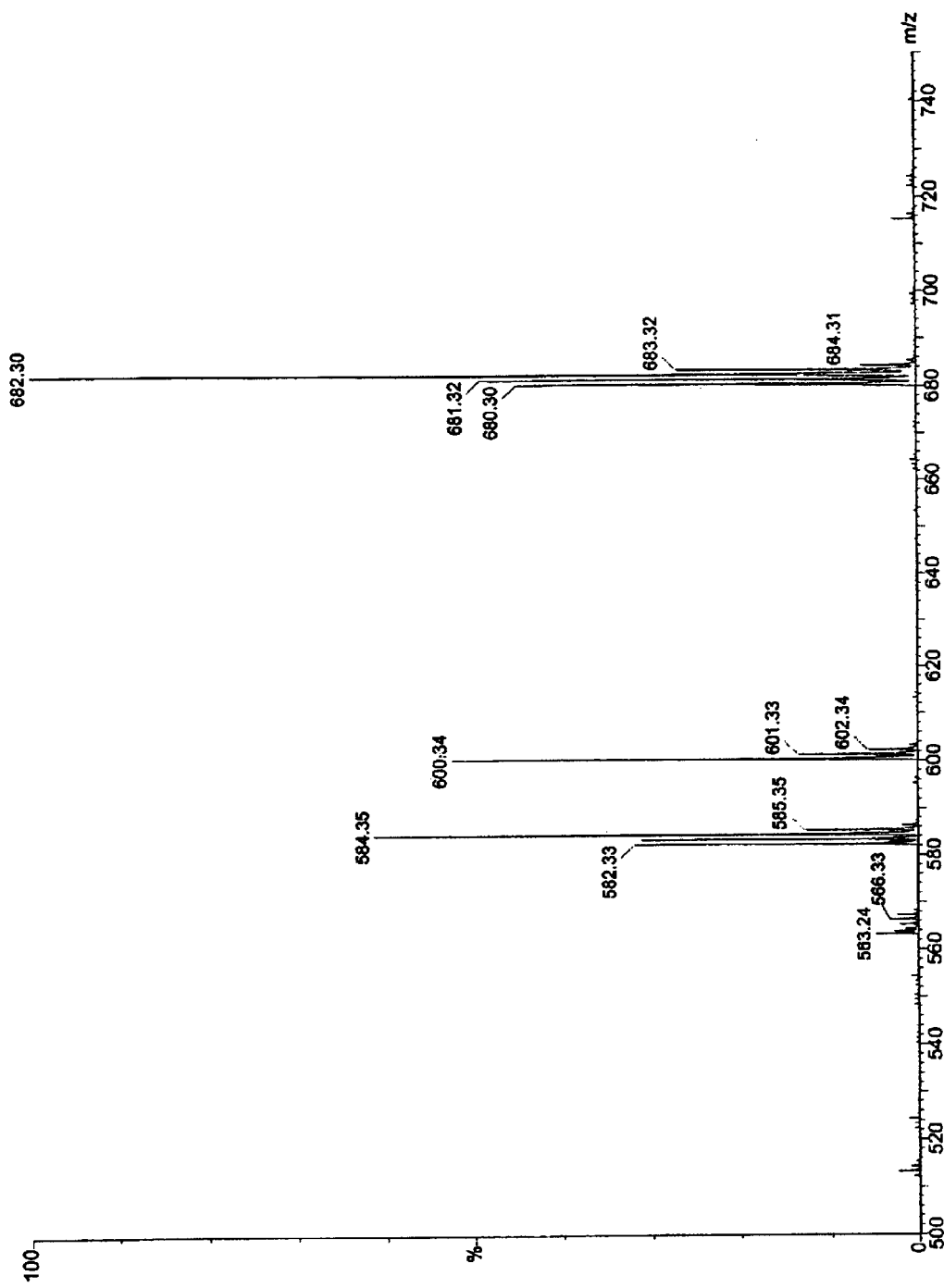
FIG. 7 is an example of a spectrum showing differentiation of reporter signal peptide fragments based on the use of stable isotopes in the reporter signal peptides.

In Table 6, the observed m/z corresponds to that in FIG. 7. Nomenclature (not industry standard): $PeptideID_M$ is fragment which contains no naturally occurring heavy isotope, $PeptideID_{M+1}$ is the peak due to naturally occurring single mass occurrences of one unit heavy isotope of the fragment, $PeptideID_{M+2}$ is the peak due to naturally occurring double mass unit heavy isotopes plus naturally occurring instances of two single mass heavy isotopes. Effect only up to M+2 are considered here but the method is extensible.

4. Second Peptides

The second set of peptides (reporter signals) is shown in Table 5 and specific aspects are addressed in these following sections. The data indicate the tryptophan, the cysteine, and the additional glycine in the second set of peptides behave well in the disclosed method.

i. Effect of Sequence

Sulfur bridge covalent bonding of reporter signals to specific binding molecules can be used. To facilitate this chemistry it is advantageous to have a cysteine as a terminal residue. Additionally, because peptide synthesis is from N to C terminus, if the cysteine is last on it can act as a purification element when the peptide is covalently attached to a specific binding molecule (compare to amine linker last on during oligonucleotide synthesis acts to purify the immobilized oligonucleotide).

To demonstrate the effect a C-terminal cysteine, peptide KER4120 (RLSGADPLSGAWGC; SEQ ID NO:33)) was synthesized which is precisely peptide KER4087 (CGWAGSLDPAGSLR; SEQ ID NO:29) in reverse sequence. The fragmentation pattern of KER4120 was similar to that of KER4087. This is consistent with a conclusion that synthesis of the peptide with the arginine on the N-terminus results in a peptide with a similar fragmentation pattern.

5. Complex Mixture

Figure 8:
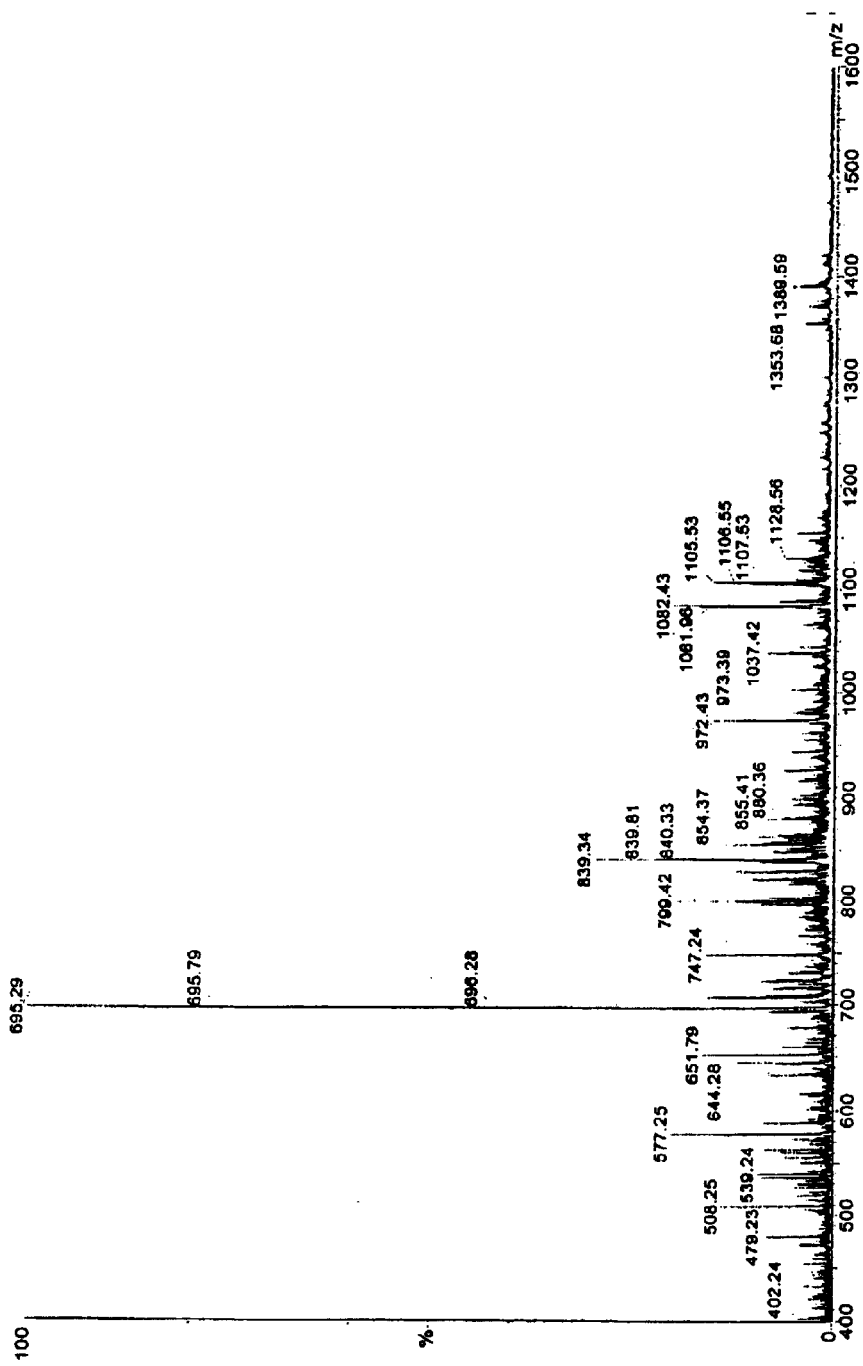
FIG. 8 is an example of a spectrum of a complex mixture of molecules that includes five reporter signal peptides (m/z=1389.6).
Figure 9:
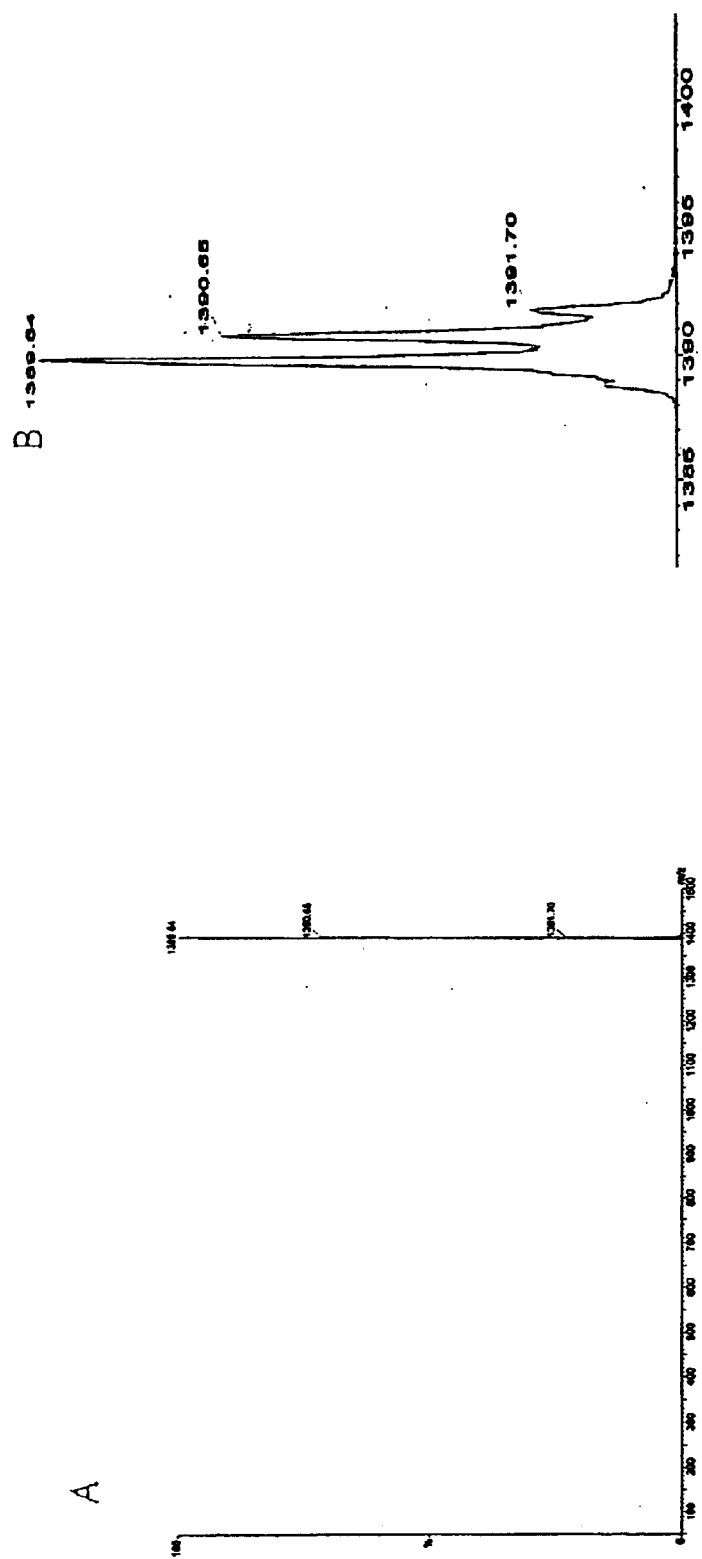
FIGS. 9A and 9B are an example of a spectrum of a set of reporter signal peptides following selection based on mass-to-charge ratio (m/z around 1390) and illustrating a nearly non-existent background everywhere except at m/z around 1390. This is the same sample (prior to selection) from which the complex spectrum of FIG. 8 was obtained.
Figure 10:
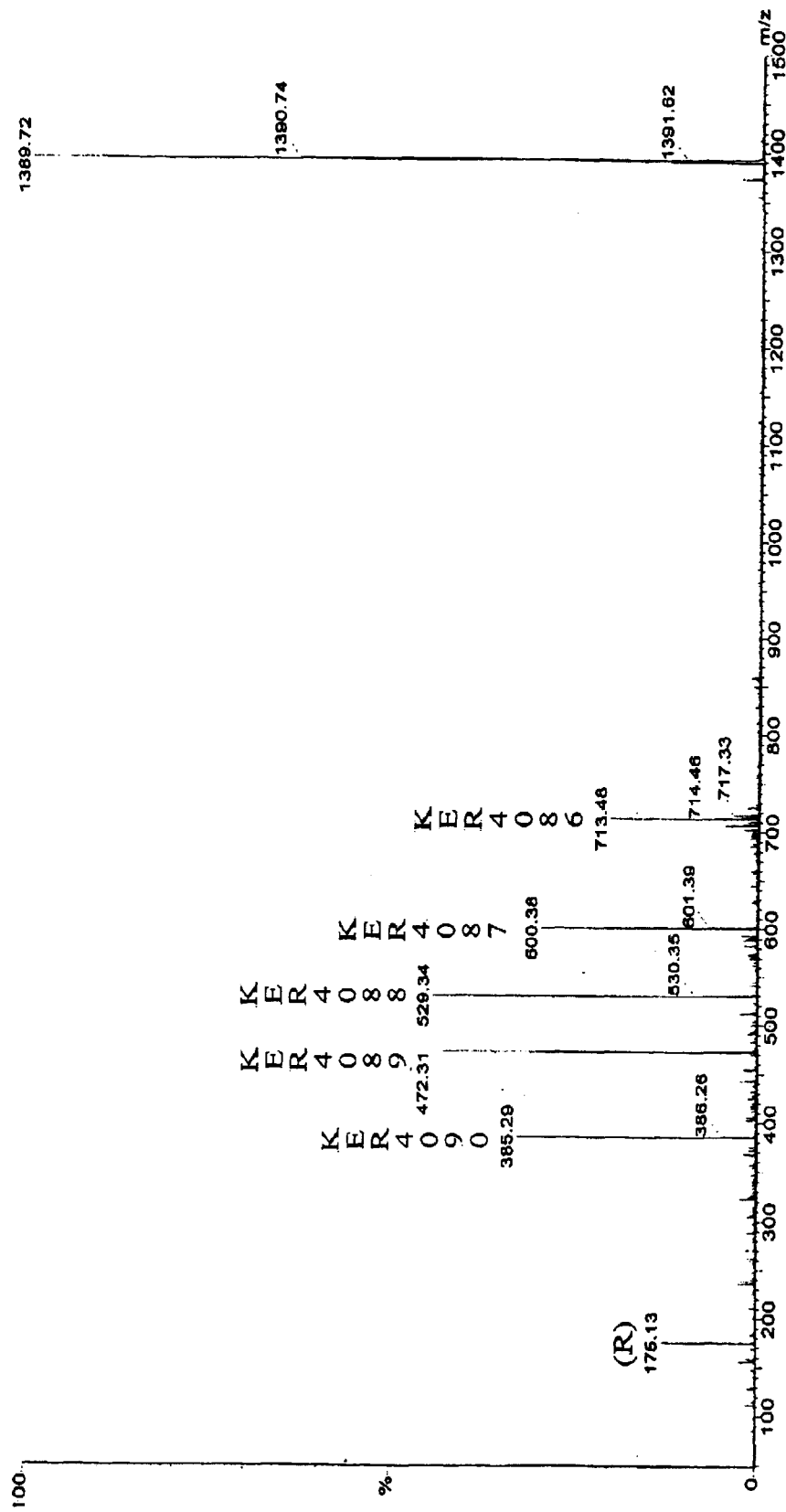
FIG. 10 is an example of a spectrum of the fragmentation products of the selected reporter signal peptides of FIG. 9 (originally in the complex sample of FIG. 8). Five prominent peaks of approximately the same magnitude appear at the expected m/z of the reporter signal peptide fragments of each of the five reporter signal peptides. Unfragmented reporter signal peptides remain in the rightmost peak (m/z near 1390).

Clear demonstration of the power of the disclosed method is seen in an example measurement in a complex mixture. To generate a reasonably complex mixture Bovine Serum Albumin (BSA) (66 kDa) and creatine phosphokinase (84 kDa) were digested using trypsin. Five peptides (KER4086 to KER4090) were added to the digestion mixture (to a final concentration of 0.1 µg/ml of each peptide). The resulting mass spectrum for this complex mixture is shown in FIG. 8. As can be seen, the mixture is quite complex, showing peaks at a wide variety of mass-to-chare ratios. The spectrum following selection of the common mass-to-charge ratio is shown in FIG. 9. As can be seen, the filtering (selection) step produces a dramatic (essentially complete) reduction in complexity. The spectrum following fragmentation of the selected mass-to-charge fraction is shown in FIG. 10. As can be seen, clear peaks, all at nearly the same level (as expected based on equal amounts of starting material for each reporter signal), appear for each of the five expected reporter signal fragments (each having a distinctive mass-to-charge ratio. FIGS. 8 through 10 give a powerful representation of the progression from a complex mixture to the identification and determination of relative concentrations of specific labels.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to "the antibody" is a reference to one or more antibodies and equivalents thereof known to those skilled in the art, and so forth.

Disclosed are the components to be used to prepare the disclosed compositions as well as the compositions themselves and to be used within the methods disclosed herein. These and other materials are disclosed herein, and it is understood that when combinations, subsets, interactions, groups, etc. of these materials are disclosed that while specific reference of each various individual and collective permutation of these compounds may not be explicitly disclosed, each is specifically contemplated and described herein. For example, if a particular type of reporter signal is disclosed and discussed in the context of some modes and embodiments of the disclosed method, specifically contemplated is each and every combination and permutation of the reporter signal and the various forms and embodiments of the disclosed method that are possible unless specifically indicated to the contrary. Thus, if a class of molecules A, B, and C are disclosed as well as a class of molecules D, E, and F and an example of a combination molecule, A-D is disclosed, then even if it each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

We claim:

1. A set of reporter signals comprising a plurality of reporter signal peptides,
   wherein the reporter signal peptides have a common property, wherein the common property allows the reporter signal peptides to be distinguished or separated from molecules lacking the common property,
   wherein the reporter signal peptides are capable of being altered, wherein the altered forms of each reporter signal peptide can be distinguished from every other altered form of reporter signal peptide.

2. The set of claim 1 wherein the common property is mass-to-charge ratio, wherein the reporter signal peptides are altered by altering their mass, wherein the altered forms of the reporter signal peptides can be distinguished via differences in the mass-to-charge ratio of the altered forms of reporter signal peptides.

3. The set of claim 2 wherein the mass of the reporter signal peptides is altered by fragmentation.

4. The set of claim 2 wherein alteration of the reporter signal peptides also alters their charge.

5. The set of claim 1 wherein the common property is mass-to-charge ratio, wherein the reporter signal peptides are altered by altering their charge, wherein the altered forms of the reporter signal peptides can be distinguished via differences in the mass-to-charge ratio of the altered forms of reporter signal peptides.

6. The set of claim 1 wherein the set comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal peptides.

7. The set of claim 6 wherein the set comprises ten or more different reporter signal peptides.

8. The set of claim 1 wherein the reporter signal peptides are associated with, or coupled to, specific binding molecules, wherein each reporter signal peptide is associated with, or coupled to, a different specific binding molecule.

9. The set of claim 1 wherein the reporter signal peptides are associated with, or coupled to, decoding tags, wherein each reporter signal peptide is associated with, or coupled to, a different decoding tag.

10. The set of claim 1 wherein the reporter signal peptides have the same mass-to-charge ratio.

11. The set of claim 10 wherein the peptides have the same amino acid composition.

12. The set of claim 11 wherein the peptides have the same amino acid sequence.

13. The set of claim 12 wherein each peptide contains a different distribution of heavy isotopes.

14. The set of claim 12 wherein each reporter signal peptide contains a different distribution of substituent groups.

15. The set of claim 11 wherein each peptide has a different amino acid sequence.

16. The set of claim 11 wherein each peptide has a labile or scissile bond in a different location.

17. The set of claim 1 wherein the reporter are coupled to proteins or peptides.

18. The set of claim 1 wherein the common property allows the reporter signal peptides to be distinguished or separated from molecules lacking the common property.

19. The set of claim 1 wherein the common property is not an affinity tag.

20. The set of claim 19 wherein one or more affinity tags are associated with the reporter signal peptides.

21. A method comprising:
   (a) separating a set of reporter signal peptides, where each reporter signal peptide has a common property, from molecules lacking the common property,
   (b) altering the reporter signal peptides,
   (c) detecting and distinguishing the altered forms the reporter signal peptides from each other.

22. The method of claim 21 wherein the common property is mass-to-charge ratio, wherein the reporter signal peptides are altered by altering their mass, wherein the altered forms of the reporter signal peptides are distinguished via differences in the mass-to-charge ratio of the altered forms of reporter signal peptides.

23. The method of claim 22 wherein the mass of the reporter signal peptides is altered by fragmentation.

24. The method of claim 22 wherein the reporter signal peptides are altered by cleavage at a photocleavable amino acid.

25. The method of claim 22 wherein the reporter signal peptides are fragmented in a collision cell.

26. The method of claim 22 wherein the reporter signal peptides are fragmented at an asparagineproline bond.

27. The method of claim 22 wherein alteration of the reporter sign peptides also alters their charge.

28. The method of claim 21 wherein the common property is mass-to-charge ratio, wherein the reporter signal peptides are altered by altering their charge, wherein the altered forms of the reporter signal peptides can be distinguished via differences in the mass-to-charge ratio of the altered forms of reporter signals.

29. The method of claim 21 wherein the set of reporter signal peptides comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal peptides.

30. The method of claim 29 wherein the set of reporter signal peptides comprises ten or more different reporter signal peptides.

31. The method of claim 21 wherein the reporter signal peptides are associated with, or coupled to, specific binding molecules, wherein each reporter signal peptide is associated with, or coupled to, a different specific binding molecule.

32. The method of claim 21 wherein the reporter signal peptides are associated with, or coupled to, decoding tags, wherein each reporter signal peptide is associated with, or coupled to, a different decoding tag.

33. The method of claim 21 wherein the reporter signal peptides have the same mass-to-charge ratio.

34. The method of claim 33 wherein the peptides have the same amino acid composition.

35. The method of claim 34 wherein the peptides have the same amino acid sequence.

36. The method of claim 35 wherein each peptide contains a different distribution of heavy isotopes.

37. The method of claim 35 wherein each reporter signal peptide contains a different distribution of substituent groups.

38. The method of claim 34 wherein each peptide has a different amino acid sequence.

39. The method of claim 34 wherein each peptide has a labile or scissile bond in a different location.

40. The method of claim 21 wherein the reporter signal peptides are coupled to proteins or peptides.

41. The method of claim 21 wherein the common property allows the reporter signal peptides to be distinguished or separated from molecules lacking the common property.

42. The method of claim 21 wherein the common property is not an affinity tag.

43. The method more tags of claim 42 wherein one or affinity are associated with the reporter signal peptides.

44. The method of claim 21 further comprising, prior to step (a), associating the reporter signal peptides with one or more analytes, wherein each reporter signal peptide is associated with, or coupled to, a different specific binding molecule, wherein each specific binding molecule can interact specifically with a different one of the analytes, wherein the reporter signal peptides are associated with the analytes via interaction of the specific binding molecules with the analytes.

45. The method of claim 21 further comprising, prior to step (a), associating one or more reporter signal peptides with one or more proteins, one or more peptides, or one or more proteins and peptides from each of one or more samples.

46. The method of claim 21 wherein the reporter signal peptides are associated with a single sample.

47. The method of claim 46 wherein the sample is produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

48. The method of claim 21 wherein steps (a) through (c) are repeated one or more times using a different set of reporter signal peptides each time.

49. The method of claim 48 wherein, prior to step (a), the different sets of reporter signal peptides are associated with different samples.

50. The method of claim 49 wherein the different sets of reporter signal peptides each comprise the same reporter signals.

51. The method of claim 49 wherein the samples are produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

52. The method of claim 49 wherein the different samples are from the same protein sample.

53. The method of claim 52 wherein the different samples are obtained at different times.

54. The method of claim 49 wherein the different samples are from the same type organism.

55. The method of claim 49 wherein the different samples are from the same type of tissue.

56. The method of claim 49 wherein the different samples are from the same organism.

57. The method of claim 56 wherein the different samples are obtained at different times.

58. The method of claim 49 wherein the different samples are from different organisms.

59. The method of claim 49 wherein the different samples are from different types of tissues.

60. The method of claim 49 wherein the different samples are from different species of organisms.

61. The method of claim 49 wherein the different samples are from different strains of organisms.

62. The method of claim 49 wherein the different samples are from different cellular components.

63. The method of claim 49 further comprising identifying or preparing proteins or peptides corresponding to the proteins or peptides present in one sample but not present in another sample.

64. The method of claim 49 further comprising determining the relative amount of proteins or peptides in the different samples.

65. The method of claim 48 wherein the sets of reporter signal peptides each contain a single reporter signal peptide.

66. The method of claim 21 wherein not all of the reporter signal peptides in the set are distinguished or separated from molecules lacking the common property, not all of the reporter signal peptides are altered, and not all of the altered forms of the reporter signal peptides are detected at the same time.

67. The method of claim 66 wherein all of the reporter signal peptides in the set are distinguished or separated from molecules lacking the common property, all of the reporter signal peptides are altered, and all of the altered forms of the reporter signal peptides are detected at different times.

68. The method of claim 21 wherein steps (a) through (c) are performed separately for each reporter signal peptide.

69. The method of claim 21 wherein the altered forms of the reporter signal peptides detected collectively constitutes a catalog of proteins.

70. The method of claim 21 wherein steps (b) and (c) are performed simultaneously.

71. The method of claim 21 wherein altered forms of the reporter signal peptides detected by using mass spectrometry.

72. The method of claim 21 wherein the steps are performed with a tandem mass spectrometer.

73. The method of claim 72 wherein the tandem mass spectrometer comprises a first stage and a last stage, wherein step (a) is performed using the first stage of the tandem mass spectrometer to select ions in a narrow mass-to-charge range, wherein step (b) is performed by collision with a gas, and wherein step (c) is performed using the final stage of the tandem mass spectrometer.

74. The method of claim 73 where the first stage of the tandem mass spectrometer is a quadrupole mass filter.

75. The method of claim 74 where the final stage of the tandem mass spectrometer is a time of flight analyzer.

76. The method of claim 73 where the final stage of the tandem mass spectrometer is a time of flight analyzer.

77. The method of claim 72 wherein the mass-to-charge range is varied to cover the mass-to-charge ratio of each of the target protein fragments.

78. A kit comprising:
(a) a set of reporter molecules, wherein each reporter molecule comprises a reporter signal peptide and a decoding tag,
wherein the reporter signal peptides have a common property, wherein the common property allows the reporter signal peptides to be distinguished or separated from molecules lacking the common property,
wherein the reporter signal peptides are capable of being altered, wherein the altered forms of each reporter signal peptide can be distinguished from every other altered form of reporter signal peptide,
wherein each different reporter molecule comprises a different decoding tag and a different reporter signal peptide,
(b) a set of coding molecules, wherein each coding molecule comprises a specific binding molecule and a coding tag, wherein each specific binding molecule can interact specifically with a different analyte, wherein each coding tag can interact specifically with a different decoding tag.

79. A method comprising:
(a) separating one or more reporter signal peptides, where each reporter signal peptide has a common property, from molecules lacking the common property in each of a plurality of samples,
(b) altering the reporter signal peptides,
(c) detecting and distinguishing the altered forms the reporter signal peptides from each other.

80. A set of labeled proteins wherein each labeled protein comprises a protein or peptide and a reporter signal peptide attached to the protein or peptide, wherein the reporter signal peptides have a common property, wherein the common property allows the labeled proteins comprising the same protein or peptide to be distinguished or separated from molecules lacking the common property, wherein the reporter signal peptides are capable of being altered, wherein the altered forms of each reporter signal peptide can be distinguished from every other altered form of reporter signal peptide, wherein alteration of the reporter signal peptides alters the labeled proteins, wherein altered forms of each labeled protein can be distinguished from every other altered form of labeled protein.

81. A kit comprising a set of reporter molecules, wherein each reporter molecule comprises a reporter signal peptide and a coupling tag, wherein the reporter signal peptides have a common property, wherein the common property allows the reporter signal peptides to be distinguished or separated from molecules lacking the common property, wherein the reporter signal peptides are capable of being altered, wherein the altered forms of each reporter signal peptide can be distinguished from every other altered form of reporter signal peptide, wherein each different reporter molecule comprises a different coupling tag and a different reporter signal peptide.

82. A set of labeled proteins wherein each labeled protein comprises a protein or peptide and a reporter signal peptide attached to the protein or peptide, wherein the labeled proteins have a common property, wherein the common property allows the labeled proteins comprising the same protein or peptide to be distinguished or separated from molecules lacking the common property, wherein the reporter signal peptides are capable of being altered, wherein the altered forms of each reporter signal peptide can be distinguished from every other altered form of reporter signal peptide, wherein alteration of the reporter signal peptides alters the labeled proteins, wherein altered forms of each labeled protein can be distinguished from every other altered form of labeled protein.

83. A set of labeled proteins wherein each labeled protein comprises a protein or peptide and a reporter signal peptide attached to the protein or peptide, wherein the reporter signal peptides are capable of being altered, wherein the altered forms of each reporter signal peptide can be distinguished from every other altered form of reporter signal peptide, wherein alteration of the reporter signal peptides alters the labeled proteins, wherein altered forms of each labeled protein can be distinguished from every other altered form of labeled protein.

84. A method comprising
(a) separating a set of labeled proteins, wherein each labeled protein comprises a protein or peptide and a reporter signal peptide attached to the protein or peptide,
wherein each reporter signal peptide has a common property, wherein the common property allows the labeled proteins comprising the same protein or peptide to be distinguished or separated from molecules lacking the common property,
(b) altering the reporter signal peptides, thereby altering the labeled proteins,
(c) detecting and distinguishing the altered forms of the labeled proteins from each other.

85. The method of claim 84 further comprising, prior to step (a), attaching the reporter signal peptides to one or more proteins, one or more peptides, or one or more proteins and peptides.

86. The method of claim 85 wherein steps are repeated one or more a using a different set of reporter signal peptides each time.

87. The method of claim 86 wherein, prior to step (a), the different sets of reporter signal peptides are attached to proteins or peptides in different samples.

88. The method of claim 87 wherein the different sets of reporter signal peptides each comprise the same reporter signal peptides.

89. The method of claim 86 wherein the sets of reporter signal peptides each contain a single reporter signal peptide.

90. A set of labeled proteins wherein each labeled protein comprises a protein or a peptide and a reporter signal attached to the protein or peptide, wherein the reporter signals comprise peptides, wherein the reporter signal peptides have the same mass-to-charge ratio.

91. A method comprising:
(a) separating one or more labeled proteins, wherein each labeled protein comprises a protein or peptide and a reporter signal peptide attached to the protein or peptide,
wherein each reporter signal peptide has a common property, wherein the common property allows the labeled proteins comprising the same protein or peptide to be distinguished or separated from molecules lacking the common property in each of one or more samples,
(b) altering the reporter signal peptides, thereby altering the labeled proteins,
(c) detecting and distinguishing the altered forms the labeled proteins from each other.

92. The method of claim 91 wherein the pattern of the presence, amount, presence and amount, or absence of labeled proteins in one of the samples constitutes a catalog of proteins in the sample.

93. The method of claim 92 wherein the pattern of the presence, amount, presence and amount, or absence of labeled proteins in a second one of the samples constitutes a catalog of proteins in the second sample, wherein the catalog of proteins in the first sample is a first catalog and the catalog of proteins in the second sample is a second catalog, the method further comprising comparing the first catalog and the second catalog.

94. A method comprising:
(a) separating a set of labeled proteins, wherein each labeled protein comprises a protein or peptide and a reporter signal peptide attached to the protein or peptide,
wherein each labeled protein has a common property, wherein the common property allows the labeled proteins comprising the same protein or peptide to be distinguished or separated from molecules lacking the common property,
(b) altering the reporter signal peptides, thereby altering the labeled proteins,
(c) detecting and distinguishing the altered forms of the labeled proteins from each other.

95. A method comprising:
(a) altering labeled proteins, wherein each labeled protein comprises a protein or peptide and a reporter signal peptide attached to the protein or peptide, wherein the labeled proteins are altered by altering the reporter signal peptides,
(b) detecting and distinguishing the altered forms of the labeled proteins from each other.

96. A method comprising
(a) separating one or more labeled proteins from other molecules, wherein the labeled proteins are derived from one or more samples, wherein each labeled protein comprises a protein or peptide and a reporter signal peptide attached to the protein or peptide,
(b) altering the reporter signal peptides, thereby altering the labeled proteins,
(c) detecting and distinguishing the altered forms the labeled proteins from each other.

97. The method of claim 96 further comprising, prior to step (a), associating one or more reporter signal peptides with one or more proteins, one or more peptides, or one or more proteins and peptides from each of the one or more samples.

98. The method of claim 96 wherein the one or more labeled proteins are derived from a single sample.

99. The method of claim 98 wherein a single labeled protein is distinguished or separated from other molecules.

100. The method of claim 98 wherein a plurality of labeled proteins are distinguished or separated from other molecules.

101. The method of claim 98 wherein the detected altered forms of the labeled proteins constitute a catalog of proteins in the sample.

102. The method of claim 96 wherein one or more labeled proteins are derived from each of a plurality of samples.

103. The method of claim 102 wherein a single labeled protein derived from each of the samples is distinguished or separated from other molecules.

104. The method of claim 102 wherein a plurality of labeled proteins derived from each of the samples are distinguished or separated from other molecules.

105. The method of claim 102 wherein the detected altered forms of the labeled proteins derived from each sample constitute a catalog of proteins in the sample.

106. A catalog of proteins and peptides comprising, proteins and peptides in a sample detected by:
(a) separating one or more labeled proteins from other molecules, wherein the labeled proteins are derived from the sample, wherein each labeled protein comprises a protein or peptide and a reporter signal peptide attached to the protein or peptide, (b) altering the reporter signal peptides, thereby altering the labeled proteins, (c) detecting and distinguishing the altered forms the labeled proteins from each other.

107. A catalog of proteins and peptides comprising, proteins and peptides in one or more samples detected by:

(a) separating one or more labeled proteins from other molecules, wherein the labeled proteins are derived from the one or more samples, wherein each labeled protein comprises a protein or peptide and a reporter signal peptide attached to the protein or peptide, (b) altering the reporter signal peptides, thereby altering the labeled proteins, (c) detecting and distinguishing the altered forms the labeled proteins from each other.

108. A method of producing a protein signature, the method comprising:

(a) treating a protein sample to produce protein fragments, wherein the protein fragments comprise a set of target protein fragments, wherein the target protein fragments can be altered, wherein the altered forms of the target protein fragments can be distinguished from the other altered forms of the target protein fragments, (b) mixing the target protein fragments with a set of reporter signal calibrators, wherein the reporter signal calibrators comprise peptides, wherein each target protein fragment shares a common property with at least one of the reporter signal calibrators, wherein the common property allows the target protein fragments and reporter signal calibrators having the common property to be distinguished or separated from molecules lacking the common property, wherein the target protein fragment and reporter signal calibrator that share a common property correspond to each other, wherein the reporter signal calibrators are capable of being altered, wherein the altered form of each reporter signal calibrator can be distinguished from the altered form of the target protein fragment with which the reporter signal calibrator shares a common property, (c) separating the target protein fragments and reporter signal calibrators from other molecules based on the common properties of the target protein fragments and reporter signal calibrators, (d) altering the target protein fragments and reporter signal calibrators, (e) detecting the altered forms of the target protein fragments and reporter signal calibrators, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

109. The method of claim 108 wherein a predetermined amount of each reporter signal calibrator is mixed with the target protein fragments, wherein the amount of each altered form of reporter signal calibrator detected provides a standard for assessing the amount of the altered form of the corresponding target protein fragment.

110. The method of claim 109 wherein the amount of at least two of the reporter signal calibrators is different.

111. The method of claim 109 wherein the relative amount each reporter signal calibrator is based on the relative amount of each corresponding target protein fragment expected to be in the protein sample.

112. The method of claim 109 wherein the amount of each of the reporter signal calibrators is the same.

113. The method of claim 108 wherein the protein fragments are produced by protease digestion of the protein sample.

114. The method of claim 113 wherein the protein fragments are produced by digestion of the protein sample with a serine protease.

115. The method of claim 114 wherein the serine protease is trypsin.

116. The method of claim 113 wherein the protein fragments are produced by digestion of the protein sample with Factor Xa or Enterokinase.

117. The method of claim 108 wherein the protein fragments are produced by cleavage at a photocleavable amino acid.

118. The method of claim 108 wherein the set of target protein fragments comprises two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different target protein fragments.

119. The method of claim 108 further comprising comparing the protein signature to one or more other protein signatures.

120. The method of claim 108 wherein at least one of the target protein fragments comprises at least one modified amino acid.

121. The method of claim 120 wherein the modified amino avid is a phosphorylated amino acid, an acylated amino acid, or a glycosylated amino acid.

122. The method of claim 120 wherein at least one of the target protein fragments is the same as the target protein fragment comprising the modified amino acid except for the modified amino acid.

123. The method of claim 108 further comprising
performing steps (a) through (e) on a control protein sample, identifying differences between the protein signatures produced from the protein sample and the control protein sample.

124. The method of claim 108 further comprising performing steps (a) through (e) on a plurality of protein samples.

125. The method of claim 124 further comprising identifying differences between the protein signatures produced from the protein samples.

126. The method of claim 124 further comprising performing steps (a) through (e) on a control protein sample, identifying differences between the protein signatures produced from the protein samples and the control protein sample.

127. The method of claim 126 wherein the differences are differences in the presence, amount, presence and amount, or absence of target protein fragments in the protein samples and the control protein sample.

128. The method of claim 124 wherein the steps (a) through (e) are performed on a control protein sample and a tester protein sample, wherein the tester protein sample, or the source of the tester protein sample, is treated, prior to step (a), so as to destroy, disrupt or eliminate one or more protein molecules in the tester protein sample, wherein the target protein fragments corresponding to the destroyed, disrupted, or eliminated protein molecules will be produced from the control protein sample but not the tester protein sample.

129. The method of claim 128 wherein the tester protein sample is treated so as to destroy, disrupt or eliminate one or more protein molecules in the tester protein sample.

130. The method of claim 129 wherein one or more protein molecules in the tester sample are eliminated by separating the one or more protein molecules from the tester protein sample.

131. The method of claim 130 wherein the one or more protein molecules are separated by affinity separation.

132. The method of claim 128 wherein the source of the tester protein sample is treated so as to destroy, disrupt or eliminate one or more protein molecules in the tester protein sample.

133. The method of claim 132 wherein the treatment of the source is accomplished by exposing cells from which the tester sample will be derived with a compound, composition, or condition that will reduce or eliminate expression of one or more genes.

134. The method of claim 128 further comprising identifying differences in the target protein fragments in the control protein sample and tester protein sample.

135. The method of claim 124 further comprising identifying differences between the target protein fragments in the protein samples.

136. The method of claim 124 wherein the plurality of protein samples are produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

137. The method of claim 136 wherein the protein samples are different fractions or samples produced by the same separation procedure.

138. The method of claim 108 further comprising performing steps (a) through (e) on a second protein sample.

139. The method of claim 108 further comprising producing a second protein signature from a second protein sample and comparing the first protein signature and second protein signature, wherein differences in the first and second protein signatures indicate differences in source or condition of the source of the first and second protein samples.

140. The method of claim 108 further comprising producing a second protein signature from a second protein sample and comparing the first protein signature and second protein signature, wherein differences in the first and second protein signatures indicate differences in protein modification of the first and second protein samples.

141. The method of claim 140 wherein the second protein sample is a sample from the same type of cells as the first protein sample except that the cells from which the first protein sample is derived are modification-deficient relative to the cells from which the second protein sample is derived.

142. The method of claim 140 wherein the second protein sample is a sample from a different type of cells than the first protein sample, and wherein the cells from which the first protein sample is derived are modification-deficient relative to the cells from which the second protein sample is derived.

143. The method of claim 108 wherein the protein sample is derived from one or more cells.

144. The method of claim 143 wherein the protein signature indicates the physiological state of the cells.

145. The method of claim 143 wherein the protein signature indicates the effect of a treatment of the cells.

146. The method of claim 145 wherein the cells are derived from an organism, wherein the cells are treated by treating the organism.

147. The method of claim 146 wherein the organism is treated by administering a compound to the organism.

148. The method of claim 146 wherein the organism is human.

149. The method of claim 108 wherein the protein sample is produced by a separation procedure, wherein the separation procedure comprises liquid chromatography, gel electrophoresis, two-dimensional chromatography, two-dimensional gel electrophoresis, isoelectric focusing, thin layer chromatography, centrifugation, filtration, ion chromatography, immunoaffinity chromatography, membrane separation, or a combination of these.

150. The method of claim 108 wherein the set of reporter signal calibrators consists of a single reporter signal calibrator.

151. The method of claim 150 wherein the protein signature of the protein sample represents the presence, absence, amount, or presence and amount of the target protein fragment in the protein sample that corresponds to the reporter signal calibrator.

152. A method of producing a protein signature, the method comprising detecting altered forms of target protein fragments and reporter signal calibrators, wherein the reporter signal calibrators comprise peptides, wherein the altered forms of the target protein fragments can be distinguished from the other altered forms of the target protein fragments, wherein each target protein fragment shares a common property with at least one of the reporter signal calibrators, wherein the common property allows the target protein fragments and reporter signal calibrators having the common property to be distinguished or separated from molecules lacking the common property, wherein the target protein fragment and reporter signal calibrator that share a common property correspond to each other, wherein the altered form of each reporter signal calibrator can be distinguished from the altered form of the target protein fragment with which the reporter signal calibrator shares a common property, wherein the presence, absence, amount, or presence and amount of the altered forms of the target protein fragments indicates the presence, absence, amount, or presence and amount in a protein sample of the target protein fragments from which the altered forms of the target protein fragments are derived, wherein the presence, absence, amount, or presence and amount of the target protein fragments in the protein sample constitutes a protein signature of the protein sample.

153. The method of claim 152 wherein the target protein fragments and reporter signal calibrators are distinguished or separated from other molecules based on the common properties of the target protein fragments and reporter signal calibrators.

154. The method of claim 153 wherein the target protein fragments and reporter signal calibrators are altered following separation.

155. The method of claim 152 wherein the target protein fragments are produced by treating the protein sample.

156. A method of producing a protein signature, the method comprising
    (a) treating a protein sample to produce protein fragments, wherein the protein fragments comprise a set of target protein fragments, wherein the target protein fragments can be altered, wherein the altered forms of the target protein fragments can be distinguished from the other altered forms of the target protein fragments, (b) separating the target protein fragments from other protein fragments in the protein sample, (c) altering the target protein fragments, (d) detecting the altered forms of the target protein fragments, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

157. The method of claim 156 further comprising, prior to or simultaneous with step (b), mixing the target protein fragments with a set of reporter signal calibrators, wherein the reporter signal calibrators comprise peptides, wherein each target protein fragment shares a common property with at least one of the reporter signal calibrators, wherein the common property allows the target protein fragments and reporter signal calibrators having the common property to be distinguished or separated from molecules lacking the common property, wherein the reporter signal calibrators are capable of being altered, wherein the altered form of each reporter signal calibrator can be distinguished from the altered form of the target protein fragment with which the reporter signal calibrator shares a common property.

158. A method of producing a protein signature, the method comprising (a) separating a plurality of target protein fragments from other protein fragments in a protein sample, (b) altering the target protein fragments, (c) detecting the altered forms of the target protein fragments, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

159. A method of analyzing a protein sample, the method comprising (a) mixing a protein sample with a predetermined amount of a reporter signal calibrator, wherein the reporter signal calibrator comprises a peptide, wherein the protein sample has a known amount of protein, wherein the protein sample comprises a target protein fragment, wherein the target protein fragment can be altered, wherein the reporter signal calibrator are capable of being altered, wherein the altered form of the reporter signal calibrator can be distinguished from the altered form of the target protein fragment, (b) altering the target protein fragment and reporter signal calibrator, (c) detecting the altered forms of the target protein fragment and reporter signal calibrator.

160. The method of claim 159 further comprising determining the ratio of the amount of the target protein fragment and the amount of the reporter signal calibrator detected, and comparing the determined ratio with the predicted ratio of the amount of the target protein fragment and the amount of the reporter signal calibrator, wherein the predicted ratio is based on the predicted amount of target protein fragment in the protein sample and the predetermined amount of reporter signal calibrator, wherein the predicted amount of target protein fragment is the amount of target protein fragment the protein sample would have if the known amount of protein in the protein sample consisted of the target protein fragment, wherein the difference between the determined ratio and the predicted ratio is a measure of the purity of the protein sample for the target protein fragment, wherein the closer the determined ratio is to the predicted ratio, the purer the protein sample.

161. A method of analyzing a protein sample, the method comprising (a) treating a protein sample to produce protein fragments, wherein the protein sample has a known amount of protein, wherein the protein sample comprises a target protein, wherein the protein fragments comprise a target protein fragment derived from the target protein, (b) mixing the protein sample with a predetermined amount of a reporter signal calibrator, wherein the reporter signal calibrator comprises peptides, wherein the target protein fragment can be altered, wherein the reporter signal calibrator are capable of being altered, wherein the altered form of the reporter signal calibrator can be distinguished from the altered form of the target protein fragment, (c) altering the target protein fragment and reporter signal calibrator, (d) detecting the altered forms of the target protein fragment and reporter signal calibrator.

162. The method of claim 161 further comprising determining the ratio of the amount of the target protein fragment and the amount of the reporter signal calibrator detected, and comparing the determined ratio with the predicted ratio of the amount of the target protein fragment and the amount of the reporter signal calibrator, wherein the predicted ratio is based on the predicted amount of target protein fragment in the protein sample and the predetermined amount of reporter signal calibrator, wherein the predicted amount of target protein fragment is the amount of target protein fragment the protein sample would have if the known amount of protein in the protein sample consisted of the target protein, wherein the difference between the determined ratio and the predicted ratio is a measure of the purity of the protein sample for the target protein, wherein the closer the determined ratio is to the predicted ratio, the purer the protein sample.

163. A set of reporter signal calibrators, wherein each reporter signal calibrator comprises a peptide, wherein each reporter signal calibrator shares a common property with a target protein fragment in a set of target protein fragments, wherein the common property allows the target protein fragments and reporter signal calibrators having the common property to be distinguished or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators are capable of being altered, wherein the altered form of each reporter signal calibrator can be distinguished from the altered form of the target protein fragment with which the reporter signal calibrator shares a common property.

164. The set of claim 163 wherein the set includes a predetermined amount of each reporter signal calibrator.

165. The set of claim 164 wherein the amount of at least two of the reporter signal calibrators is different.

166. The set of claim 164 wherein the relative amount each reporter signal calibrator is based on the relative amount of each corresponding target protein fragment expected to be in the protein sample.

167. The set of claim 164 wherein the amount of each of the reporter signal calibrators is the same.

168. A kit for producing a protein signature, the kit comprising (a) a set of reporter signal calibrators, wherein each reporter signal calibrator comprises a peptide, wherein each reporter signal calibrator shares a common property with a target protein fragment in a set of target protein fragments, wherein the common property allows the target protein fragments and reporter signal calibrators having the common property to be distinguished or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators are capable of being altered, wherein the altered form of each reporter signal calibrator can be distinguished from the altered form of the target protein fragment with which the reporter signal calibrator shares a common property, (b) one or more reagents for treating a protein sample to produce protein fragments.

169. A mixture comprising a set of reporter signal calibrators and a set of target protein fragments, wherein each reporter signal calibrator comprises a peptide, wherein each reporter signal calibrator shares a common property with a target protein fragment in the set of target protein fragments, wherein the common property allows the target protein fragments and reporter signal calibrators having the common property to be distinguished or separated from molecules lacking the common property, wherein the target protein fragment and reporter signal calibrator that share a common property correspond to each other, wherein the target protein fragments can be altered, wherein the altered forms of the target protein fragments can be distinguished from the other altered forms of the target protein fragments, wherein the reporter signal calibrators are capable of being altered, wherein the altered form of each reporter signal calibrator can be distinguished from the altered form of the target protein fragment with which the reporter signal calibrator shares a common property.

170. A set of target protein fragments, wherein each target protein fragment shares a common property with a reporter signal calibrator in a set of reporter signal calibrators, wherein each reporter signal calibrator comprises a peptide, wherein the common property allows the target protein fragments and reporter signal calibrators having the common property to be distinguished or separated from molecules lacking the common property, wherein the target protein fragment and reporter signal calibrator that share a common property correspond to each other, wherein the target protein can be altered, wherein the altered forms of the target protein fragments can be distinguished from the other altered forms of the target protein fragments, wherein the reporter signal calibrators are capable of being altered, wherein the altered form of each reporter signal calibrator can be distinguished from the altered form of the target protein fragment with which the reporter signal calibrator shares a common property.

171. A method of producing a protein signature, the method comprising (a) treating a protein sample to produce protein fragments, wherein the protein fragments comprise a set of target protein fragments, wherein each of the target protein fragments can be altered, wherein the altered forms of each target protein fragment can be distinguished from every other altered form of target protein fragment, (b) mixing the target protein fragments with a set of reporter signal calibrators, wherein each reporter signal calibrator comprises a peptide, wherein each target protein fragment shares a common property with at least one of the reporter signal calibrators, wherein the common property allows each of the target protein fragments and reporter signal calibrators having the common property to be distinguished or separated from molecules lacking the common property, wherein the target protein fragment and reporter signal calibrator that share a common property correspond to each other, wherein each of the reporter signal calibrators are capable of being altered, wherein the altered form of each reporter signal calibrator can be distinguished from the altered form of the target protein fragment with which the reporter signal calibrator shares a common property, (c) separating the target protein fragments and reporter signal calibrators from other molecules based on the common properties of the target protein fragments and reporter signal calibrators, (d) altering the target protein fragments and reporter signal calibrators, (e) detecting the altered forms of the target protein fragments and reporter signal calibrators, wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

172. A method of producing a protein signature, the method comprising detecting altered forms of target protein fragments and reporter signal calibrators, wherein each reporter signal calibrator comprises a peptide,
  wherein the altered forms of each target protein fragment can be distinguished from every other altered form of target protein fragment, wherein each target protein fragment shares a common property with at least one of the reporter signal calibrators, wherein the common property allows each of the target protein fragments and reporter signal calibrators having the common property to be distinguished or separated from molecules lacking the common property, wherein the target protein fragment and reporter signal calibrator that share a common property correspond to each other, wherein the altered form of each reporter signal calibrator can be distinguished from the altered form of the target protein fragment with which the reporter signal calibrator shares a common property,
  wherein the presence, absence, amount, or presence and amount of the altered forms of the target protein fragments indicates the presence, absence, amount, or presence and amount in a protein sample of the target protein fragments from which the altered forms of the target protein fragments are derived, wherein the presence, absence, amount, or presence and amount of the target protein fragments in the protein sample constitutes a protein signature of the protein sample.

173. A method of producing a protein signature, the method comprising
  (a) treating a protein sample to produce protein fragments, wherein the protein fragments comprise a set of target protein fragments,
    wherein each of the target protein fragments can be altered, wherein the altered forms of each target protein fragment can be distinguished from every other altered form of target protein fragment,
  (b) separating the target protein fragments from other protein fragments in the protein sample,
  (c) altering the target protein fragments,
  (d) detecting the altered forms of the target protein fragments,
  wherein the presence, absence, amount, or presence and amount of the altered forms of the target protein fragments indicates the presence, absence, amount, or presence and amount in the protein sample of the target protein fragments from which the altered forms of the target protein fragments are derived, wherein the presence, absence, amount, or presence and amount of the target protein fragments in the protein sample constitutes a protein signature of the protein sample.

174. The method of claim 173 further comprising, prior to or simultaneous with step (b), mixing the target protein fragments with a set of reporter signal calibrators, wherein each reporter signal calibrator comprises a peptide,
  wherein each target protein fragment shares a common property with at least one of the reporter signal calibrators, wherein the common property allows each of the target protein fragments and reporter signal calibrators having the common property to be distinguished or separated from molecules lacking the common property,
  wherein each of the reporter signal calibrators are capable of being altered, wherein the altered form of each reporter signal calibrator can be distinguished from the altered form of the target protein fragment with which the reporter signal calibrator shares a common property.

175. A set of reporter signal calibrators, wherein each reporter signal calibrator comprises a peptide,
  wherein each reporter signal calibrator shares a common property with a target protein fragment in a set of target protein fragments, wherein the common property allows each of the target protein fragments and reporter signal calibrators having the common property to be distinguished or separated from molecules lacking the common property, wherein the target protein fragment and reporter signal calibrator that share a common property correspond to each other,
  wherein each of the target protein fragments can be altered, wherein the altered forms of each target protein fragment can be distinguished from every other altered form of target protein fragment,
  wherein each of the reporter signal calibrators are capable of being altered, wherein the altered form of each reporter signal calibrator can be distinguished from the altered form of the target protein fragment with which the reporter signal calibrator shares a common property.

176. A kit for producing a protein signature, the kit comprising
  (a) a set of reporter signal calibrators, wherein each reporter signal calibrator comprises a peptide,
    wherein each reporter signal calibrator shares a common property with a target protein fragment in a set of target protein fragments, wherein the common property allows each of the target protein fragments and reporter signal calibrators having the common property to be distinguished or separated from molecules lacking the common property, wherein the target protein fragment and reporter signal calibrator that share a common property correspond to each other,
    wherein each of the target protein fragments can be altered, wherein the altered forms of each target protein fragment can be distinguished from every other altered form of target protein fragment,
    wherein each of the reporter signal calibrators are capable of being altered, wherein the altered form of each reporter signal calibrator can be distinguished from the altered form of the target protein fragment with which the reporter signal calibrator shares a common property,
  (b) one or more reagents for treating a protein sample to produce protein fragments.

177. A mixture comprising a set of reporter signal calibrators and a set of target protein fragments, wherein each reporter signal calibrator comprises a peptide,
  wherein each reporter signal calibrator shares a common property with a target protein fragment in the set of target protein fragments, wherein the common property allows each of the target protein fragments and reporter signal calibrators having the common property to be distinguished or separated from molecules lacking the common property, wherein the target protein fragment and reporter signal calibrator that share a common property correspond to each other,
  wherein each of the target protein fragments can be altered, wherein the altered forms of each target protein fragment can be distinguished from every other altered form of target protein fragment,
  wherein each of the reporter signal calibrators are capable of being altered, wherein the altered form of each reporter signal calibrator can be distinguished from the altered form of the target protein fragment with which the reporter signal calibrator shares a common property.

178. A set of target protein fragments,
wherein each target protein fragment shares a common property with a reporter signal calibrator in a set of reporter signal calibrators, wherein each reporter signal calibrator comprises a peptide, wherein the common property allows each of the target protein fragments and reporter signal calibrators having the common property to be distinguished or separated from molecules lacking the common property, wherein the target protein fragment and reporter signal calibrator that share a common property correspond to each other,
wherein each of the target protein fragments can be altered, wherein the altered forms of each target protein fragment can be distinguished from every other altered form of target protein fragment,
wherein each of the reporter signal calibrators are capable of being altered, wherein the altered form of each reporter signal calibrator can be distinguished from the altered form of the target protein fragment with which the reporter signal calibrator shares a common property.

179. A set of nucleic acid molecules wherein each nucleic acid molecule comprises a nucleotide segment encoding an amino acid segment comprising a reporter signal peptide and a protein or peptide of interest,
wherein the reporter signal peptides have a common property, wherein the common property allows the reporter signal peptides to be distinguished or separated from molecules lacking the common property,
wherein the reporter signal peptides are capable of being altered, wherein the altered form of each reporter signal peptide can be distinguished from the altered forms of the other reporter signal peptides.

180. The set of claim 179 wherein each nucleic acid molecule further comprises expression sequences, wherein the expression sequences are operably linked to the nucleotide segment such that the amino acid segment can be expressed.

181. The set of claim 180 wherein the expression sequences comprise translation expression sequences.

182. The set of claim 181 wherein the expression sequences further comprise transcription expression sequences.

183. The set of claim 180 wherein the amino acid segment can be expressed in vitro.

184. The set of claim 180 wherein the amino acid segment can be expressed in vivo.

185. The set of claim 184 wherein the amino acid segment can be expressed in cell culture.

186. The set of claim 180 wherein the expression sequences of each nucleic acid molecule are different.

187. The set of claim 186 wherein the different expression sequences are differently regulated.

188. The set of claim 186 wherein the expression sequences are similarly regulated.

189. The set of claim 188 wherein a plurality of the expression sequences are expression sequences of, or derived from, genes expressed as part of the same expression cascade.

190. The set of claim 180 wherein the expression sequences of each nucleic acid molecule are the same.

191. The set of claim 190 wherein the expression sequences are similarly regulated.

192. The set of claim 180 wherein the expression sequences of at least two nucleic acid molecules are different.

193. The set of claim 180 wherein the expression sequences of at least two nucleic acid molecules are the same.

194. The set of claim 179 wherein each nucleic acid molecule further comprises replication sequences, wherein the replication sequences allow replication of the nucleic acid molecules.

195. The set of claim 194 wherein the nucleic acid molecules can be replicated in vitro.

196. The set of claim 194 wherein the nucleic acid molecules can be replicated in vivo.

197. The set of claim 196 wherein the nucleic acid molecules can be replicated in cell culture.

198. The set of claim 179 wherein each nucleic acid molecule further comprises integration sequences, wherein the integration sequences allow integration of the nucleic acid molecules into other nucleic acids.

199. The set of claim 198 wherein the nucleic acid molecules can be integrated into a chromosome.

200. The set of claim 199 wherein the nucleic acid molecules can be integrated into a chromosome at a predetermined location.

201. The set of claim 179 wherein the nucleic acids molecules are produced by replicating nucleic acids in one or more nucleic acid samples.

202. The set of claim 201 wherein the nucleic acids are replicated using pairs of primers, wherein each of the first primers in the primer pairs used to produce the nucleic acid molecules comprises a nucleotide sequence encoding the reporter signal peptide.

203. The set of claim 202 wherein each first primer further comprises expression sequences.

204. The set of claim 203 wherein the nucleotide sequence of each first primer also encodes an epitope tag.

205. The set of claim 179 wherein each amino acid segment further comprises an epitope tag.

206. The set of claim 205 wherein the epitope tag of each amino acid segment is different.

207. The set of claim 205 wherein the epitope tag of each amino acid segment is the same.

208. The set of claim 205 wherein the epitope tag of at least two amino acid segments are different.

209. The set of claim 205 wherein the epitope tag of at least two amino acid segments are the same.

210. The set of claim 179 wherein the reporter signal peptide of each amino acid segment is different.

211. The set of claim 179 wherein the reporter signal peptide of each amino acid segment is the same.

212. The set of claim 179 wherein the reporter signal peptide of at least two amino acid segments are different.

213. The set of claim 179 wherein the reporter signal peptide of at least two amino acid segments are the same.

214. The set of claim 179 wherein the nucleic acid molecules are in cells.

215. The set of claim 214 wherein each nucleic acid molecule is in a different cell.

216. The set of claim 214 wherein each nucleic acid molecule is in the same cell.

217. The set of claim 216 wherein each nucleic acid molecule further comprises expression sequences, wherein the expression sequences are operably linked to the nucleotide segment such that the amino acid segment can be expressed.

218. The set of claim 217 wherein the expression sequences of each nucleic acid molecule are different.

219. The set of claim 218 wherein the expression sequences are similarly regulated.

220. The set of claim 219 wherein a plurality of the expression sequences are expression sequences of, or derived from, genes expressed as part of the same expression cascade.

221. The set of claim 214 wherein the nucleic acid molecules are integrated into a chromosome of the cell.

222. The set of claim 221 wherein the nucleic acid molecules are integrated into the chromosome at a predetermined location.

223. The set of claim 221 wherein the chromosome is an artificial chromosome.

224. The set of claim 214 wherein the nucleic acid molecules are, or are integrated into, a plasmid.

225. The set of claim 214 wherein the cells are cell lines.

226. The set of claim 225 wherein each nucleic acid molecule is in a different cell line.

227. The set of claim 225 wherein each nucleic acid molecule is in the same cell line.

228. The set of claim 179 wherein the nucleic acid molecules are in organisms.

229. The set of claim 228 wherein each nucleic acid molecule is in a different organism.

230. The set of claim 228 wherein each nucleic acid molecule is in the same organism.

231. The set of claim 230 wherein each nucleic acid molecule further comprises expression sequences, wherein the expression sequences are operably linked to the nucleotide segment such that the amino acid segment can be expressed.

232. The set of claim 231 wherein the expression sequences of each nucleic acid molecule are different.

233. The set of claim 232 wherein the expression sequences are similarly regulated.

234. The set of claim 233 wherein a plurality of the expression sequences are expression sequences of, or derived from, genes expressed as part of the same expression cascade.

235. The set of claim 228 wherein the nucleic acid molecules are integrated into a chromosome of the organism.

236. The set of claim 235 wherein the nucleic acid molecules are integrated into the chromosome at a predetermined location.

237. The set of claim 235 wherein the chromosome is an artificial chromosome.

238. The set of claim 228 wherein the nucleic acid molecules are, or are integrated a plasmid.

239. The set of claim 228 wherein each nucleic acid molecule is in a different organism.

240. The set of claim 228 wherein each nucleic acid molecule is in the same organism.

241. The set of claim 179 wherein the nucleic acid molecules are in cells of an organism.

242. The set of claim 241 wherein the nucleic acid molecules are in substantially all of the cells of the organism.

243. The set of claim 241 wherein the nucleic acid molecules are in some of the cells organism.

244. The set of claim 241 wherein the amino acid segments are expressed in substantially all of the cells of the organism.

245. The set of claim 241 wherein the amino acid segments are expressed in some of the cells of the organism.

246. The set of claim 179 wherein the protein or peptide of interest of each amino acid segment is different.

247. The set of claim 179 wherein the protein or peptide of interest of each amino acid segment is the same.

248. The set of claim 179 wherein the protein or peptide of interest of at least two amino acid segments are different.

249. The set of claim 179 wherein the protein or peptide of interest of at least two amino acid segments are the same.

250. The set of claim 246 wherein the proteins or peptides of interest have common motifs.

251. The set of claim 250 wherein the proteins or peptides of interest are proteins produced in the same cascade.

252. The set of claim 250 wherein the proteins or peptides of interest are proteins expressed under the same conditions.

253. The set of claim 250 wherein the proteins or peptides of interest are proteins associated with the same disease.

254. The set of claim 250 wherein the proteins or peptides of interest are proteins associated with the same cell type.

255. The set of claim 250 wherein the proteins or peptides of interest are proteins associated with the same tissue type.

256. The set of claim 250 wherein the proteins or peptides of interest are proteins in the same enzymatic pathway.

257. The set of claim 179 wherein the nucleotide segment encodes a plurality of amino acid segments each comprising a reporter signal peptide and a protein or peptide of interest.

258. The set of claim 257 wherein the protein or peptide of interest of at least two of the amino acid segments in one of the nucleotide segments are different.

259. The set of claim 257 wherein the protein or peptide of interest of the amino acid segments in one of the nucleotide segments are different.

260. The set of claim 257 wherein the protein or peptide of interest of at least two of the amino acid segments in each of the nucleotide segments are different.

261. The set of claim 257 wherein the protein or peptide of interest of the amino acid segments in each of the nucleotide segments are different.

262. The set of claim 257 wherein the set consists of a single nucleic acid molecule.

263. The set of claim 179 wherein the set consists of a single nucleic acid molecule, wherein the nucleic acid molecule comprises a plurality of nucleotide segments each encoding an amino acid segment.

264. The set of claim 179 wherein the amino acid segment comprises a cleavage site near the junction between the reporter signal peptide and the protein or peptide of interest.

265. The set of claim 264 wherein the cleavage site is a trypsin cleavage site.

266. The set of claim 264 wherein the cleavage site is at the junction between the reporter signal peptide and the protein or peptide of interest.

267. The set of claim 179 wherein each amino acid segment further comprises a self-cleaving segment.

268. The set of claim 267 wherein the self-cleaving segment is between the reporter signal peptide and the protein or peptide of interest.

269. The set of claim 267 wherein the self-cleaving segment is an intein segment.

270. A set of nucleic acid molecules wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein alteration of the reporter signal peptides alters the amino acid segments, wherein the altered form of each amino acid segment can be distinguished from the altered forms of the other amino acid segments.

271. A set of nucleic acid molecules wherein each nucleic acid molecule comprises a nucleotide segment encoding an amino acid segment comprising a reporter signal peptide and a protein or peptide of interest,
  wherein the amino acid segments have a common property, wherein the common property allows the amino acid segments to be distinguished or separated from molecules lacking the common property,
  wherein the reporter signal peptides are capable of being altered, wherein the altered form of each reporter signal peptide can be distinguished from the altered forms of the other reporter signal peptides.

272. A set of nucleic acid molecules wherein each nucleic acid molecule comprises a nucleotide segment encoding an amino acid segment comprising a reporter signal peptide and a protein or peptide of interest,
  wherein the amino acid segments have a common property, wherein the common property allows the amino acid segments to be distinguished or separated from molecules lacking the common property,
  wherein the reporter signal peptides are capable of being altered, wherein alteration of the reporter signal peptides alters the amino acid segments, wherein the altered form of each amino acid segment can be distinguished from the altered forms of the other amino acid segments.

273. A set of nucleic acid molecules wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide,
  wherein the amino acid subsegments have a common property, wherein the common property allows the amino acid subsegments to be distinguished or separated from molecules lacking the common property,
  wherein the reporter signal peptides are capable of being altered, wherein the altered form of each reporter signal peptide can be distinguished from the altered forms of the other reporter signal peptides.

274. A set of nucleic acid molecules wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide,
  wherein the amino acid subsegments have a common property, wherein the common property allows the amino acid subsegments to be distinguished or separated from molecules lacking the common property,
  wherein the reporter signal peptides are capable of being altered, wherein alteration of the reporter signal peptides alters the amino acid subsegments, wherein the altered form of each amino acid subsegment can be distinguished from the altered forms of the other amino acid subsegments.

275. A set of amino acid segments wherein each amino acid segment comprises a reporter signal peptide and a protein or peptide of interest,
  wherein the reporter signal peptides have a common property, wherein the common property allows the reporter signal peptides to be distinguished or separated from molecules lacking the common property,
  wherein the reporter signal peptides are capable of being altered, wherein the altered form of each reporter signal peptide can be distinguished from the altered forms of the other reporter signal peptides.

276. The set of claim 275 wherein the amino acid segment is a protein or peptide.

277. The set of claim 275 wherein the set consists of a single amino acid segment wherein the amino acid segment comprises a plurality of reporter signal peptides.

278. A cell comprising a set of nucleic acid molecules wherein each nucleic acid molecule comprises a nucleotide segment encoding an amino acid segment comprising a reporter signal peptide and a protein or peptide of interest,
  wherein the reporter signal peptides have a common property, wherein the common property allows the reporter signal peptides to be distinguished or separated from molecules lacking the common property,
  wherein the reporter signal peptides are capable of being altered, wherein the altered form of each reporter signal peptide can be distinguished from the altered forms of the other reporter signal peptides.

279. A set of cells wherein each cell comprises a nucleic acid molecule wherein each nucleic acid molecule comprises a nucleotide segment encoding an amino acid segment comprising a reporter signal peptide and a protein or peptide of interest,
  wherein the reporter signal peptides have a common property, wherein the common property allows the reporter signal peptides to be distinguished or separated from molecules lacking the common property,
  wherein the reporter signal peptides are capable of being altered, wherein the altered form of each reporter signal peptide can be distinguished from the altered forms of the other reporter signal peptides.

280. The set of claim 279 wherein each cell further comprises additional nucleic acid molecules.

281. The set of claim 279 wherein the set consists of a single cell, wherein the cell comprises a plurality of nucleic acid molecules.

282. The set of claim 279 wherein the set consists of a single cell, wherein the cell comprises a set of nucleic acid molecules, wherein the set of nucleic acid molecules consists of a single nucleic acid molecule,
  wherein the nucleic acid molecule encodes a plurality of nucleic acid segments.

283. An organism comprising a set of nucleic acid molecules wherein each nucleic acid molecule comprises a nucleotide segment encoding an amino acid segment comprising a reporter signal peptide and a protein or peptide of interest,
  wherein the reporter signal peptides have a common property, wherein the common property allows the reporter signal peptides to be distinguished or separated from molecules lacking the common property,
  wherein the reporter signal peptides are capable of being altered, wherein the altered form of each reporter signal peptide can be distinguished from the altered forms of the other reporter signal peptides.

284. A set of organisms each organism comprises a nucleic acid molecule wherein each nucleic acid molecule comprises a nucleotide segment encoding an amino acid segment comprising a reporter signal peptide and a protein or peptide of interest,
  wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides.

285. The set of claim 284 wherein each organism further comprises additional nucleic acid molecules.

286. The set of claim 284 wherein the set consists of a single organism, wherein the organism comprises a plurality of nucleic acid molecules.

287. The set of claim 284 wherein the set consists of a single organism, wherein the organism comprises a set of nucleic acid molecules, wherein the set of nucleic acid molecules consists of a single nucleic acid molecule, wherein the nucleic acid molecule encodes a plurality of nucleic acid segments.

288. A method of detecting expression, the method comprising detecting a target altered reporter signal peptide derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates expression of the amino acid segment that comprises the reporter signal peptide from which the target altered reporter signal peptide is derived.

289. The method of claim 288 further comprising determining the amount of the target altered reporter signal peptide detected, wherein the amount of the target altered reporter signal peptide indicates the amount present in the one or more expression samples of the amino acid segment that comprises the reporter signal peptide from which the target altered reporter signal peptide is derived.

290. The method of claim 289 wherein the amount of the amino acid segment present is proportional to the amount of the target altered reporter signal peptide detected.

291. The method of claim 288 further comprising detecting a plurality of the altered reporter signal peptides, wherein detection of each altered reporter signal peptide indicates expression of the amino acid segment that comprises the reporter signal peptide from which that altered reporter signal peptide is derived.

292. The method of claim 291 further comprising determining the amount of the altered reporter signal peptides detected, wherein the amount of each altered reporter signal peptide indicates the amount present in the one or more expression samples of the amino acid segment that comprises the reporter signal peptide from which that altered reporter signal peptide is derived.

293. The method of claim 292 wherein the amount of the amino acid segment present is proportional to the amount of the altered reporter signal peptide detected.

294. The method of claim 291 wherein the presence, absence, amount, or presence and amount of the altered forms of the reporter signal peptides indicates the presence, absence, amount, or presence and amount in the expression sample of the reporter signal peptides from which the altered forms of the reporter signal peptides are derived, wherein the presence, absence, amount, or presence and amount of the reporter signal peptides in the expression sample a protein signature of the expression sample.

295. The method of claim 294 wherein the altered forms of the reporter signal peptides are detected by using mass spectrometry.

296. The method of claim 295 wherein the altered forms of the reporter signal peptides are detected with a tandem mass spectrometer.

297. The method of claim 296 wherein the mass spectrometer includes a quadrupole set for single-ion filtering, a collision cell, and a time-of-flight spectrometer.

298. The method of claim 294 wherein the reporter signal peptides are altered by fragmentation.

299. The method of claim 298 wherein the reporter signal peptides are altered by cleavage at a photocleavable amino acid.

300. The method of claim 298 wherein the reporter signal peptides are fragmented in a collision cell.

301. The method of claim 298 wherein the reporter signal peptides are fragmented at an asparagine-proline bond, a methionine, or a phosphorylated amino acid.

302. The method of claim 294 wherein the common property is mass-to-charge ratio, wherein the reporter signal peptides are altered by altering their mass, their charge, or their mass and charge, wherein the altered forms of the reporter signal peptides can be distinguished via differences in the mass-to-charge ratio of the altered forms of the reporter signal peptides.

303. The method of claim 294 wherein there are two or more, three or more, four or more, five or more, six or more, seven or more, eight or more, nine or more, ten or more, twenty or more, thirty or more, forty or more, fifty or more, sixty or more, seventy or more, eighty or more, ninety or more, or one hundred or more different reporter signal peptides.

304. The method of claim 303 wherein there are ten or more different reporter signal peptides.

305. The method of claim 304 wherein each reporter signal peptide has a labile or scissile bond in a different location.

306. The method of claim 294 further comprising comparing the protein signature to one or more other protein signatures.

307. The method of claim 294 wherein the detected altered reporter signal peptides are derived from a plurality of expression samples.

308. The method of claim 307 wherein some of the detected altered reporter signal peptides are derived from a control expression sample, wherein the method further comprises identifying differences between the protein signatures produced from the expression samples and the control expression sample.

309. The method of claim 308 wherein the differences are differences in the presence, amount, presence and amount, or absence of reporter signal peptides in the expression samples and the control expression sample.

310. The method of claim 307 wherein the plurality of expression samples comprises a control expression sample and a tester expression sample, wherein the tester expression sample, or the source of the tester expression sample, is treated so as to destroy, disrupt or eliminate one or more of the amino acid segments in the tester expression sample, wherein the reporter signal peptides corresponding to the destroyed, disrupted, or eliminated amino acid segments will be produced from the control expression sample but not the tester expression sample.

311. The method of claim 310 wherein the tester expression sample is treated so as to destroy, disrupt or eliminate one or more of the amino acid segments in the tester expression sample.

312. The method of claim 311 wherein one or more of the amino acid segments in the tester sample are eliminated by separating the one or more of the amino acid segments from the tester expression sample.

313. The method of claim 312 wherein the one or more of the amino acid segments are separated by affinity separation.

314. The method of claim 310 wherein the source of the tester expression sample is treated so as to destroy, disrupt or eliminate one or more of the amino acid segments in the test expression sample.

315. The method of claim 314 wherein the treatment of the source is accomplished by exposing cells from which the tester sample will be derived with a compound, composition, or condition that will reduce or eliminate expression of one or more of the nucleotide segments.

316. The method of claim 310 further comprising identifying differences in the reporter signal peptides in the control expression sample and tester expression sample.

317. The method of claim 307 further comprising identifying differences between the reporter signal peptides in the expression samples.

318. The method of claim 307 wherein at least two of the expression samples, or the sources of the at least two expression samples, are subjected to different conditions.

319. The method of claim 318 wherein the sources of the expression samples are cells.

320. The method of claim 318 wherein differences in the protein signatures of the at least two expression samples indicate the effect of the different conditions.

321. The method of claim 318 wherein the different conditions are exposure to different compounds.

322. The method of claim 318 wherein the different conditions are exposure to a compound and no exposure to the compound.

323. The method of claim 294 further comprising producing a second protein signature from a second expression sample and comparing the first protein signature and second protein signature,
wherein differences in the first and second protein signatures indicate differences in source or condition of the source of the first and second expression samples.

324. The method of claim 294 further comprising producing a second protein signature from a second expression sample and comparing the first protein signature and second protein signature,
wherein differences in the first and second protein signatures indicate differences in protein modification of the first and second expression samples.

325. The method of claim 324 wherein the second expression sample is a sample from the same type of cells as the first expression sample except that the cells from which the first expression sample is derived are modification-deficient relative to the cells from which the second expression sample is derived.

326. The method of claim 324 wherein the second expression sample is a sample from a different type of cells than the first expression sample, and wherein the cells from which the first expression sample is derived are modification-deficient relative to the cells from which the second expression sample is derived.

327. The method of claim 294 wherein the expression sample is derived from one or more cells.

328. The method of claim 327 wherein the protein signature indicates the physiological state of the cells.

329. The method of claim 327 wherein the protein signature indicates the effect of a treatment of the cells.

330. The method of claim 329 wherein the cells are derived from an organism, wherein the cells are treated by treating the organism.

331. The method of claim 330 wherein the organism is treated by administering a compound to the organism.

332. The method of claim 330 wherein the organism is human.

333. The method of claim 291 wherein altered reporter signal peptides are detected in a first and a second expression sample.

334. The method of claim 333 wherein the second expression sample is a sample from the same type of organism as the first expression sample.

335. The method of claim 333 wherein the second expression sample is a sample from the same type of tissue as the first expression sample.

336. The method of claim 333 wherein the second expression sample is a sample from the same organism as the first expression sample.

337. The method of claim 336 wherein the second expression sample is obtained at a different time than the first expression sample.

338. The method of claim 333 wherein the second expression sample is a sample from a different organism than the first expression sample.

339. The method of claim 333 wherein the second expression sample is a sample from a different type of tissue than the first expression sample.

340. The method of claim 333 wherein the second expression sample is a sample from a different species of organism in the first expression sample.

341. The method of claim 333 wherein the second expression sample is a sample from a different strain of organism than the first expression sample.

342. The method of claim 333 wherein the second expression sample is a sample from a different cellular compartment than the first expression sample.

343. The method of claim 288 further comprising altering the reporter signal peptides.

344. The method of claim 343 wherein the reporter signal peptides are altered by fragmentation.

345. The method of claim 344 wherein the reporter signal peptides are altered by cleavage at a photocleavable amino acid.

346. The method of claim 344 wherein the reporter signal peptides are fragmented in a collision cell.

347. The method of claim 344 wherein the reporter signal peptides are fragmented at an asparagineproline bond, a methionine, or a phosphorylated amino acid.

348. The method of claim 288 further comprising separating the reporter signal peptides from the expression samples.

349. The method of claim 348 wherein the reporter signal peptides are distinguished or separated from the expression samples based on the common property.

350. The method of claim 288 further comprising cleaving the reporter signal peptides from the proteins or peptides of interest.

351. The method of claim 350 wherein the reporter signal peptides are distinguished or separated from the proteins or peptides of interest based on the common property.

352. The method of claim 288 further comprising cleaving the amino acid segments into a reporter signal peptide portion and a protein portion.

353. The method of claim 288 further comprising mixing two or more of the expression samples together.

354. The method of claim 288 further comprising mixing two or more amino acid segments together, wherein the mixed amino acid segments were derived from two or more different expression samples.

355. The method of claim 288 wherein expression of the amino acid segment that comprises the reporter signal peptide from which the target altered reporter signal peptide is derived identifies the expression sample from which the target altered reporter signal peptide is derived.

356. The method of claim 355 wherein the expression samples are derived from one or more cells, wherein expression of the amino acid segment that comprises the reporter signal peptide from which the target altered reporter signal peptide is derived identifies the cell from which the identified expression sample is derived.

357. The method of claim 355 wherein the expression samples are derived from one or more organisms, wherein expression of the amino acid segment that comprises the reporter signal peptide from which the target altered reporter signal peptide is derived identifies the organism from which the identified expression sample is derived.

358. The method of claim 355 wherein the expression samples are derived from one or more tissues, wherein expression of the amino acid segment that comprises the reporter signal peptide from which the target altered reporter signal peptide is derived identifies the tissue from which the identified expression sample is derived.

359. The method of claim 355 wherein the expression samples are derived from one or more cell lines, wherein expression of the amino acid segment that comprises the reporter signal peptide from which the target altered reporter signal peptide is derived identifies the cell line from which the identified expression sample is derived.

360. The method of claim 288 wherein each nucleic acid molecule further comprises expression sequences, wherein the expression sequences are operably linked to the nucleotide segment such that the amino acid segment is expressed.

361. The method of claim 360 wherein the expression sequences comprise translation expression sequences.

362. The method of claim 361 wherein the expression sequences further comprise transcription expression sequences.

363. The method of claim 360 wherein the amino acid segment is expressed in vitro.

364. The method of claim 360 wherein the amino acid segment is expressed in vivo.

365. The method of claim 364 wherein the amino acid segment is expressed in cell culture.

366. The method of claim 360 wherein the expression sequences of each nucleic acid molecule are different.

367. The method of claim 366 wherein the different expression sequences are differently regulated.

368. The method of claim 366 wherein the expression sequences are similarly regulated.

369. The method of claim 368 wherein a plurality of the expression sequences are expression sequences of, or derived from, genes expressed as part of the same expression cascade.

370. The method of claim 360 wherein the expression sequences of each nucleic acid molecule are the same.

371. The method of claim 370 wherein the expression sequences are similarly regulated.

372. The method of claim 360 wherein the expression sequences of at least two nucleic acid molecules are different.

373. The method of claim 360 wherein the expression sequences of at least two nucleic acid molecules are the same.

374. The method of claim 360 wherein expression of the amino acid segment is induced.

375. The method of claim 288 wherein each nucleic acid molecule further comprises replication sequences, wherein the replication sequences mediate replication of the nucleic acid molecules.

376. The method of claim 375 wherein the nucleic acid molecules are replicated in vitro.

377. The method of claim 375 wherein the nucleic acid molecules are replicated in vivo.

378. The method of claim 377 wherein the nucleic acid molecules are replicated in cell culture.

379. The method of claim 288 wherein each nucleic acid molecule further comprises integration sequences, wherein the integration sequences mediate integration of the nucleic acid molecules into other nucleic acids.

380. The method of claim 379 wherein the nucleic acid molecules are integrated into a chromosome.

381. The method of claim 380 wherein the nucleic acid molecules are integrated into a chromosome at a predetermined location.

382. The method of claim 288 wherein the nucleic acids molecules are produced by replicating nucleic acids in one or more nucleic acid samples.

383. The method of claim 382 wherein the nucleic acids are replicated using pairs of primers, wherein each of the first primers in the primer pairs used to produce the nucleic acid molecules comprises a nucleotide sequence encoding the reporter signal peptide.

384. The method of claim 383 wherein each first primer further comprises expression sequences.

385. The method of claim 384 wherein the nucleotide sequence of each first primer also encodes an epitope tag.

386. The method of claim 288 wherein each amino acid segment further comprises an epitope tag.

387. The method of claim 386 wherein the epitope tag of each amino acid segment is different.

388. The method of claim 386 wherein the epitope tag of each amino acid segment is the same.

389. The method of claim 386 wherein the epitope tag of at least two amino acid segments are different.

390. The method of claim 386 wherein the epitope tag of at least two amino acid segments are the same.

391. The method of claim 386 wherein the amino acid segments are distinguished or separated from the one or more expression samples via the epitope tags.

392. The method of claim 288 wherein the reporter signal peptide of each amino acid segment is different.

393. The method of claim 288 wherein the reporter signal peptide of each amino acid segment is the same.

394. The method of claim 288 wherein the reporter signal peptide of at least two amino avid segments are different.

395. The method of claim 288 wherein the reporter signal peptide of at least two amino acid segments are the same.

396. The method of claim 288 wherein the nucleic acid molecules are in cells.

397. The method of claim 396 wherein each nucleic acid molecule is in a different cell.

398. The method of claim 396 wherein each nucleic acid molecule is in the same cell.

399. The method of claim 398 wherein each nucleic acid molecule further comprises expression sequences, wherein the expression sequences are operably linked to the nucleotide segment such that the amino acid segment can be expressed.

400. The method of claim 399 wherein the expression sequences of each nucleic acid molecule are different.

401. The method of claim 400 wherein the expression sequences are similarly regulated.

402. The method of claim 401 wherein a plurality of the expression sequences are expression sequences of, or derived from, genes expressed as part of the same expression cascade.

403. The method of claim 396 wherein the nucleic acid molecules are integrated into a chromosome of the cell.

404. The method of claim 403 wherein the nucleic acid molecules are integrated into the chromosome at a predetermined location.

405. The method of claim 403 wherein the chromosome is an artificial chromosome.

406. The method of claim 396 wherein the nucleic acid molecules are, or are integrated into, a plasmid.

407. The method of claim 396 wherein the cells are cell lines.

408. The method of claim 407 wherein each nucleic acid molecule is in a different cell line.

409. The method of claim 407 wherein each nucleic acid molecule is in the same cell line.

410. The method of claim 396 wherein the expression samples are produced from the cells.

411. The method of claim 410 wherein each expression sample is produced from cells from a cell sample, wherein each expression sample is produced from a different cell sample.

412. The method of claim 411 wherein each cell sample is subjected to different conditions.

413. The method of claim 412 wherein each cell sample is brought into contact with a different test compound.

414. The method of claim 412 wherein each cell sample is cultured under different conditions.

415. The method of claim 412 wherein each cell sample is derived from a different organism.

416. The method of claim 412 wherein each cell sample is derived from a different tissue.

417. The method of claim 412 wherein each cell sample is taken from the same source different times.

418. The method of claim 410 wherein the expression samples are produced by lysing the cells.

419. The method of claim 288 wherein the nucleic acid molecules are in organism.

420. The method of claim 419 wherein each nucleic acid molecule is in a different organism.

421. The method of claim 419 wherein each nucleic acid molecule is in the same organism.

422. The method of claim 421 wherein each nucleic acid molecule further comprises expression sequences, wherein the expression sequences are operably linked to the nucleotide segment such that the amino acid segment can be expressed.

423. The method of claim 422 wherein the expression sequences of each nucleic acid molecule are different.

424. The method of claim 423 wherein the expression sequences are similarly regulated.

425. The method of claim 424 wherein a plurality of the expression sequences are expression sequences of, or derived from, genes expressed as part of the same expression cascade.

426. The method of claim 419 wherein the nucleic acid molecules are integrated into a chromosome of the organism.

427. The method of claim 426 wherein the nucleic acid molecules are integrated into the chromosome at a predetermined location.

428. The method of claim 426 wherein the chromosome is an artificial chromosome.

429. The method of claim 419 wherein the nucleic acid molecules are, or are integrated into, a plasmid.

430. The method of claim 419 wherein each nucleic acid molecule is in a different organism.

431. The method of claim 419 wherein each nucleic acid molecule is in the same organism.

432. The method of claim 288 wherein the nucleic acid molecules are in cells of organism.

433. The method of claim 432 wherein the nucleic acid molecules are in substantially all of the cells of the organism.

434. The method of claim 432 wherein the nucleic acid molecules are in some of the cells of the organism.

435. The method of claim 432 wherein the amino acid segments are expressed in substantially all of the cells of the organism.

436. The method of claim 432 wherein the amino acid segments are expressed in some of the cells of the organism.

437. The method of claim 288 wherein the protein or peptide of interest of each amino acid segment is different.

438. The method of claim 288 wherein the protein or peptide of interest of each amino acid segment is the same.

439. The method of claim 288 wherein the protein or peptide of interest of at least two amino acid segments are different.

440. The method of claim 288 wherein the protein or peptide of interest of at least two amino acid segments are the same.

441. The method of claim 437 wherein the proteins or peptides of interest have common motifs.

442. The method of claim 441 wherein the proteins or peptides of interest are proteins produced in the same cascade.

443. The method of claim 441 wherein the proteins or peptides of interest are proteins expressed under the same conditions.

444. The method of claim 441 wherein the proteins or peptides of interest are proteins associated with the same disease.

445. The method of claim 441 wherein the proteins or peptides of interest are proteins associated with the same cell type.

446. The method of claim 441 wherein the proteins or peptides of interest are proteins associated with the same tissue type.

447. The method of claim 441 wherein the proteins or peptides of interest are proteins in the same enzymatic pathway.

448. The method of claim 288 wherein the nucleotide segment encodes a plurality of amino acid segments each comprising a reporter signal peptide and a protein or peptide of interest.

449. The method of claim 448 wherein the protein or peptide of interest of at least two of the amino acid segments in one of the nucleotide segments are different.

450. The method of claim 448 wherein the protein or peptide of interest of the amino acid segments in one of the nucleotide segments are different.

451. The method of claim 448 wherein the protein or peptide of interest of at least two of the amino acid segments in each of the nucleotide segments are different.

452. The method of claim 448 wherein the protein or peptide of interest of the amino acid segments in each of the nucleotide segments are different.

453. The method of claim 448 wherein the set consists of a single nucleic acid molecule.

454. The method of claim 288 wherein the set consists of a single nucleic acid molecule, wherein the nucleic acid molecule comprises a plurality of nucleotide segments each encoding an amino acid segment.

455. The method of claim 288 wherein the amino acid segment comprises a cleavage site near the junction between the reporter signal peptide and the protein or peptide of interest.

456. The method of claim 455 wherein the cleavage site is cleaved.

457. The method of claim 456 wherein the reporter signal peptide is distinguished or separated from the peptide or protein of interest.

458. The method of claim 455 wherein the cleavage site is a trypsin cleavage site.

459. The method of claim 455 wherein the cleavage site is at the junction between the reporter signal peptide and the protein or peptide of interest.

460. The method of claim 288 wherein each amino acid segment further comprises a self-cleaving segment.

461. The method of claim 460 wherein the self-cleaving segment is between the reporter signal peptide and the protein or peptide of interest.

462. The method of claim 461 wherein the self-cleaving segment cleaves the amino acid segment.

463. The method of claim 462 wherein the reporter signal peptide is distinguished or separated from the peptide or protein of interest.

464. The method of claim 460 wherein the self-cleaving segment is an intein segment.

465. The method of claim 288 wherein a plurality of different altered reporter signal peptides are detected, wherein detection of each altered reporter signal peptide indicates expression of the amino acid segment that comprises the reporter signal peptide from which that altered reporter signal peptide is derived.

466. The method of claim 465 wherein different expression samples comprise different nucleic acid molecules, wherein detection of each altered reporter signal peptide indicates expression in the expression sample that comprises the nucleic acid molecule that comprises the nucleotide segment encoding the amino acid segment that comprises the reporter signal peptide from which that altered reporter signal peptide is derived.

467. The method of claim 288 wherein there are a plurality of different expression samples, wherein each different expression sample comprises different nucleic acid molecules, wherein detection of an altered reporter signal peptide indicates expression in the expression sample that comprises the nucleic acid molecule that comprises the nucleotide segment encoding the amino acid segment that comprises the reporter signal peptide from which the detected altered reporter signal peptide is derived.

468. A method of detecting expression, the method comprising detecting a target altered reporter signal peptide derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates expression of the nucleotide segment encoding the amino acid segment that comprises the reporter signal peptide from which the target altered reporter signal peptide is derived.

469. The method of claim 468 further comprising determining the amount of the target altered reporter signal peptide detected, wherein the amount of the target altered reporter signal peptide indicates the amount present in the one or more expression samples of the nucleotide segment that comprises the reporter signal peptide from which the target altered reporter signal peptide is derived.

470. The method of claim 469 wherein the amount of the nucleotide segment present is proportional to the amount of the target altered reporter signal peptide detected.

471. A The method of claim 468 further comprising detecting a plurality of the altered reporter signal peptides, wherein detection of each altered reporter signal peptide indicates expression of the nucleotide segment that comprises the reporter signal peptide from which that altered reporter signal peptide is derived.

472. The method of claim 471 further comprising determining the amount of the altered reporter signal peptides detected, wherein the amount of each altered reporter signal peptide indicates the amount present in the one or more expression samples of the nucleotide segment that comprises the reporter signal peptide from which that altered reporter signal peptide is derived.

473. The method of claim 472 wherein the amount of the nucleotide segment present is proportional to the amount of the altered reporter signal peptide detected.

474. A method of detecting expression, the method comprising detecting a target altered amino acid segment derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished or separated from molecules lacking the common property, wherein the reporter signal peptides are capable of being altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates expression of the amino acid segment from which the target altered amino acid segment is derived.

475. A method of detecting expression, the method comprising detecting an altered amino acid subsegment derived from one or more expression samples, wherein the one or more expression samples collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished or separated from molecules lacking the common property, wherein the reporter signal peptides are capable of being altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates expression of the amino acid segment from which the target altered amino acid subsegment is derived.

476. A method of detecting cells, the method comprising detecting a target altered reporter signal peptide derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell from which the target altered reporter signal peptide is derived.

477. The method of claim 476 wherein each cell is engineered to contain at least one of the nucleic acid molecules, wherein the reporter signal peptide of the amino acid segment encoded by the nucleotide segment of the nucleic acid molecule in each cell is different.

478. The method of claim 477 wherein each cell having a trait of interest comprises the same reporter signal peptide.

479. The method of claim 478 wherein the trait of interest is a heterologous gene.

480. The method of claim 479 wherein the heterologous gene comprises the nucleic acid molecule.

481. The method of claim 478 wherein the heterologous gene encodes the amino acid segment.

482. The method of claim 476 wherein a plurality of different altered reporter signal peptides are detected, wherein detection of each altered reporter signal peptide indicates the presence of the cell from which that altered reporter signal peptide is derived.

483. The method of claim 482 wherein different cells comprise different nucleic acid molecules, wherein detection of each altered reporter signal peptide indicates the presence of the cell that comprises the nucleic acid molecule that comprises the nucleotide segment encoding the amino acid segment that comprises the reporter signal peptide from which that altered reporter signal peptide is derived.

484. The method of claim 476 wherein there are a plurality of different cells, wherein each different cell comprises different nucleic acid molecules, wherein detection of an altered reporter signal peptide indicates the presence of the cell that comprises the nucleic acid molecule that comprises the nucleotide segment encoding the amino acid segment that comprises the reporter signal peptide from which the detected altered reporter signal peptide is derived.

485. A method of detecting cell samples, the method comprising detecting a target altered reporter signal peptide derived from one or more cell samples, wherein the one or more cell samples collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell sample from which the target altered reporter signal peptide is derived.

486. The method of claim 485 wherein a plurality of different altered reporter signal peptides are detected, wherein detection of each altered reporter signal peptide indicates the presence of the cell sample from which that altered reporter signal peptide is derived.

487. The method of claim 485 wherein different cell samples comprise different nucleic acid molecules, wherein detection of each altered reporter signal peptide indicates the presence of the cell sample that comprises the nucleic acid molecule that comprises the nucleotide segment encoding the amino acid segment that comprises the reporter signal peptide from which that altered reporter signal peptide is derived.

488. The method of claim 485 wherein there are a plurality of different cell samples, wherein each different cell sample comprises different nucleic acid molecules, wherein detection of an altered reporter signal peptide indicates the presence of the cell sample that comprises the nucleic acid molecule that comprises the nucleotide segment encoding the amino acid segment that comprises the reporter signal peptide from which the detected altered reporter signal peptide is derived.

489. A method of detecting cells, the method comprising detecting a target altered reporter signal peptide derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the cell from which the target altered reporter signal peptide is derived.

490. A method of detecting cells, the method comprising detecting a target altered amino acid segment derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished or separated from molecules lacking the common property, wherein the reporter signal peptides are capable of being altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates the presence of the cell from which the target altered amino acid segment is derived.

491. A method of detecting cells, the method comprising detecting an altered amino acid subsegment derived from one or more cells, wherein the one or more cells collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished or separated from molecules lacking the common property, wherein the reporter signal peptides are capable of being altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates the presence of the cell which the target altered amino acid subsegment is derived.

492. A method of detecting organisms, the method comprising detecting a target altered reporter signal peptide derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the organism from which the target altered reporter signal peptide is derived.

493. The method of claim 492 wherein each organism is engineered to contain at least one of the nucleic acid molecules, wherein the reporter signal peptide of the amino acid segment encoded by the nucleotide segment of the nucleic acid molecule in each organism is different.

494. The method of claim 493 wherein each organism having a trait of interest comprises the same reporter signal peptide.

495. The method of claim 494 wherein the trait of interest is a transgene.

496. The method of claim 495 wherein the transgene gene comprises the nucleic acid molecule.

497. The method of claim 494 wherein the transgene gene encodes the amino acid segment.

498. The method of claim 492 wherein a plurality of different altered reporter signal peptides are detected, wherein detection of each altered reporter signal peptide indicates the presence of the organism from which that altered reporter signal peptide is derived.

499. The method of claim 498 wherein different organisms comprise different nucleic acid molecules, wherein detection of each altered reporter signal peptide indicates the presence of the organism that comprises the nucleic acid molecule that comprises the nucleotide segment encoding the amino acid segment that comprises the reporter signal peptide from which that altered reporter signal peptide is derived.

500. The method of claim 492 wherein there are a plurality of different organisms, wherein each different organism comprises different nucleic acid molecules, wherein detection of an altered reporter signal peptide indicates the presence of the organism that comprises the nucleic acid molecule that comprises the nucleotide segment encoding the amino acid segment that comprises the reporter signal peptide from which the detected altered reporter signal peptide is derived.

501. A method of detecting organisms, the method comprising detecting a target altered reporter signal peptide derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the reporter signal peptides have a common property, wherein the common property allows the reporter signal peptides to be distinguished or separated from molecules lacking the common property, wherein the reporter signal peptides are capable of being altered, wherein the altered form of each reporter signal peptide can be distinguished from the altered forms of the other reporter signal peptides, wherein the target altered reporter signal peptide is one of the altered reporter signal peptides, wherein detection of the target altered reporter signal peptide indicates the presence of the organism from which the target altered reporter signal peptide is derived.

502. A method of detecting organisms, the method comprising detecting a target altered amino acid segment derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the amino acid segments have a common property, wherein the common property allows the amino acid segments to be distinguished or separated from molecules lacking the common property, wherein the reporter signal peptides are capable of being altered, wherein alteration of the reporter signal peptides alters the amino acid segments, wherein the altered form of each amino acid segment can be distinguished from the altered forms of the other amino acid segments, wherein the target altered amino acid segment is one of the altered amino acid segments, wherein detection of the target altered amino acid segment indicates the presence of the organism from which the target altered amino acid segment is derived.

503. A method of detecting organisms, the method comprising detecting an altered amino acid subsegment derived from one or more organisms, wherein the one or more organisms collectively comprise a set of nucleic acid molecules, wherein each nucleic acid molecule comprises a nucleotide segment encoding an amino acid segment comprising a reporter signal peptide and a protein or peptide of interest, wherein the amino acid segments each comprise an amino acid subsegment, wherein each amino acid subsegment comprises a portion of the protein or peptide of interest and all or a portion of the reporter signal peptide, wherein the amino acid subsegments have a common property, wherein the common property allows the amino acid subsegments to be distinguished or separated from molecules lacking the common property, wherein the reporter signal peptides are capable of being altered, wherein alteration of the reporter signal peptides alters the amino acid subsegments, wherein the altered form of each amino acid subsegment can be distinguished from the altered forms of the other amino acid subsegments, wherein the target altered amino acid subsegment is one of the altered amino acid subsegments, wherein detection of the target altered amino acid subsegment indicates the presence of the organism from which the target altered amino acid subsegment is derived.

504. A method comprising:
(a) associating one of a plurality of reporter signal peptides with one or more analytes in each of a plurality of samples,
wherein each reporter signal has a common property, wherein the common property allows each reporter signal to be separated from molecules lacking the common property,
(b) separating the analytes contained in each sample,
(c) altering the reporter signals, and
(d) detecting the altered forms the reporter signals.

505. The method of claim 504 further comprising, following step (a) and prior to step (b), combining two or more of the samples.

506. The method of claim 504 wherein analytes in each sample are associated with only one reporter signal peptide, wherein the reporter signal peptide associated with analytes in each sample is different.

507. The method of claim 504 wherein the analytes are separated by contact with a capture array.

508. A method comprising:
(a) associating one of a plurality of coding tags with one or more analytes in at least one sample,
(b) separating the analytes contained in each sample;
(c) associating the coding tags with one or more reporter molecules, wherein each reporter molecule comprises a reporter signal peptide and a decoding tag,
wherein each reporter signal peptide has a common property, wherein the common property allows each reporter signal peptide to be separated from molecules lacking the common property, wherein each decoding tag is specific for one or more of the coding tags,
(d) altering the reporter signal peptides, and
(e) detecting the altered forms the reporter signal peptides.

509. The method of claim 508 wherein the coding tags are oligonucleotides, and wherein the decoding tags are peptide nucleic acids.

510. A method comprising:
(a) associating one of a plurality of coding tags with one or more analytes in at least one sample,
(b) separating the analytes contained in each sample;
(c) associating the coding tags with one or more reporter signal peptides,
wherein each reporter signal peptide has a common property, wherein the common property allows each reporter signal peptide to be separated from molecules lacking the common property, wherein each reporter signal peptide is specific for one or more of the coding tags,
(d) altering the reporter signal peptides, and
(e) detecting the altered forms the reporter signal peptides.

511. The method of claim 510 wherein the coding tags are oligonucleotides, and wherein the reporter signals are peptide nucleic acids.

512. A method comprising:
(a) associating one of a plurality of reporter signal peptides with one or more analytes in each of a plurality of samples to form reporter signal/analyte conjugates,
wherein each reporter signal/analyte conjugate has a common property, wherein the common property allows each reporter signal/analyte conjugate to be separated from molecules lacking the common property,
(b) separating the analytes contained in each sample, wherein separation is not based on the common property of the reporter signal/analyte conjugates,
(c) altering the reporter signal peptides thereby altering the reporter signal/analyte conjugates, and
(d) detecting the altered forms the reporter signal/analyte conjugates.

513. A method comprising:
(a) associating one of a plurality of coding tags with one or more analytes in at least one sample,
(b) separating the analytes contained in each sample;
(c) associating the coding tags with one or more reporter molecules, wherein each reporter molecule comprises a reporter signal peptide and a decoding tag, wherein each reporter molecule has a common property, wherein the common property allows each reporter molecule to be separated from molecules lacking the common property, wherein each decoding tag is specific for one or more of the coding tags, (d) altering the reporter signal peptides thereby altering the reporter molecules, and (e) detecting the altered forms the reporter molecules.

* * * * *

UNITED STATES PATENT AND TRADEMARK OFFICE
CERTIFICATE OF CORRECTION

PATENT NO.       : 6,824,981 B2
APPLICATION NO.  : 09/929266
DATED            : November 30, 2004
INVENTOR(S)      : Brian T. Chait et al.

It is certified that error appears in the above-identified patent and that said Letters Patent is hereby corrected as shown below:

On column 75, line 26, the word "asparagine" should be replaced with --aspartic acid--.
On column 76, line 55, the word "asparagine" should be replaced with --aspartic acid--.
On column 78, line 15, the word "asparagine" should be replaced with --aspartic acid--.
On column 79, line 39, the word "asparagine" should be replaced with --aspartic acid--.
On column 119, line 51, the word "asparagine" should be replaced with --aspartic acid--.
On column 127, line 24, the word "asparagine" should be replaced with --aspartic acid--.
On column 129, line 48, the word "asparagine" should be replaced with --aspartic acid--.
On column 187, line 34, the word "asparagineproline" should be replaced with --aspartic acid-proline--.
On column 210, line 23, the word "asparagine" should be replaced with --aspartic acid--.
On column 212, line 54, the word "asparagineproline" should be replaced with --aspartic acid-proline--.

Signed and Sealed this

Eighteenth Day of July, 2006

JON W. DUDAS
*Director of the United States Patent and Trademark Office*